US012590123B2

(12) United States Patent
Janetka et al.

(10) Patent No.: US 12,590,123 B2

(45) Date of Patent: Mar. 31, 2026

(54) COMPOUNDS AND METHODS FOR TREATING CANCER, VIRAL INFECTIONS, AND ALLERGIC CONDITIONS

(71) Applicant: Washington University, St. Louis, MO (US)

(72) Inventors: James W. Janetka, St. Louis, MO (US); Vishnu Damalanka, St. Louis, MO (US)

(73) Assignee: Washington University, St. Louis, MO (US)

( * ) Notice: Subject to any disclaimer, the term of this patent is extended or adjusted under 35 U.S.C. 154(b) by 998 days.

(21) Appl. No.: 17/620,169

(22) PCT Filed: Jun. 25, 2020

(86) PCT No.: PCT/US2020/039659

§ 371 (c)(1),
(2) Date: Dec. 17, 2021

(87) PCT Pub. No.: WO2020/264187

PCT Pub. Date: Dec. 30, 2020

(65) Prior Publication Data

US 2022/0380407 A1 Dec. 1, 2022

Related U.S. Application Data

(60) Provisional application No. 63/031,340, filed on May 28, 2020, provisional application No. 62/866,069, filed on Jun. 25, 2019.

(51) Int. Cl.

| | |
|---|---|
| ***A61K 38/04*** | (2006.01) |
| ***A61K 38/12*** | (2006.01) |
| ***A61K 45/06*** | (2006.01) |
| ***A61K 47/54*** | (2017.01) |
| ***A61P 31/14*** | (2006.01) |
| ***C07K 5/04*** | (2006.01) |
| ***C07K 5/117*** | (2006.01) |
| ***C07K 5/12*** | (2006.01) |

(52) U.S. Cl.

CPC .............. *C07K 5/126* (2013.01); *A61K 45/06* (2013.01); *A61K 47/545* (2017.08); *A61P 31/14* (2018.01); *C07K 5/1024* (2013.01)

(58) Field of Classification Search

CPC .... C07K 5/126; C07K 5/1024; C07K 5/1021; C07K 5/1019; A61K 45/06; A61K 47/545; A61K 38/12; A61P 31/14; A61P 35/00

See application file for complete search history.

(56) References Cited

U.S. PATENT DOCUMENTS

2018/0066015 A1 3/2018 Janetka et al.

FOREIGN PATENT DOCUMENTS

WO 2013014074 A1 1/2013

OTHER PUBLICATIONS

Grabowska et al, "Structure-activity relationship study of a small cyclic peptide H-c[Lys-Pro-Glu]-Arg-OH: a potent inhibitor of Vascular Endothelial Growth Factor interaction with Neuropilin-1," Bioorg Med Chem 25:597-602 (2017) (Year: 2017).*

Moulin et al, "synthesis of peptide aldehydes," J Pept Syn 13:1-15 (2007) (Year: 2007).*

Steinmetzer, T., et al., "Chapter 11 The Antiviral Potential of Host Protease Inhibitors," Activation of Viruses by Host Proteases, E. Bottcher-Friebertshauser et al. (Eds.), Springer International Publishing AG, 2018, pp. 279-325, 47 pages.

Steinmetzer, T., et al., "Secondary Amides of Sulfonylated 3-Amidinophenylalanine. New Potent and Selective Inhibitors of Matriptase," 2006, J Med Chem, 49:4116-4126.

Venukadasula, P.K.M., et al., "Design and Synthesis of Nonpeptide Inhibitors of Hepatocyte Growth Factor Activation," 2016, ACS Med Chem Lett, 177-181, 5 pages.

Wang, M-H., et al., "Oncogenic and Invasive Potentials of Human Macrophage-Stimulating Protein Receptor, the RON Receptor Tyrosine Kinase," 2003, Carcinogenesis, 23/8:1291-1300, 10 pages.

Wang, M-H., et al., "Proteolytic Activation of Single-Chain Precursor Macrophage-Stimulating Protein by Nerve Growth Factor-gamma and Epidermal Growth Factor-Binding Protein, Members of the Kallikrein Family," 1994, J Biol Chem, 269:13806-13810, 5 pages.

Weerawarna, P.M., et al., "Structure-based Design and Synthesis of Triazole-based Macrocyclic Inhibitors of Norovirus Protease: Structural, Biochemical, Spectroscopic, and Antiviral Studies," 2016, Eur J Med Chem, 119:300-318, 20 pages.

White, G.V., et al., " Kallikrein 5 Inhibitors Identified Through Structure Based Drug Design in Search for a Treatment for Netherton Syndrome," 2019, Bioorg Medic Chem Lett, 29:821-825, 5 pages.

Yao, H.P., et al., "MSP-RON Signalling in Cancer: Pathogenesis and Therapeutic Potential," 2013, Nat Rev Cancer, 13:466-481, 16 pages.

International Preliminary Report on Patentability issued in PCT/US2020/039659, dated Jan. 6, 2022, 7 pages.

International Search Report and Written Opinion issued in PCT/US2020/039659, dated Nov. 24, 2020, 10 pages.

(Continued)

*Primary Examiner* — Julie Ha

*Assistant Examiner* — Kristina M Hellman

(74) *Attorney, Agent, or Firm* — Stinson LLP

(57) ABSTRACT

The present invention generally relates to compounds that are useful for inhibiting one or more trypsin-like S1 serine proteases, HGFA, matriptase, hepsin, KLK5 and/or TMPRSS2 as well as cysteine proteases including trypsin-like cysteine proteases (e.g. Cathepsin B). The present invention also relates to various methods of using the inhibitor compounds to treat or prevent viral infections, including those caused by coronaviruses and influenza, conditions associated with KLK5, various malignancies, pre-malignant conditions, and cancer.

10 Claims, 17 Drawing Sheets

Specification includes a Sequence Listing.

(56) References Cited

OTHER PUBLICATIONS

Azouz, N.P., et al., "The Antiprotease SPINK7 Serves as an Inhibitory Checkpoint for Esophageal Epithelial Inflammatory Responses," 2018, Sci Transl Med, 10:3aap9736, 15 pages.
Beliveau, F., et al., "Probing the Substrate Specificities of Matriptase, Matriptase-2, Hepsin and DESC1 with Internally Quenched Fluorescent Peptides," 2009, FEBS J, 276:2213-2226, 14 pages.
Bestle, D., et al., "TMPRSS2 and Furin are Both Essential for Proteolytic Activation of SARS-CoV-2 in Human Airway Cells," 2020, Life Science Alliance, 3/9:3202000786, 14 pages.
Chevillet, J.R., et al., "Identification and Characterization of Small-Molecule Inhibitors of Hepsin," 2008, Mol Cancer Ther, 7:3343-3351, 9 pages.
Colombo, E., et al., "Design and Synthesis of Potent, Selective Inhibitors of Matriptase," 2012, ACW Med Chem Lett, 3/7:530-534, 5 pages.
Craik, D.J., et al., "The Future of Peptide-Based Drugs," 2013, Chem Biol Drug Des, 81:136-147, 12 pages.
Damalanka, V.C., et al., "Recent Progress on Inhibitors of the Type II Transmembrane Serine Proteases, Hepsin, Matripetase and Matriptase-2," 2019, Future Med Chem, 11/7:743-769, 27 pages.
Damalanka, V.C., et al., "Discovery of Selective Matriptase and Hepsin Serine Protease Inhibitors: Useful Chemical Tools for Cancer Cell Biology," 2019, J Med Chem, 62:480-490, 11 pages.
Damalanka, V.C., et al., "Structure-guided Design, Synthesis and Evaluation of Exazolidinone-based Inhibitors of Norovirus 3CL Protease," 2018, Eur J Med Chem, 143:881-890, 10 pages.
Damalanka, V.C., et al., "Design, Synthesis, and Evaluation of a Novel Series of Macrocyclic Inhibitors of Norovirus BCL Protease," 2017, Eur J Med Chem, 127:41-61, 21 pages.
Debela, M., et al., "Structures and Specificity of the Human Kallikrein-Related Peptidases KLK 4, 5, 6, and 7," 2008, Biol Chem, 389:623-632, 10 pages.
Enyedy, I.J., et al., "Structure-Based Approach for the Discovery of Bis-benzamidines as Novel Inhibitors of Matriptase," 2001, J Med Chem, 44:1349-1355, 7 pages.
Farady, C.J., et al., "The Mechanism of Inhibition of Antibody-Based Inhibitors of Membrane-Type Serine Protease 1 (MT-SP1)," 2007, J Mol Biol, 369:1041-1051, 22 pages.
Fedosejevs, E.T., et al., "The Signal Metabolite Trehalose-6-Phosphate Inhibits the Sucrolytic Activity of Sucrose Synthase from Developing Castor Beans," 2018, FEBS Letters, 592:2525-2532, 8 pages.
Franco, F.M., et al., "Structure-based discovery of small molecule hepsin and HGFA protease inhibitors: Evaluation of Potency and Selectivity Derived from Distinct Binding Pocket," 2015, Bioorg Med Chem, 23:2328-2343, Abstact Only.
Friis, S., et al., "The Protease Inhibitor HAI-2, but Not HAI-1, Regulates Matriptase Activation and Shedding through Prostasin*," 2014, J Biol Chem, 289:22319-22332, 14 pages.
Gak, E., et al., "Processing of Hepatocyte growth Factor to the Heterodimeric Form is Required for Biological Activity," 1992, FEBS Lett, 311/1:17-21, 5 pages.
Galasiti Kankanamalage, A.C., et al., "Structure-guided Design of Potent and Permeable Inhibitors of MERS Coronavirus 3CL Protease that Utilize a Piperidine Moiety as a Novel Design Element," 2018, Eur J Med Chem, 150:334-346, 13 pages.
Ganesan, R., et al., "Proteolytic Activation of Pro-Mmacrophage-Stimulating Protein by Hepsin," 2011, Mol Cancer Res, 9:1175-1186, 13 pages.
Ganesan, R., et al., "Unraveling the Allosteric Mechanism of Serine Protease Inhibition by an Antibody," 2009, Structure, 17:1614-1624, 11 pages.
Gherardi, E., et al., "Targeting MET in Cancer: Rationale and Progress," 2012, Nat Rev Cancer, 12:89-103, 16 pages.
Giordanetto, F., et al., "Macrocyclic Drugs and Clinical Candidates: What Can Medicinal Chemists Learn from Their Properties?," 2014, J Med Chem, 57:278-295, 18 pages.
Goswami, R., et al., "Discovery of Pyridyl Bis(oxy)dibenzimidamide Derivatives as Selective Matriptase Inhibitors," 2013, ACS Med Chem Lett, 4:1152-1157, 6 pages.
Gaudino, G., et al., "RON is a heterodimeric tyrosine kinase receptor activated by the HGF homologue MSP," 1994, Embo J, 13:3524-3532, 9 pages.
Hammami, M., et al., New 3-Amidinophenylalanine-Derived Inhibitors of Matriptase, 2012, Med Chem Comm, 3:807-813, 7 pages.
Han, Z., et al., "α-Ketobenzothiazole Serine Protease Inhibitors of Aberrant HGF/c-MET and MSP/RON Kinase Pathway Signaling in Cancer," 2016, Chem Med Chem, 11:585-599, Abstract only, 2 pages.
Han, Z., et al., "Inhibitors of HGFA, Matriptase, and Hepsin Serine Proteases: A Nonkinase Strategy to Block Cell Signaling in Cancer," 2014, ACS Med Chem Lett, 5/11:1219-1224, 6 pages.
Hjerter, S., et al., "Hepatocyte Growth Factor is a Serine Protease Implicated in Prostate and Ovarian Cancers," 2005, Biochem J, 390/Pt 1:125-136, 12 pages.
Hoffman, M., et al., "SARS-CoV-2 Cell Entry Depends on ACE2 and TMPRSS2 and is Blocked by a Clinically Proven Protease Inhibitor," 2020, Cell, 181/2:271-280, 19 pages.
Kataoka, H., et al., "Roles of Hepatocyte Growth Factor (HGF) Activator and HGF Activator Inhibitor in the Pericellular Activation of HGF/Scatter Factor," 2003, Cancer Metastasis Rev, 22/2-3:223-236, 14 pages.
Kataoka, H., et al., "Pericellular Activation of Hepatocyte Growth Factor/Scatter Factor (HGF/SF) in Colorectal Carcinomas: Roles of HGF Activator (HGFA) and HGFA Inhibitor Type 1 (HAI-1)," 2001, Hum Cell, 14:83-93, 11 pages.
Kawaguchi, M., et al., "Herpatocyte Growth Factor Activator is a Serum Activator of Single-Chain Pre-Macrophase-Stimulating Protein," 2009, FEBS J, 276:3481-3490, 10 pages.
Li, P., et al., "Synthesis and Evaluation of Analogs of SFTI-1, Potent Inhibitors of the Type II Transmembrane Serine Protease, Matriptase," 2007, J Med Chem, 50:5976-5983, 8 pages.
Lin, J.H., "Pharmacokinetics of Biotech Drugs: Peptides, Proteins and Monoclonal Antibodies," 2009, Curr Drug Metab, 10:661-691. 31 pages.
Liu, X., et al., "Development of c-MET Pathway Inhibitors ," 2011, Expert Opin Investig Drugs, 20:1225-1241, 18 pages.
Lopez-Otin, C., et al., "Proteases: Multifunctional Enzymes in Life and Disease," 2008, J Biol Chem, 283:30433-30437, 5 pages.
Lucas, J.M., et al., "The Androgen-Regulated Protease TMPRSS2 Activates aProteolytic Cascade Involving Components of the Tumor Microenvironment and Promotes Prostate Cancer Metastasis," 2014, Cancer Discov, 1/11:1310-1325, 29 pages.
Mathiowetz, A.M., et al., "Chapter 10—Optimizing the Permeability and Oral Bioavailability of Macrocycles," 2015, The Royal Society of Chemistry, 367-397, 31 pages.
Meyer, D., et al., "Identification of the First Synthetic Inhibitors of the Type II Transmembrane Serine Protease TMPRSS2 Suitable for Inhibition of Influenza Virus Activation," 2013, Biochem J., 452:31-343, 13 pages.
Naka, D., et al., "Activation of Hepatocyte Growth Factor by Proteolytic Conversion of a Single Chain Form to a Heterodimer," 1992, J Biol Chem, 267/28:20114-20119, 6 pages.
Oberst, M.D., et al., "Expression of the Serine Protease Matriptase and its Inhibitor HAI-1 in Epithelial Ovarian Cancer: Correlation with Clinical Outcome and Tumor Clinicopathological Parameters," 2002, Clin Cancer Res, 8:1101-1107, 8 pages.
Organ, S.L, et al., "An Overview of the c-MET Signaling Pathway," 2011, Ther Adv Med Oncol, 3:S7-S19, 14 pages.
Owen, K.A., et al., "Pericellular Activation of Hepatocyte Growth Factor by the Transmembrane Serine Proteases Matriptase and Hepsin, But Not by the Membrane-Associated Protease uPA," 2010, Biochem J, 426:219-228, 22 pages.
Owusu, B.Y., et al., "Inhibition of Pro-HGF Activation by SRI31215, A Novel Approach to Block Oncogenic HGF/MET Signaling," 2016, Oncotarget, 7:29492-29506, 15 pages.
Pant, S.M., et al., "Design, Synthesis, and Testing of Potent, Selective Hepsin Inhibitors via Application of an Automated Closed-Loop Optimization Platform," 2018, J Med Chem, 61:4335-4347.

(56) References Cited

OTHER PUBLICATIONS

Parr, C., et al., "Hepatocyte Growth Factor Activation Inhibitors—Therapeutic Potential in Cancer," 2010, Anticancer Agents Med Chem, 10:47-57.
Sakai, K., et al., "Hepatocyte Growth Factor and Met in Drug Discovery," 2015, J Biochem, 157:271-284, 14 pages.
Shimomura, T., et al., "A Novel Protease Obtained from FBS-Containing Culture Supernatant, that Processes Single Chain Form Hepatocyte Growth Factor to Two Chain Form in Serum-Free Culture," 1992, Cytotechnology, 8:219-229, 11 pages.
Smyth, E.C., et al., "Emerging Molecular Targets in Oncology: clinical Potential of MET/Hepatocyte Growth-Factor Inhibitors," 2014, Onco Target: Ther, 78:1001-1014, 14 pages.
St-Georges, C., et al., "Modulating the Selectivity of Matriptase-2 Inhibitors with Unnatural Amino Acids," 2017, Eur J Med Chem, 129:110-123, 14 pages.

* cited by examiner m = 1,2

A)

B)

Scheme 1

Scheme 2

A

2a

2b

B 3 a-c a = Phenyl;b = Benzyl; c = Phenethyl 3 d-e d = Phenyl; e = Benzyl

A

B

COMPOUNDS AND METHODS FOR TREATING CANCER, VIRAL INFECTIONS, AND ALLERGIC CONDITIONS

GOVERNMENT LICENSE RIGHTS

This invention was made with government support under CA224832 awarded by the National Institutes of Health. The government has certain rights in the invention.

FIELD OF THE INVENTION

The present invention generally relates to compounds that are useful for inhibiting one or more proteases including various serine proteases such as Hepatocyte Growth Factor Activator (HGFA), matriptase, and hepsin. The compounds are also useful as inhibitors of kallikrein related peptidase 5 (KLK5) and TMPRSS2 (required for the host cellular entry of SARS-CoV-2). The present invention also relates to various methods of using the inhibitor compounds to treat and/or prevent infections, including those caused by coronaviruses and influenza viruses, conditions associated with KLK5 activity (e.g. inflammation), various other malignancies, pre-malignant conditions, and/or cancer.

BACKGROUND OF THE INVENTION

Proteases, also known as proteinases, peptidases, or proteolytic enzymes, are enzymes that process proteins by hydrolyzing peptide bonds between amino acid residues. It is known that proteases regulate numerous physiological processes which enable or stimulate the growth, proliferation, transformation, motility, survival, and metastasis of tumor cells. Metastasis involves the proteolytic degradation of the extracellular matrix proteins (e.g. collagen) surrounding the tumor cells by proteases, which enables the invasion of tumor cells metastasizing from the primary tumors into the surrounding tissue and the lymph system or the blood system. Theses degradation proteases include matrix metalloproteases (MMPs) and cysteine proteases including various subfamily members of the cathepsins. Proteases are also involved in the activation of growth factors, cytokines, and other proteins that stimulate the growth, proliferation, motility, and survival of cancer cells, thus enabling tumors to develop and expand in size. These include multiple members of trypsin-like S1 serine protease such as HGFA, KLK5 and of the subfamily of serine proteases called type II transmembrane serine proteases (TTSPs) such as matriptase, hepsin, and TMPRSS2 which have been found to be important in tissue homeostasis, infection, other diseases, and in cancer, including tumor progression and metastasis.

One member of the TTSP enzyme class, matriptase (matriptase-1, MT-SP1, TADG-15, CAP3, epithin, and ST14), is a trypsin-like serine protease expressed by cells of epithelial origin and overexpressed in a wide variety of human cancers. Unlike most proteases, which are either secreted from or retained in the cell, matriptase is located on the cell surface and hence an attractive therapeutic target for a variety of therapies, including vaccines, monoclonal antibodies and small molecule compounds. Inhibition of matriptase results in concomitant inhibition of the processing and activation of multiple potential substrates important in cancer and tumor progression, including protease active receptor-2 (PAR2) and two other crucial mediators of tumorigenesis, hepatocyte growth factor (HGF) and the urokinase-type plasminogen activator (uPA).

Hepsin is another member of the type II transmembrane serine protease family. Hepsin has been reported to play a role in cancer cell growth and is known to be widely expressed with noticeably high levels in the liver and kidney as well as in cancer cells such as ovarian, breast, renal, colon, gastric and prostate. Like matriptase inhibition of hepsin results in concomitant inhibition of the processing and Activiation of multiple potential substrates important in cancer and tumor progression. Hepatocyte Growth Factor Activator (HGFA) is an S1 trypsin-like protease but is secreted and present in the blood, like other coagulation cascade proteases such as thrombin and Factor Xa. It has been associated with many tumor types similar to those described for matriptase and hepsin but also including hematological malignancies such as multiple myeloma.

Hepsin, matriptase and HGFA are differentially expressed and have upregulated function in numerous tumor types including multiple myeloma, breast, prostate, lung (and other thoracic), colon, gastric, ovarian, testicular, liver, bladder, kidney, glioblastoma and pancreatic. These proteases cleave the single-chain zymogen precursors, pro-HGF (hepatocyte growth factor), and pro-MSP (macrophage stimulating protein) into active two-chain heterodimeric forms. Active two-chain HGF and MSP are activating ligands for the receptor tyrosine kinases (RTKs), c-MET and RON, respectively.

Increased activity of hepsin, matriptase, and/or HGFA, resulting from either overexpression or upregulation of these proteases and/or downregulation of their endogenous serine protease inhibitors (serpins), HAI-1 (SPINT1), HAI-2 (SPINT2), and protein C inhibitor (PCI), has been demonstrated in tumor types driven by c-MET and/or RON receptor tyrosine kinase (RTK) pathway signaling. This increased protease function has been clearly associated with the development and elevation of metastatic cancer phenotypes, and direct inhibition of this protease activity through genetic ablation or with small molecule or antibody inhibitors has been demonstrated to reduce this metastatic potential in multiple tumor types. The biological reason for the redundancy of activation by these three different proteases and the tight regulation by serpins in cancer is not yet understood. Furthermore, since HGF/c-MET and MSP/RON signaling are necessary for development and normal cell physiology, selective inhibitors of each protease involved in individual tumors need to be identified when developing as therapeutics in order to understand and limit potential toxicities.

Matriptase inhibitors are of high therapeutic importance, but development has been a challenging task. To date, a number of small molecule inhibitors and inhibitory antibodies have been reported. See, for example, Enyedy et al., *J. Med. Chem.* 2001, 44, 1349-1355; Steinmetzer et al., J. Med. Chem., 2006, 49: 4116-4126, and Farady et al, *J Mol Biol,* 2007, 369: 1041-1051. Also, a series of inhibitors was recently described by Marsault et al., ACS Med Chem. Lett., 2012, 3: 530-534. Inhibitory antibodies have also been developed against matriptase.

As compared to matriptase, inhibitory antibodies have also been reported for HGFA and hepsin but relatively few inhibitors are known for either hepsin or HGFA. Small molecule hepsin inhibitors were discovered through high-throughput screening (Chevillet, J. R., et al. *Mol. Cancer Ther.* 2008, 7, 3343) but the reported HGFA inhibitors are the non-selective serine protease inhibitors, Nafamostat and Leupeptin (Shimomura, T., et al., *Cytotechnology,* 1992, 8, 219). Various small molecule inhibitors of HGFA, hepsin, and matriptase are described in U.S. Patent Application Publication 2018/0066015, which is hereby incorporated by reference herein.

Although progress has been made toward the development of inhibitors of matriptase, hepsin, and HGFA, there remains a need for small molecular weight inhibitors that are both potent and selective for one or more of more of these enzymes. Such compounds have significant therapeutic value, in particular for the treatment of cancer and other conditions but most importantly those diseases involving the survival, migration, abnormal cell differentiation and proliferation of tumor cells leading to metastasis. Compounds having improved selectivity, solubility, metabolic stability, half-life, and oral bioavailability are particularly desirable.

Like matriptase and hepsin, TMPRSS2 is a TTSP and has been shown to be essential for host-cell viral entry and replication of SARS-CoV-2, SARS-CoV and other coronaviruses MERS-CoV and influenza. SARS-CoV-2 cell entry involves binding to the host (human) cell receptor ACE2. The binding of SARS-CoV-2 to ACE2 requires proteolytic priming of the Spike protein by TMPRSS2 (host (human) cell protease), suggesting that TMPRSS2 inhibitors would be effective therapeutics for COVID-19 by blocking the adherence, invasion, and replication of coronaviruses. Accordingly, TMPRSS2-expressing human lung epithelial Calu-3 cells which express both TMPRSS2 and ACE2 are highly susceptible to SARS-CoV-2 infection and other infections caused by other coronaviruses and influenza viruses which also utilize this same mechanism.

Aside from its role in SARS-CoV-2 infection, TMPRSS2 plays a role in prostate cancer (and possibly other cancers) progression and metastasis. This has been established through its ability to activate hepatocyte growth factor (HGF) (as discussed above, the sole ligand for MET receptor kinase), via proteolytic processing of pro-HGF. Thus, TMPRSS2 shares pro-hepatocyte growth factor (pro-HGF) as a protein substrate with HGFA, hepsin and matriptase. Accordingly, there remains a high unmet need for inhibitors of TMPRSS2.

Human kallikrein-related peptidases (KLKs) are a large family of S1 trypsin-like serine proteinases which are expressed in a variety of tissues such as prostate, ovary, breast, testes, brain, and skin. Although their physiological functions have been only partly elucidated, many of the KLKs appear to be useful prognostic cancer markers, showing distinct correlations between their expression levels and different stages of cancer. Of the fifteen KLKs, KLK5 is critical since it plays a role in activating many others in the family. In addition, KLK5 has been shown to activate pro-HGFA to active HGFA in cancer. Furthermore, KLK5 is known to be important in certain immune system and inflammatory conditions including allergic disorders. Accordingly, there remains a need for inhibitors of KLK5.

BRIEF SUMMARY OF THE INVENTION

Generally, the present invention relates to compounds that are useful for inhibiting one or more proteases including various serine proteases not limited to Hepatocyte Growth Factor Activator (HGFA), matriptase, hepsin, thrombin, factor Xa, TMPRSS2, KLK5 and cysteine proteases including trypsin-like cysteine proteases (e.g. Cathepsin B) along with various methods of use for these compounds. In various aspects, the present invention is directed to compounds of Formula (I), salts thereof, and stereoisomers thereof:

(I)

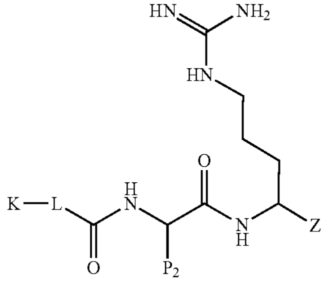

wherein:

$P_2$ is H or a side chain of a natural or unnatural amino acid; L is —O— or NH;

K is a substituted or unsubstituted heterocycle, or substituted or unsubstituted $-(CH_2)_x$heterocycle;

L is —O— or NH;

x is 0, 1, or 2;

Z is

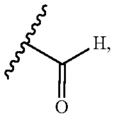

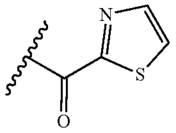

,

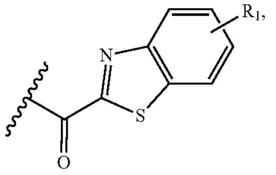

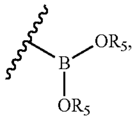

or

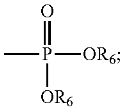

$R_1$ is hydrogen,

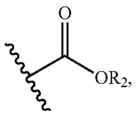

or

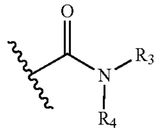

;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

Further aspects of the present invention relate to cyclic compounds of Formulas (IIA)-(IIH), salts thereof, and stereoisomers thereof:

(IIA)

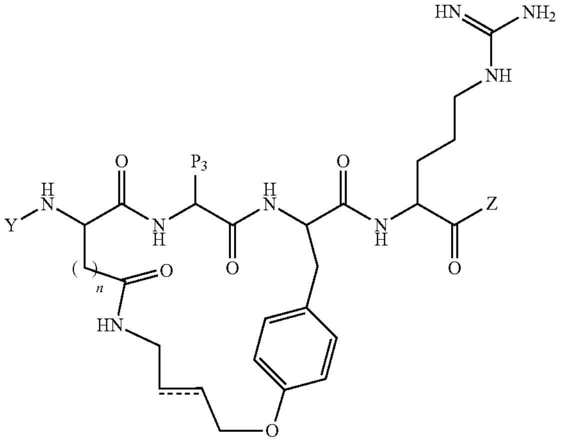

(IIB)

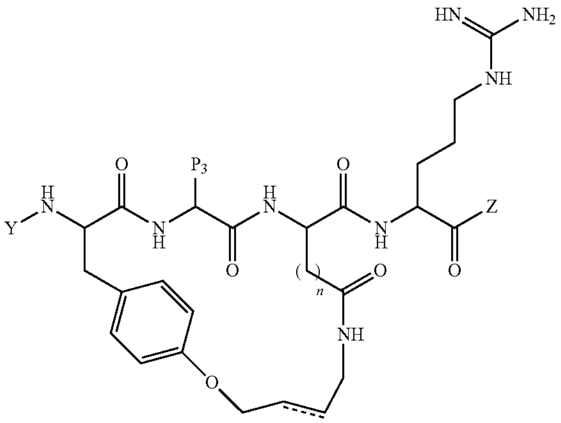

(IIC)

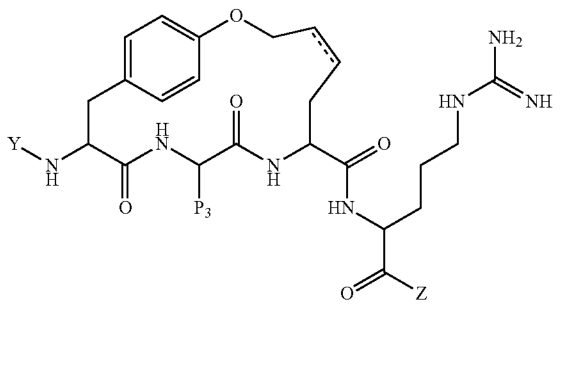

-continued (IID)

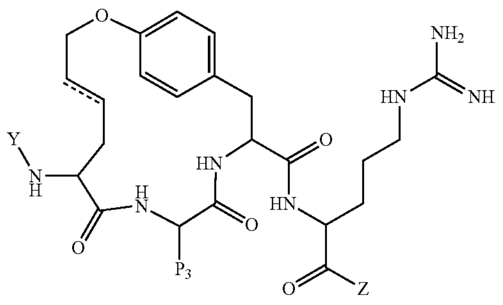

(IIE)

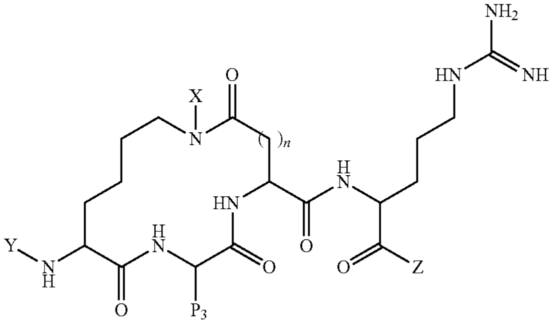

(IIF)

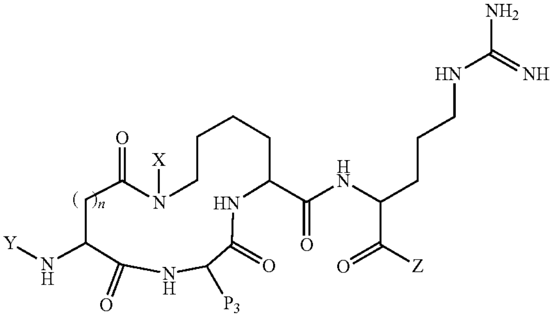

(IIG)

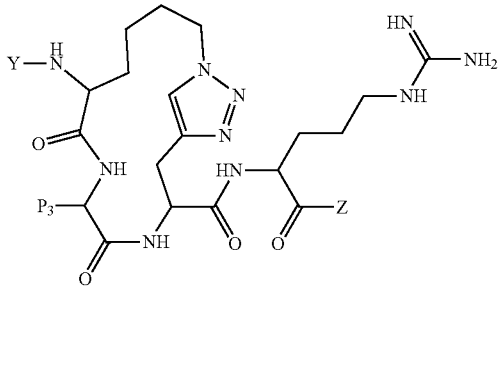

-continued (IIH)

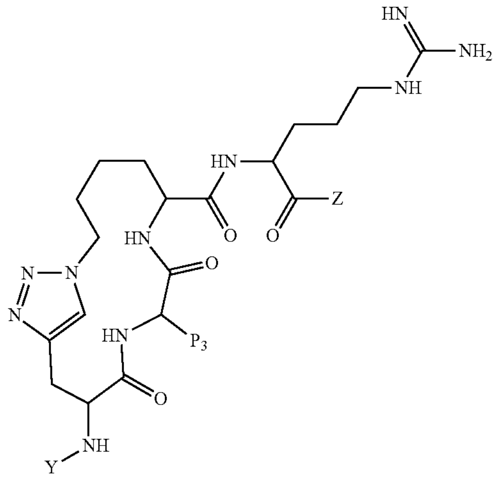

wherein:

each n is independently 1 or 2;

each $P_3$ is independently H or a side chain of a natural or unnatural amino acid;

each X is independently H or methyl;

each Y is independently H, acetyl, tert-butyloxycarbonyl (Boc), benzyloxycarbonyl (Cbz), fluorenylmethyloxycarbonyl (Fmoc), benzyl, —C(O)R, —SOOR, —COOR, —C(O)NHR, substituted or unsubstituted $—(CH_2)_x$aryl, substituted or unsubstituted $—(CH_2)_x$heteroaryl, substituted or unsubstituted $—(CH_2)_x$cycloalkyl, or substituted or unsubstituted $—(CH_2)_x$heterocycle;

each x is independently 0, 1, or 2;

each R is independently $C_1$ to $C_6$ alkyl, $C_3$ to $C_6$ cycloalkyl, heterocycle, alkylheterocycle, aralkyl, or aryl; and each Z is independently

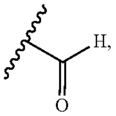

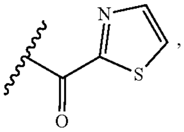

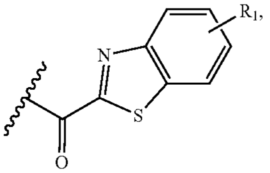

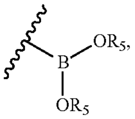 or

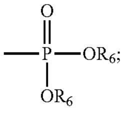

$R_1$ is hydrogen,

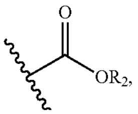 or 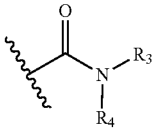 ;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

Further aspects of the present invention relate to compounds of Formula (IIIA), (IIIB), or (IIIC), a salt thereof, or a stereoisomer thereof:

(IIIA)

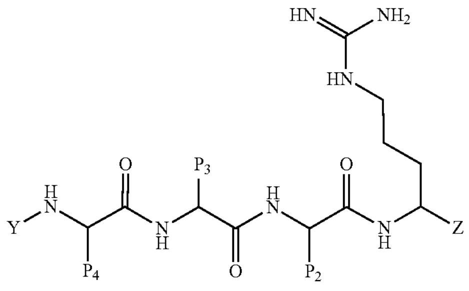

(IIIB)

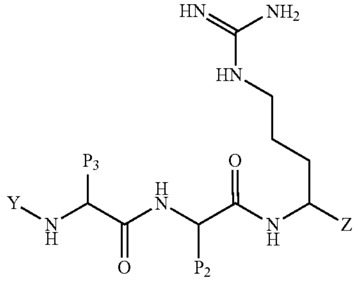

(IIIC)

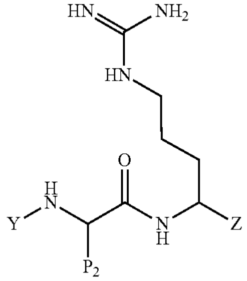

wherein:

each $P_2$ is independently a side chain of Phe, Leu, hLeu, Ala, Thr, Asn, NptGly, L-Orn, L-Cha, Igl, Phe(3,4-F2), Phe(3-Cl), Phe(4-F), or Glu(Bzl);

each $P_3$ is independently a side chain of Arg, hArg, Trp, D-Trp, Lys, hTyr, Gln, D-Gln, L-Nle(OBzl), Agp, L-Orn, hCha, hPhe, His(3-Bom), or Phe(4-$NO_2$);

$P_4$ is a side chain of Arg, Ile, Gly, Pro, Met, Leu, hArg, $Arg(Z)_2$, L-Arg($NO_2$), Trp, D-Trp, Ser, Lys, Lys(2-Cl—Z), Agp, L-DAB(Z), L-Orn, L-Nle(OBzl), or His (3-Bom);

Y is H, acetyl, tert-butyloxycarbonyl (Boc), benzyloxycarbonyl (Cbz), fluorenylmethyloxycarbonyl (Fmoc), benzyl, —C(O)R, —SOOR, —COOR, —C(O)NHR, substituted or unsubstituted $—(CH_2)_x$aryl, substituted or unsubstituted $—(CH_2)_x$heteroaryl, substituted or unsubstituted $—(CH_2)_x$cycloalkyl, or substituted or unsubstituted $—(CH_2)_x$heterocycle;

each x is independently 0, 1, or 2;

each R is independently $C_1$ to $C_6$ alkyl, $C_3$ to $C_6$ cycloalkyl, heterocycle, alkylheterocycle, aralkyl, or aryl;

each Z is independently

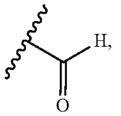

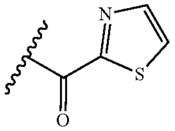

,

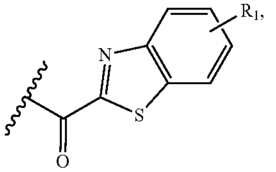

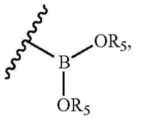

or

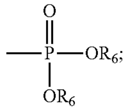

$R_1$ is hydrogen,

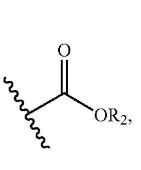

or

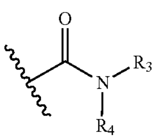

;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

The present invention further relates to pharmaceutical compositions comprising a therapeutically effective amount of at least one compound as described herein.

The present invention also relates to various methods of use including a method of inhibiting one or more trypsin-like S1 serine proteases (e.g., matriptase, hepsin, or HGFA) cysteine proteases including trypsin-like cysteine proteases (e.g. Cathepsin B) comprising administering to a subject in need thereof a pharmaceutical composition comprising a therapeutically effective amount of at least one compound as described herein. Another method includes a method of inhibiting HGF/MET oncogenic signaling comprising administering to a subject in need thereof a pharmaceutical composition comprising a therapeutically effective amount of at least one compound as described herein.

Other methods include a method of inhibiting carcinoma progression and/or metastasis and a method of treating a malignancy, a pre-malignant condition, or cancer comprising administering to the subject in need thereof a pharmaceutical composition comprising a therapeutically effective amount of at least one compound as described herein.

Further aspects include methods of treating or preventing a viral infection in a subject comprising administering to the subject in need thereof a pharmaceutical composition comprising a therapeutically effective amount of at least one compound of (a) Formula (I), (IIA)-(IIH), or (IIIA)-(IIIC); (b) a polypeptide-based inhibitor; and/or (c) a benzamidine-based inhibitor. Certain aspects relate to methods of inhibiting TMPRSS2 and/or matriptase in an organism comprising administering to the organism a composition comprising an effective amount of at least one compound of (a) Formula (I), (IIA)-(IIH), or (IIIA)-(IIIC); (b) a polypeptide-based inhibitor; and/or (c) a benzamidine-based inhibitor.

Still other aspects of the invention relate to methods of treating or preventing a condition at least in part associated with KLK5 in a subject comprising administering to the subject in need thereof a pharmaceutical composition comprising a therapeutically effective amount of at least one compound of (a) (I), (IIA)-(IIH), or (IIIA)-(IIIC); (b) a polypeptide-based inhibitor; and/or (c) a benzamidine-based inhibitor. Some aspects also relate to methods of inhibiting KLK5 in an organism comprising administering to the organism a composition comprising an effective amount of at least one compound of (a) Formula (I), (IIA)-(IIH), or (IIIA)-(IIIC); (b) a polypeptide-based inhibitor; and/or (c) a benzamidine-based inhibitor.

Other objects and features will be in part apparent and in part pointed out hereinafter.

DETAILED DESCRIPTION OF THE INVENTION

Figure 1:
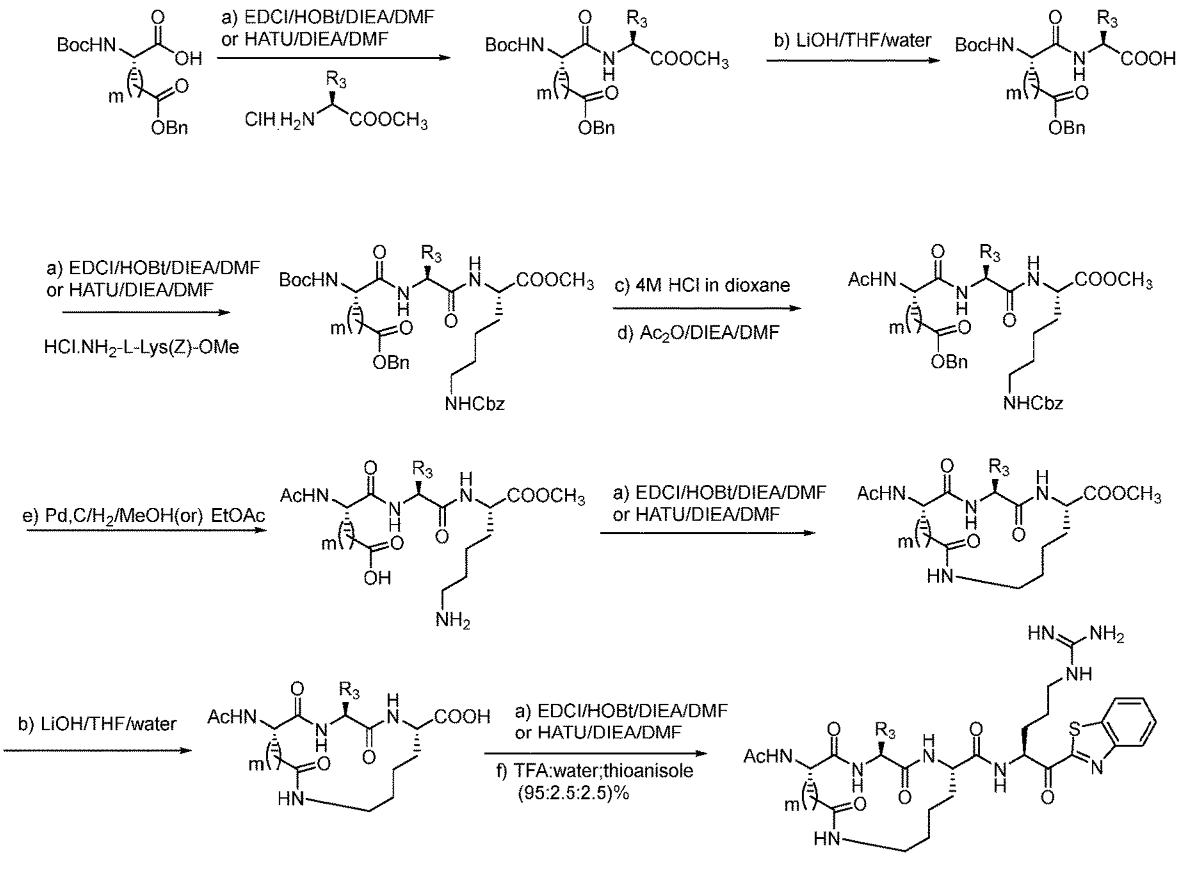
FIG. 1 presents a general synthetic route for macrocycles of Formula IIF in solution phase.

The present invention generally relates to compounds that are useful for inhibiting one or more various proteases including serine proteases such as Hepatocyte Growth Factor Activator (HGFA), matriptase, and hepsin as well as cysteine proteases including trypsin-like cysteine proteases (e.g. Cathepsin B). The compounds are also useful as inhibitors of KLK5 and TMPRSS2 (a necessary signal molecule for cellular entry of SARS-CoV-2). The present invention also relates to various methods of using the inhibitor compounds to treat or prevent viral infections, including those caused by coronaviruses and influenza, conditions associated with upregulated KLK5, various malignancies, pre-malignant conditions, or cancer. These methods include administering an effective amount of an inhibitor to a subject in need thereof.

Compounds of Formula (I)

In accordance with the present invention, one class of compounds useful for inhibiting one or more serine proteases includes compounds of Formula (I), salts thereof, and stereoisomers thereof:

(I)

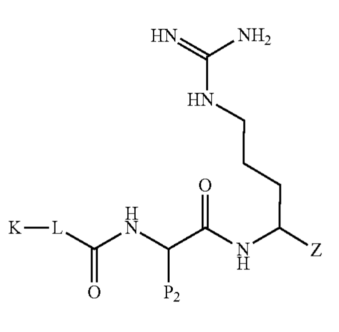

wherein:

$P_2$ is H or a side chain of a natural or unnatural amino acid;

K is a substituted or unsubstituted heterocycle, or substituted or unsubstituted $-(CH_2)_x$heterocycle;

L is —O— or NH;

x is 0, 1, or 2;

Z is

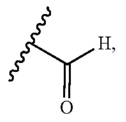

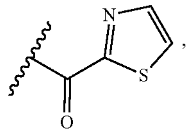

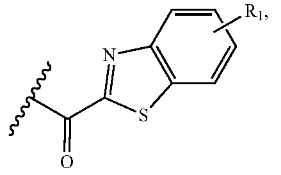

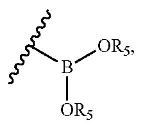

or

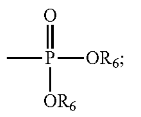

$R_1$ is hydrogen,

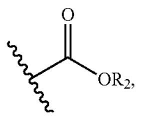

or

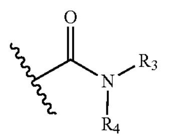

;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

In various embodiments, K is a substituted or unsubstituted piperidine ring. For example, in some embodiments, K can be selected from the group consisting of:

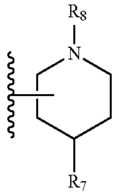

and

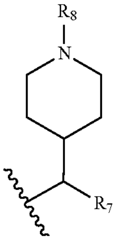

wherein $R_7$ is hydrogen, substituted or unsubstituted alkyl, substituted or unsubstituted aryl, substituted or unsubstituted heterocycle, or substituted or unsubstituted aralkyl; $R_8$ is hydrogen, substituted or unsubstituted alkyl, substituted or unsubstituted aralkyl (e.g. benzyl), —C(O)$R_9$, or —SOOR$_{10}$; $R_9$ is hydrogen, substituted or unsubstituted alkyl, substituted or unsubstituted aryl, substituted or unsubstituted heterocycle or substituted or unsubstituted aralkyl; and $R_{10}$ is hydrogen, substituted or unsubstituted alkyl, substituted or unsubstituted aryl, substituted or unsubstituted heterocycle, or substituted or unsubstituted aralkyl.

In certain embodiments, $R_7$ is hydrogen, $C_1$-$C_6$ alkyl, halo-substituted $C_1$-$C_6$ alkyl, aryl, alkyl-substituted aryl, halo-substituted aryl, nitro-substituted aryl, alkyl-substituted aralkyl, halo-substituted aralkyl, or nitro-substituted aralkyl. For example, in some embodiments $R_7$ is hydrogen, methyl, ethyl, propyl, butyl, phenyl, benzyl, or phenethyl.

In various embodiments, $R_9$ is hydrogen, $C_1$-$C_6$ alkyl, halo-substituted $C_1$-$C_6$ alkyl, aryl, alkyl-substituted aryl, halo-substituted aryl, nitro-substituted aryl, alkyl-substituted aralkyl, halo-substituted aralkyl, or nitro-substituted aralkyl. For example, in some embodiments, $R_9$ is hydrogen, methyl, or ethyl.

In various embodiments, $R_{10}$ is hydrogen, $C_1$-$C_6$ alkyl, halo-substituted $C_1$-$C_6$ alkyl, aryl, aryl substituted with at least one group selected from the group consisting of alkyl, alkoxy, halo, nitro and combinations thereof. In some embodiments, $R_{10}$ is hydrogen, methyl, ethyl, propyl, butyl, phenyl, phenyl aryl substituted with at least one group selected from the group consisting of alkyl, alkoxy, halo, nitro and combinations thereof.

In various embodiments, K is selected from the group consisting of:

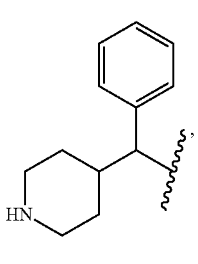

,

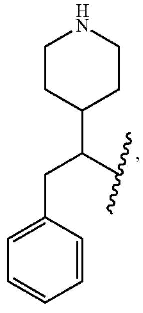

,

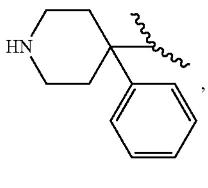

,

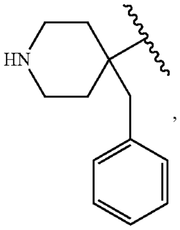

,

-continued

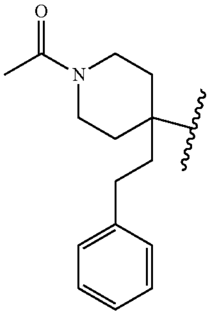

,

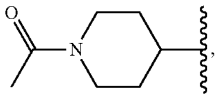

,

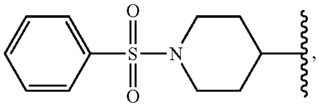

,

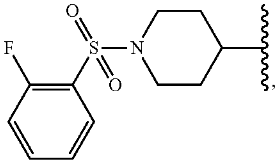

,

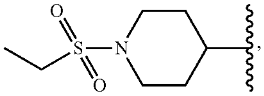

,

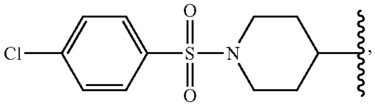

,

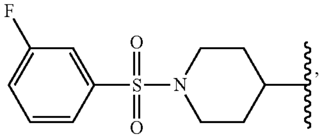

,

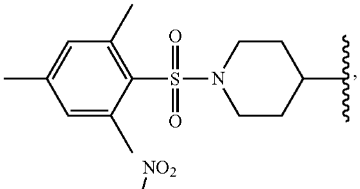

,

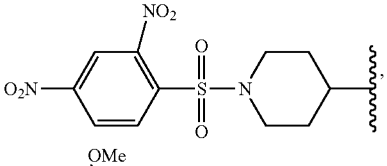

, and

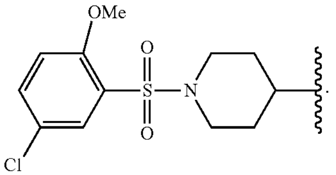 [SMILES: *C1CCN(S(=O)(=O)c2cc(Cl)ccc2OC)CC1]

.

In various embodiments, L is —O—.

In various embodiments, $P_2$ is a side chain of Leu, Cha, hLeu, Nle, NptGly, hTyr, Orn, Thr, Asn, Nva, Igl, Phe, hPhe, Phe(3,4-F2), Phe(3-Cl), Phe(4-F), Phe(3-F), Glu(Bzl), Trp, Bta, hCha, hArg, Arg(Z)$_2$, Lys(2-ClZ), Chg, or hTyr(Me). In some embodiments, $P_2$ is a side chain of Leu or Cha.

In certain embodiments, $R_2$ and $R_3$ are each independently hydrogen, alkyl, cycloalkyl, aryl, aralkyl, heteroaryl, or heteroarylalkyl. For example, in certain embodiments, $R_2$ and $R_3$ are each independently hydrogen, $C_1$-$C_6$ alkyl, $C_3$-$C_{10}$ cycloalkyl, phenyl or benzyl.

In certain embodiments, $R_4$ is hydrogen, alkyl, or a residue of an amino acid, or $R_3$ and $R_4$ can form a piperazine or piperidine ring In various embodiments, each $R_5$ is independently hydrogen, alkyl, or the $R_5$ moieties can form a ring.

In various embodiments, $R_6$ is aryl.

In various embodiments, Z is

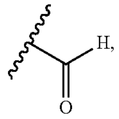
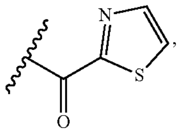
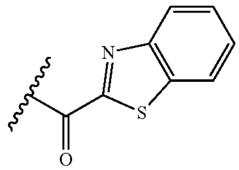
or
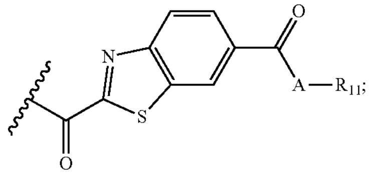

wherein A is —O— or NH and $R^{11}$ is hydrogen, methyl, benzyl, optionally substituted alkyl, optionally substituted aryl, heterocycle, or residue of an α-amino acid. In some embodiments, A is NH and A and $R^{11}$ form a residue of an α-amino acid.

In certain embodiments, Z is:

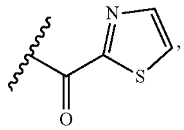
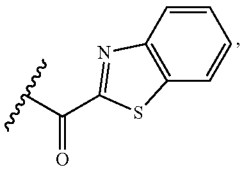
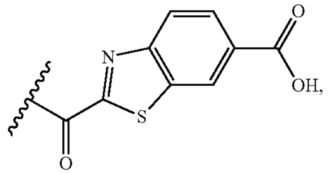
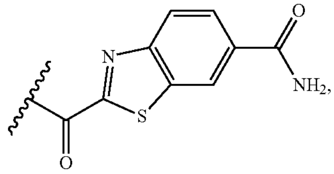
or
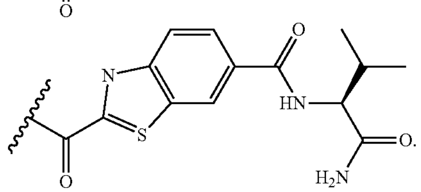

In some embodiments, Z is:

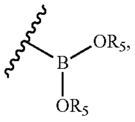

wherein each $R_5$ is as defined herein. In certain embodiments, Z is:

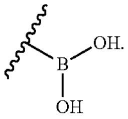 [SMILES: *B(O)O]

In some embodiments, Z is

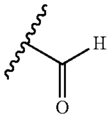
or
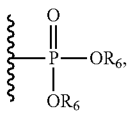

wherein $R_6$ each is substituted or unsubstituted aryl.

In certain embodiments, each Z is independently is:

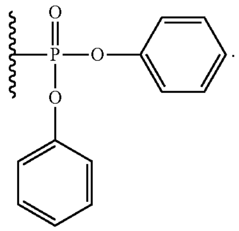 [SMILES: *P(=O)(Oc1ccccc1)Oc1ccccc1]

In various embodiments, the compound of Formula (I) is selected from the group consisting of:

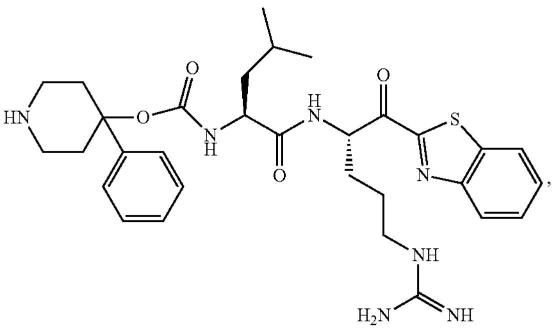

-continued
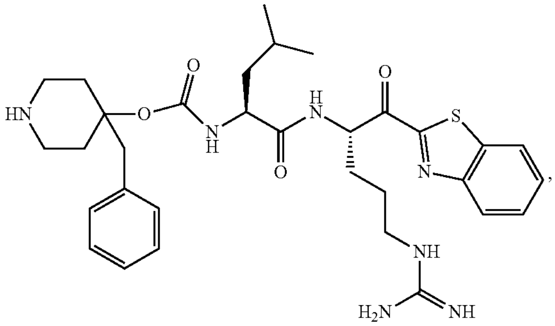
,
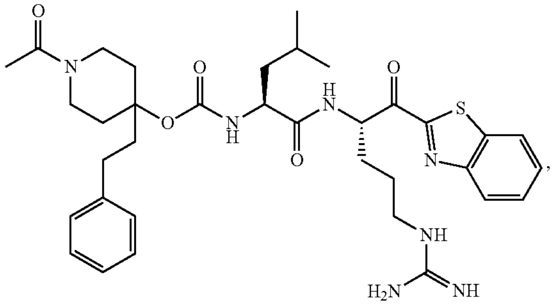
,
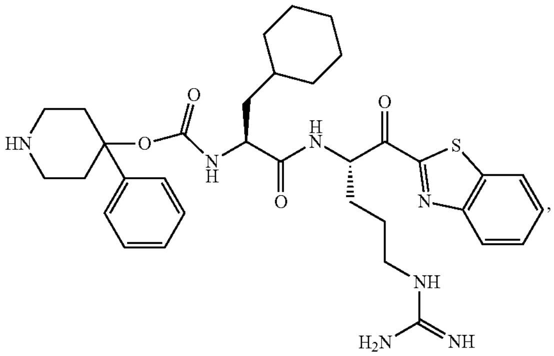
,
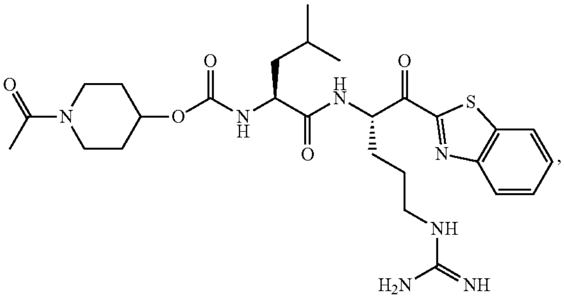
,
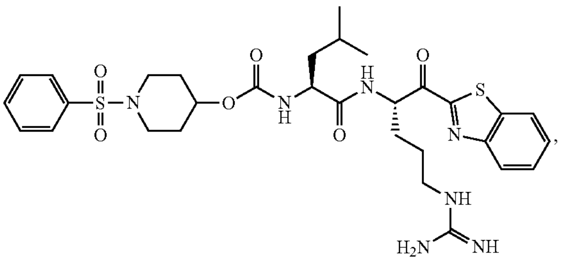
,
-continued
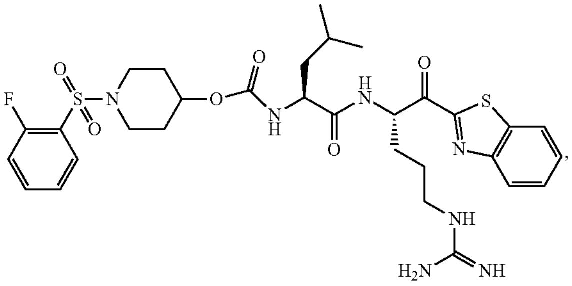
,
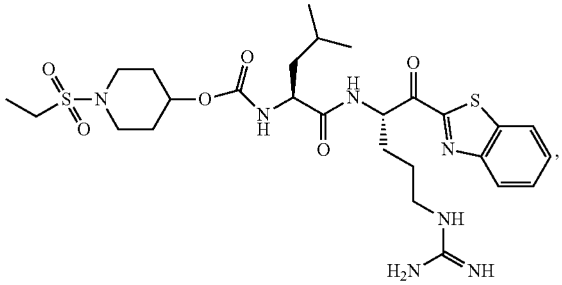
,
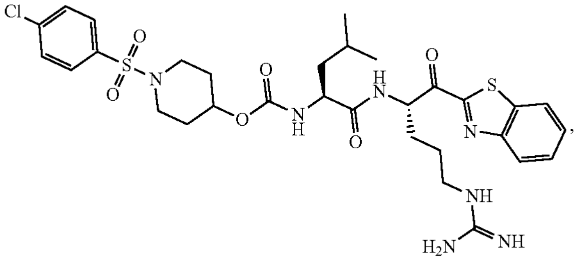
,
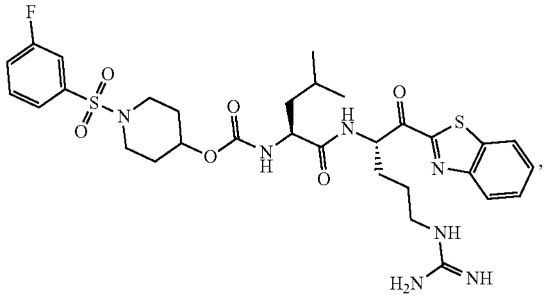
,
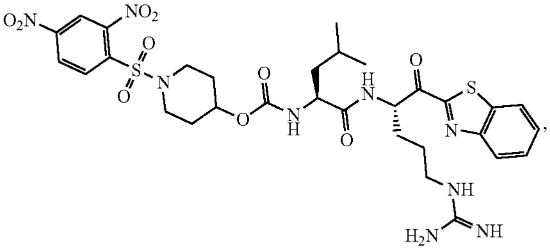
,
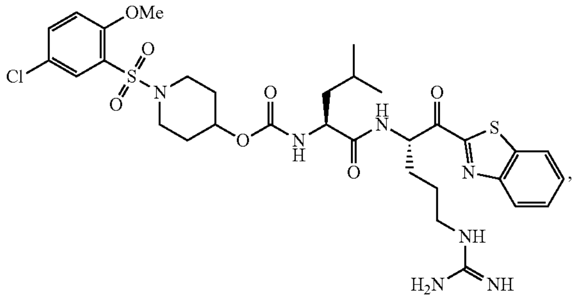
, -continued
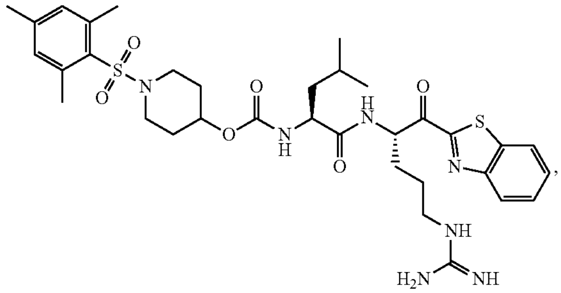
,
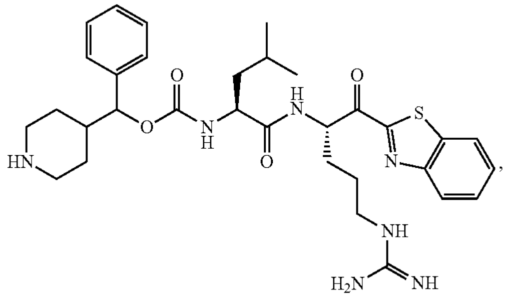
, and
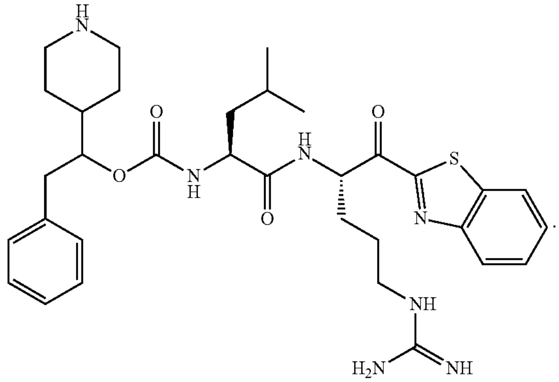
.
Compounds of Formulas (IIA)-(IIH)
In accordance with the present invention, another class of compounds useful for inhibiting one or more serine proteases includes compounds of Formulas (IIA)-(IIH), salts thereof, and stereoisomers thereof:
(IIA)
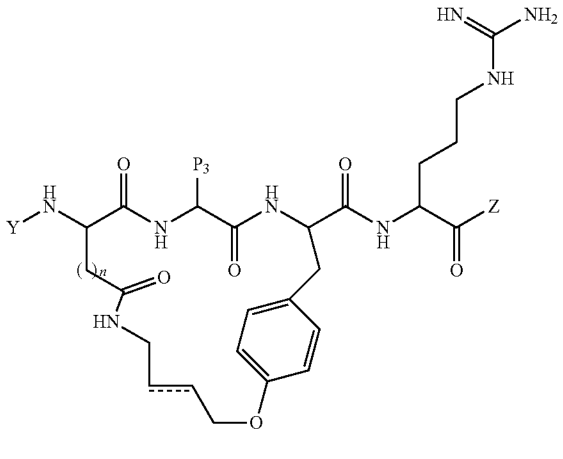
-continued
(IIB)
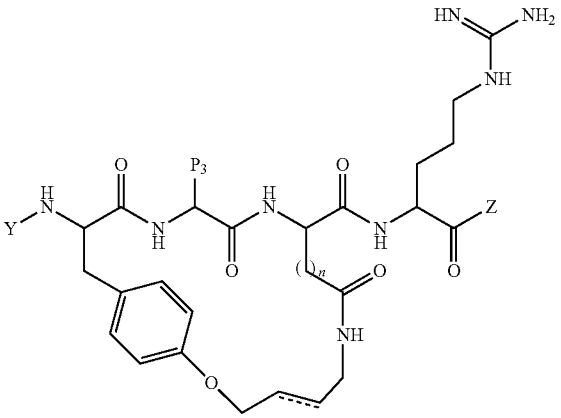
(IIC)
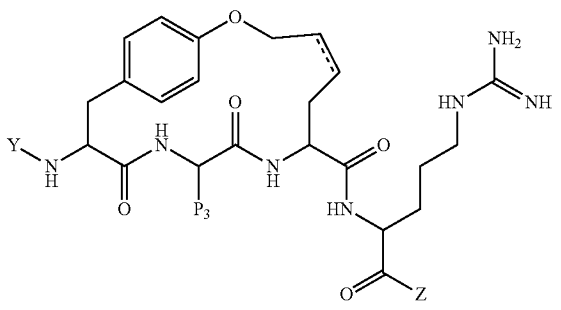
(IID)
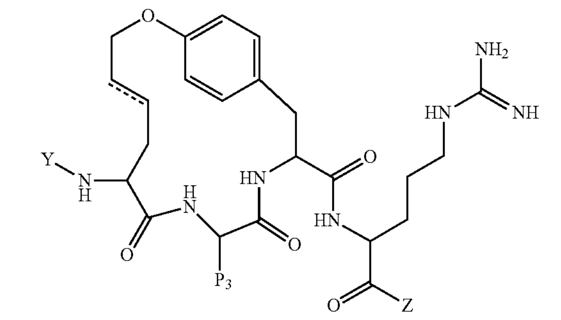
(IIE)
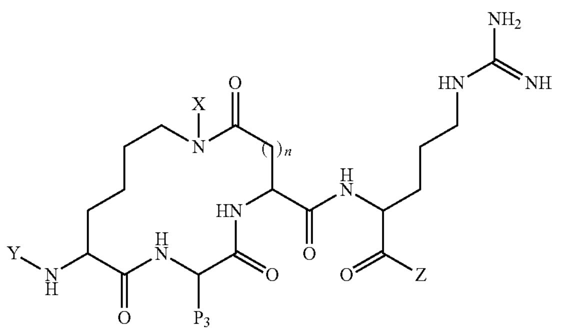

-continued (IIF)

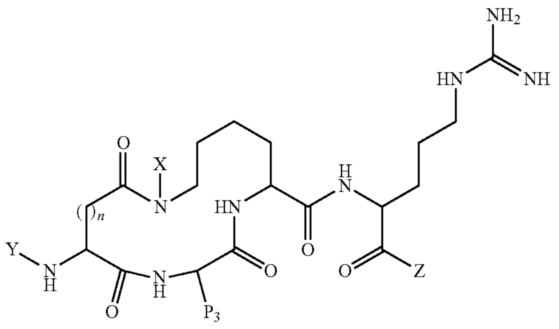

(IIG)

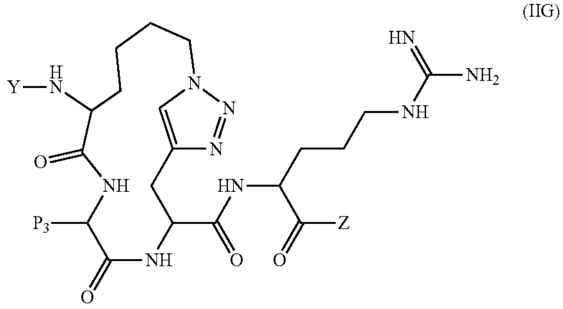

(IIH)

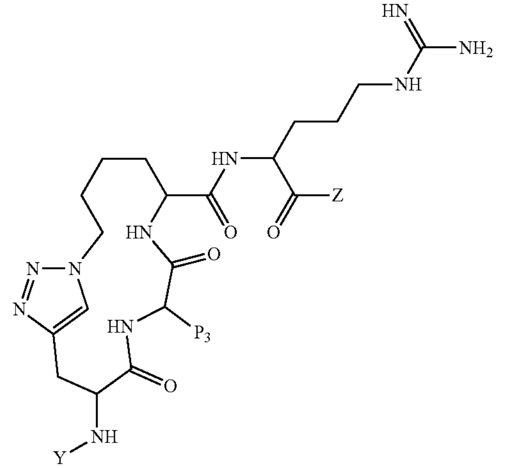

wherein:

each n is independently 1 or 2;

each $P_3$ is independently hydrogen or a side chain of a natural or unnatural amino acid;

each X is independently hydrogen or methyl;

each Y is independently hydrogen, acetyl, tert-butyloxycarbonyl (Boc), benzyloxycarbonyl (Cbz), fluorenylmethyloxycarbonyl (Fmoc), benzyl, —C(O)R, —SOOR, —COOR, —C(O)NHR, substituted or unsubstituted $-(CH_2)_x$aryl, substituted or unsubstituted $-(CH_2)_x$heteroaryl, substituted or unsubstituted $-(CH_2)_x$cycloalkyl, or substituted or unsubstituted $-(CH_2)_x$heterocycle;

each x is independently 0, 1, or 2;

each R is independently $C_1$ to $C_6$ alkyl, $C_3$ to $C_6$ cycloalkyl, heterocycle, alkylheterocycle, aralkyl, or aryl;

each Z is independently

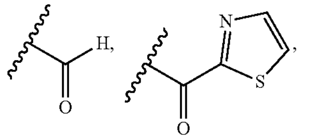

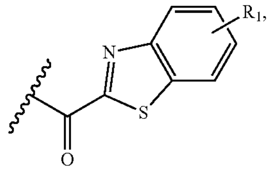

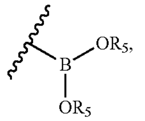

or

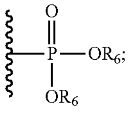

$R_1$ is hydrogen,

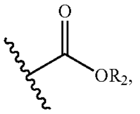

or

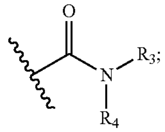

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

In various embodiments, the compounds of Formulas (IIA)-(IIH) include one or more of the following:

each Y is independently hydrogen, acetyl, tert-butyloxycarbonyl (Boc), benzyloxycarbonyl(Cbz), or fluorenylmethyloxycarbonyl (Fmoc); and/or each $P_3$ is independently a side chain of Ala, Gly, Val, Leu, Lys, D-Lys, Arg, D-Arg, Asn, Phe, Gln, D-Gln, Thr, D-Trp, Tyr, Met, Agp, hCha, hTyr, hPhe, Orn, Dab, Dab(Z), Nle (O-Bzl), $Arg(NO_2)$, $Arg(Z)_2$, Lys(2-ClZ), dhLeu, Dht, Idc, IgI, Chg, dhAbu, Hyp, Glu(Bzl), Met(O), Dap, Phe(F5), Glu(Me), or hArg.

In certain embodiments, each Y is independently hydrogen or acetyl.

In certain embodiments, each $P_3$ is independently a side chain of an amino acid selected from the group consisting of Ala, Gly, Val, Leu, Lys, Arg, Asn, Phe, Gln, Thr, D-Trp, Tyr, Met, Agp, hCha, hTyr, hPhe, Orn, DAB, DAB(Z), Nle(O-Bzl), $Arg(NO_2)$, $Arg(Z)_2$, Lys(2-ClZ), hLeu, Dht, Idc, IgI, Chg, hAbu, Hyp, Glu(Bz), Met(O), Dap, Phe(F5), Glu(Me), and hArg.

In certain embodiments, $R_2$ and $R_3$ are each independently hydrogen, alkyl, cycloalkyl, aryl, aralkyl, heteroaryl, or heteroarylalkyl. For example, $R_2$ and $R_3$ can each independently be hydrogen, $C_1$-$C_6$ alkyl, $C_1$-$C_{10}$ cycloalkyl, phenyl or benzyl.

In certain embodiments, $R_4$ is hydrogen, alkyl, or a residue of an amino acid, or $R_3$ and $R_4$ can form a piperazine or piperidine ring.

In various embodiments, each $R_5$ is independently hydrogen, alkyl, or the $R_5$ moieties can form a ring.

In various embodiments, $R_6$ is aryl.

In various embodiments, each Z is independently

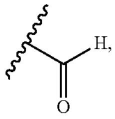
,
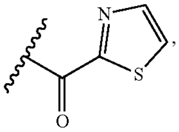
,
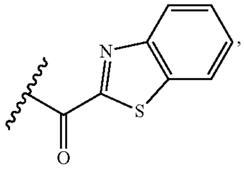
, or
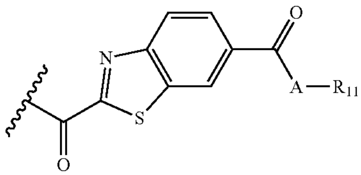

wherein A is —O— or NH and $R_{11}$ is H, methyl, benzyl, optionally substituted alkyl, optionally substituted aryl, heterocycle, or a residue of an α-amino acid.

In various embodiments, A is NH and $R_{11}$ form a residue of an α-amino acid.

In various embodiments, each Z is independently:

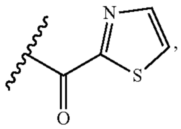
,
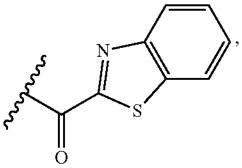
, or
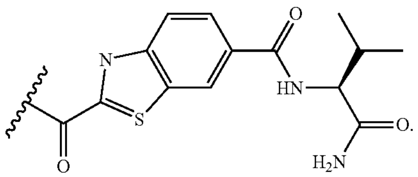

In some embodiments, each Z is independently:

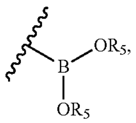

wherein each $R_5$ is as defined herein. In certain embodiments, each Z is independently:

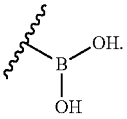 [SMILES: *B(O)O]

In some embodiments, each Z is independently:

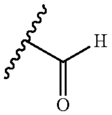
or
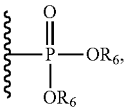

wherein $R_6$ each is substituted or unsubstituted aryl.

In certain embodiments, each Z is independently is:

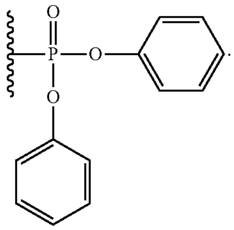 [SMILES: *P(=O)(Oc1ccccc1)Oc1ccccc1]

In various embodiments, the compounds of Formulas (IIA)-(IIH) are selected from the group consisting of:

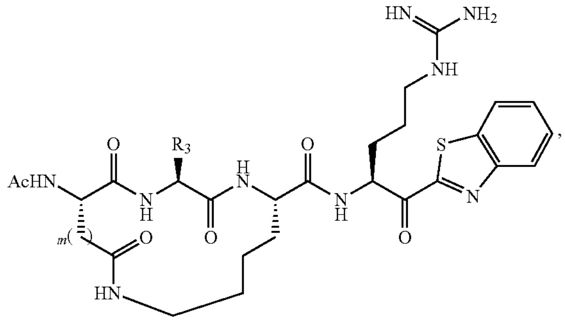
,
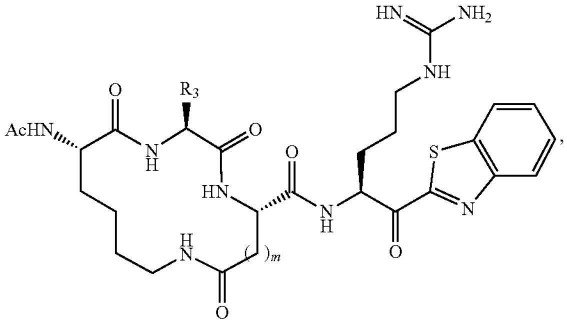
,

-continued

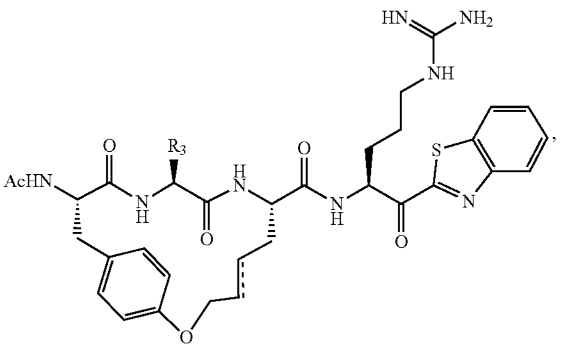

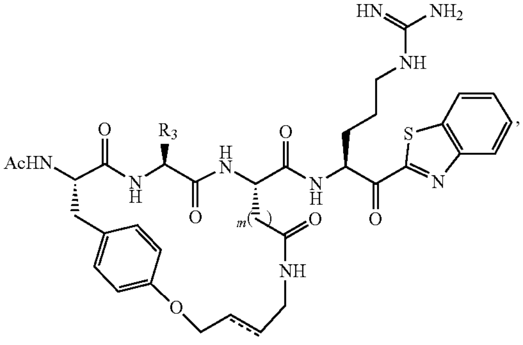

and

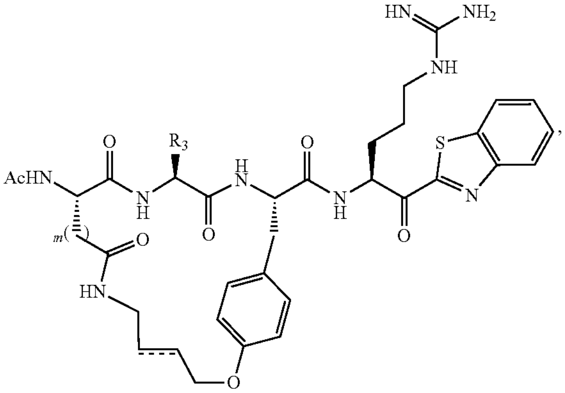

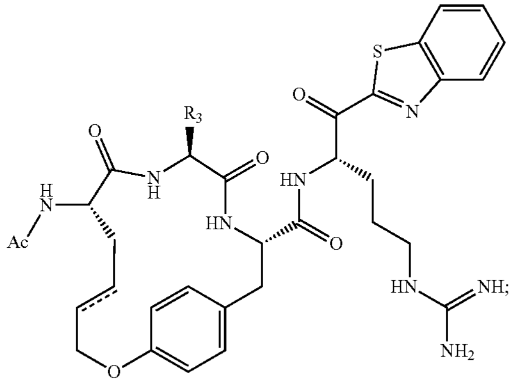

wherein each m is independently 1 or 2, and each $R_3$ is independently a side chain of an amino acid selected from the group consisting of Ala, Gly, Val, Leu, Lys, Arg, Asn, Phe, Gln, Thr, D-Trp, Tyr, Met, Agp, hCha, hTyr, hPhe, Orn, DAB, DAB(Z), Nle(O-Bzl), Arg($NO_2$), $Arg(Z)_2$, Lys(2-ClZ), hLeu, Dht, Idc, IgI, Chg, hAbu, Hyp, Glu(Bz), Met (O), Dap, Phe($F_5$), Glu(Me), and hArg.

In various embodiments, the compound of Formulas (IIA)-(IIH) are selected from the group consisting of:

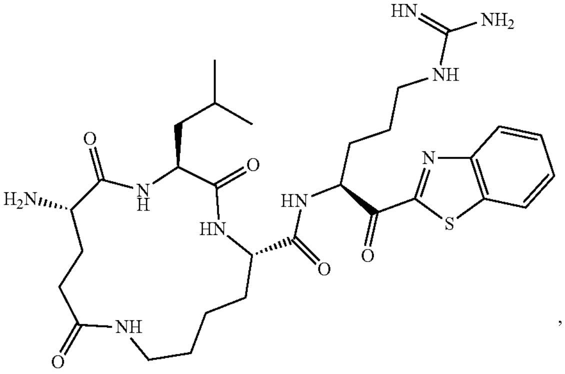

,

-continued
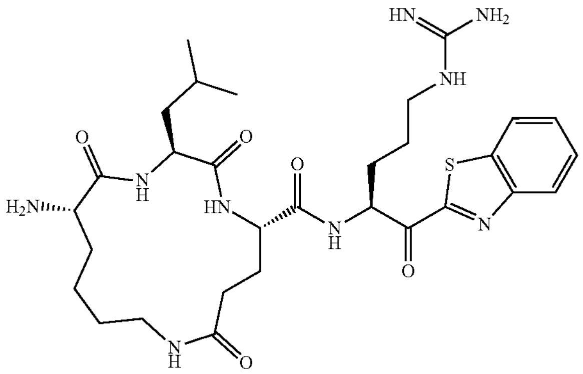
,
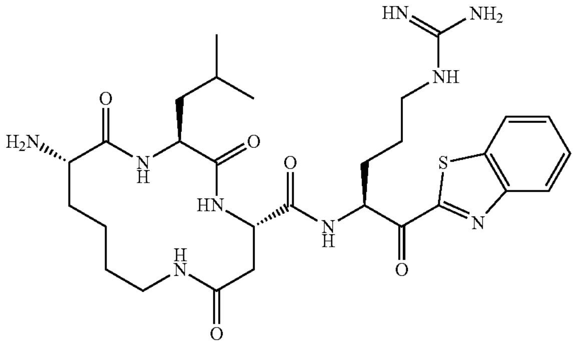
,
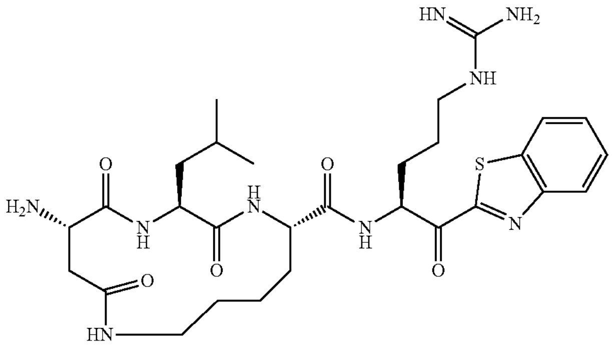
,
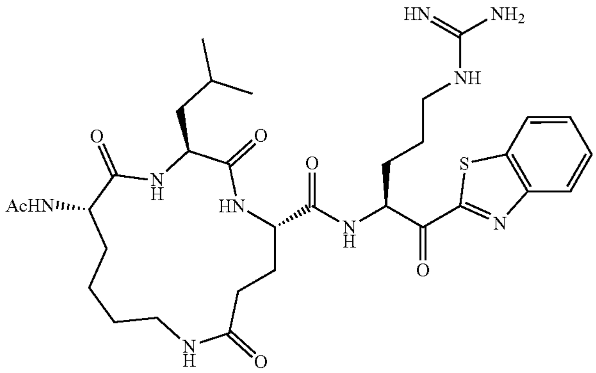
,

-continued
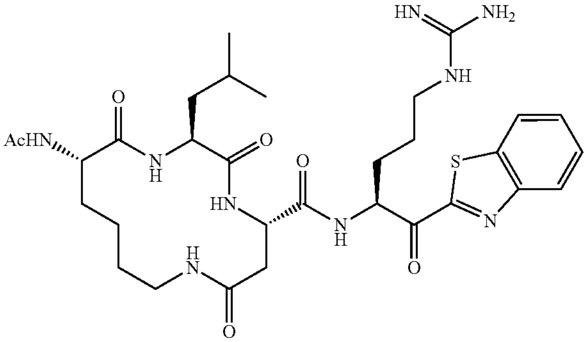
,
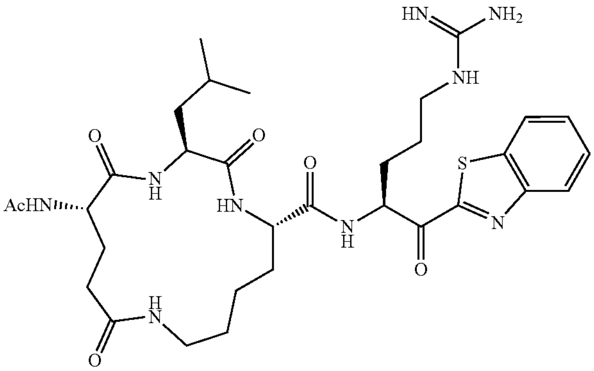
,
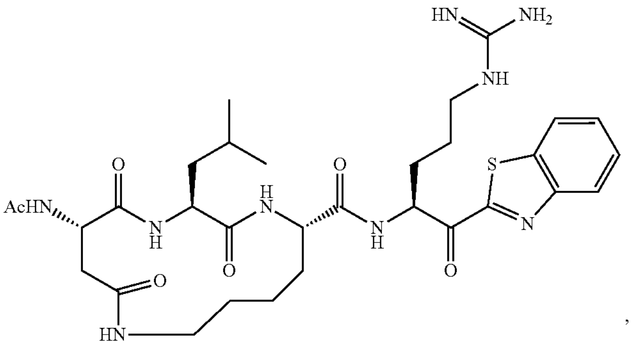
,
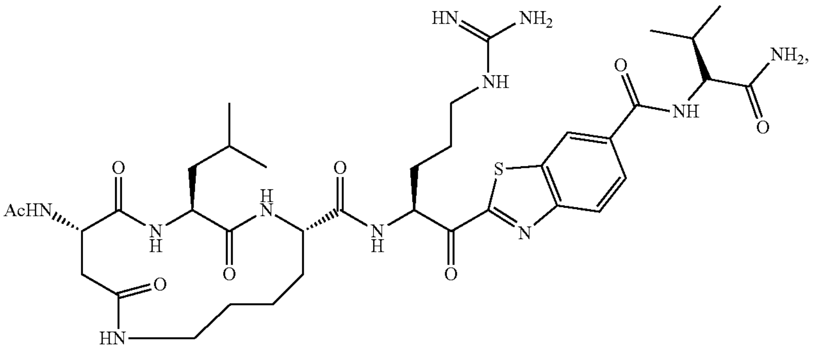

-continued
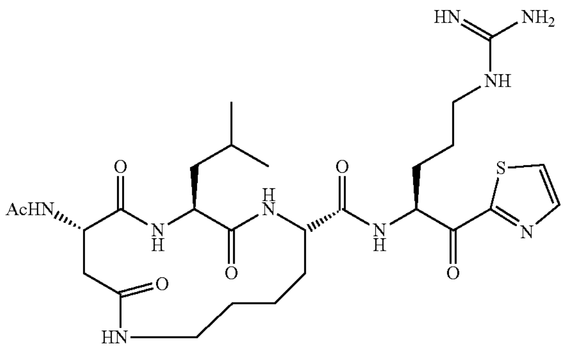
,
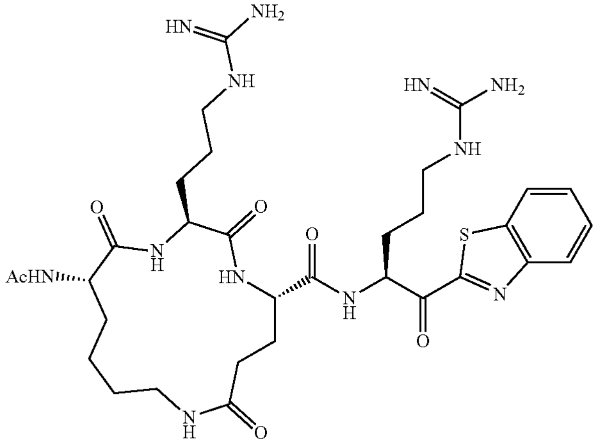
,
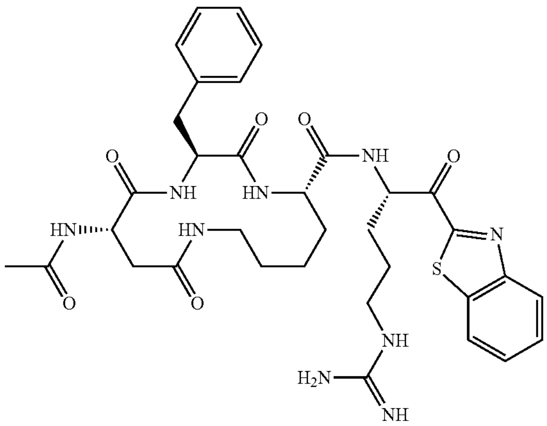
,
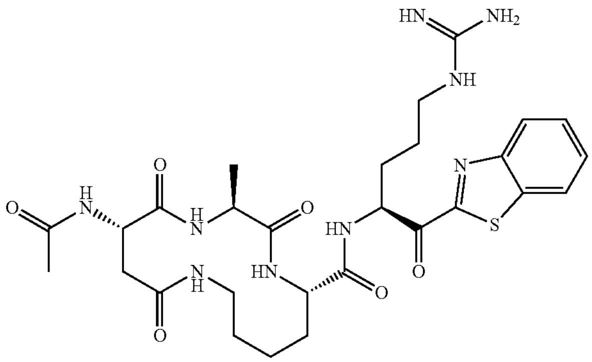
,

-continued
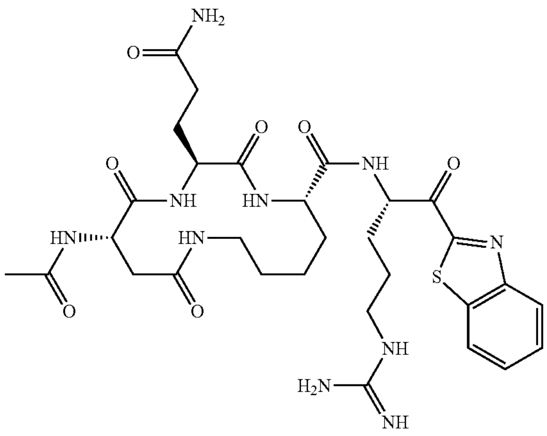
,
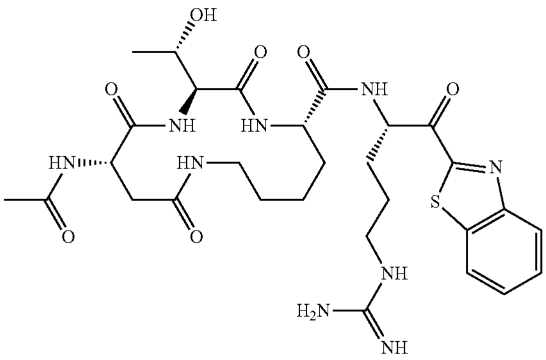
,
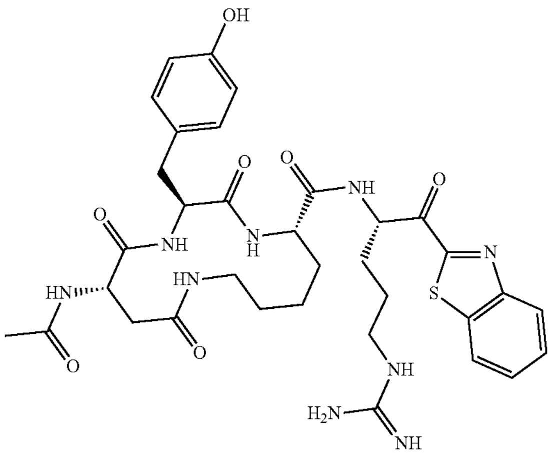
,
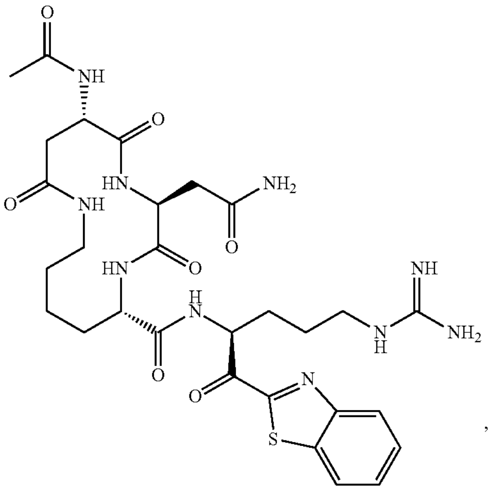
,
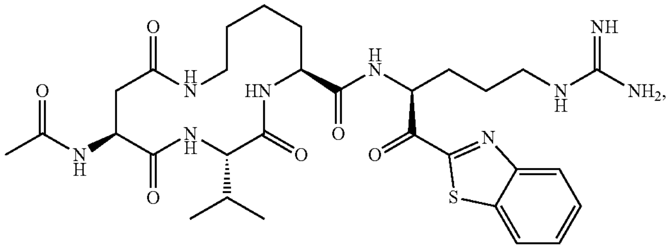
,
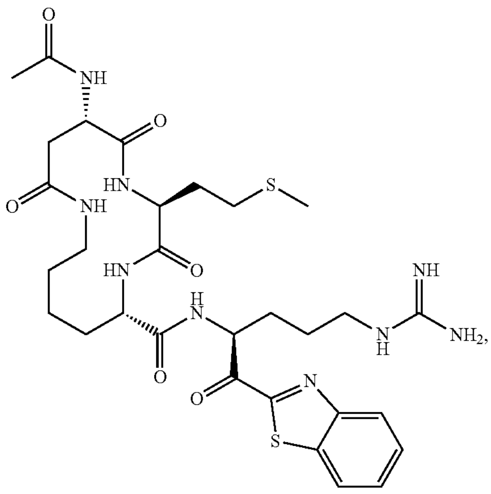
, -continued
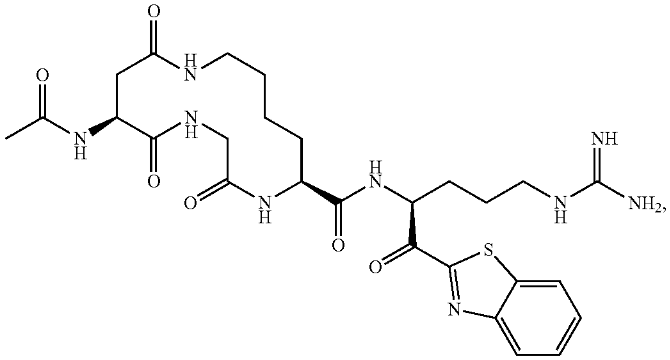
,
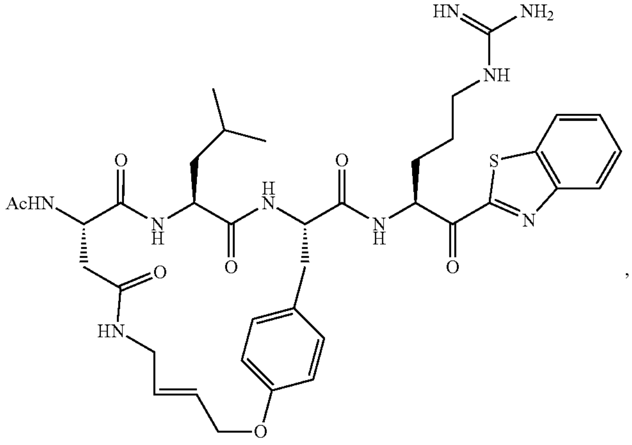
,
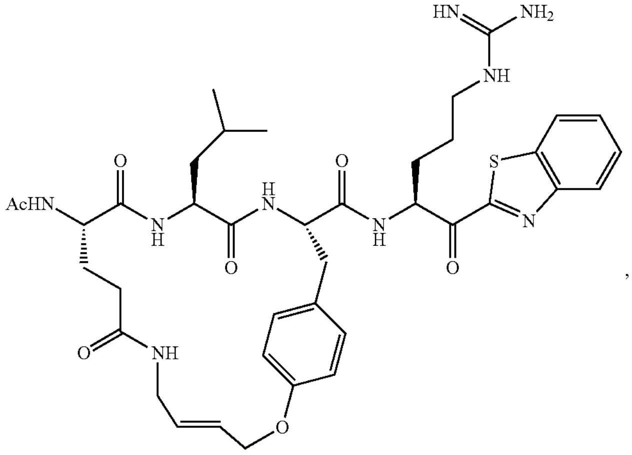
,
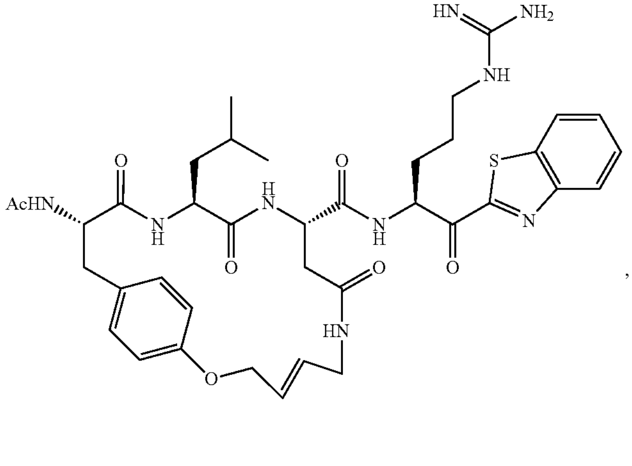
, -continued
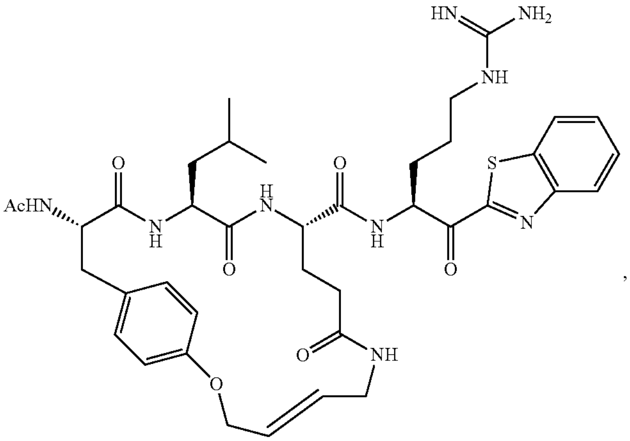
,
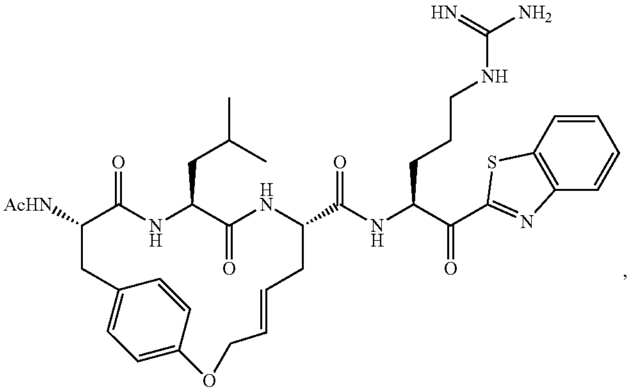
,
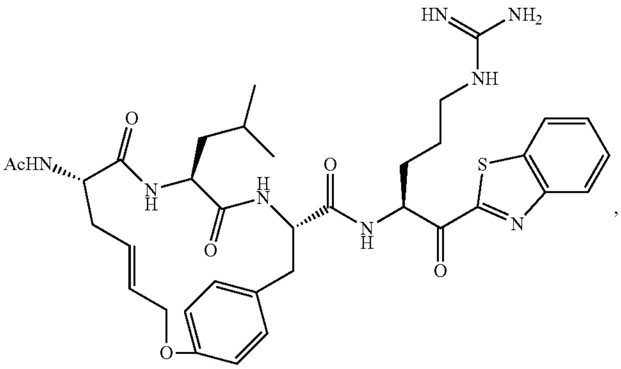
,
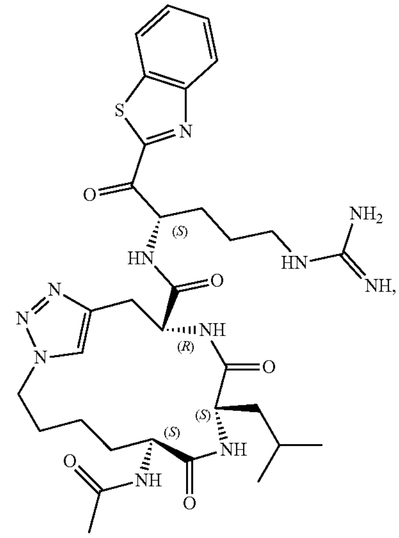

-continued
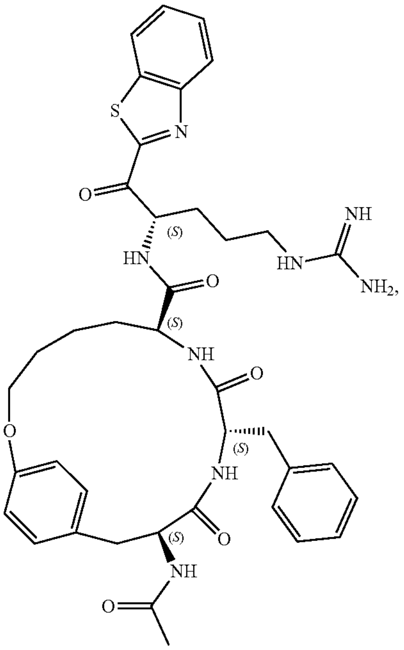
,
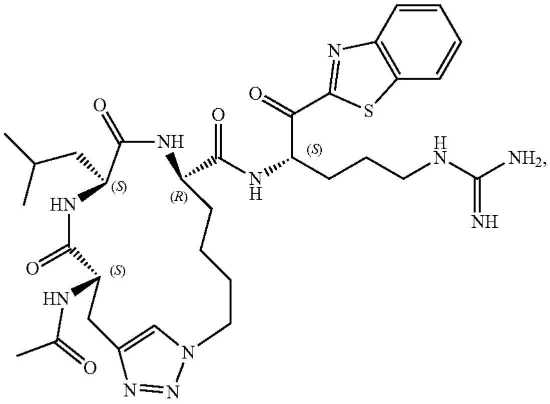
,
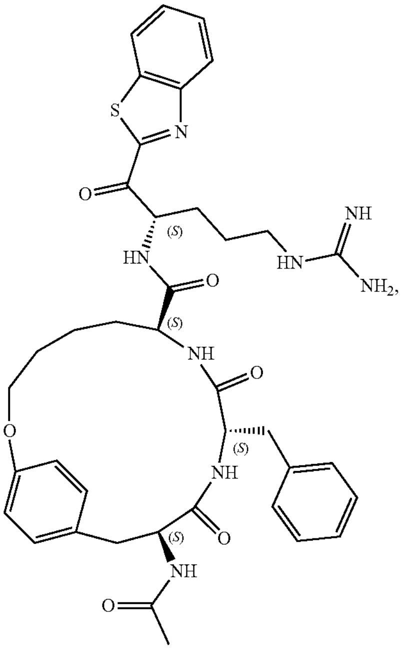
,
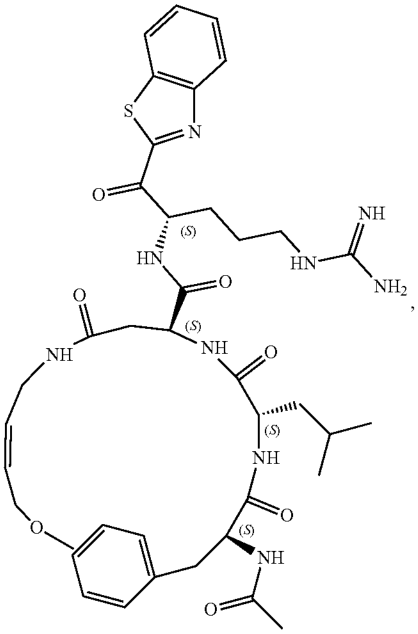
,

-continued
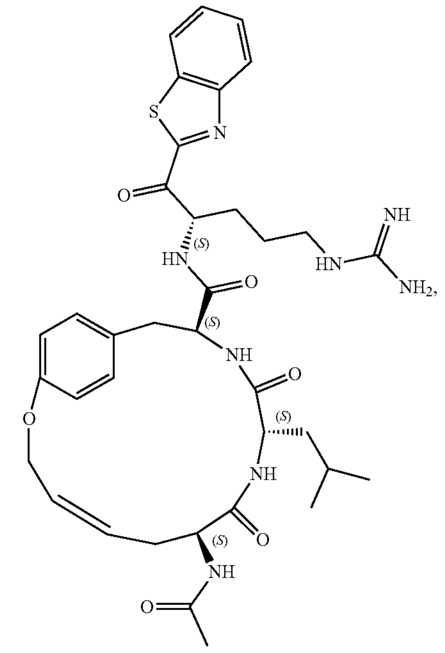
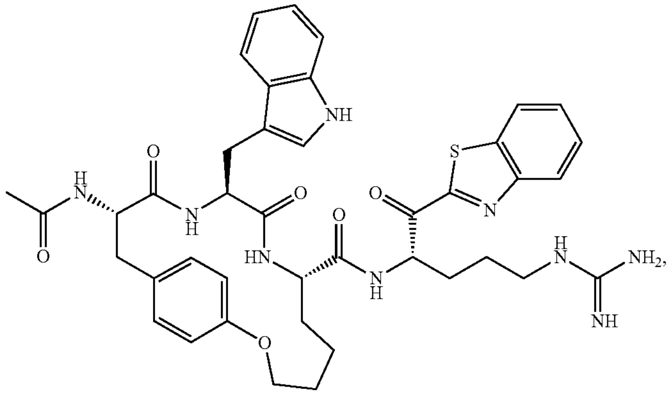
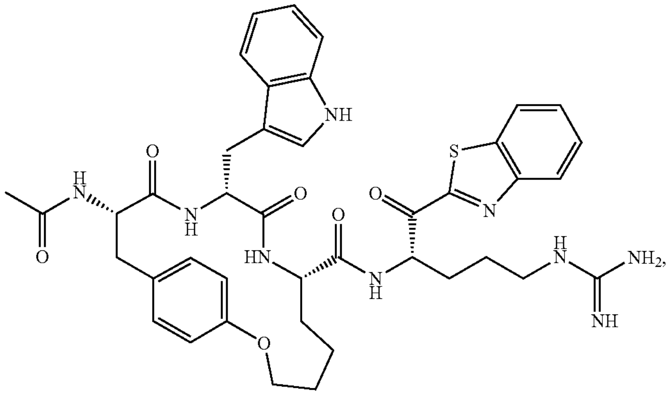
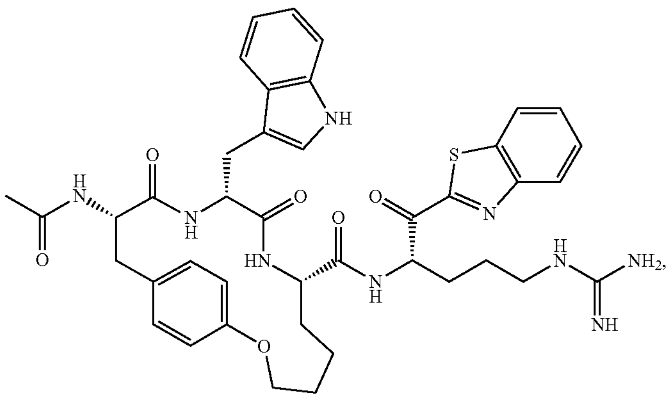

-continued
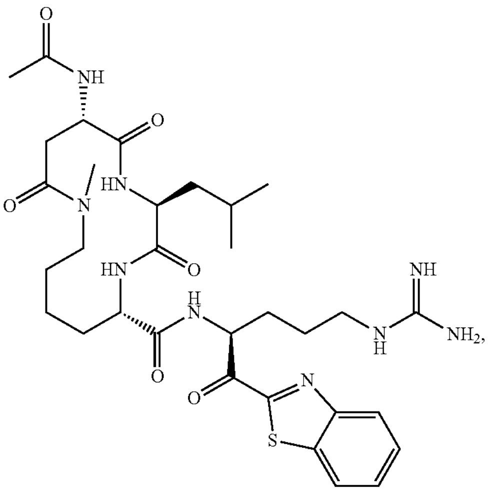
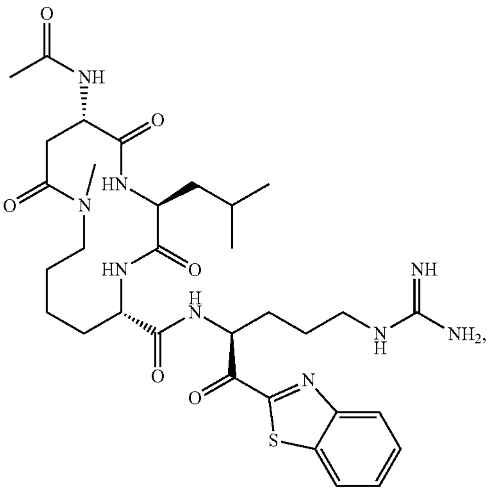
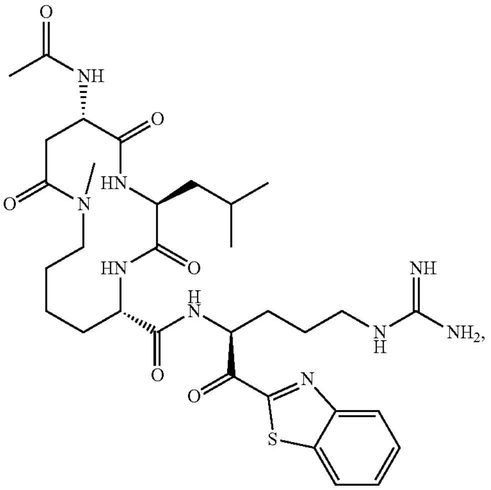
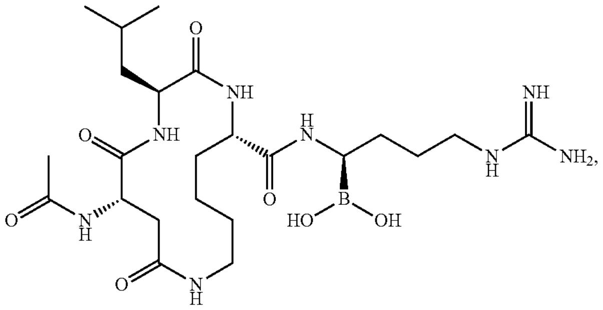
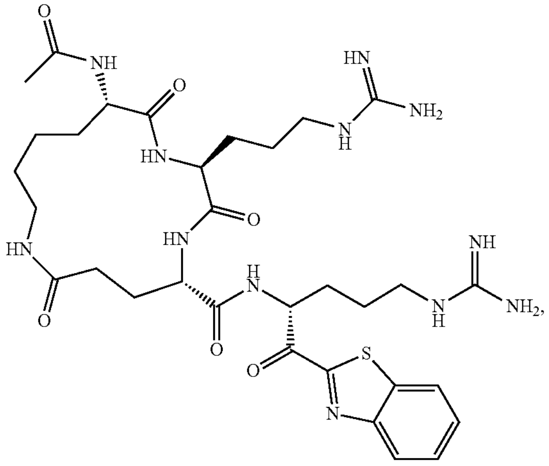
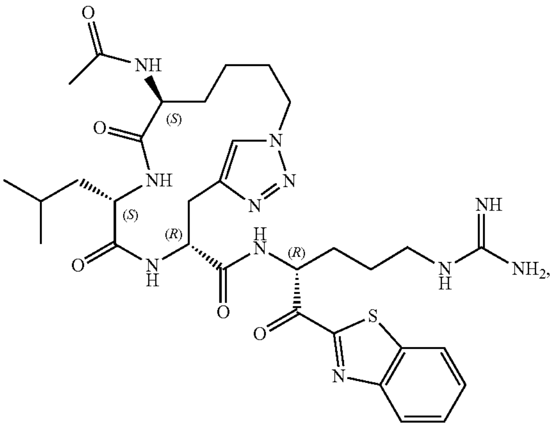

-continued
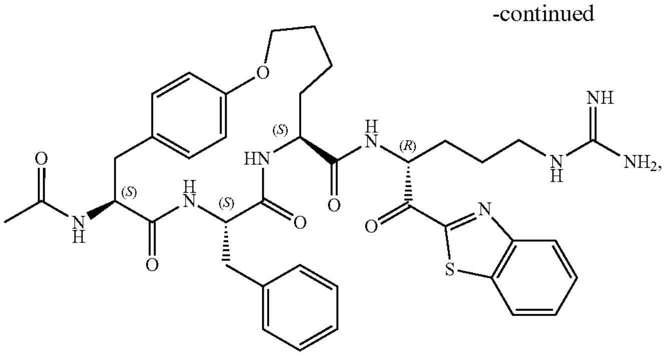
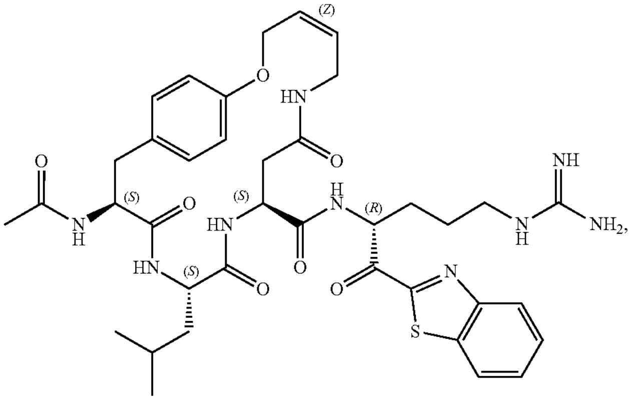
and
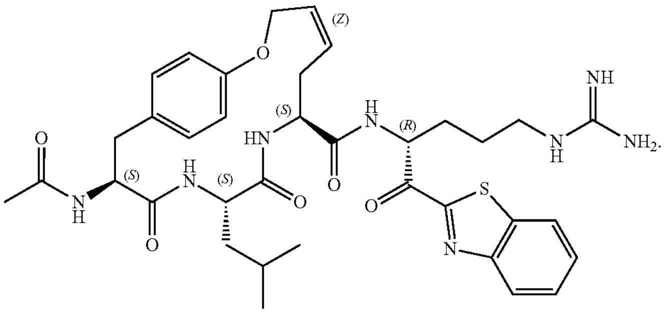
Compounds of Formulas (IIIA)-(IIIC)
In accordance with the present invention, another class of compounds useful for inhibiting one or more serine proteases includes compounds of Formulas (IIIA), (IIIB), (IIIC), salts thereof, or stereoisomers thereof:
(IIIA)
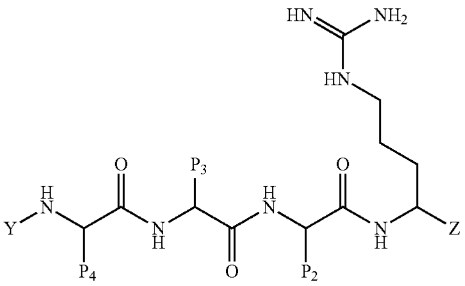
-continued
(IIIB)
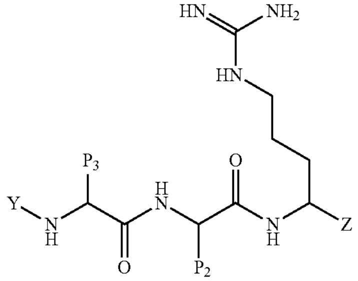

-continued (IIIC)

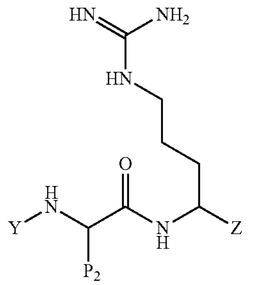

wherein:

each $P_2$ is independently a side chain of Phe, Leu, hLeu, Ala, Thr, Asn, NptGly, L-Orn, L-Cha, IgI, Phe(3,4-F2), Phe(3-Cl), Phe(4-F), or Glu(Bzl);

each $P_3$ is independently a side chain of Arg, hArg, Trp, D-Trp, Lys, hTyr, Gln, D-Gln, L-Nle(OBzl), Agp, L-Orn, hCha, hPhe, His(3-Bom), or Phe(4-$NO_2$);

$P_4$ is a side chain of Arg, Ile, Gly, Pro, Met, Leu, hArg, Arg$(Z)_2$, L-Arg($NO_2$), Trp, D-Trp, Ser, Lys, Lys(2-Cl—Z), Agp, L-DAB(Z), L-Orn, L-Nle(OBzl), or His (3-Bom);

Y is H, acetyl, tert-butyloxycarbonyl (Boc), benzyloxycarbonyl (Cbz), fluorenylmethyloxycarbonyl (Fmoc), benzyl, —C(O)R, —SOOR, —COOR, —C(O)NHR, substituted or unsubstituted —$(CH_2)_x$aryl, substituted or unsubstituted —$(CH_2)_x$heteroaryl, substituted or unsubstituted —$(CH_2)_x$cycloalkyl, or substituted or unsubstituted —$(CH_2)_x$heterocycle;

each x is independently 0, 1, or 2;

each R is independently $C_1$ to $C_6$ alkyl, $C_3$ to $C_6$ cycloalkyl, heterocycle, alkylheterocycle, aralkyl, or aryl;

each Z is independently

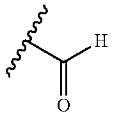
,
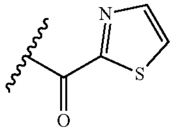
,
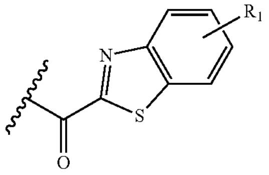
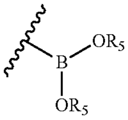
, or
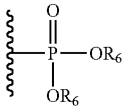
;

$R_1$ is hydrogen,

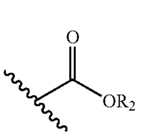
, or
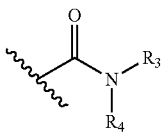
;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or the $R_5$ moieties can form a ring; and each $R_6$ is substituted or unsubstituted aryl.

In certain instances, the side chain of the amino acid forms a ring with the terminal amino group. For example, when $P_4$ is a side chain of Pro, the side chain of Pro forms a ring with the terminal amino group, as illustrated in the compound below:

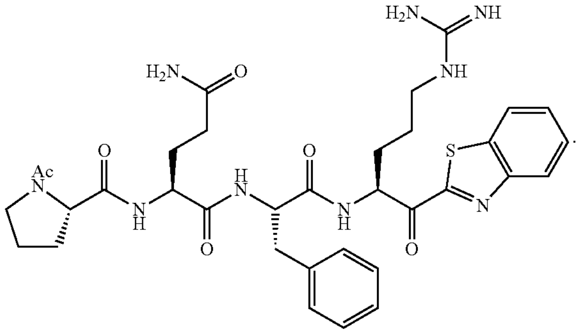

In various embodiments, the compound of Formula (IIIA), (IIIB), or (IIIC) is an inhibitor of HGFA.

In various embodiments, $P_2$ is independently a side chain of Leu, hLeu, or NptGly; each $P_3$ is independently a side chain of Arg, hArg, D-Trp, hTyr, Agp, hCha, or hPhe; and/or $P_4$ is a side chain of Lys(2-Cl—Z), Agp, or His(3-Bom).

In various embodiments, the compound of Formula (IIIA), (IIIB), or (IIIC) is an inhibitor of hepsin. For example, in various embodiments, each $P_2$ is independently a side chain of Leu, Thr, Asn, L-Orn, or L-Cha; each $P_3$ is independently a side chain of Arg, Lys, D-Gln, L-Nle(Obzl), Agp, or L-Orn; and/or $P_4$ is a side chain of Arg, L-Arg($NO_2$), Lys, Agp, L-DAB(Z), L-Orn, or L-Nle(OBzl).

In various embodiments, the compound of Formula (IIIA), (IIIB), or (IIIC) is an inhibitor of matriptase. In various embodiments, each $P_2$ is independently a side chain of IgI, Phe(3,4-F2), Phe(3-Cl), Phe(4-F), or Glu(Bzl); each $P_3$ is independently a side chain of Arg, Lys, L-Nle(Obzl), Agp, or L-Orn; and/or $P_4$ is a side chain of Arg, hArg, Arg$(Z)_2$, Lys, or L-Orn.

In various embodiments at least one of $P_2$, $P_3$, and $P_4$ is a side chain of an unnatural amino acid.

In certain embodiments, $R_2$ and $R_3$ are each independently hydrogen, alkyl, cycloalkyl, aryl, aralkyl, heteroaryl, or heteroarylalkyl. For example, $R_2$ and $R_3$ can each independently be hydrogen, $C_1$-$C_6$ alkyl, $C_3$-$C_{10}$ cycloalkyl, phenyl, or benzyl.

In certain embodiments, $R_4$ is hydrogen, alkyl, or a residue of an amino acid, or $R_3$ and $R_4$ can form a piperazine or piperidine ring In various embodiments, each $R_5$ is independently hydrogen, alkyl, or the $R_5$ moieties can form a ring.

In various embodiments, $R_6$ is aryl.

In various embodiments, each Z is independently:

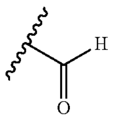 , 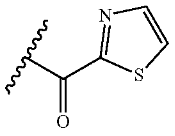 ,

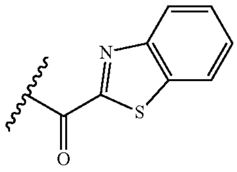 , or

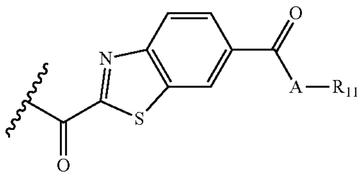

wherein A is —O— or NH and $R_{11}$ is H, methyl, benzyl, optionally substituted alkyl, optionally substituted aryl, heterocycle, or a residue of an α-amino acid. In various embodiments, A is NH and A and Ru form a residue of an α-amino acid.

In various embodiments, each Z is independently

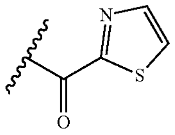 , 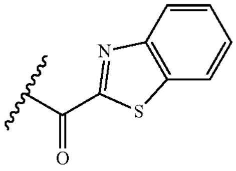 , or

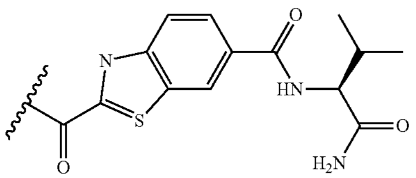 .

In some embodiments, each Z is independently:

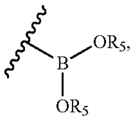

wherein each $R_5$ is as defined herein. In certain embodiments, each Z is independently:

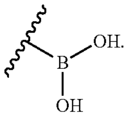 [SMILES: *B(O)O]

In some embodiments, each Z is independently:

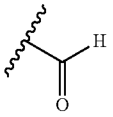 , or 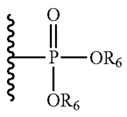 , wherein $R_6$ each is substituted or unsubstituted aryl.

In certain embodiments, each Z is independently is:

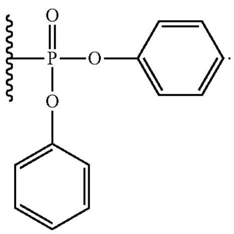 [SMILES: *P(=O)(Oc1ccccc1)Oc1ccccc1]

In various embodiments, the compound of the compound of Formula (IIIA), (IIIB), or (IIIC) is selected from the group consisting of:

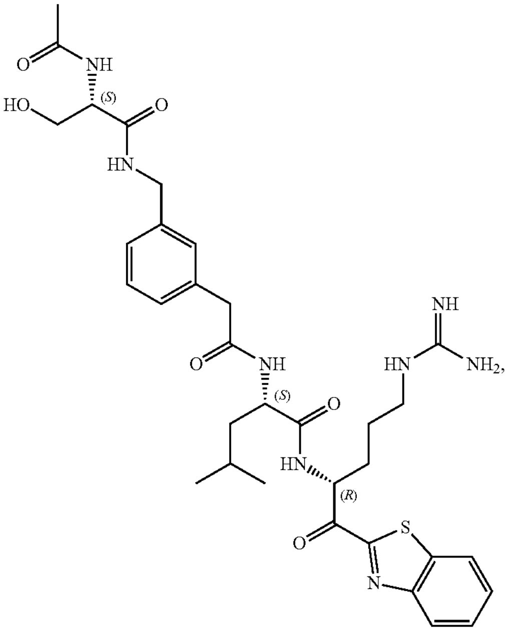
,
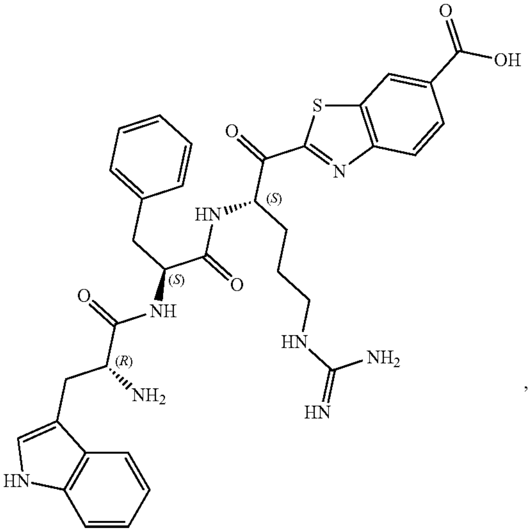
,
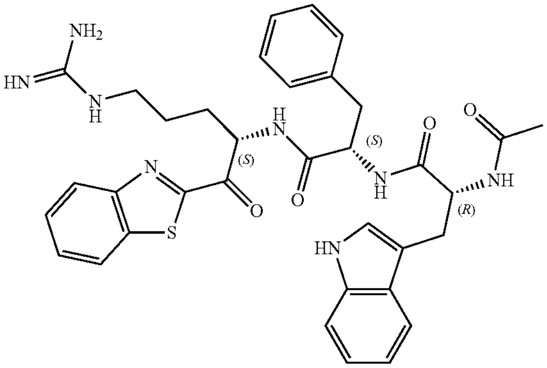
,
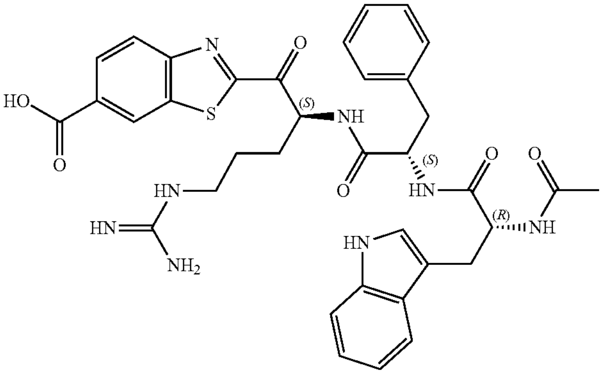
,

-continued
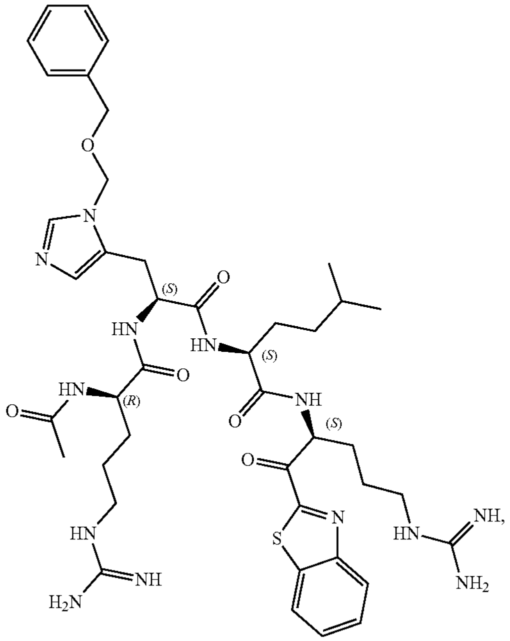
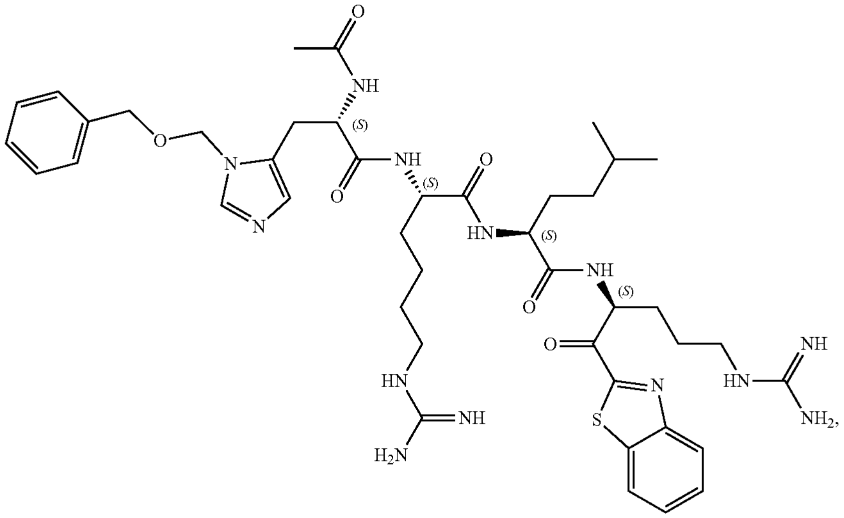
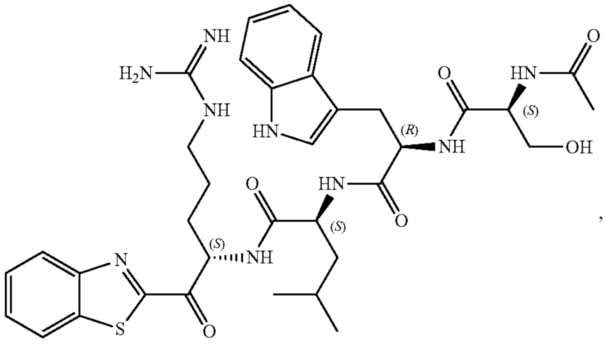
,

-continued
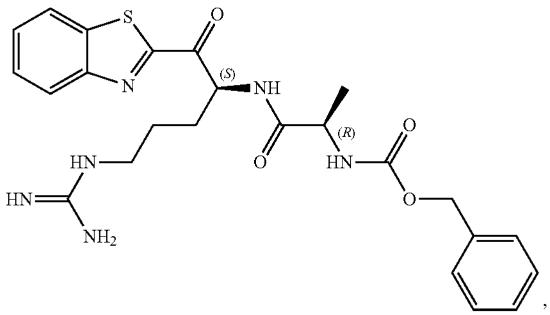
,
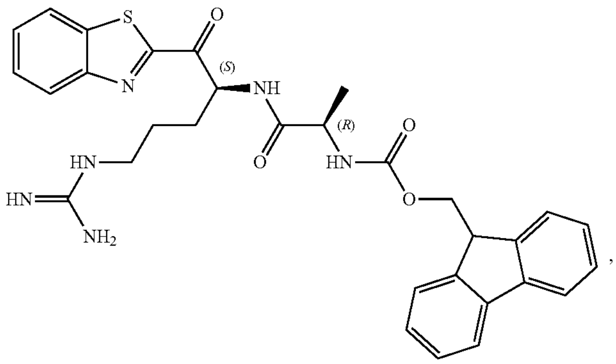
,
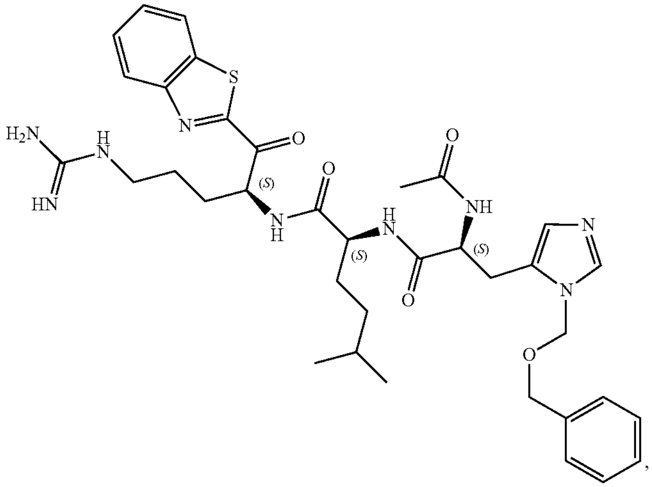
,
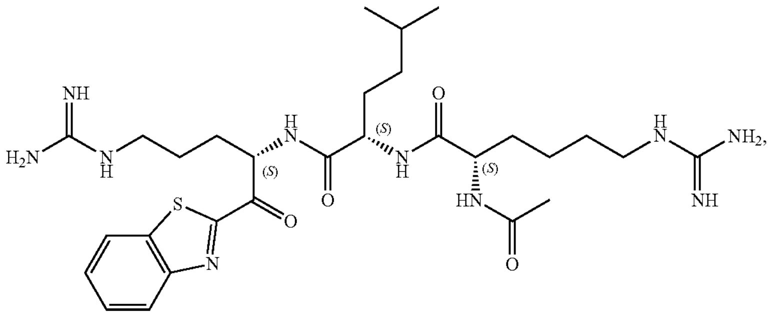
,

-continued
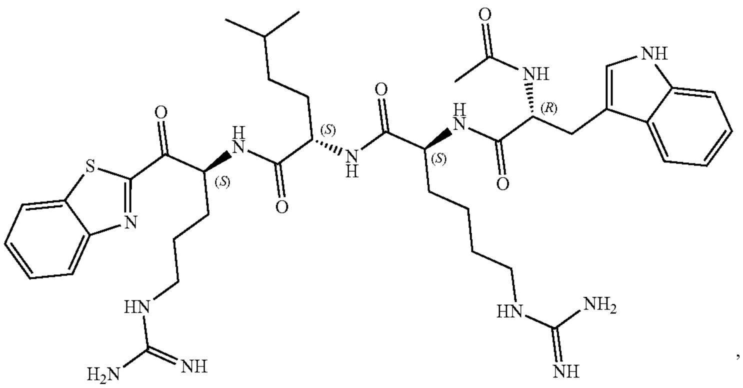
,
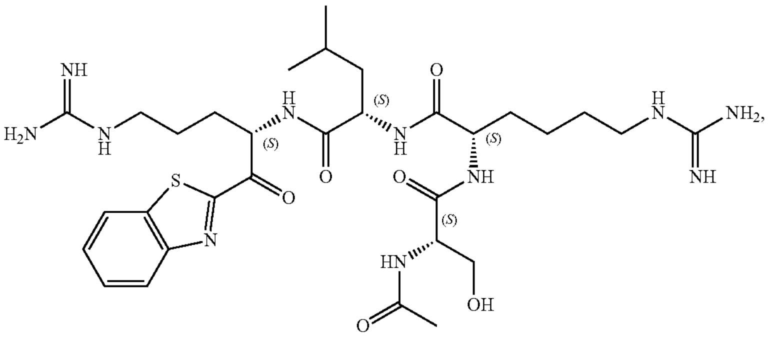
,
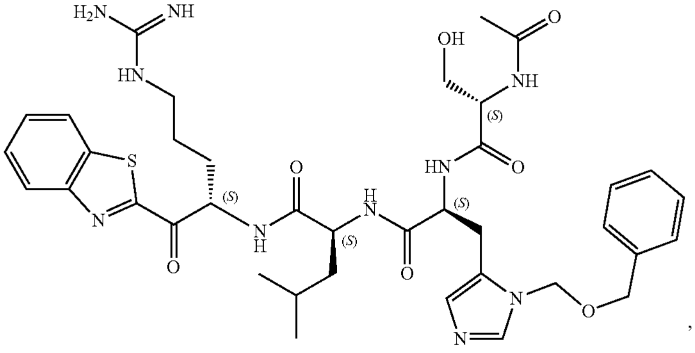
,
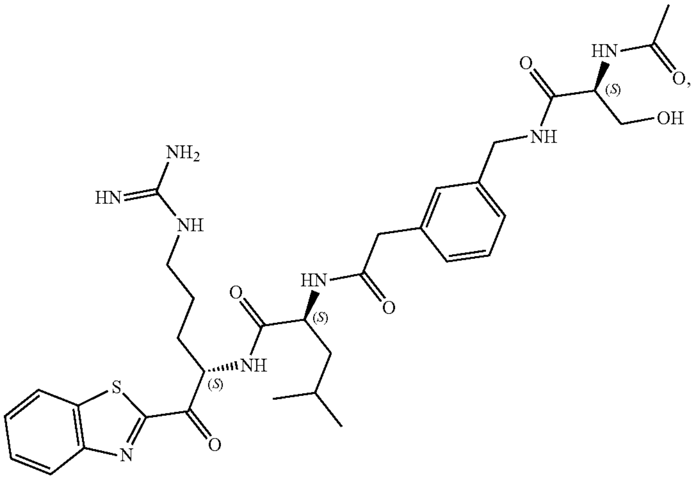
,

-continued
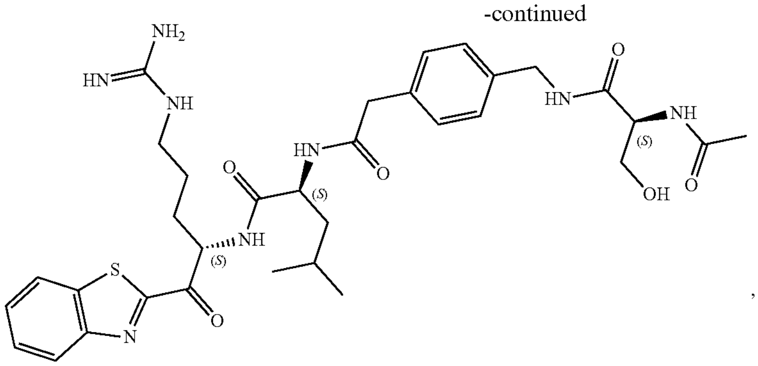
,
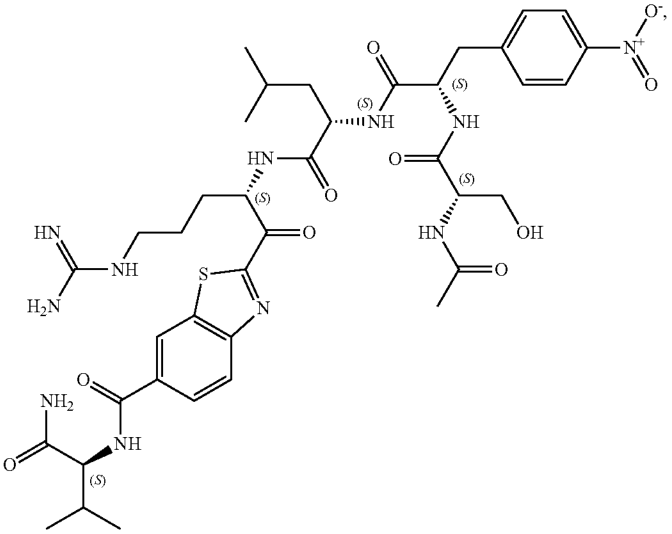
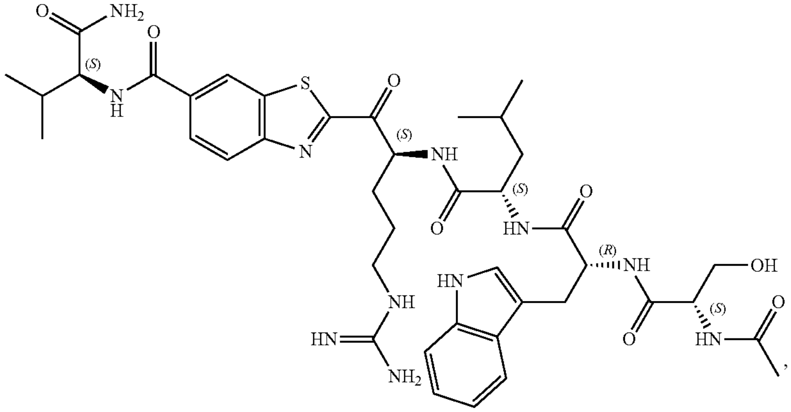
,
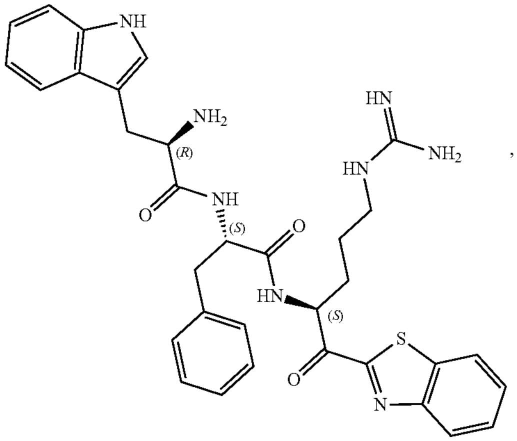
,

-continued
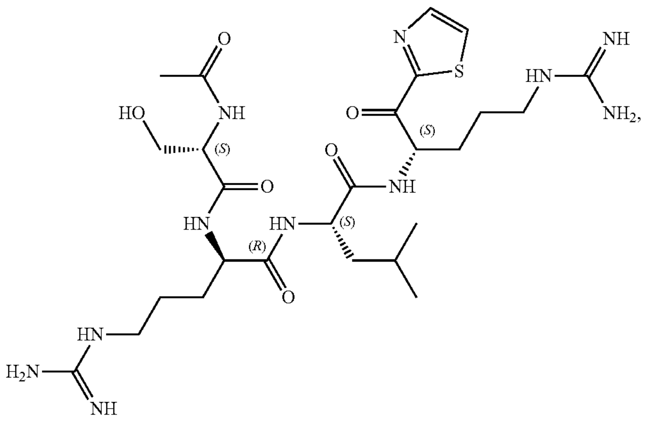
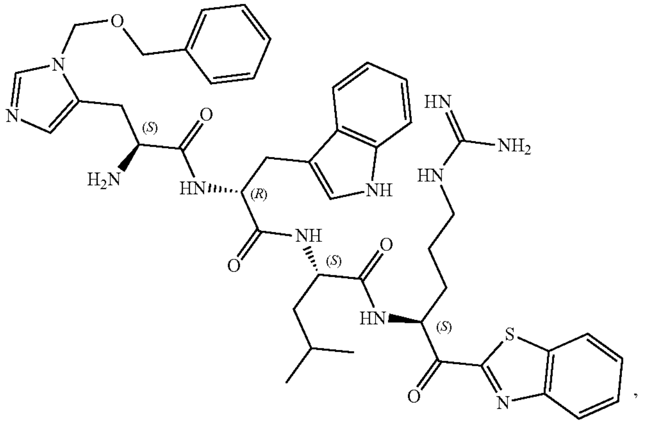
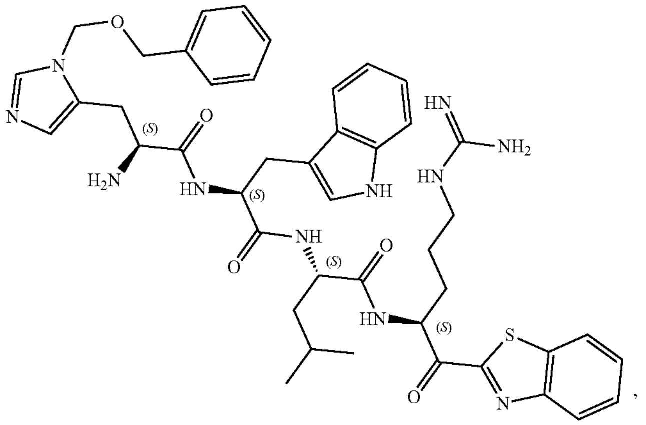
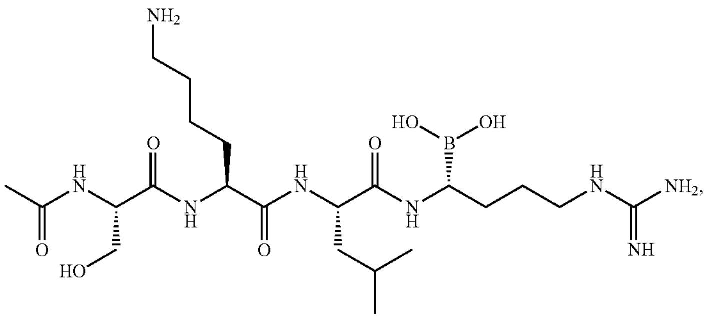

-continued
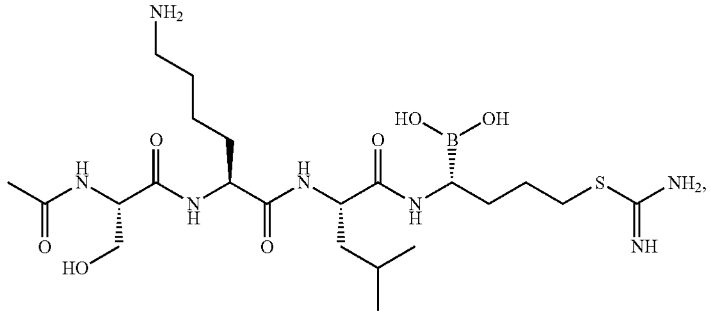
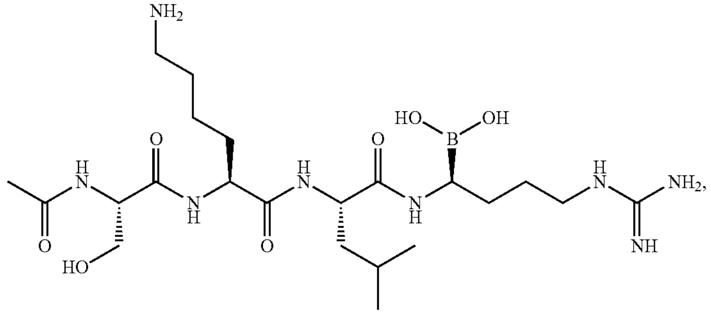
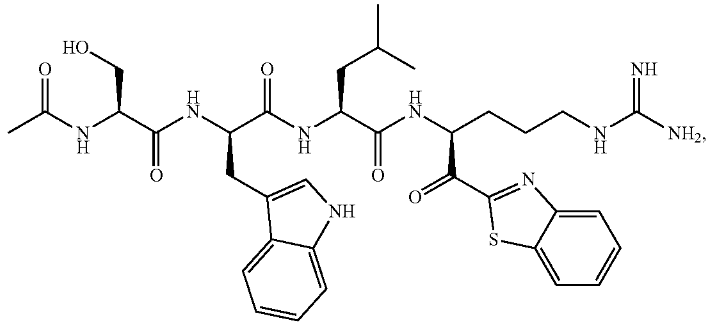
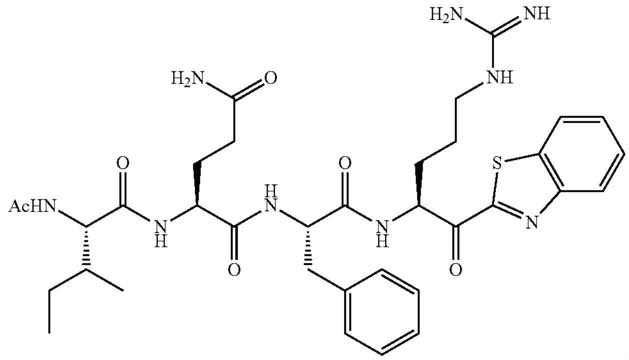
,
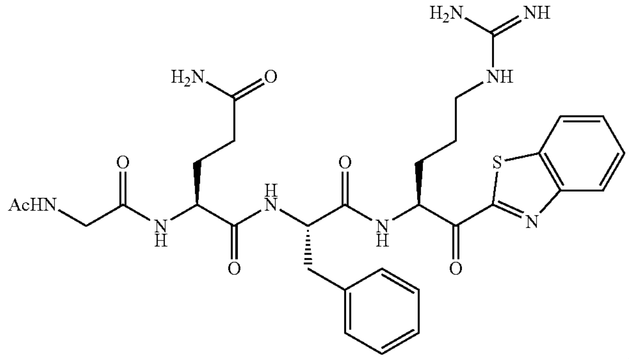
,

-continued
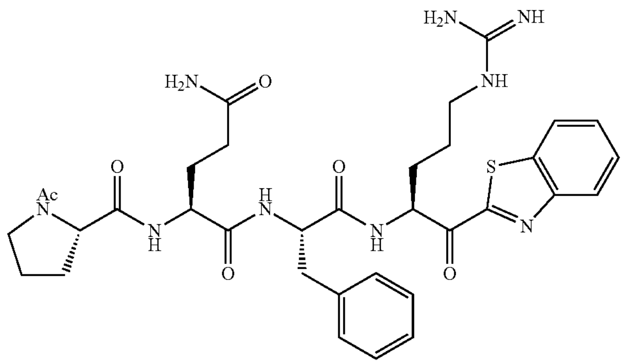
,
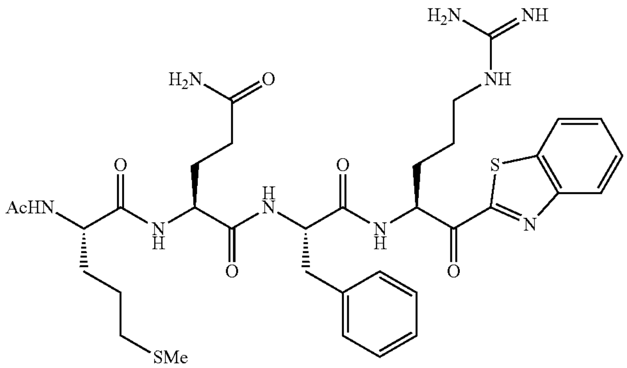
,
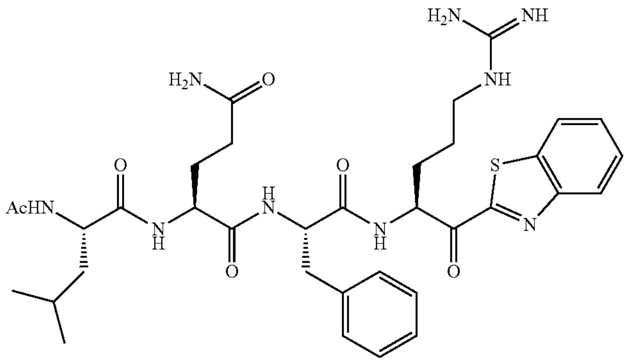
,
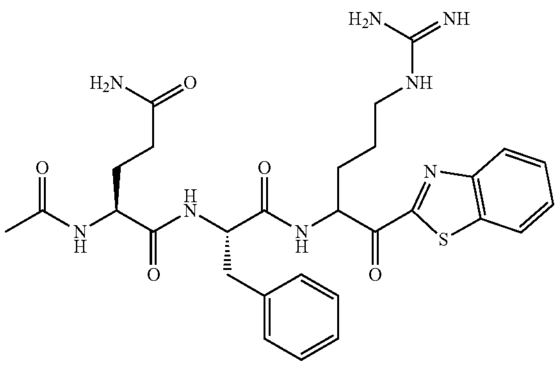
,

-continued

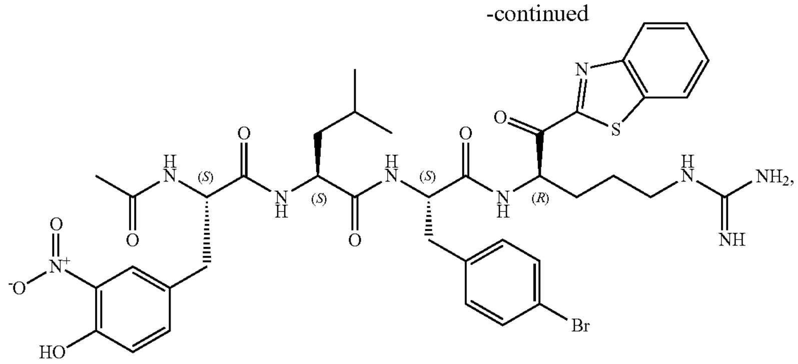

and

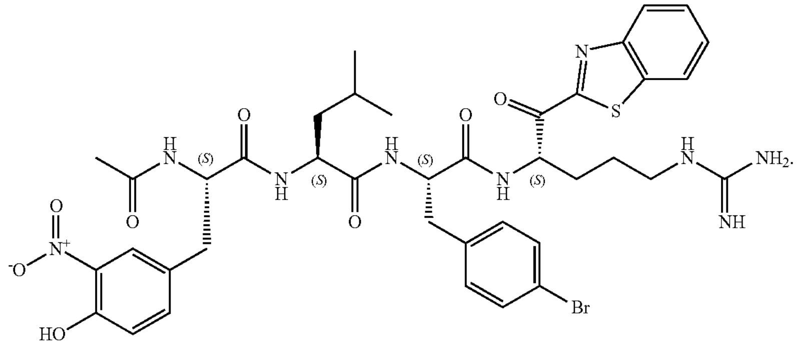

As used herein, the abbreviations of the naturally occurring amino acids are as follows:

| Amino acid | Three letter code | One letter code |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gin | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

The naturally occurring amino acids described herein are the L-isomer unless denoted as a D-isomer.

Unless otherwise specified, the unnatural amino acids can be selected from the group listed in the table below. The unnatural amino acids can be the D and/or L-isomers.

| Unnatural Alpha-Amino Acids | |
|---|---|
| Abbreviation | Structure |
| His(3-Bom) | 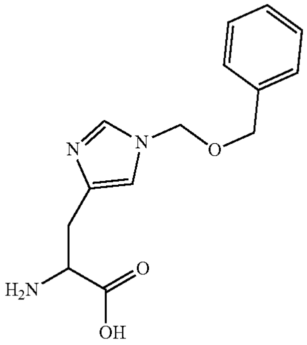 [SMILES: NC(Cc1cn(COCc2ccccc2)cn1)C(=O)O] |
| Thyr | 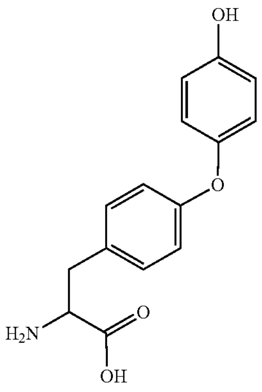 [SMILES: NC(Cc1ccc(Oc2ccc(O)cc2)cc1)C(=O)O] |

-continued
Unnatural Alpha-Amino Acids
| Abbreviation | Structure |
|---|---|
| Agp | 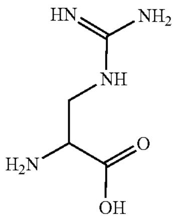 |
| Inp | 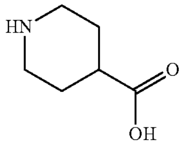 |
| Lys(2-Cl-Z) | 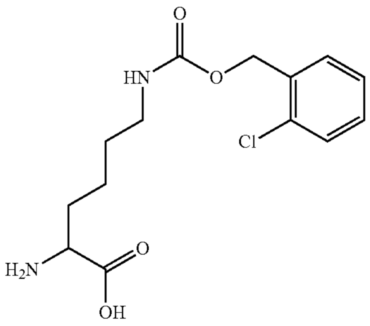 [SMILES: NC(CCCCNC(=O)OCc1ccccc1Cl)C(=O)O] |
| Pip | 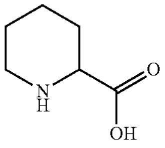 |
| hArg | 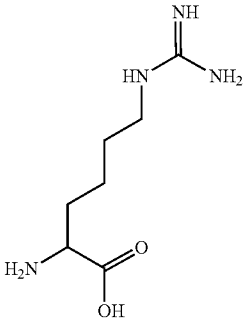 [SMILES: N=C(N)NCCCCC(N)C(=O)O] |
| Phg | 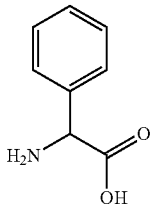 |
-continued
Unnatural Alpha-Amino Acids
| Abbreviation | Structure |
|---|---|
| hTyr | 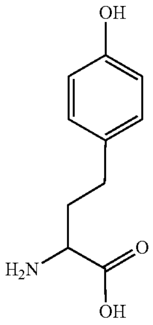 |
| 3-Pal | 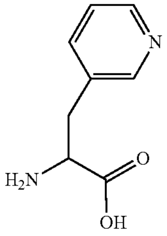 [SMILES: NC(Cc1cccnc1)C(=O)O] |
| hPhe | 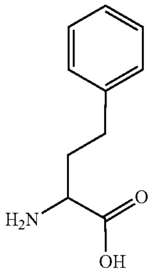 [SMILES: NC(CCc1ccccc1)C(=O)O] |
| 4-Pal | 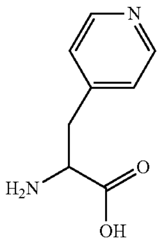 [SMILES: NC(Cc1ccncc1)C(=O)O] |
| hLeu | 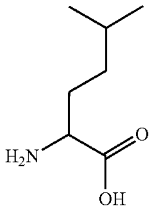 |

-continued
| Unnatural Alpha-Amino Acids | |
|---|---|
| Abbreviation | Structure |
| hCha | 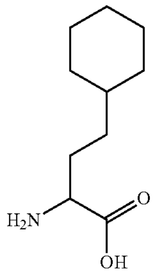 |
| NptGly | 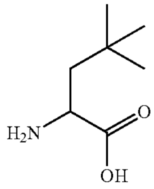 |
| Orn | 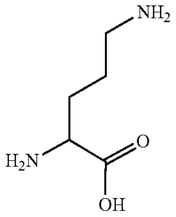 |
| DAB(Z) | 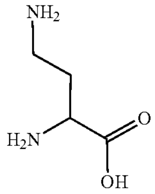 |
| Met(O) | 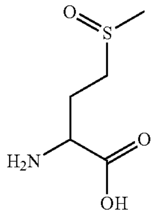 |
| Nle(OBzl) | 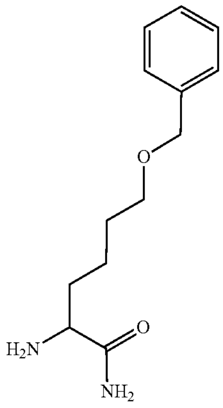 [SMILES: NC(=O)C(N)CCCCOCc1ccccc1] |
-continued
| Unnatural Alpha-Amino Acids | |
|---|---|
| Abbreviation | Structure |
| Cha | 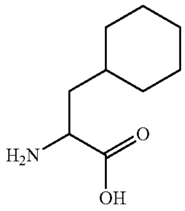 [SMILES: NC(CC1CCCCC1)C(=O)O] |
| Arg($NO_2$) | 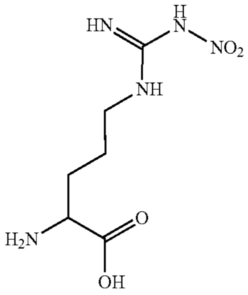 [SMILES: N=C(NCCCC(N)C(=O)O)N[N+](=O)[O-]] |
| Nle | 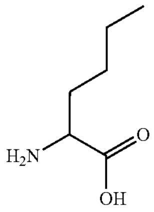 |
| Hyp | 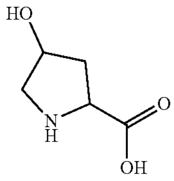 |
| MeAla | 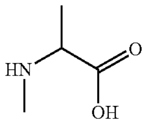 |
| Oic | 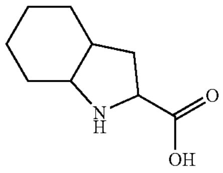 [SMILES: O=C(O)C1CC2CCCCC2N1] |
| βAla | 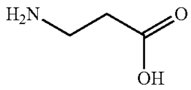 |
| hPro | 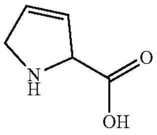 |

-continued
| Unnatural Alpha-Amino Acids | |
| --- | --- |
| Abbreviation | Structure |
| Gla | 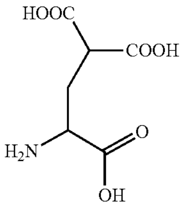 [SMILES: NC(CC(C(=O)O)C(=O)O)C(=O)O] |
| Hyp(Bzl) | 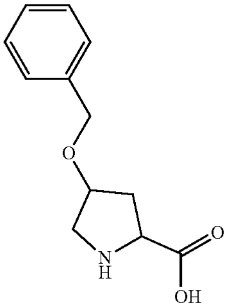 [SMILES: O=C(O)C1CC(OCc2ccccc2)CN1] |
| Asp(Me) | 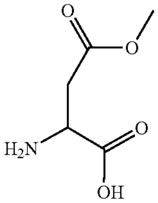 |
| Asp(All) | 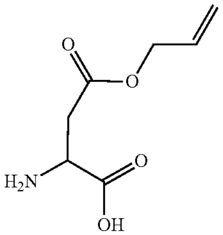 |
| Glu(Me) | 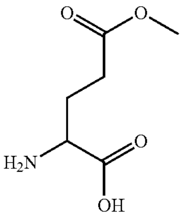 |
| Asp(Bzl) | 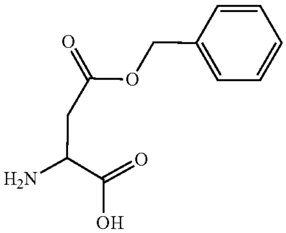 [SMILES: NC(CC(=O)OCc1ccccc1)C(=O)O] |
| Glu(All) | 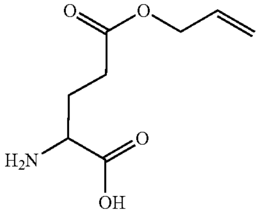 |
| Glu(Chx) | 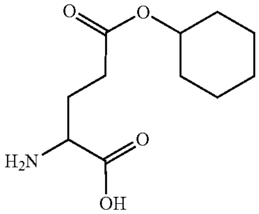 [SMILES: NC(CCC(=O)OC1CCCCC1)C(=O)O] |
| Aad | 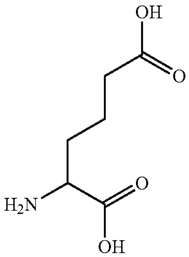 |
| Glu(Bzl) | 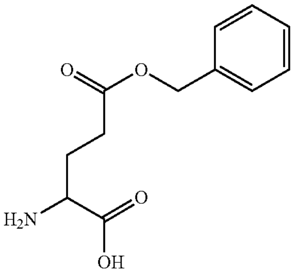 [SMILES: NC(CCC(=O)OCc1ccccc1)C(=O)O] |
| Cit | 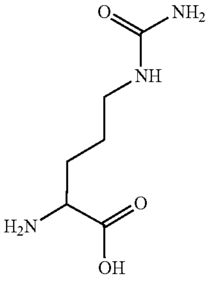 [SMILES: NC(=O)NCCCC(N)C(=O)O] |
| Api | 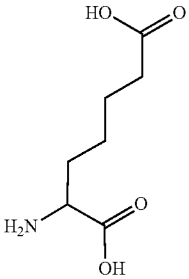 [SMILES: NC(CCCCC(=O)O)C(=O)O] |

-continued
| Unnatural Alpha-Amino Acids | |
|---|---|
| Abbreviation | Structure |
| hCit | 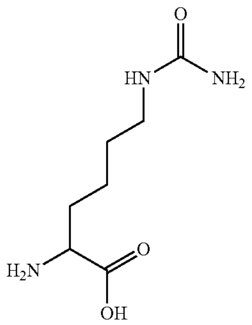 [SMILES: NC(=O)NCCCCC(N)C(=O)O] |
| Dap | 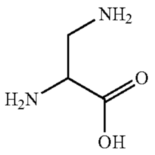 |
| Lys(Ac) | 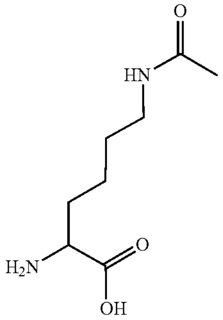 |
| Lys(TFA) | 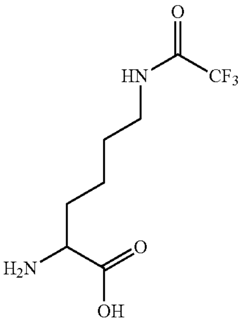 [SMILES: NC(CCCCNC(=O)C(F)(F)F)C(=O)O] |
| Lys(2Cl-Z) | 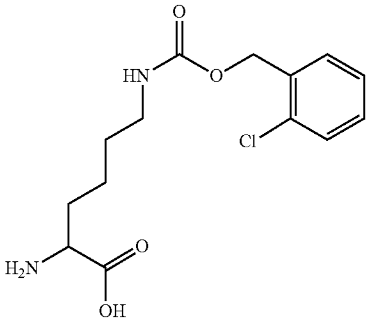 [SMILES: NC(CCCCNC(=O)OCc1ccccc1Cl)C(=O)O] |
-continued
| Unnatural Alpha-Amino Acids | |
|---|---|
| Abbreviation | Structure |
| His(Bzl) | 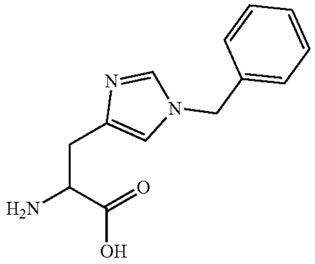 [SMILES: NC(Cc1cn(Cc2ccccc2)cn1)C(=O)O] |
| Arg(Me) | 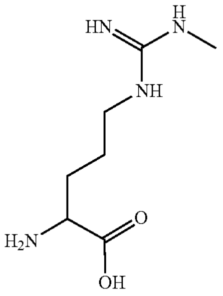 |
| $Arg(Me)_2$ | 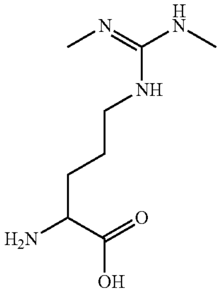 |
| $Phe(4-NH)_2$ | 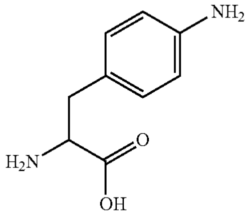 [SMILES: Nc1ccc(CC(N)C(=O)O)cc1] |
| 3-Pal | 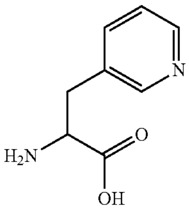 [SMILES: NC(Cc1cccnc1)C(=O)O] |
| Phe(2-F) | 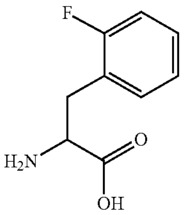 [SMILES: NC(Cc1ccccc1F)C(=O)O] |

-continued
| Unnatural Alpha-Amino Acids | |
|---|---|
| Abbreviation | Structure |
| 4-Pal | 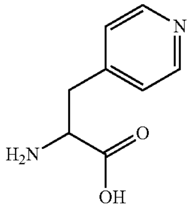 [SMILES: NC(Cc1ccncc1)C(=O)O] |
| Phe(3-F) | 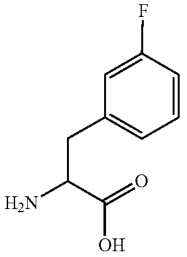 [SMILES: NC(Cc1cccc(F)c1)C(=O)O] |
| Phe(4-F) | 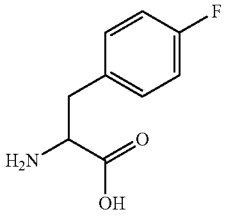 [SMILES: NC(Cc1ccc(F)cc1)C(=O)O] |
| Phe(2-Cl) | 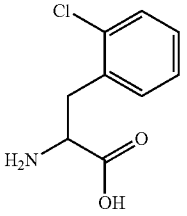 [SMILES: NC(Cc1ccccc1Cl)C(=O)O] |
| Phe(3,4-F) | 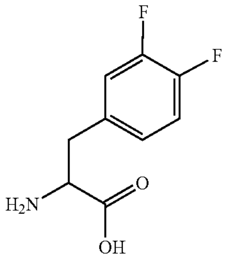 [SMILES: NC(Cc1ccc(F)c(F)c1)C(=O)O] |
| Phe(3-Cl) | 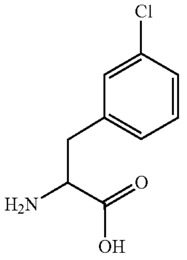 [SMILES: NC(Cc1cccc(Cl)c1)C(=O)O] |
-continued
| Unnatural Alpha-Amino Acids | |
|---|---|
| Abbreviation | Structure |
| Phe($F_5$) | 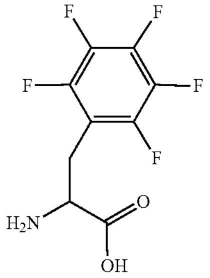 [SMILES: NC(Cc1c(F)c(F)c(F)c(F)c1F)C(=O)O] |
| Phe(4-Cl) | 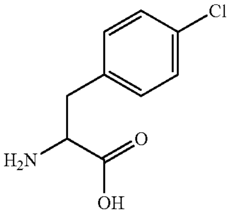 [SMILES: NC(Cc1ccc(Cl)cc1)C(=O)O] |
| Phe(3,4-Cl) | 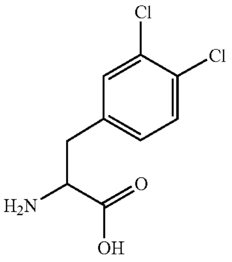 [SMILES: NC(Cc1ccc(Cl)c(Cl)c1)C(=O)O] |
| Phe(4-I) | 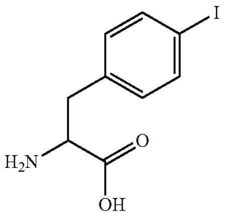 [SMILES: NC(Cc1ccc(I)cc1)C(=O)O] |
| Phe(3-I) | 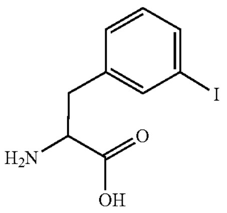 [SMILES: NC(Cc1cccc(I)c1)C(=O)O] |
| Phe(4-Br) | 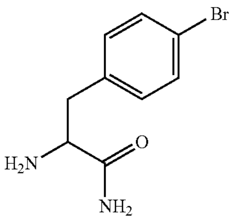 [SMILES: NC(=O)C(N)Cc1ccc(Br)cc1] |

-continued
| Unnatural Alpha-Amino Acids | |
|---|---|
| Abbreviation | Structure |
| Phe(4-$NO_2$) | 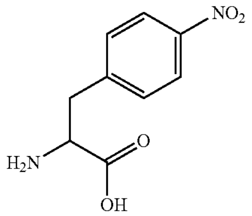 |
| Phe(4-Me) | 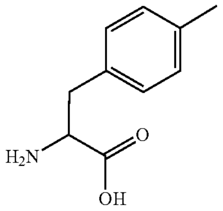 |
| Phe(4-guan) | 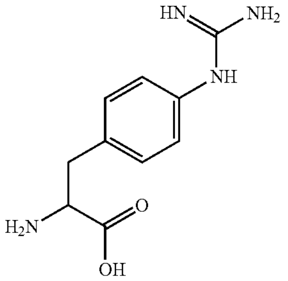 [SMILES: N=C(N)Nc1ccc(CC(N)C(=O)O)cc1] |
| Ala(2-th) | 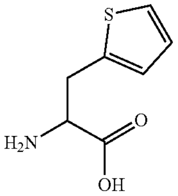 [SMILES: NC(Cc1cccs1)C(=O)O] |
| Ser(Bzl) | 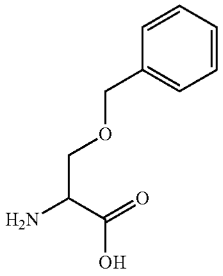 |
| Cys(4-MeBzl) | 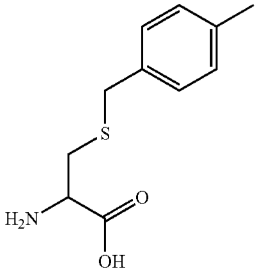 |
-continued
| Unnatural Alpha-Amino Acids | |
|---|---|
| Abbreviation | Structure |
| hSer(Bzl) | 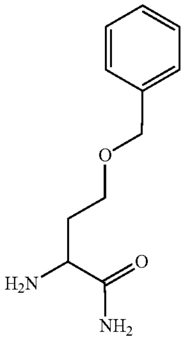 [SMILES: NC(=O)C(N)CCOCc1ccccc1] |
| Cys(4-MeOBzl) | 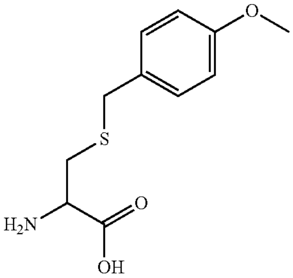 [SMILES: COc1ccc(CSCC(N)C(=O)O)cc1] |
| Thr(Bzl) | 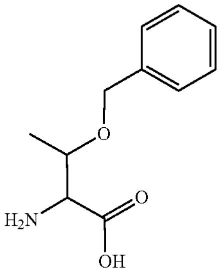 |
| Tyr(Bzl) | 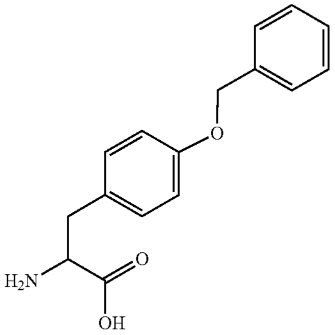 [SMILES: NC(Cc1ccc(OCc2ccccc2)cc1)C(=O)O] |
| Cys(Bzl) | 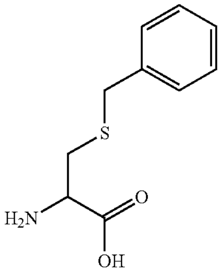 [SMILES: NC(CSCc1ccccc1)C(=O)O] |

-continued
| Unnatural Alpha-Amino Acids | |
|---|---|
| Abbreviation | Structure |
| Dht | 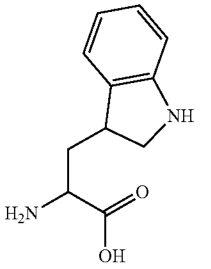 [SMILES: NC(CC1CNc2ccccc21)C(=O)O] |
| Tyr(Me) | 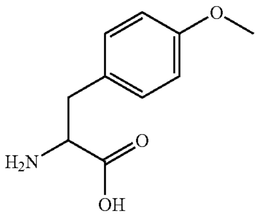 |
| Trp(Me) | 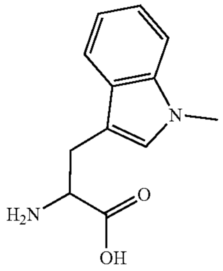 [SMILES: Cn1cc(CC(N)C(=O)O)c2ccccc21] |
| hTyr(Me) | 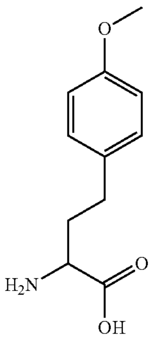 |
| Abu(Bth) | 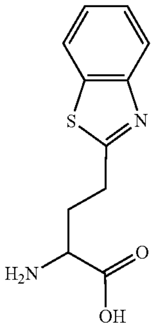 [SMILES: NC(CCc1nc2ccccc2s1)C(=O)O] |
-continued
| Unnatural Alpha-Amino Acids | |
|---|---|
| Abbreviation | Structure |
| Tyr(2,6-Cl-Bzl) | 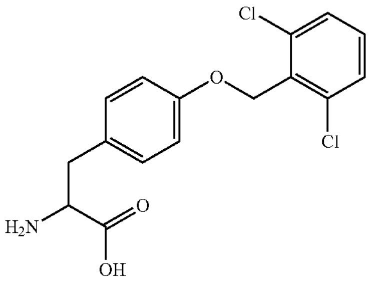 [SMILES: NC(Cc1ccc(OCc2c(Cl)cccc2Cl)cc1)C(=O)O] |
| Bip | 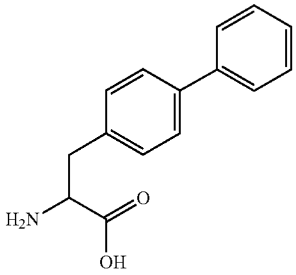 [SMILES: NC(Cc1ccc(-c2ccccc2)cc1)C(=O)O] |
| Bpa | 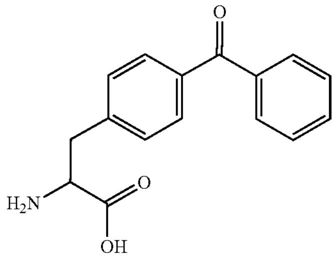 [SMILES: NC(Cc1ccc(C(=O)c2ccccc2)cc1)C(=O)O] |
| hSer | 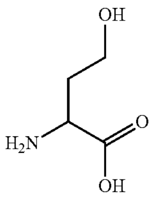 |
| 1-Nal | 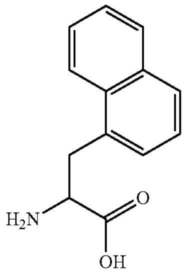 [SMILES: NC(Cc1cccc2ccccc12)C(=O)O] |
| Hnv | 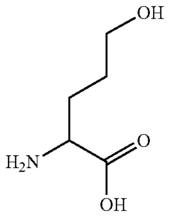 |

-continued
Unnatural Alpha-Amino Acids
| Abbreviation | Structure |
| --- | --- |
| 2-Nal | 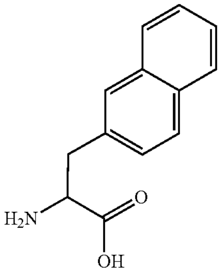 [SMILES: NC(Cc1ccc2ccccc2c1)C(=O)O] |
| Met($O_2$) | 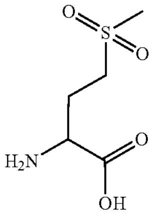 |
| Abu | 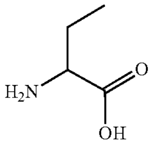 |
| AC5C | 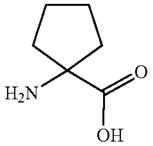 |
| Nva | 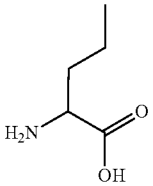 |
| Chg | 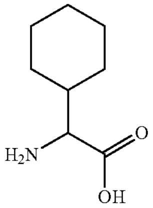 |
| 2-Aoc | 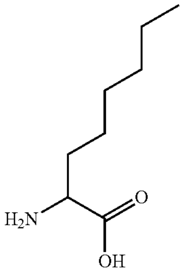 |
-continued
Unnatural Alpha-Amino Acids
| Abbreviation | Structure |
| --- | --- |
| Tic | 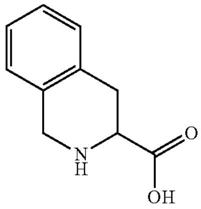 [SMILES: O=C(O)C1Cc2ccccc2CN1] |
| Tle | 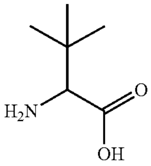 |
| AllyGly | 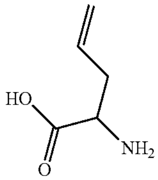 |
| 4-$NO_2$-3-F-Phe | 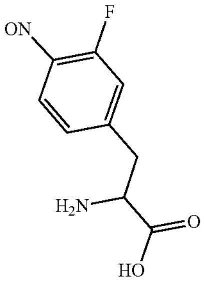 |
| Igl | 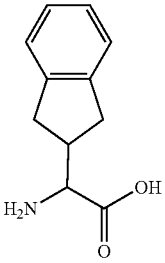 [SMILES: NC(C(=O)O)C1Cc2ccccc2C1] |
| DAB | 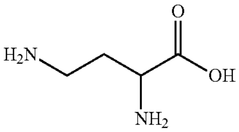 |
| L-Idc | 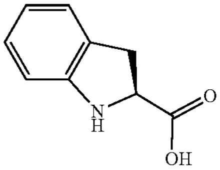 [SMILES: O=C(O)[C@@H]1Cc2ccccc2N1] |

-continued

| Unnatural Alpha-Amino Acids | |
|---|---|
| Abbreviation | Structure |
| Arg(Z)2 | 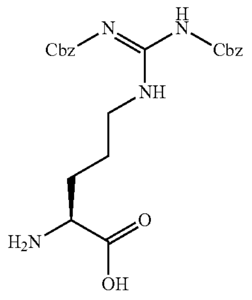 [SMILES: N[C@@H](CCCN/C(=N\C(=O)OCc1ccccc1)NC(=O)OCc1ccccc1)C(=O)O] |
| hAbu | 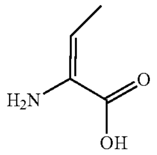 |

Unless otherwise indicated, the alkyl, alkenyl, and alkynyl groups described herein preferably contains from 1 to 20 carbon atoms in the principal chain. They may be straight or branched chain or cyclic (e.g., cycloalkyls). Alkenyl and alkenylene groups can contain saturated or unsaturated carbon chains so long as at least one carbon-carbon double bond is present. Alkynyl and alkynylene groups can contain saturated or unsaturated carbon chains so long as at least one carbon-carbon triple bond is present. Unless otherwise indicated, the alkoxy groups described herein contain saturated or unsaturated, branched or unbranched carbon chains having from 1 to 20 carbon atoms in the principal chain.

Unless otherwise indicated herein, the term "aryl" refers to monocyclic, bicyclic or tricyclic aromatic groups containing from 6 to 14 ring carbon atoms and including, for example, phenyl. The term "heteroaryl" refers to monocyclic, bicyclic or tricyclic aromatic groups having 5 to 14 ring atoms and containing carbon atoms and at least 1, 2 or 3 oxygen, nitrogen or sulfur heteroatoms. Unless otherwise indicated herein, the terms "aralkyl" or "arylalkyl" refer to a moiety of the formula $—(CH_2)q$-Y, wherein q is an integer from 1, 2, 3, 4, 5, or 6, and "Y" is a monocyclic, bicyclic or tricyclic aromatic groups containing from 6 to 14 ring carbon atoms and including, for example, phenyl or naphthyl. Various substituted groups referred to herein can each be substituted by, for example, 1, 2, or 3 substituents independently selected from, for example, halogen, —OH, —CN, —NO, $—NH_2$, alkyl, alkoxy, or $—CF_3$.

Methods of Use

Any of the compounds described herein are useful for inhibiting one or more trypsin-like S1 serine proteases. In particular, compounds of Formulas (I), (IIA)-(IIH), and (IIIA)-(IIIC) are useful for inhibiting one or more of matriptase, hepsin, and/or HGFA. Accordingly, the present invention is also directed to a method of inhibiting a trypsin-like S1 serine protease (e.g., matriptase, hepsin, KLK5, TMPRSS2 and/or HGFA) comprising administering to a subject in need thereof a pharmaceutical composition comprising a therapeutically effective amount of at least one compound of Formula (I), (IIA)-(IIH), or (IIIA)-(IIIC) as described herein. In certain, embodiments the compounds are highly selective for one of matriptase, hepsin, or HGFA.

As noted, trypsin-like S1 serine proteases like matriptase, hepsin, HGFA, KLK5, and TMPRSS2 are involved in various cancerous disease conditions. Thus, the present invention is directed to various methods of using the inhibitor compounds to treat cancer in a subject (e.g., a human). One method includes inhibiting HGF/MET oncogenic signaling by administering to a subject in need thereof a pharmaceutical composition comprising a therapeutically effective amount of at least one compound of Formula (I), (IIA)-(IIH), or (IIIA)-(IIIC) as described herein. Another method includes inhibiting MSP/RON oncogene signaling by administering to a subject in need thereof a pharmaceutical composition comprising a therapeutically effective amount of at least one compound of Formula (I), (IIA)-(IIH), or (IIIA)-(IIIC) as described herein. Yet another method including reversing resistance to a kinase inhibitor by blocking HGF and/or MPS production and/or activation by administering to a subject in need thereof a pharmaceutical composition comprising a therapeutically effective amount of at least one compound of Formula (I), (IIA)-(IIH), or (IIIA)-(IIIC) as described herein.

Further methods include overcoming and preventing resistance to a DNA-damaging agent including gemcitabine comprising administering to a subject in need thereof a pharmaceutical composition comprising a therapeutically effective amount of at least one compound of Formula (I), (IIA)-(IIH), or (IIIA)-(IIIC) as described herein. Still other methods include overcoming and preventing resistance to an immunotherapy agent including a PD-1 antagonist comprising administering to a subject in need thereof a pharmaceutical composition comprising a therapeutically effective amount of at least one compound of Formula (I), (IIA)-(IIH), or (IIIA)-(IIIC) as described herein.

Another method includes inhibiting carcinoma progression and metastasis comprising administering to the subject in need thereof a pharmaceutical composition comprising a therapeutically effective amount of at least one compound of Formula (I), (IIA)-(IIH), or (IIIA)-(IIIC) as described herein.

A further method includes treating a malignancy, a premalignant condition, or cancer in a subject comprising administering to the subject in need thereof a pharmaceutical composition comprising a therapeutically effective amount of at least one compound of Formula (I), (IIA)-(IIH), or (IIIA)-(IIIC) as described herein. The cancer can be selected from the group consisting of breast, ovarian, prostate, endometrial, colon, pancreatic, head and neck, gastric, renal, brain, liver, bladder, kidney, lung, esophageal, leukemia, multiple myeloma, lymphoma, and melanoma. For example, the malignancy and the pre-malignant condition can be a condition of the breast, lung, colon, and/or pancreas. Also, the pre-malignant condition can be selected from the group consisting of a typical ductal hyperplasia of the breast, actinic keratosis, leukoplakia, Barrett's epithelium (columnar metaplasia) of the esophagus, ulcerative colitis, adenomatous colorectal polyps, erythroplasia of Queyrat, Bowen's disease, bowenoid papulosis, vulvar intraepthelial neoplasia, and dysplastic changes to the cervix. In various methods, the cancer can also be metastasized.

Methods of Inhibiting TMPRSS2 and KLK5

As noted, TMPRSS2 is a type II transmembrane serine protease (TTSP) is essential for host-cell viral entry and replication of SARS-CoV-2 2-4, SARS-CoV and other coronaviruses such as MERS-CoV, and influenza. SARS-CoV-2 cell entry involves binding to the host cell receptor ACE2 which requires proteolytic priming of the Spike protein by TMPRSS2, such that TMPRSS2 inhibitors offer promise as effective therapeutics for COVID-19.

Accordingly, methods of the present invention include methods of treating or preventing a viral infection in a subject comprising administering to the subject in need thereof a pharmaceutical composition comprising a therapeutically effective amount of at least one compound of (a) Formula (I), (IIA)-(IIH), or (IIIA)-(IIIC); (b) a polypeptide-based inhibitor; and/or (c) a benzamidine-based inhibitor. In various embodiments, the viral infection is caused by a coronavirus. For example, in some embodiments, the coronavirus is selected from the group consisting of SARS-CoV, SARS-CoV-2, and MERS-CoV. In further embodiments, the viral infection is caused by an influenza virus.

Other embodiments relate to methods of inhibiting TMPRSS2 in an organism comprising administering to the organism a composition comprising an effective amount of at least one compound of (a) Formula (I), (IIA)-(IIH), or (IIIA)-(IIIC); (b) a polypeptide-based inhibitor; and/or (c) a benzamidine-based inhibitor.

In some embodiments, the compound for inhibiting TMPRSS2 comprises at least one of:

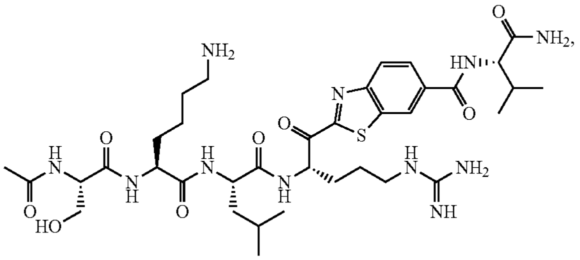

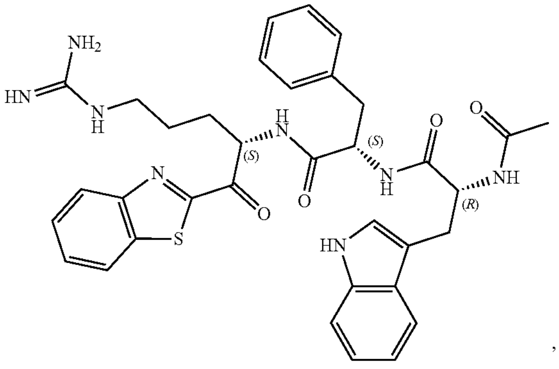

,

-continued

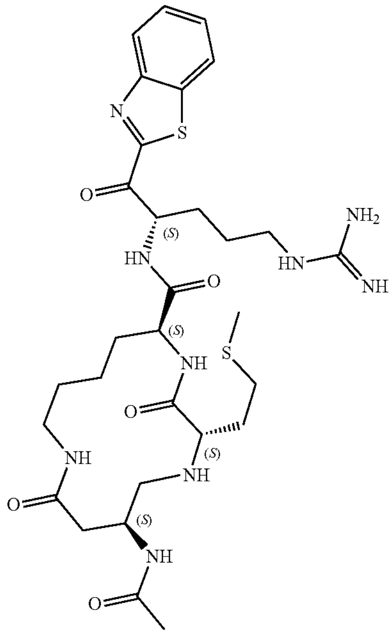

,

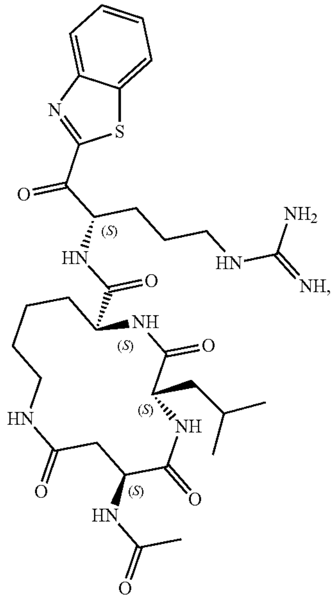

-continued
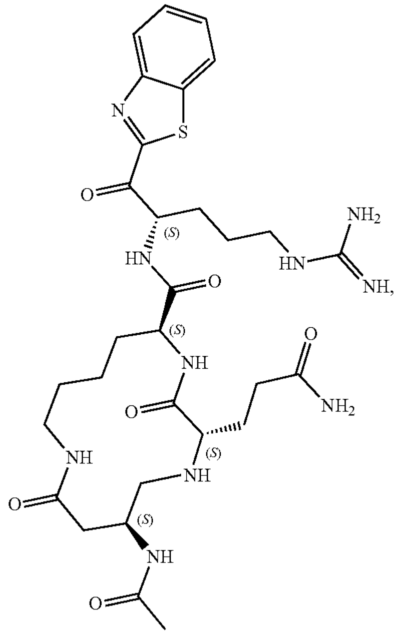
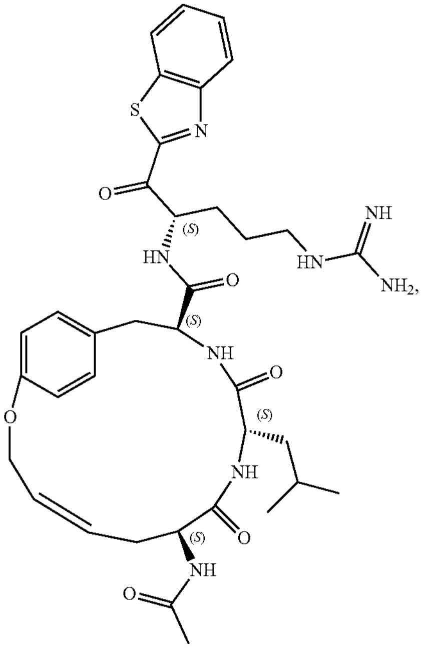
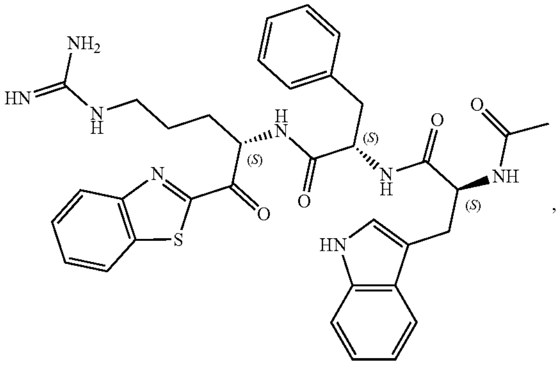
,
-continued
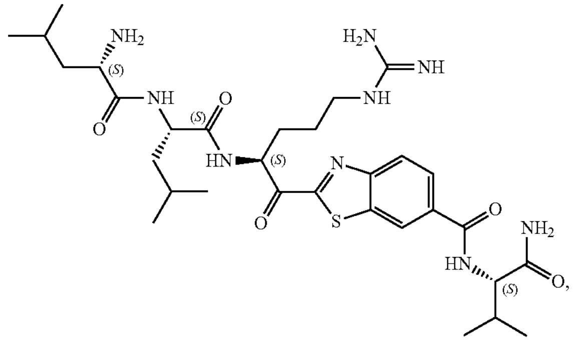
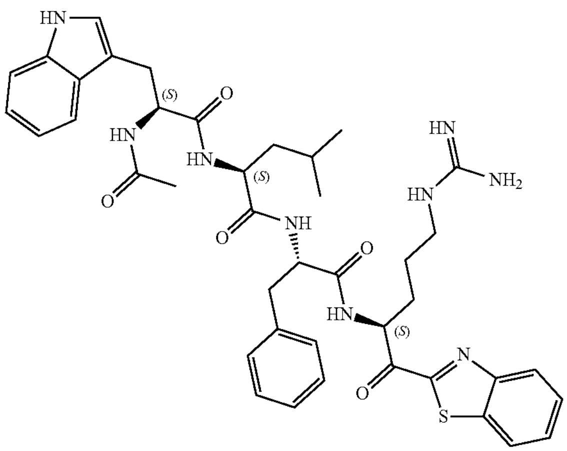
,
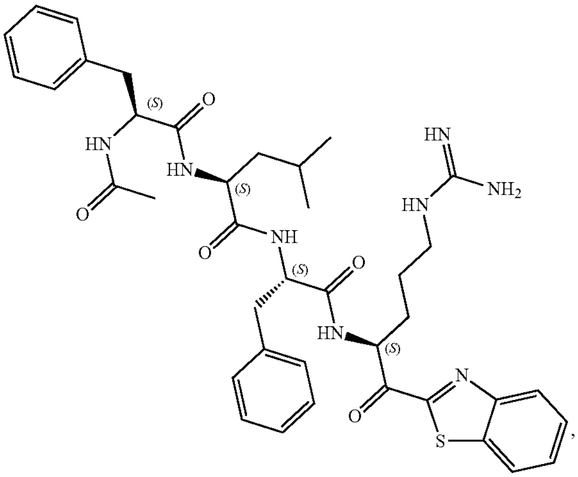
,
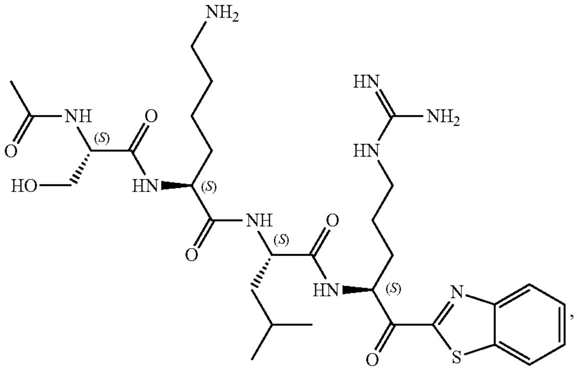
, -continued
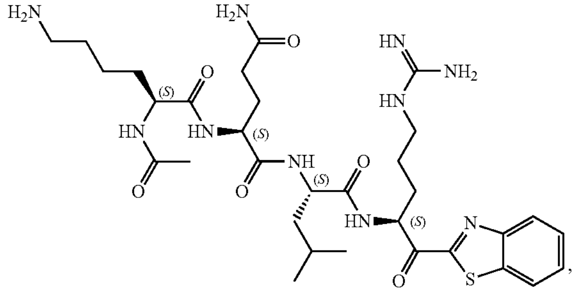
,
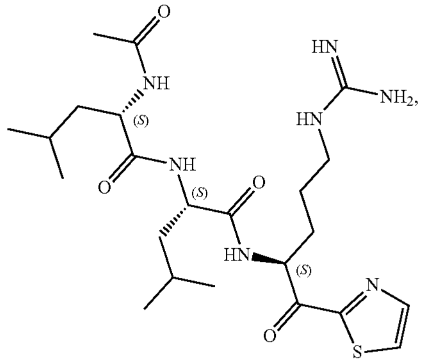
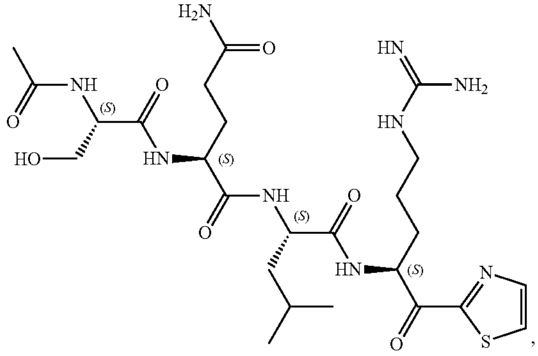
,
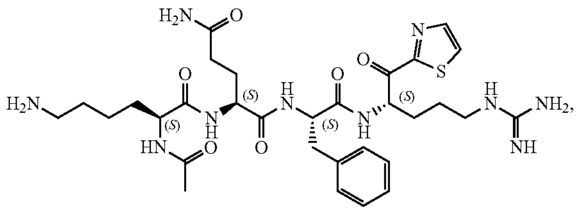
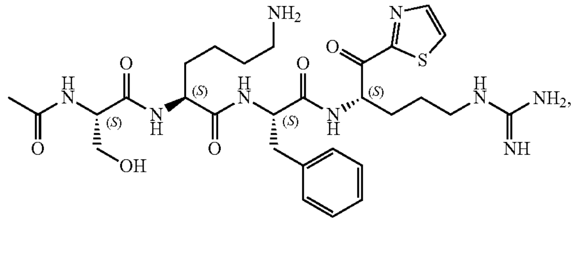
-continued
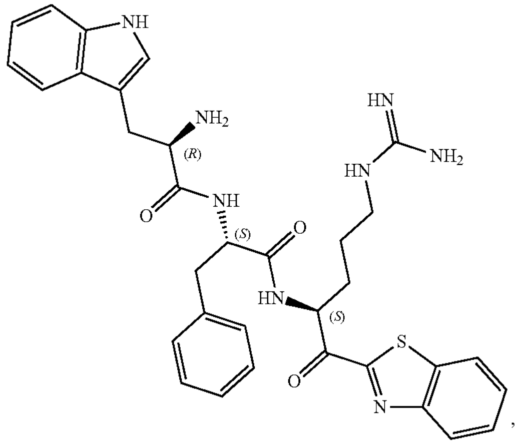
,
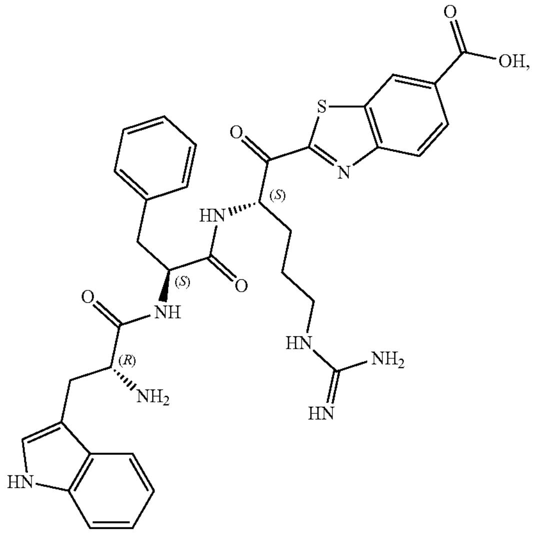
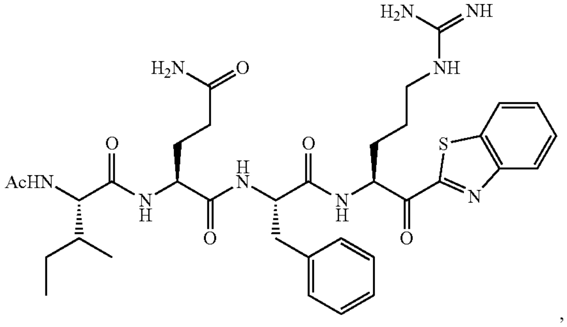
,
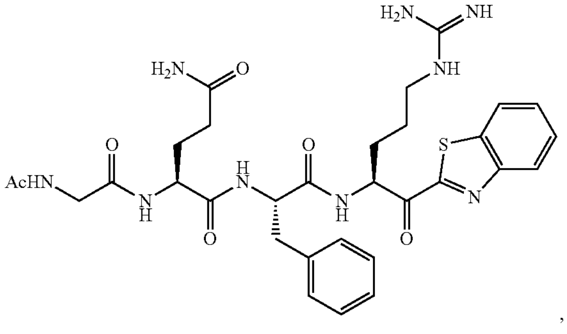
, -continued

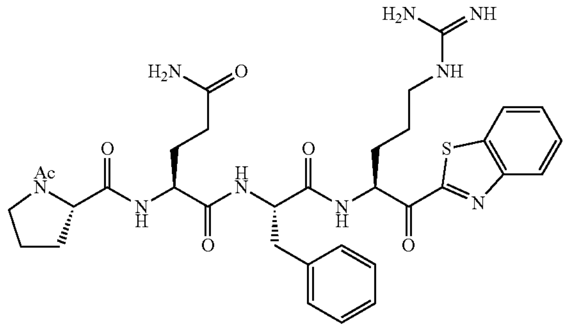

,

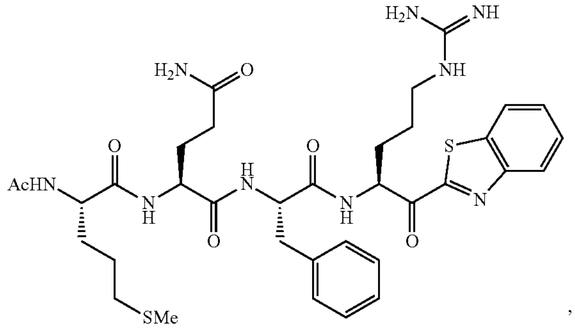

,

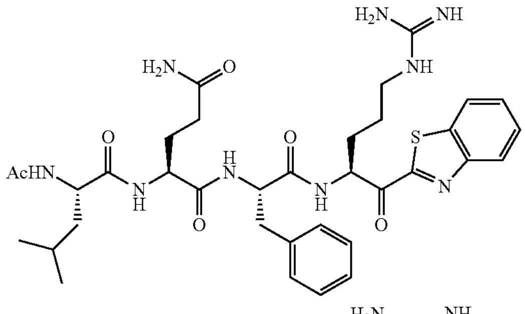

, or

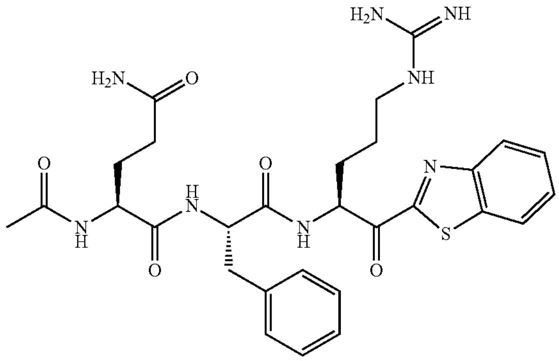

.

KLK5 is a serine protease heavily involved in epidermal cell shedding (desquamation). It has also been linked to carcinogenic properties in various cancers (e.g., breast and ovarian cancer). Accordingly, various embodiments relate to methods of treating or preventing a condition at least in part associated with upregulated KLK5 in a subject comprising administering to the subject in need thereof a pharmaceutical composition comprising a therapeutically effective amount of at least one compound of (a) (I), (IIA)-(IIH), or (IIIA)-(IIIC); (b) a polypeptide-based inhibitor; and/or (c) a benzamidine-based inhibitor. In some embodiments, the condition at least in part associated with upregulated KLK5 comprises cancer (e.g., ovarian and/or breast cancer). In other embodiments, the condition comprises an allergic condition (e.g., eosinophilic esophagitis). In various embodiments, the condition comprises a skin disorder (e.g., Netherton syndrome).

Other embodiments relate to methods of inhibiting KLK5 in an organism comprising administering to the organism a composition comprising an effective amount of at least one compound of (a) Formula (I), (IIA)-(IIH), or (IIIA)-(IIIC); (b) a polypeptide-based inhibitor; and/or (c) a benzamidine-based inhibitor.

The polypeptide-based inhibitors and a benzamidine-based inhibitors useful in these methods include those described in U.S. Patent Application Publication 2018/0066015, which is hereby incorporated by reference herein.

For example, various polypeptide-based inhibitors described in US2018/0066015 include compounds of Formula (IV):

$$Y—(P_5)_b—(P_4)_n—(P_3)_m—P_2—P_1—Z \qquad (IV)$$

wherein n is 0 or 1;

m is 0 or 1;

b is 0 or 1;

Y is H, acetyl, tert-butyloxycarbonyl, benzyloxymethyl acetyl, carboxybenzyl, FMOC, benzyl, —C(O)$R_9$, —SOO$R_9$, —COO$R_9$, —C(O)NH$R_9$, —$(CH_2)_x$aryl-$R_9$, heteroaryl-$R_9$, -cycloalkyl-$R_9$, or a fluorophore;

x is 0, 1, or 2;

$R_9$ is $C_1$ to $C_{12}$ alkyl, cycloalkyl, alkylaryl, or aryl;

$P_1$ is a residue of an amino acid selected from the group consisting of Arg, D-Arg, Lys, substituted Lys, and an alpha-amino acid of the following:

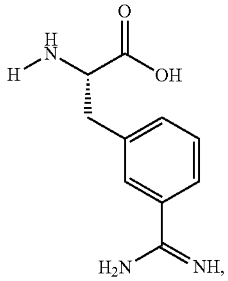

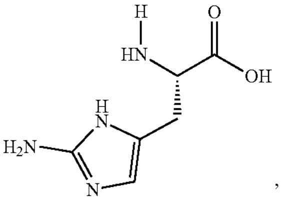

,

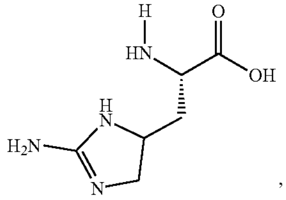

,

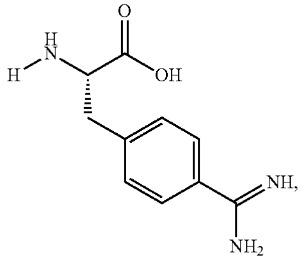

-continued

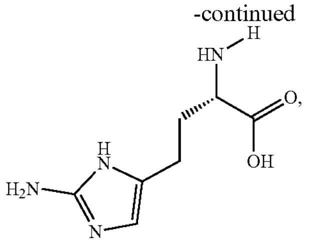

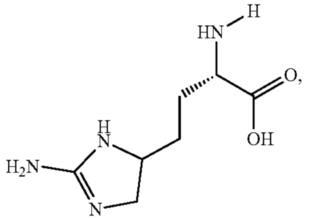

or an unnatural amino acid residue;

$P_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orn, L-Cha, Nle, hTyr, Nva, Orn, Cha, and an unnatural amino acid residue;

$P_3$ is a residue of an amino acid selected from the group consisting Asp, Glu, Arg, Lys, Met, Trp, Leu, Gln, Phe, Tyr, His, hArg, D-Trp, L-Orn, D-Gln, L-Met(O), L-Nle (OBzl), Agp, hCha, hTyr, hPhe, D-Arg, Nle(OBzl), Orn, Met(O), and an unnatural amino acid residue;

$P_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg($NO_2$), L-Nle(OBzl), L-DAB(Z) and an unnatural amino acid residue;

$P_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, Asn, and an unnatural amino acid residue; and Z is Val, Ser, Lys, Ala, Gly, Trp, Tyr, Phe, Arg, Thr, Leu, Ile, Met, His, Nle, Phg, Pro, Gln, Asn, —$CH_2Cl$, or a substituted or unsubstituted ring substituent selected from the group consisting of:

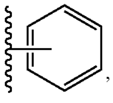, 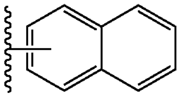, 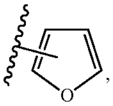,

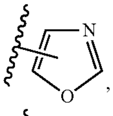, 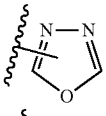, 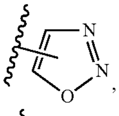, 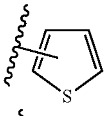,

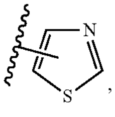, 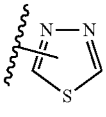, 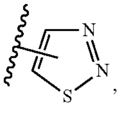, 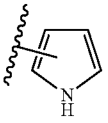,

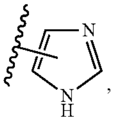, 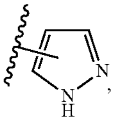, 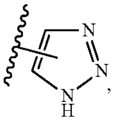, 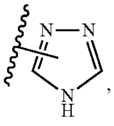,

-continued

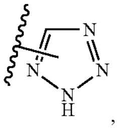, 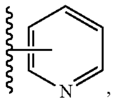, 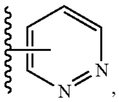, 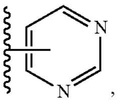,

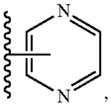, 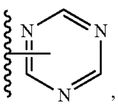, 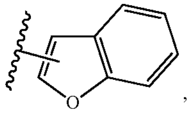,

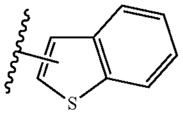, 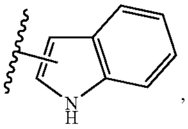,

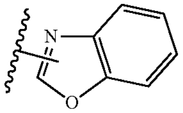, 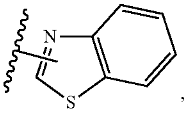,

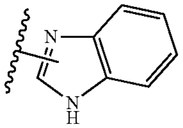, 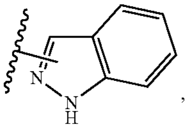,

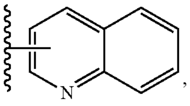, 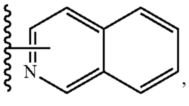,

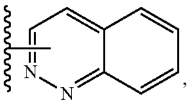, 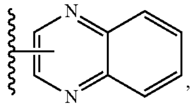,

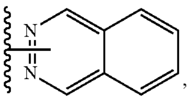, and 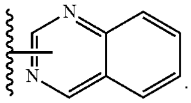.

As understood, when two or more amino acids combine to form a peptide (e.g., of Formula (IV)), the elements of water are removed, and what remains of each amino acid is called an amino-acid residue.

In various embodiments, the compound of Formula (IV) include one or more of the following:

Y is H, acetyl, tert-butyloxycarbonyl, benzyloxymethyl acetyl, carboxybenzyl, FMOC, benzyl, —C(O)$R_9$, —SOOR$_9$, —COOR$_9$, —C(O)NHR$_9$, —$(CH_2)_x$aryl-$R_9$, heteroaryl-$R_9$, -cycloalkyl-$R_9$, or a fluorophore;

x is 0, 1, or 2;

$R_9$ is $C_1$ to $C_{12}$ alkyl, cycloalkyl, alkylaryl, or aryl;

$P_1$ is a residue of an amino acid selected from the group consisting Arg, D-Arg, Lys, and substituted Lys;

$P_2$ is a residue of an amino acid selected from the group consisting Leu, Phe, Met, Thr, Val, Tyr, Trp, Ser, Pro, His, Glu, Gln, Asp, Arg, Lys, Ile, Ala, Gly, Asn, hLeu, NptGly, L-Orn, L-Cha, Nle, hTyr, Nva, Orn, and Cha;

$P_3$ is a residue of an amino acid selected from the group consisting Asp, Glu, Arg, Lys, Met, Trp, Leu, Gln, Phe, Tyr, His, hArg, D-Trp, L-Orn, D-Gln, L-Met(O), L-Nle (OBzl), Agp, hCha, hTyr, hPhe, D-Arg, Nle(OBzl), Orn, and Met(O);

$P_4$ is a residue of an amino acid selected from the group consisting Arg, Lys, Met, Try, Trp, Ser, His, Phe, Thr, Asn, Pro, Gln, Asp, Glu, Chg, Idc, dhLeu, Agp, D-Ser, Agp, His(3-Bom), Lys(2-Cl—Z), L-Orn, L-Arg($NO_2$), L-Nle(OBzl), and L-DAB(Z);

$P_5$ is a residue of an amino acid selected from the group consisting Lys, Arg, Leu, Phe, Met, Thr, Val, Tyr, Trp, Ser, Pro, His, Glu, Gln, Asp, Ile, Ala, Gly, and Asn; and Z is Val, Ser, Lys, Ala, Gly, Trp, Tyr, Phe, Arg, Thr, Leu, Ile, Met, His, Nle, Phg, Pro, Gln, Asn, —$CH_2Cl$,

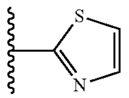
,
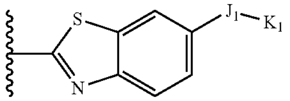
,
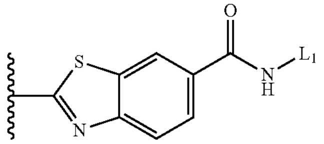
;

$J_1$ is C(O), $SO_2$, $CH_2$, or heterocyclo;

$K_1$ is a D- or L-amino acid, wherein the C-terminus is —COOH, —$C(O)NH_2$, —OH, —$OR_{10}$, —$NH_2$, —$NR_{11}R_{12}$, —H, or heterocyclo;

$R_{10}$ is $C_1$ to $C_{12}$ alkyl, cycloalkyl, alkylaryl, or aryl;

$R_{11}$ and $R_{12}$ are each independently H, $C_1$ to $C_{12}$ alkyl, cycloalkyl, alkylaryl, aryl, or heterocyclo; and Ru and $R_{12}$ together can form a ring; and/or $L_1$ is H, alkyl, cycloalkyl, alkylaryl, benzyl, substituted benzyl, 2- or 3- or 4-piperdinyl, 2- or 3- or 4-pyridinyl, alkyl, cycloalkyl, aryl, heterocyclo, or heteroaryl.

In various embodiments, in Formula (IV), $P_1$ is an amino acid residue of Arg; $P_2$ is an amino acid residue of Leu, Phe, Met, Tyr, Trp, hLeu, NptGly, Nle, hTyr, or Nva; $P_3$ is an amino acid residue of His, Gln, Arg, Lys, Leu, Phe, Trp, Tyr, hArg, D-Trp, Agp, hCha, hTyr, hPhe, or D-Arg; and/or $P_4$ is an amino acid residue of Thr, Asn, Ser, Arg, Lys, Phe, Trp, His(Bom), Agp, Lys(2-Cl—Z), dhLeu, Idc, or Chg.

In some embodiments, in Formula (IV), $P_1$ is an amino acid residue of Arg or Lys; $P_2$ is an amino acid residue of Phe, Ala, Arg, Asn, Gln, Glu, Gly, His, Leu, Lys, Met, Pro, or Ser; $P_3$ is an amino acid residue of Arg, Leu, Trp, Phe, His, Gln, Lys, D-Trp, or D-Arg; and/or $P_4$ is an amino acid residue of Pro, Phe, Thr, Asn, Trp, Gln, Ser, Lys, Arg, or His(Bom).

In certain embodiments, $P_1$ is an amino acid residue of Arg; $P_2$ is an amino acid residue of Pro, Arg, Asn, Asp, Gln, Ile, Leu, Lys, Phe, Thr, Trp, Tyr, Orn, Cha, Nle, or Nva; $P_3$ is an amino acid residue of Leu, Trp, Phe, His, Gln, Lys, Arg, D-Gln, Agp, Nle (OBzl), Orn, Met(O), D-Trp, or D-Arg; and/or $P_4$ is an amino acid residue of Pro, Phe, Thr, Asn, Trp, Gln, Ser, Arg, Lys, Agp, DAB(Z), Nle (OBzl), Orn, Arg ($NO_2$), or His(Bom).

In some embodiments, m is 1, n is 1, and $P_4$—$P_3$-$P_2$—$P_1$ of Formula (IV) is a tetrapeptide selected from the group consisting of SEQ ID NO 1, SEQ ID NO 2, SEQ ID NO 3, SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, and mixtures thereof.

In some embodiments, $P_3$ can form a bond with $P_5$ and form a cyclic peptide. In other embodiments, $P_2$ can form a bond with $P_4$ and form a cyclic peptide.

In certain embodiments, $P_2$, $P_3$, $P_4$, and $P_5$ are independently selected from the group consisting of Asp, Glu, Lys, Tyr, 4-$NO_2$-3-F-Phe, or allyGly.

In some embodiments, in Formula (IV), Z is

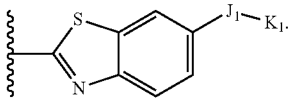

In other embodiments, Z is

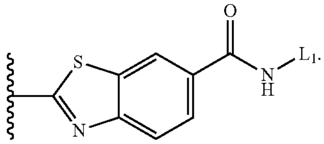

In some embodiments, $L_1$ is a substituted benzyl group.

In various embodiments, Y is acetyl; $J_1$ is C(O); and/or $K_1$ is amino acid residue of Val.

In certain embodiments, Y is a fluorophore, biotin, or a reporter tag. For example, the fluorophore can be selected from the group consisting of Cy3, Cy3.5, Cy5, Cy5.5, Cy7, and Cy7.5.

In some embodiments, the compound of Formula (IV) is a tetrapeptide selected from the group consisting of:

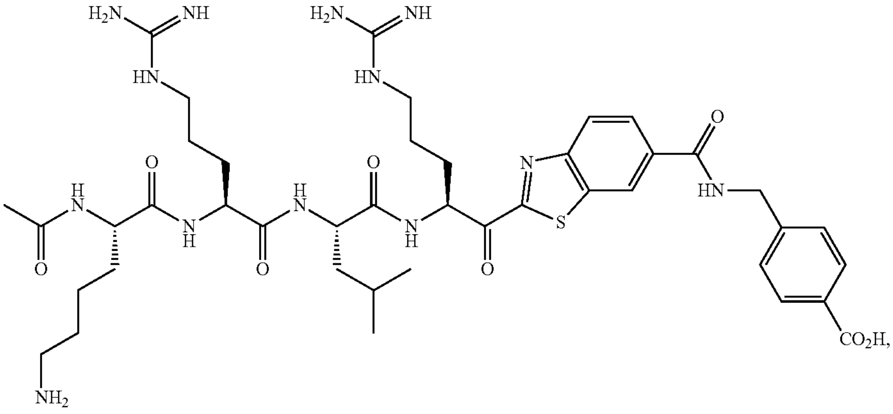
,

-continued
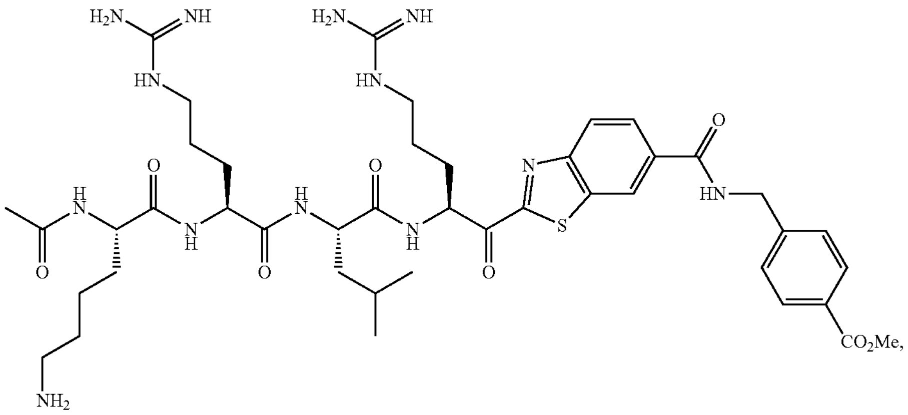
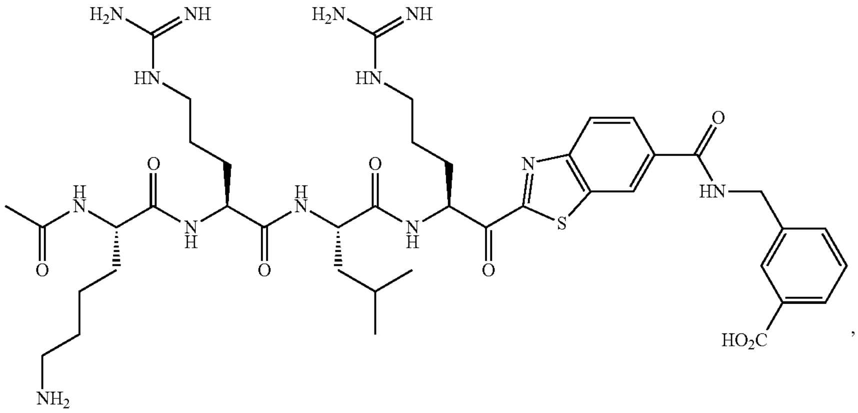
,
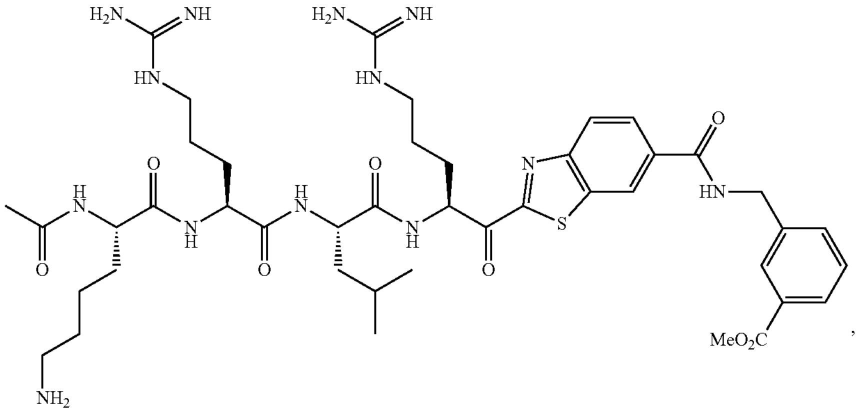
,
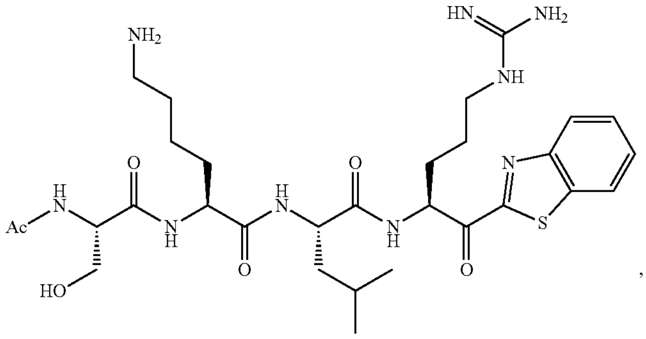
,

-continued
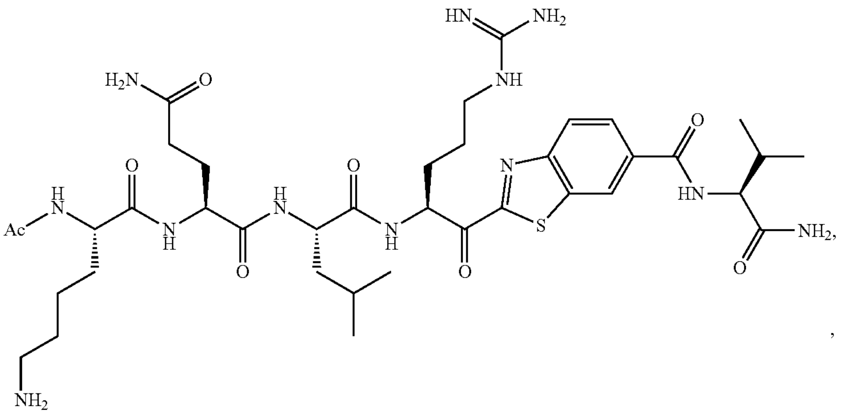
,
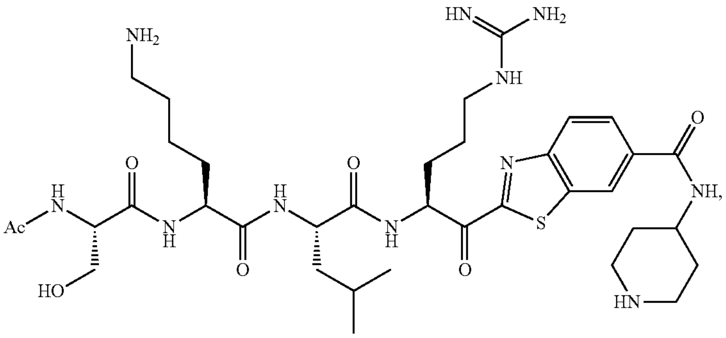
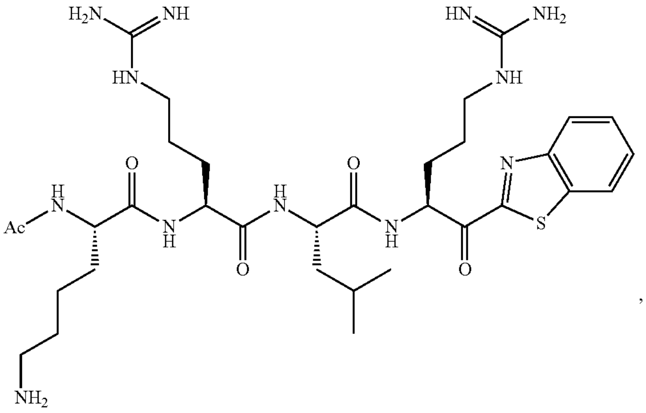
,
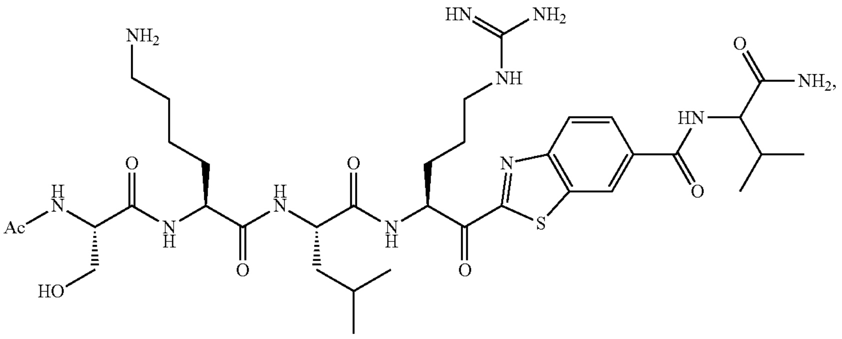

-continued
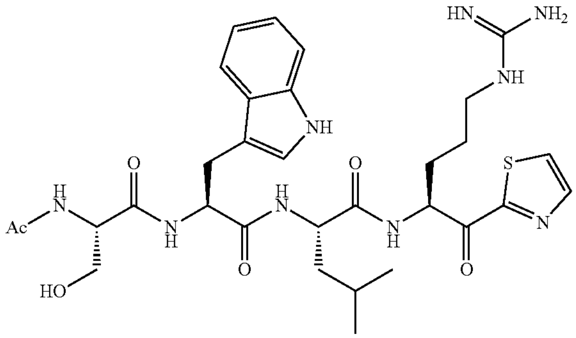
,
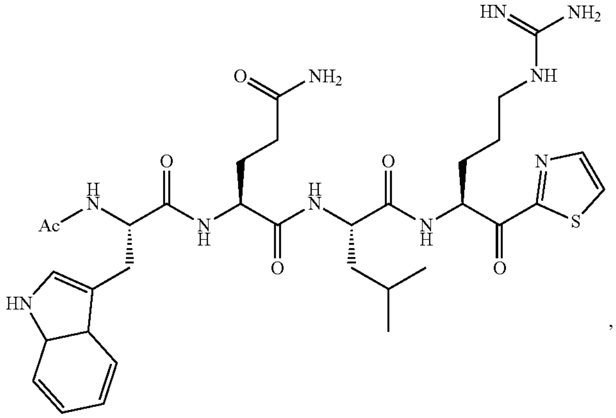
,
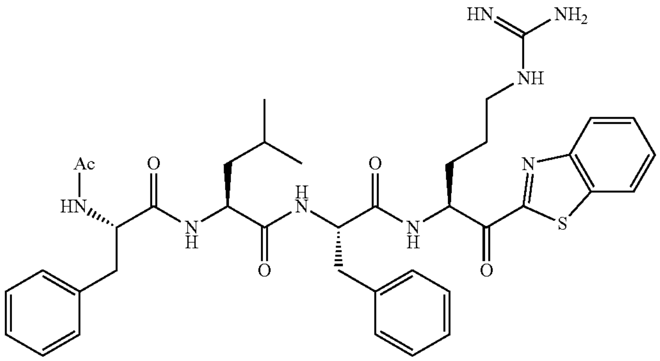
,
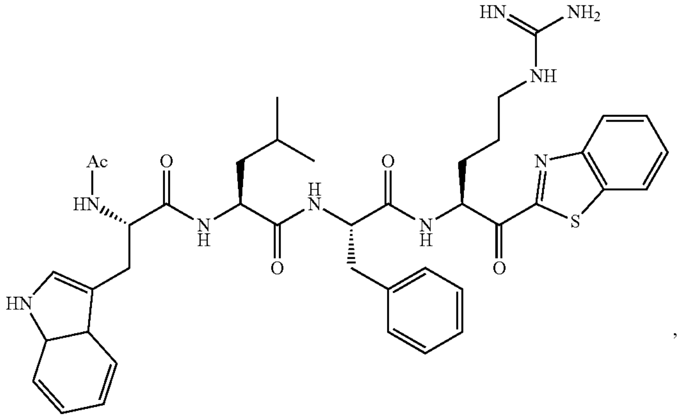
,

-continued
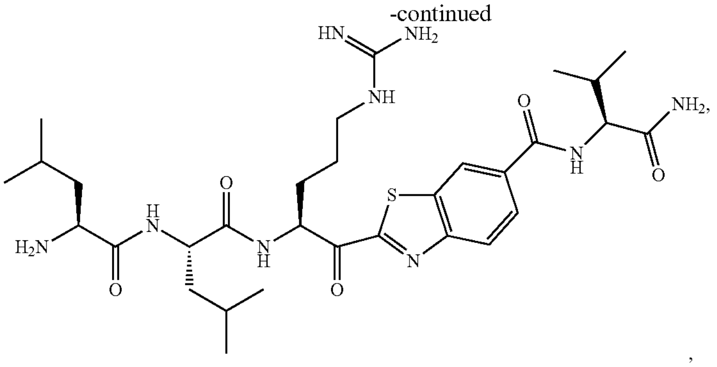
,
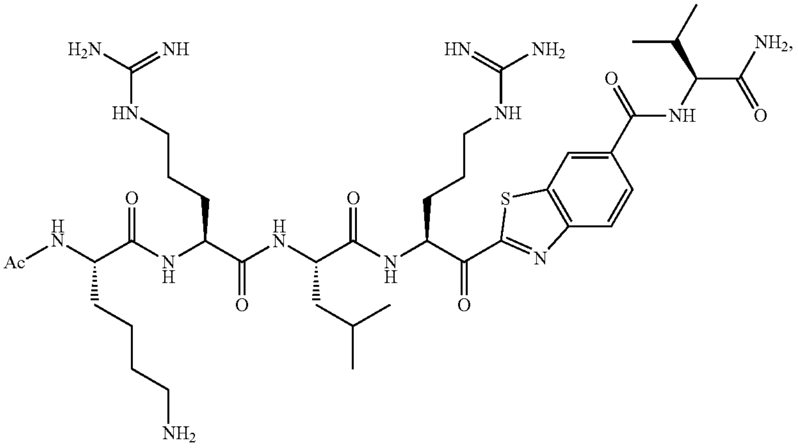
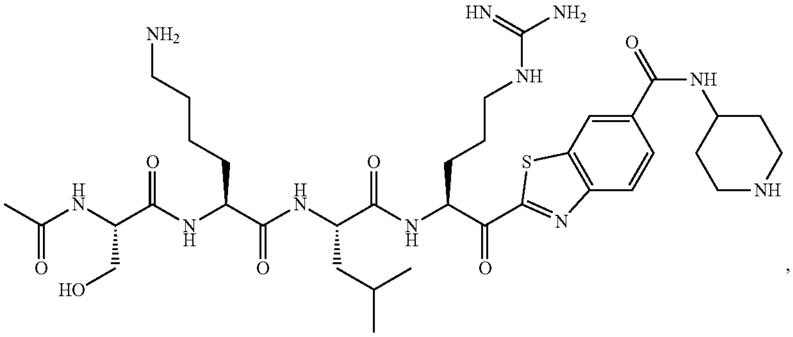
, and
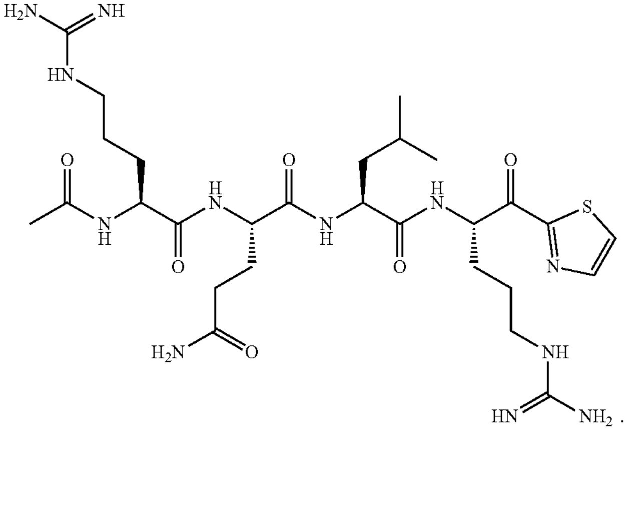 [SMILES: CC(=O)N[C@@H](CCCNC(=N)N)C(=O)N[C@@H](CCC(N)=O)C(=O)N[C@@H](CC(C)C)C(=O)N[C@@H](CCCNC(=N)N)C(=O)c1nccs1]
.

In some embodiments, the compound of Formula (IV) is a tripeptide selected from the group consisting of:
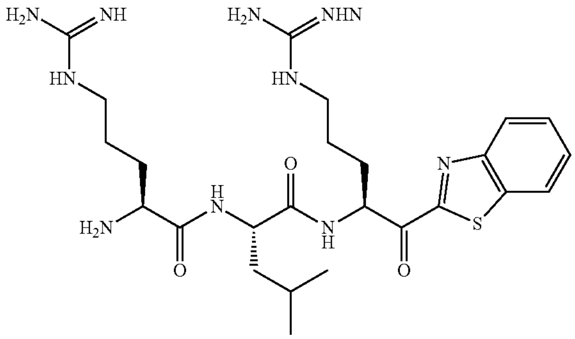
,
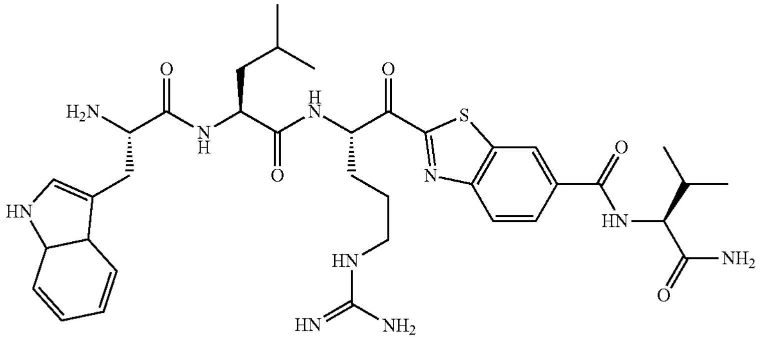
, and
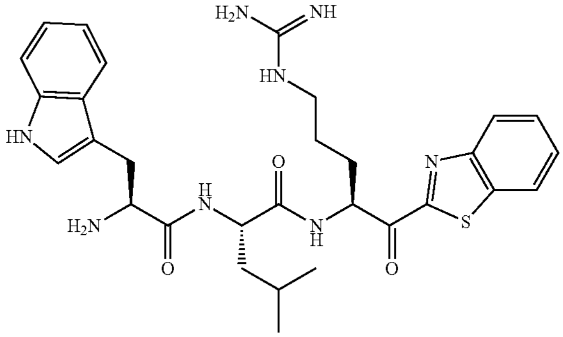
.
In some embodiments, the compound of Formula (IV) is a dipeptide selected from the group consisting of:
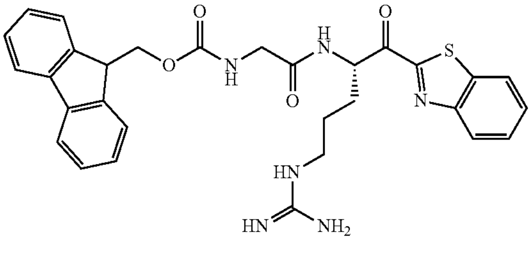
, and
-continued
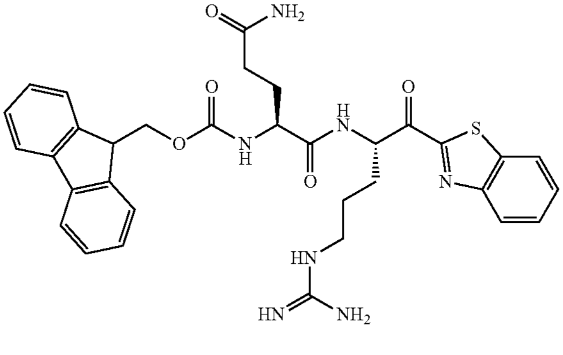
, In some embodiments, the compound of Formula (IV) is a cyclic peptide of the following structure:

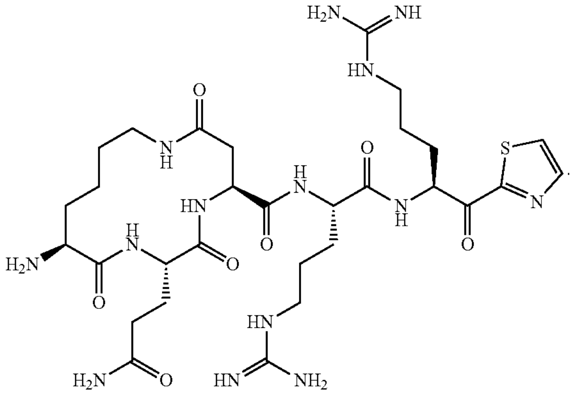 [SMILES: N=C(N)NCCC[C@H](NC(=O)[C@@H]1CC(=O)NCCCC[C@H](N)C(=O)N[C@@H](CCC(N)=O)C(=O)N1)C(=O)N[C@@H](CCCNC(=N)N)C(=O)c1nccs1]

In various embodiments, Y is a fluorophore. The fluorophore can be selected from the group consisting of Cy3, Cy3.5, Cy5, Cy5.5, Cy7, and Cy7.5.

In some embodiments, the compound of Formula (IV) is selected from the group consisting of:

Various benzamidine-based inhibitors described in US2018/0066015 include compounds of Formula (V), as a single stereoisomer or as a mixture thereof, or a salt thereof:

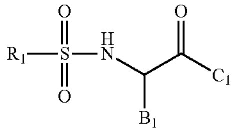

(V)

wherein $R_1$ is substituted or unsubstituted alkyl, substituted or unsubstituted aryl, or substituted or unsubstituted heteroaryl;

$B_1$ is selected from the group consisting of:

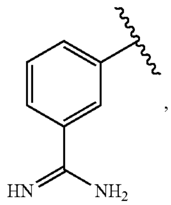

,

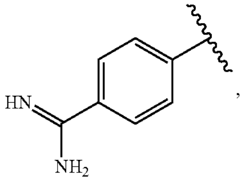

,

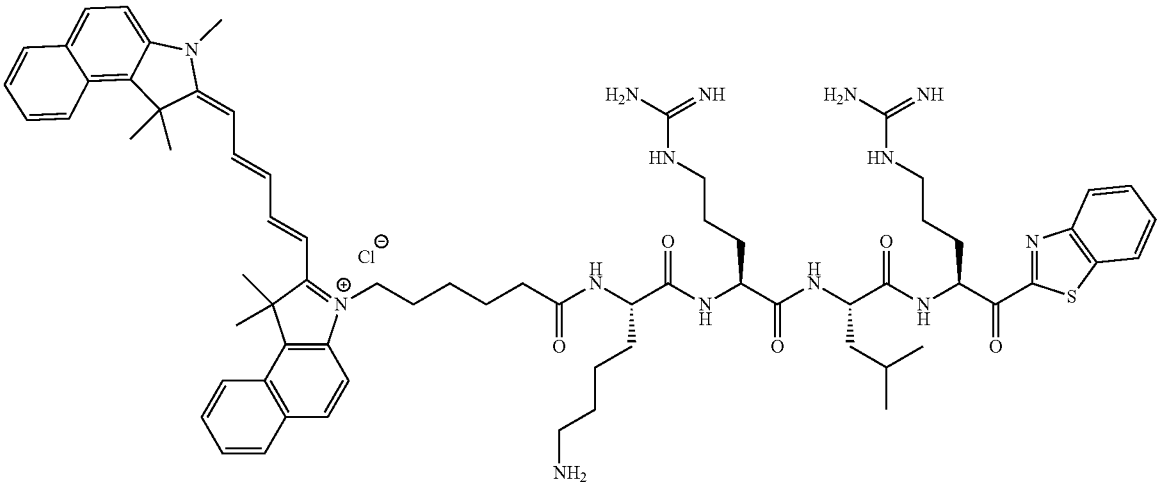

and

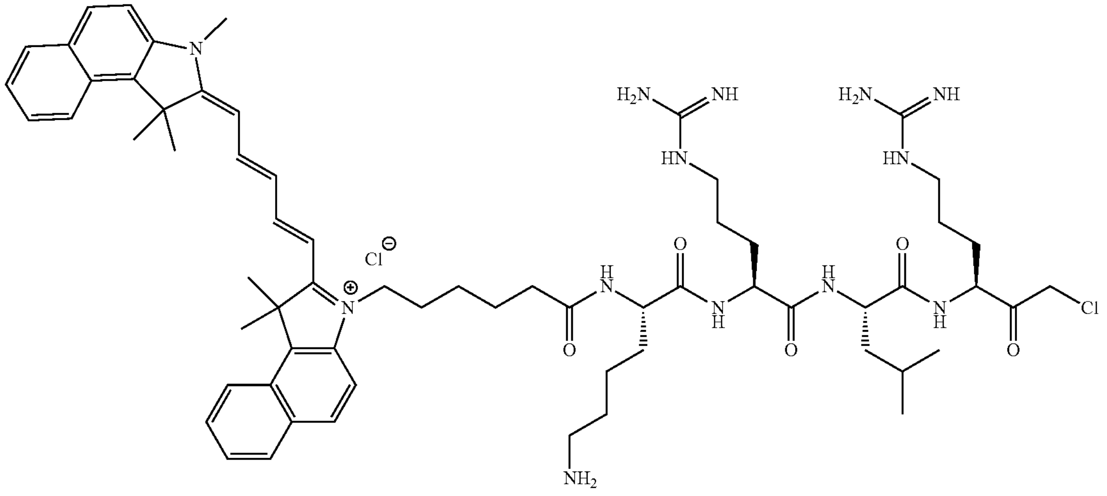

-continued

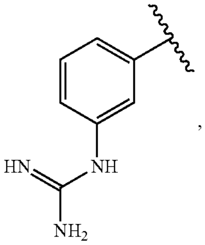,
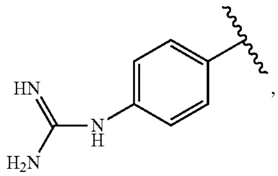,
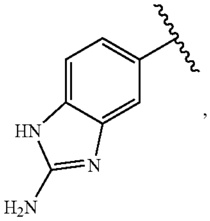,
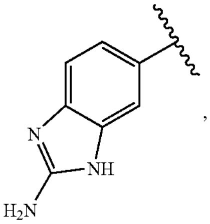,
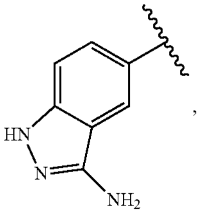,
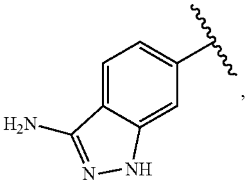,
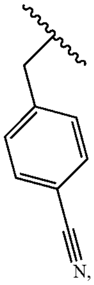 and
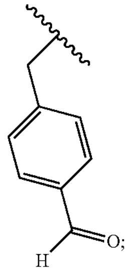;

$C_1$ is a group selected from the group consisting of:

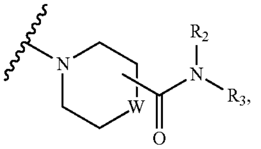
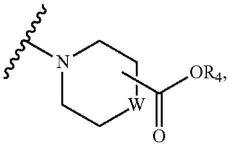
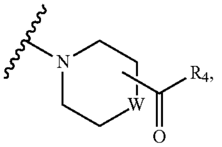
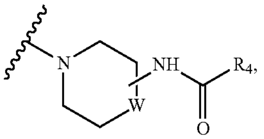
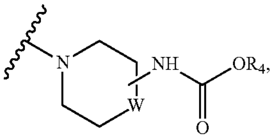
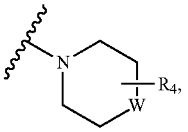
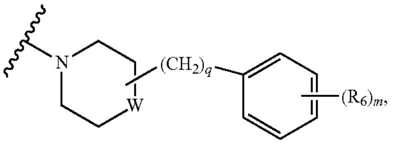

-continued

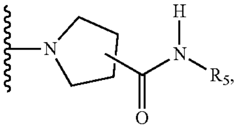
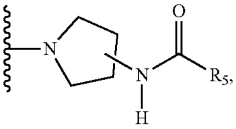
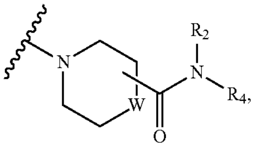
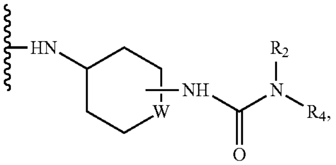
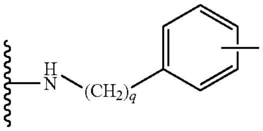 and
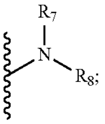;

W is CH, $CH_2$, N, or NH;

$R_2$, $R_3$, $R_4$, $R_5$, $R_6$, $R_7$, and $R_8$ are each independently hydrogen, substituted or unsubstituted alkyl or cycloalkyl, substituted or unsubstituted alkylaryl, substituted or unsubstituted heterocyclic ring, substituted or unsubstituted aryl or heteroaryl, with the proviso that when $R_2$ is methyl, then $R_3$ cannot also be methyl and vice versa; and m is 0 to 5.

In various embodiments, $R_1$ is substituted or unsubstituted $C_1$-$C_6$ alkyl, substituted or unsubstituted $C_3$-$C_6$ cycloalkyl, substituted or unsubstituted phenyl, substituted or unsubstituted naphthyl, or a substituted or unsubstituted nitrogen-containing aromatic ring. For example, the substituted $C_1$-$C_6$ alkyl, substituted $C_3$-$C_6$ cycloalkyl, substituted phenyl, substituted naphthyl, or substituted nitrogen-containing aromatic ring can comprise one or more substituents comprising halo, hydroxy, $C_1$-$C_6$ alkyl, $C_1$-$C_6$ alkoxy, halo-substituted $C_1$-$C_4$ alkyl, or amino. In certain embodiments, $R_1$ is an group selected from the group consisting of:

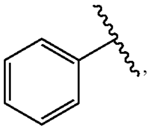,
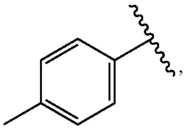,
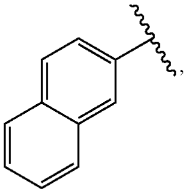,
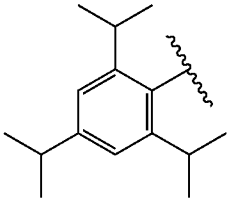,

-continued

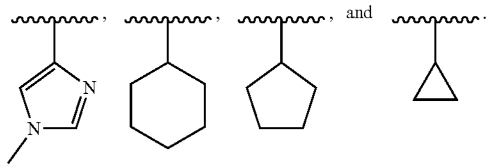

, , , and .

In some embodiments, $C_1$ is a group selected from the group consisting of:

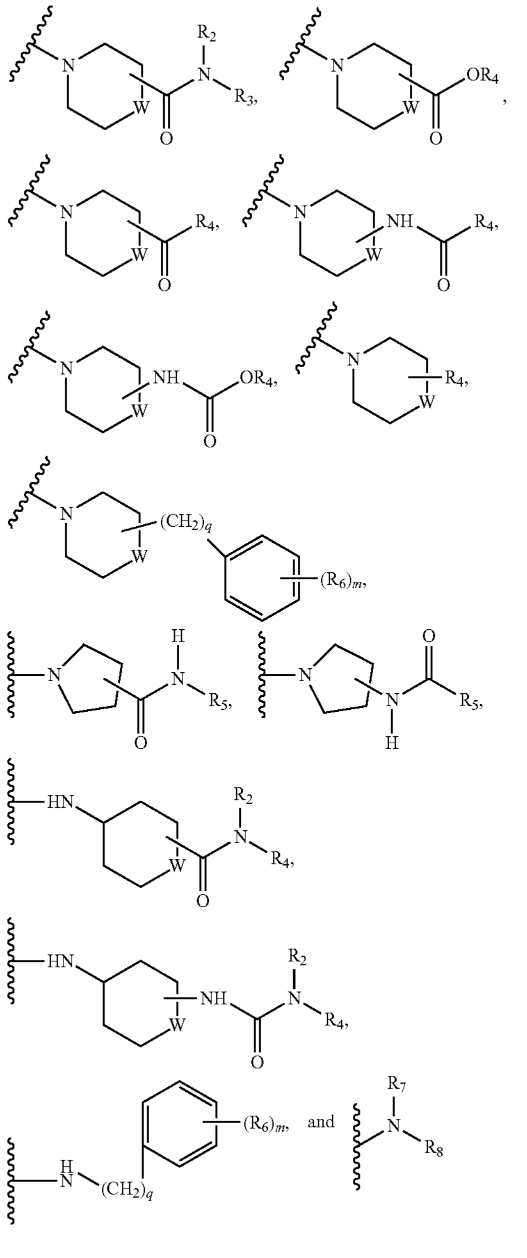

and

W is CH or N;

$R_2$, $R_3$, $R_4$, $R_5$, $R_6$, $R_7$, and $R_8$ are each independently hydrogen, substituted or unsubstituted alkyl or cycloalkyl, substituted or unsubstituted alkylaryl, substituted or unsubstituted heterocyclic ring, substituted or unsubstituted aryl or heteroaryl, with the proviso that when $R_2$ is methyl, then $R_3$ cannot also be methyl and vice versa; and m is 0 to 5, or a pharmaceutically acceptable salt thereof.

In some embodiments, $R_2$, $R_3$, $R_4$, $R_5$, $R_6$, $R_7$, and $R_8$ are each independently hydrogen, substituted or unsubstituted $C_1$-$C_{10}$ alkyl or cycloalkyl, substituted or unsubstituted heterocyclic ring, substituted or unsubstituted aryl, or substituted or unsubstituted heteroaryl. In particular embodiments, $R_2$ is hydrogen; $R_3$ is hydrogen, $C_1$-$C_6$ alkyl, benzyl, or halo-substituted benzyl; $R_4$ and $R_5$ are each independently hydrogen, $C_1$-$C_6$ alkyl, halo- or alkoxy-substituted $C_1$-$C_6$ alkyl, phenyl, phenethyl, benzyl, halo- or alkoxy-substituted benzyl; substituted or unsubstituted 3-benzothiophenyl, or substituted or unsubstituted 1-morpholinyl; $R_6$ is hydrogen, $C_1$-$C_4$ alkoxy; and/or $R_7$ and $R_8$ are each independently hydrogen or $C_1$-$C_6$ alkyl.

In certain embodiments, $C_1$ is

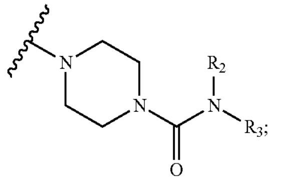

$R_2$ is hydrogen; and $R_3$ is hydrogen, $C_1$-$C_6$ alkyl, benzyl, halo-substituted benzyl, aryl, cycloalkyl, alkylaryl, or hetercyclo.

In the various methods of the present invention, the compounds of Formula (I), (IIA)-(IIH), or (IIIA)-(IIIC) can also be administered in combination with one or more additional pharmaceutical drugs, therapies, or procedures such as an anticancer compound, radiation therapy, a compound that induces apoptosis, a surgical procedure, or any combination thereof.

In accordance with the various methods of the present invention, a pharmaceutical composition comprising a compound of Formula (I), (IIA)-(IIH), or (IIIA)-(IIIC) is administered to the subject in need thereof. The pharmaceutical composition can be administered by a route including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. In various embodiments, administration is selected from the group consisting of oral, intranasal, intraperitoneal, intravenous, subcutaneous, intramuscular, intratumoral, rectal, topical, and transdermal.

The determination of a therapeutically effective dose for any one or more of the inhibitor compounds described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Typically, the normal dosage amount of the inhibitor can vary from about 0.05 to about 100 mg per kg body weight depending upon the route of administration. Guidance as to particular dosages and methods of delivery is provided in the literature and generally available to practitioners in the art. It will generally be administered so that a daily oral dose in the range, for example, from about 0.1 mg to about 75 mg, from about 0.5 mg to about 50 mg, or from about 1 mg to about 25 mg per kg body weight is given. The active ingredient can be administered in a single dose per day, or alternatively, in divided does (e.g., twice per day, three time a day, four times a day, etc.). In general, lower doses can be administered when a parenteral route is employed. Thus, for example, for intravenous administration, a dose in the range, for example, from about 0.05 mg to about 30 mg, from about 0.1 mg to about 25 mg, or from about 0.1 mg to about 20 mg per kg body weight can be used.

A pharmaceutical composition for oral administration can be formulated using pharmaceutically acceptable carriers known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. In certain embodiments, the composition is formulated for parenteral administration. Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

In addition to the active ingredients (e.g., the inhibitor compound), the pharmaceutical composition can contain suitable pharmaceutically acceptable carriers comprising excipients and auxiliaries that facilitate processing of the active compounds into preparations which can be used pharmaceutically. As used herein, the term "pharmaceutically acceptable carrier" means a non-toxic, inert solid, semi-solid or liquid filler, diluent, encapsulating material, or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil; and soybean oil; glycols such as propylene glycol; esters such as ethyl oleate and ethyl laurate; agar; detergents such as TWEEN® 80 (polysorbate 80); buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring, and perfuming agents, preservatives and antioxidants can also be present in the composition, according to the judgment of the formulator based on the desired route of administration.

The compounds of the present invention can also be used in various nuclear imaging techniques when labeled with a suitable radionuclide. Accordingly, an imaging composition in accordance with the present invention comprises a radiolabeled compound of Formula (I), (IIA)-(IIH), or (IIIA)-(IIIC), wherein the labeled compound comprises a radioisotope selected from the group consisting of $^{11}C$, $^{13}N$, $^{15}O$, $^{18}F$, $^{75}Br$, $^{124}I$, $^{125}I$, and $^{131}I$. Methods known in the art for radiolabeling the compounds of the present invention may be used.

Imaging methods in accordance with the present invention include a method of detecting cancer comprising:

- administering to a subject a radiolabeled compound of Formula (I), (IIA)-(IIH), or (IIIA)-(IIIC);
- employing a nuclear imaging technique for monitoring or visualizing a distribution of the radiolabeled compound within the body or within a portion thereof; and
- correlating the distribution of the radiolabeled compound to the existence of cancer.

In various embodiments, the nuclear imaging technique is positron emission tomography (PET) or photon emission computed tomography (SPECT).

Imaging methods in accordance with the present invention include a method of detecting cancer comprising:

- administering to a subject a fluorescent compound of Formula (I), (IIA)-(IIH), or (IIIA)-(IIIC);
- employing an imaging technique for monitoring or visualizing a distribution of the fluorescent compound within the body or within a portion thereof; and
- correlating the distribution of the fluorescent compound to the existence of cancer.

Having described the invention in detail, it will be apparent that modifications and variations are possible without departing from the scope of the invention defined in the appended claims.

EXAMPLES

The following non-limiting examples are provided to further illustrate the present invention.

Example 1. General Synthetic Route for Macrocycles in Solution Phase

Figure 2:
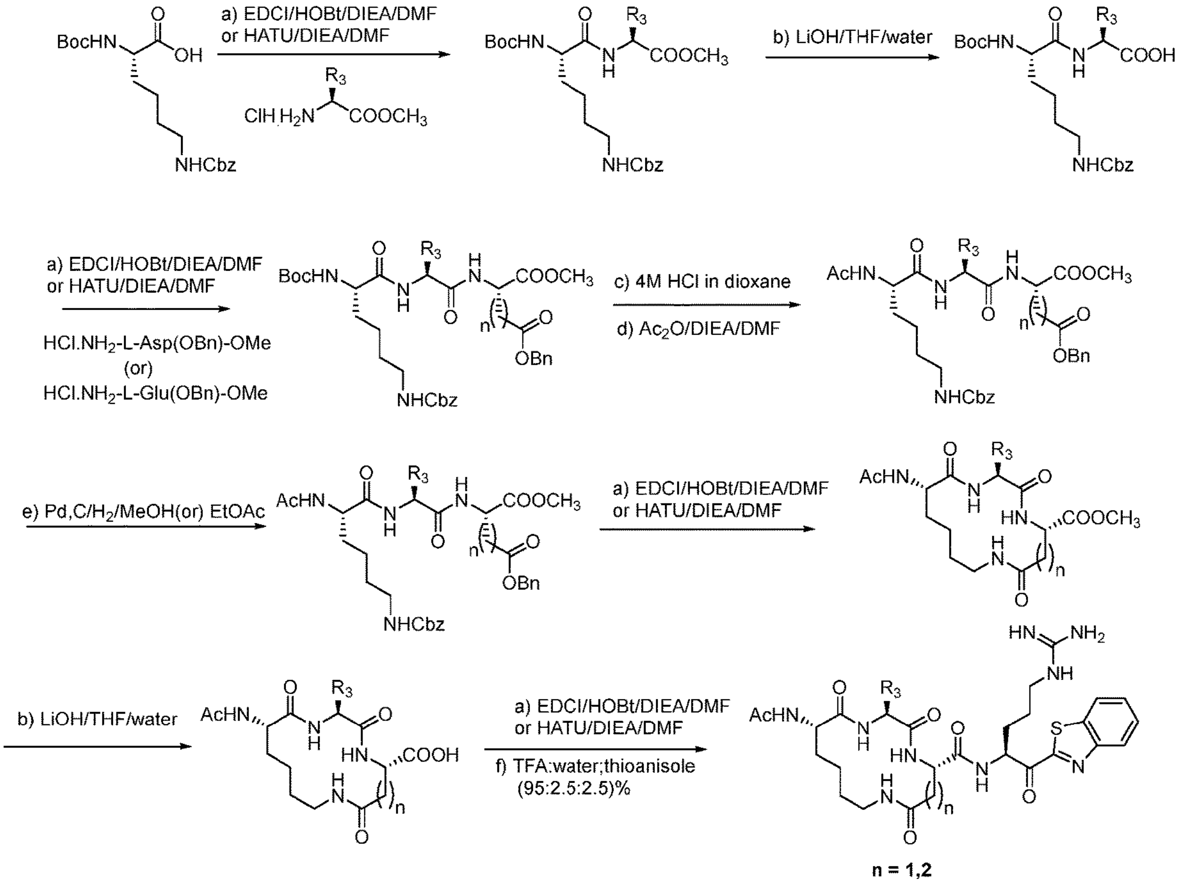
FIG. 2 presents a general synthetic route for macrocycles of Formula IIE in solution phase.

The macrocycles were synthesized in accordance with FIGS. 1 and 2 and the procedures described below.

General procedure A. Peptide coupling in solution phase: An appropriate N-protected amino acid was treated with peptide coupling reagent EDCI/HOBt or HATU (1.3 eq) in DMF for 30 min. The reaction was cooled to 0-5° C. and amino acid methyl ester hydrochloride (1.1 equiv.) was added followed by diisopropylethyl amine (3.0 equiv.) at 0-5° C. The reaction was continued with stirring for 15 minutes, then was allowed to come to room temperature and continued overnight. The reaction was monitored by TLC/LCMS. The solvent was removed under reduced pressure and the residue was partitioned between EtOAc and 5% aqueous HCl. The layers were separated and the organic layer was washed with aqueous 5% HCl, saturated $NaHCO_3$ solution (2×), and brine (1×). The organic layer was dried over anhydrous $Na_2SO_4$, filtered, and concentrated. The crude product was purified by silica column chromatography.

General procedure B. Boc-deprotection: Boc-protected peptide was treated with 4 M HCl in dioxane (10 mL/1 g) at room temperature for 3 hours. The reaction was monitored by TLC. The solvent was removed on the rotavap, the crude product was triturated with diethyl ether, and the product was filtered and used in next step.

General procedure C. Hydrogenolysis or benzyl deprotection: To a solution of benzyl ester in methanol/ethyl acetate (10-20 mL/1 g) was added 10% Pd/C (50 mol %), and the mixture was shaken on a Parr hydrogenator for 8 hours under 40-45 atm of $H_2$ while monitoring the reaction by TLC or LCMS. The reaction mixture was filtered through Celite, and the Celite bed was washed with methanol. The filtrate was concentrated under reduced pressure to yield a white solid.

General procedure D. Acetylation of peptides: The Boc de-protected compound was dissolved in DMF or DCM, cooled to 0-5° C., and N, N-diisopropylethylamine (DIEA) (3 mmol) was added followed by acetic anhydride (1.5 mmol). The reaction was stirred for 1 hour at room temperature and monitored by TLC or LCMS. The solvent was removed on reduced pressure. The residue was partitioned between ethyl acetate and ice cold water and the layers were separated. The organic layer was washed with ice cold water (2×) and saturated NaCl solution, dried over anhydrous $Na_2SO_4$, filtered, and concentrated to yield a white solid.

General procedure E. Synthesis of macrocyclic esters: To a solution of acyclic compound (0.5 mmol) in dry DMF (250 mL) was added EDCI (0.75 mmol), HOBt (0.75 mmol), and DIEA (1.5 mmol), and the mixture was stirred for 18 hours at room temperature while monitoring the reaction by TLC or LCMS. The solvent was removed and the residue partitioned between EtOAc (200 mL) and 10% aqueous citric acid (2×50 mL). The ethyl acetate layer was further washed with saturated aqueous $NaHCO_3$ (2×50 mL) followed by saturated NaCl (50 mL), dried over anhydrous $Na_2SO_4$, filtered, and concentrated. The crude product was purified by flash chromatography to yield cyclic ester.

General procedure F. Hydrolysis of esters: A solution of ester (0.1 mmol) in THF (2 mL) was treated with 1 M aqueous LiOH (2 mL). The reaction mixture was stirred for 3 hours at room temperature, and the absence of starting material was monitored by TLC. Most of the solvent was evaporated off, the residue was diluted with water and the pH was adjusted ~3.0 using 5% aqueous HCl. The product was extracted with ethyl acetate (3×100 mL). Combined ethyl acetate layers were washed with saturated NaCl (25 mL), dried over anhydrous $Na_2SO_4$, filtered, and concentrated to yield the corresponding acids.

General procedure G. De-protection of Pbf and Mtr: The resulting Pbf/Mtr protected analogs (1.0 mmol) were dissolved in TFA/thioanisole/water (95:2.5:2.5 v/v/v) and the mixture was stirred at room temperature for 2-3 hours. The reaction was monitored by LCMS. Solvent was removed in vacuo and cold ether (40 mL) was added to the residue to yield a precipitate. The ether solvent was decanted carefully and the crude product was purified by HPLC ($C_{18}$, 15×150 mm column; eluent: acetonitrile/water (0.05% TFA)) to give the resulting compound.

General procedure H. Oxidation of alcohols: The resulting alcohol (170 mg, 0.159 mmol) was dissolved in anhydrous DMF (5 mL) under nitrogen atmosphere, followed by the addition of Dess-Martin periodinane (135 mg, 0.318 mmol) at 0° C., and the reaction was stirred and allowed to come to room temperature. The absence of starting material was monitored by TLC or LCMS. After completion of the reaction, the solvent was removed under reduced pressure, water was added to the residue, and the crude product was precipitated out. The product was filtered and washed with water, dried, and purified by flash chromatography.

General Procedure I. Ring closing metathesis (RCM) macrocyclization: Acyclic precursor (250 mg, 0.512 mmol) was dissolved in DCM (400 mL, 0.2 mol). The reaction was degassed for 30 minutes by purging with nitrogen gas, and Grubbs $2^{nd}$ generation catalyst lot-1 (44 mg, 10 mol %) was added. The reaction was heated to reflux temperature and continued for 30 minutes. Grubbs $2^{nd}$ generation catalyst lot-2 (22 mg, 5 mol %) was added and the reaction was continued at reflux temperature for 18 hours under nitrogen atmosphere. The reaction was monitored by TLC or LCMS. After consumption of starting material, the reaction was cooled to room temperature and quenched by adding activated charcoal (100 mg) and stirring the reaction for 1 hour. The reaction mass was filtered through a celite bed and washed with DCM. The filtrate was concentrated and the crude product was purified by silica column. The product was collected as an off-white solid.

Figure 3:
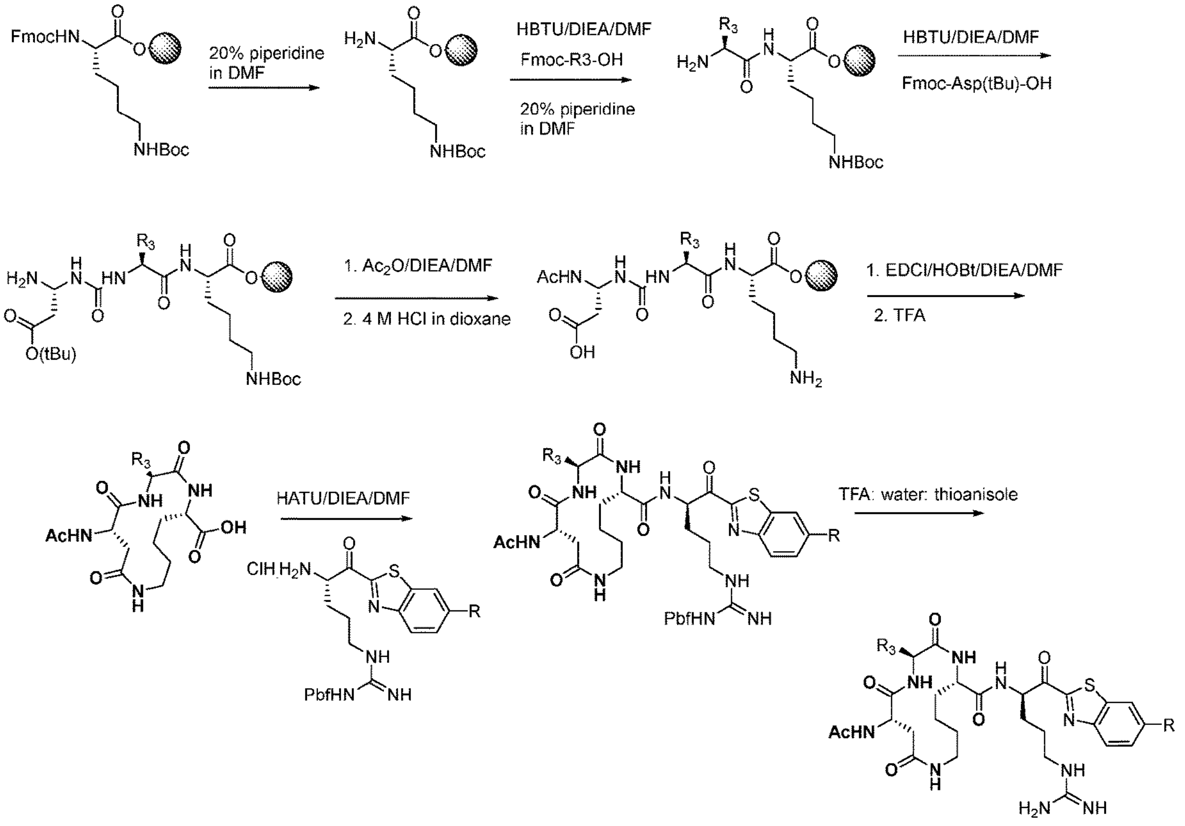
FIG. 3 presents a general synthetic route for macrocyclic inhibitors of Formula IIE and IIF in solid phase.
Figure 4:
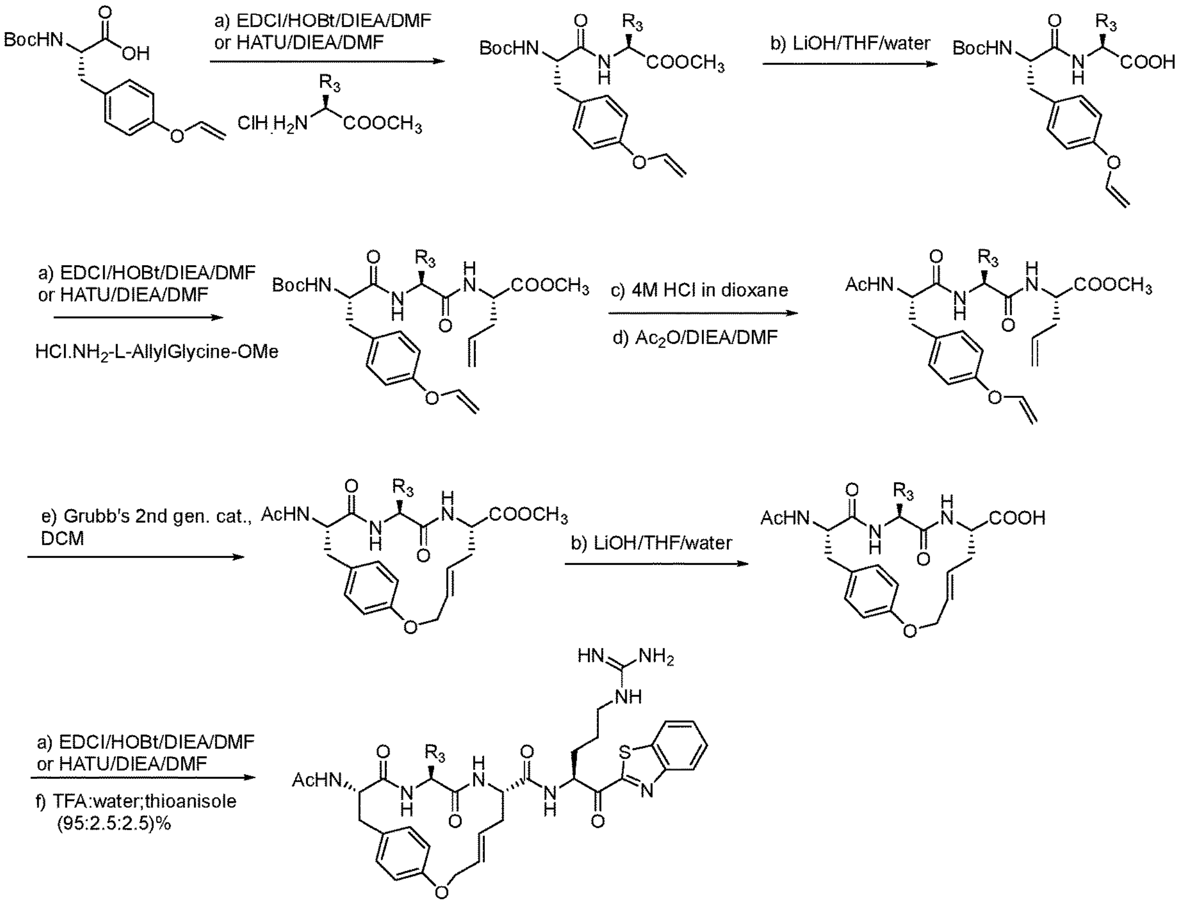
FIG. 4 presents a general synthetic route for macrocyclic analogs of Formula IIC and IID using ring-closing metathesis.
Figure 5:
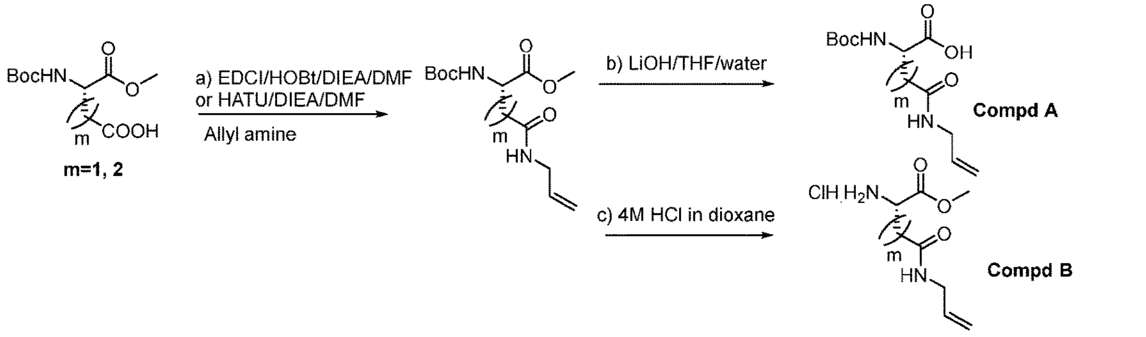
FIG. 5 presents (A) a general synthetic route for forming the building blocks for macrocyclic analogs of Formula IIB using ring-closing metathesis, and (B) a general synthetic route for forming macrocyclic analogs of Formula IIB using ring-closing metathesis.
Figure 5:
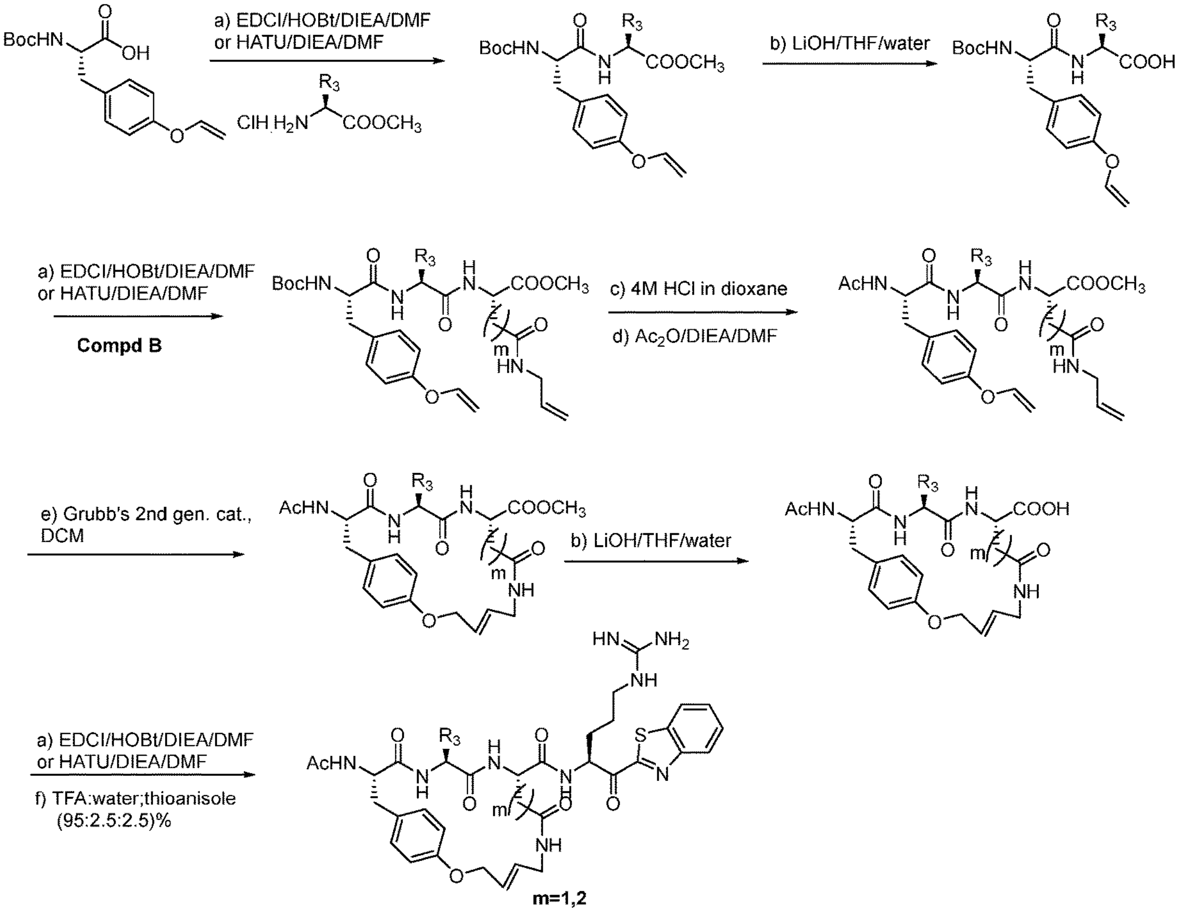
Figure 6:
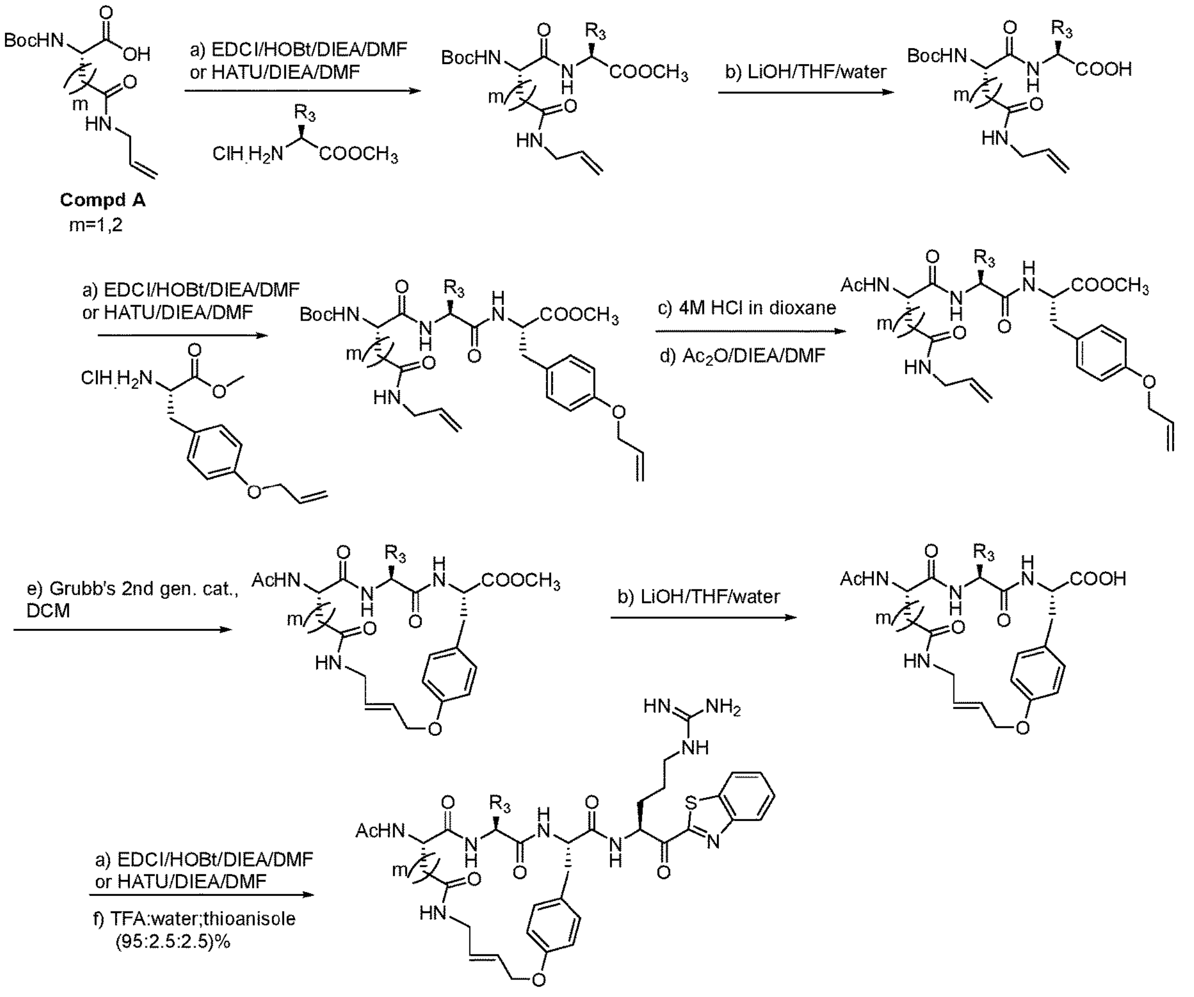
FIG. 6 presents a general synthetic route for forming macrocyclic analogs of Formula IIA using ring-closing metathesis.
Figure 7:
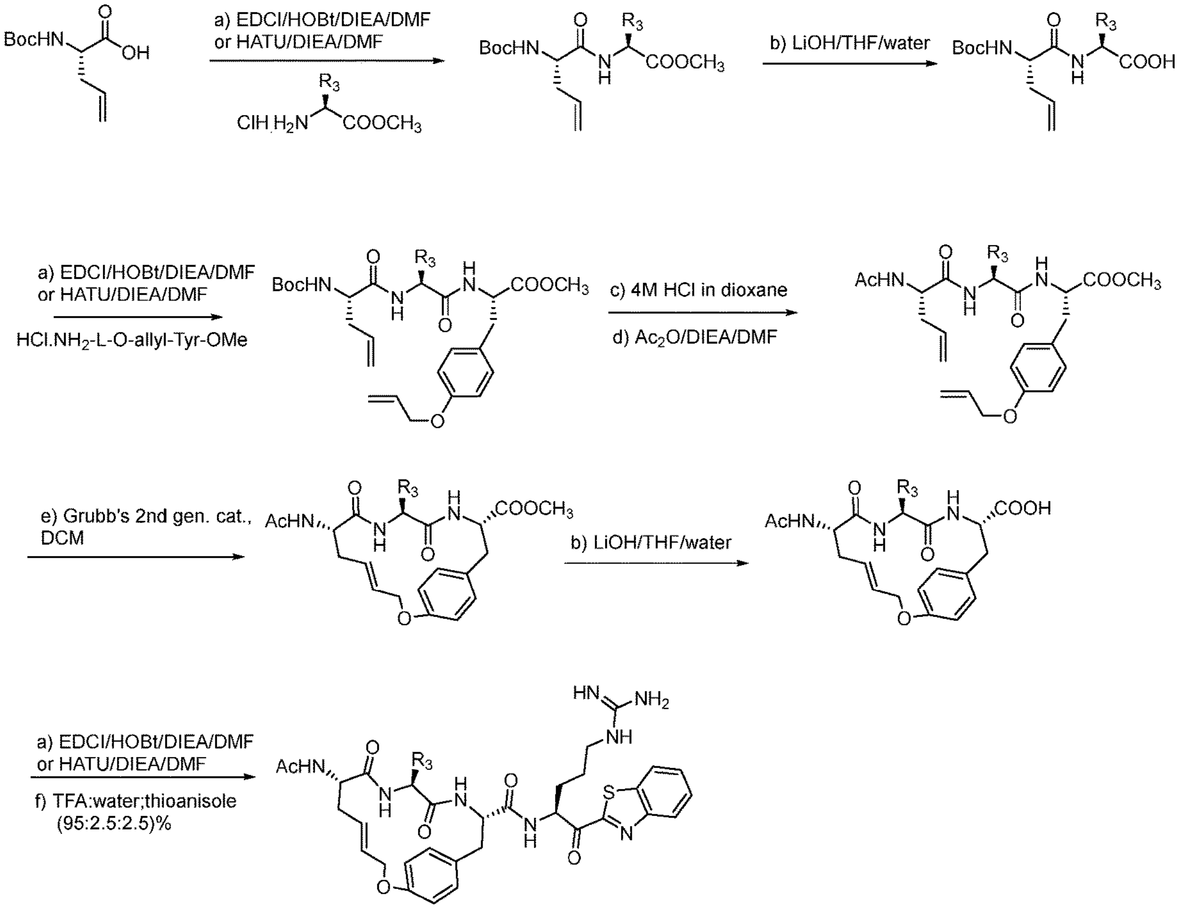
FIG. 7 presents a general synthetic route for forming macrocyclic analogs of Formula IID.
Figure 8:
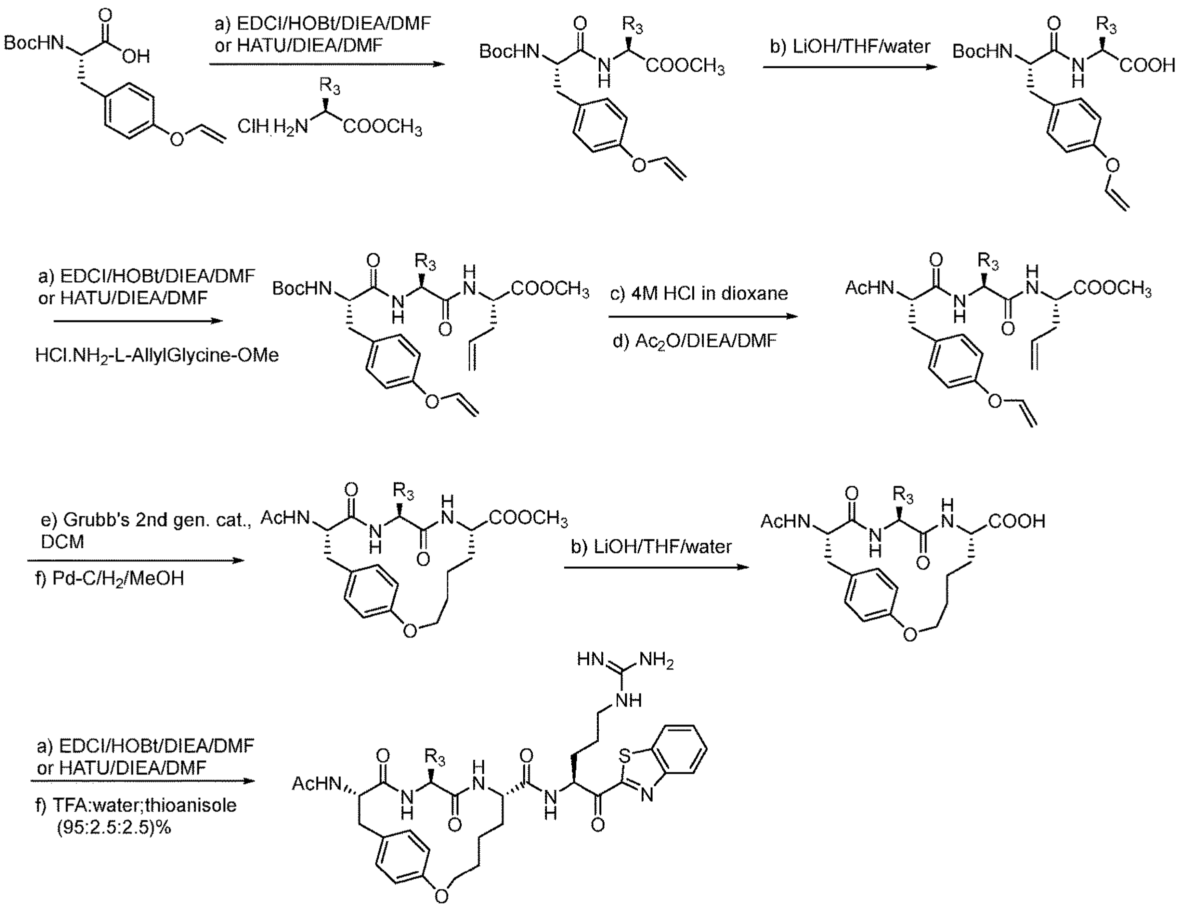
FIG. 8 presents a general synthetic route for forming a macrocyclic analog of Formula IIC.
Figure 9:
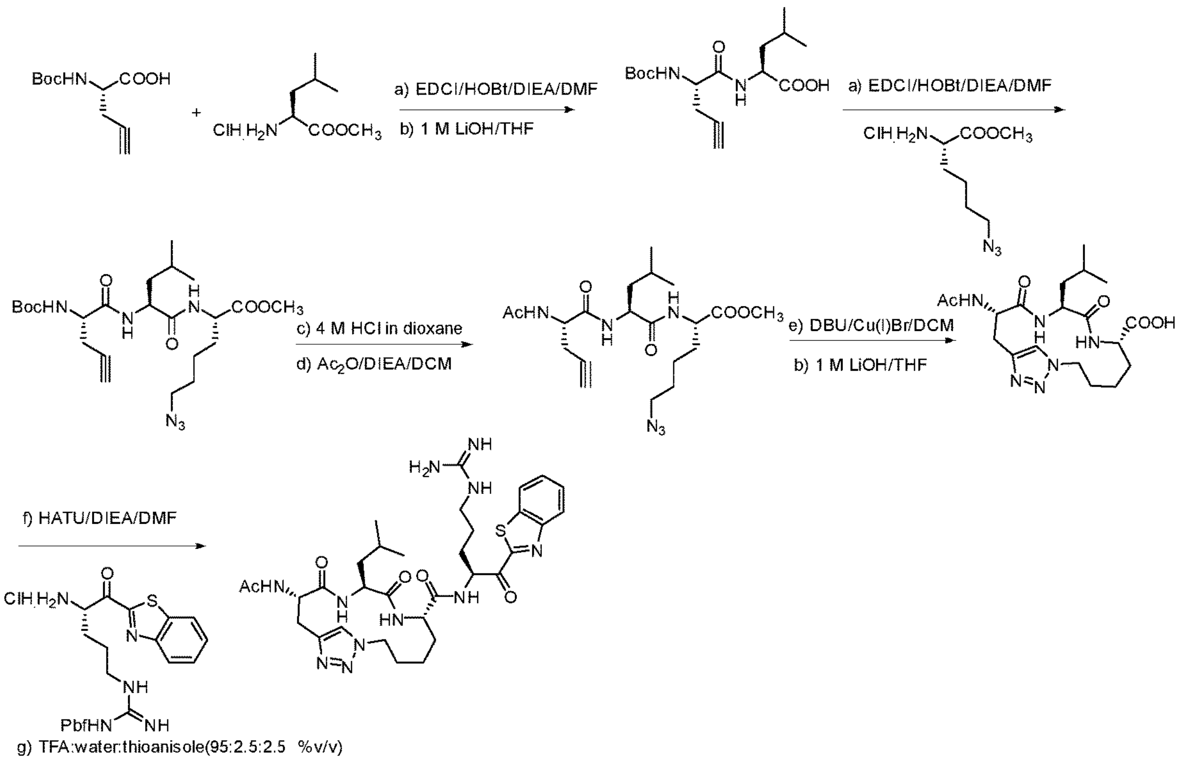
FIG. 9 presents a general synthetic route for forming a macrocyclic analog of Formula IIH.
Figure 10:
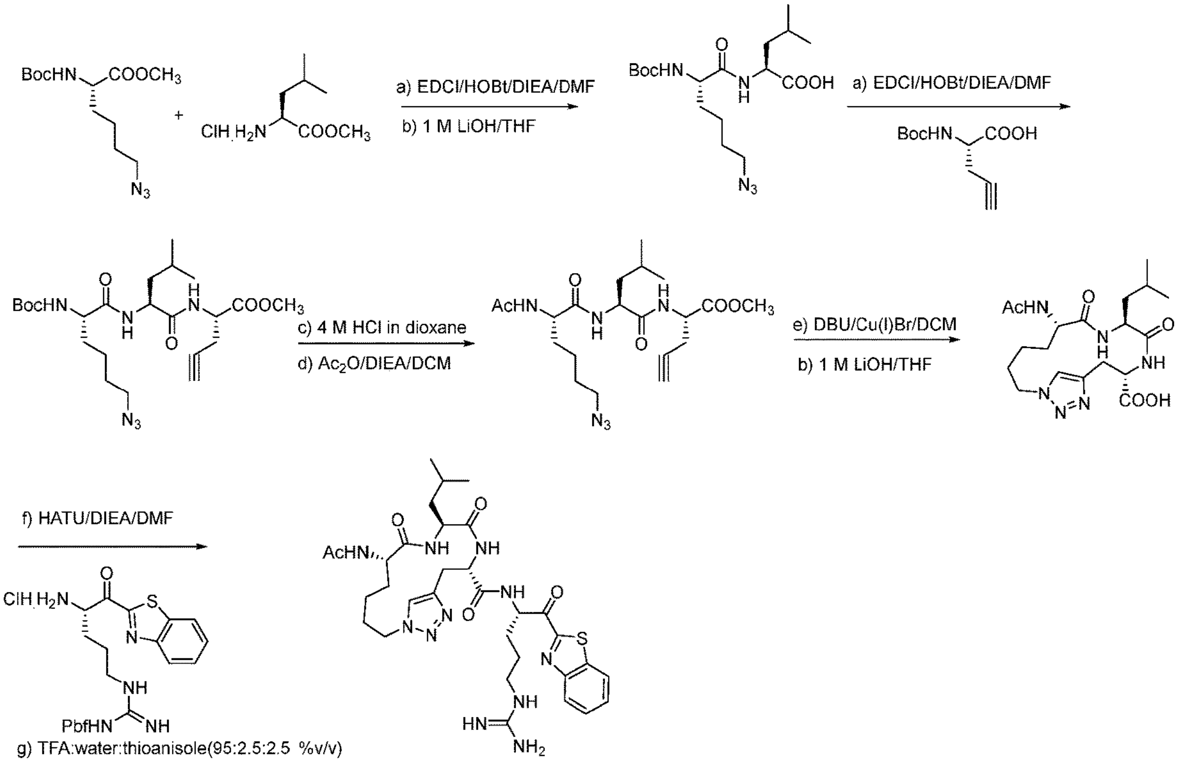
FIG. 10 presents a general synthetic route for forming a macrocyclic analog of Formula IIG.
Figure 11:
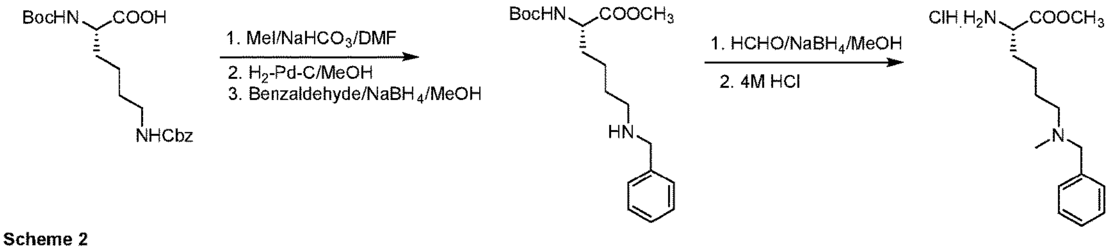
FIG. 11 presents a general synthetic route for forming a macrocyclic analog.
Figure 11:
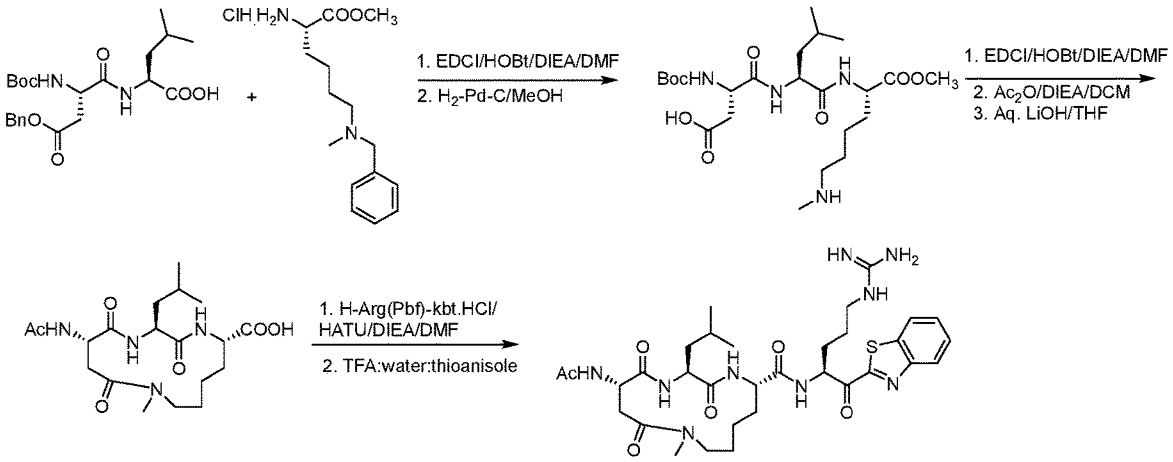

Example 2. General Synthetic Route for Macrocyclic Inhibitors in Solid Phase The macrocyclic inhibitors were synthesized in accordance FIG. 3 and the procedures described below.

Peptide coupling and deprotection steps of the Fmoc group: Into the reaction vessel (with a fritted glass resin support) containing Fmoc-L-Lys(Boc)-Wang resin (2 g, 0.68 mmol), DCM (20 mL) was added. The mixture was shaken at room temperature for 15 min, and filtered. To the resulting resin piperidine/DMF (20% v/v, 20 mL) was added and the mixture was shaken for 30 minutes at RT, then filtered. The resin was washed with DCM (2×20 mL) and DMF (2×20 mL). Fmoc-AA-OH (2.04 mmol), HBTU (2.38 mmol), $iPr_2NEt$ (4.08 mmol), and DMF (20 mL) were added to the vessel and shaken at 2 hours or overnight, then filtered. The resin was washed with DCM (2×20 mL) followed by DMF (2×20 mL).

Acetyl capping of the peptides: The peptide resin was suspended in 20 mL DMF, 1.36 mmol $Ac_2O$, and 2.72 mmol $iPr_2NEt$. The mixture was shaken at RT for 1 hour. The resin was filtered and washed with DCM (2×20 mL) followed by DMF (2×20 mL).

Cleavage of Boc and t-Bu groups of peptides: To the resin in the vessel 20 mL of 4M HCl in 1, 4-dioxane was added and shaken for 30-40 min. at room temperature. The resin was filtered, and washed with DCM (2×20 mL) followed by DMF (2×20 mL).

Cyclization of peptide in presence of resin: EDCI (2.04 mmol), HOBt (2.04 mmol), $iPr_2NEt$ (3.4 mmol), and DMF (40 mL) were added to the resin in the reaction vial and the resulting mixture was shaken overnight at room temperature. The resin was filtered and washed with DCM (2×20 mL) followed by DMF (2×20 mL).

Cleavage of macrocyclic resin: Acetyl capped macrocyclic resin was suspended in TFA (2×15 mL) and shaken for 30 min. The mixture was filtered and the resin was washed with DCM (2×20 mL). The filtrate was concentrated, cold ether was added to the residue, and the precipitate was obtained. The crude product was obtained by filtering and purified by flash chromatography.

Macrocyclic ketobenzothiazoles: The macrocyclic acid (0.334 mmol) was dissolved in dry DMF (5 mL) under nitrogen atmosphere at 0° C. HATU (0.40 mmol) was added and the reaction was stirred for 15 min, followed by addition of Pbf-protected arginine ketobenzothiazole (0.334 mmol) and $iPr_2NEt$ (1.00 mmol) at 0° C. The reaction was allowed to come to room temperature and stirred for 2-3 h. DMF was removed and the water (100 mL) was added to the resulting residue. The precipitate which formed was filtered and washed with water (2×20 mL) and dried. To this precipitate 5 mL TFA/thioanisole/water (95:2.5:2.5 v/v/v) was added and the mixture was stirred for 2 h. The solvent was removed and the cold ether (50 mL) was added. The resulting precipitate, which was the crude product, was collected by centrifugation, then by decanting out the solvents carefully. The crude product was purified by HPLC ($C_{18}$, 15×150 mm column; eluent: acetonitrile/water (0.05% TFA)) to give the resulting title compound.

Example 3. Synthesis of Specific Macrocycles and Intermediates (2S,5S,14S)-14-amino-N—((S)-1-(benzo[d]thiazol-2-yl)-5-guanidino-1-oxopentan-2-yl)-2-isobutyl-3,8,15-trioxo-1,4,9-triazacyclopentadecane-5-carboxamide (VD1135): Following general procedures A, B, C, E, and G, compound VD1135 was synthesized.

Compound was isolated as a white solid. Overall yield (30%). $^1$H NMR (400 MHz, DMSO-$d_6$) δ ppm 8.66-8.42 (m, 1H), 8.30-8.11 (m, 1H), 8.02 (br. s., 1H), 7.68-7.61 (m, 1H), 7.52 (br. s., 1H), 7.26 (d, J=7.8 Hz, 1H), 6.50 (br. s., 1H), 4.40 (d, J=7.4 Hz, 1H), 3.86 (br. s., 1H), 3.10 (br. s., 4H), 1.92 (br. s., 2H), 1.55 (br. s., 4H), 1.51-1.38 (m, 4H), 1.23-1.12 (m, 4H), 0.81 (t, J=6.5 Hz, 9H), 0.76 (d, J=6.7 Hz, 5H). ESI-MS [M+H]+ calculated for $C_{30}H_{46}N_9O_5S$+ 644.33, found 644.5.

(2S,5S,14S)-14-amino-N—((S)-1-(benzo[d]thiazol-2-yl)-5-guanidino-1-oxopentan-2-yl)-2-isobutyl-3,8,15-trioxo-1,4,9-triazacyclopentadecane-5-carboxamide (VD2056): Following general procedures A, B, C, E, and G, compound VD2056 was synthesized. Compound was isolated as a white solid. Overall yield (35%). $^1$H NMR (400 MHz, $CD_3OD$) δ ppm 0.95 (dd, J=18.78, 6.26 Hz, 6H) 1.18-1.50 (m, 3H) 1.97 (m, 8H) 2.12-2.55 (m, 4H) 2.81-3.00 (m, 2H) 3.52-3.66 (m, 1H) 4.31-4.56 (m, 2H) 5.67-5.85 (m, 1H) 7.56-7.81 (m, 2H) 8.08-8.30 (m, 2H) 8.37-8.71 (m, 1H). ESI-MS [M+H]+ calculated for $C_{30}H_{46}N_9O_5S$+ 644.33, found 644.5.

(2S,5S,13S)-13-amino-N—((S)-1-(benzo[d]thiazol-2-yl)-5-guanidino-1-oxopentan-2-yl)-2-isobutyl-3,7,14-trioxo-1,4,8-triazacyclotetradecane-5-carboxamide (VD1185): Following general procedures A, B, C, E, and G, compound VD1185 was synthesized. Compound was isolated as a white solid. Overall yield (32%). $^1$H NMR (400 MHz, DMSO-$d_6$) δ ppm 8.70 (d, J=8.6 Hz, 2H), 8.45 (d, J=7.4 Hz, 1H), 8.27 (t, J=9.6 Hz, 2H), 8.06 (br. s., 1 H), 7.69 (d, J=3.5 Hz, 1H), 6.53 (s, 3H), 4.50 (d, J=9.0 Hz, 1H), 3.13 (d, J=6.3 Hz, 7H), 2.67 (s, 2H), 2.37-2.29 (m, 6H), 1.24 (br. s, 4H), 0.90-0.76 (m, 7H), 0.83-0.75 (m, 4H). ESI-MS [M+H]+ calculated for $C_{29}H_{44}N_9O_5S$+ 630.32, found 630.5.

(3S,6S,14S)-6-amino-N—((S)-1-(benzo[d]thiazol-2-yl)-5-guanidino-1-oxopentan-2-yl)-3-isobutyl-2,5,8-trioxo-1,4,9-triazacyclotetradecane-14-carboxamide (VD2055): Following general procedures A, B, C, E, and G, compound VD2055 was synthesized. Compound was isolated as a white solid. Overall yield (30%). $^1$H NMR (400 MHz, DMSO-d6) δ ppm 8.53 (d, J=6.7 Hz, 2H), 8.27 (t, J=7.0 Hz, 2H), 7.75-7.50 (m, 2H), 6.60-6.52 (m, 1H), 5.56-5.39 (m, 2H), 3.48-3.32 (m, 1H), 3.14 (q, J=6.3 Hz, 6H), 1.89 (br. s, 6H), 1.59 (br. s., 6H), 0.95-0.77 (m, 10H). ESI-MS [M+H]+ calculated for $C_{29}H_{44}N_9O_5S$+ 630.32, found 630.4.

(2S,5S,14S)-14-acetamido-N—((S)-1-(benzo[d]thiazol-2-yl)-5-guanidino-1-oxopentan-2-yl)-2-isobutyl-3,8,15-trioxo-1,4,9-triazacyclopentadecane-5-carboxamide (VD2064): Following general procedures A, B, C, D, E, and G, compound VD2064 was synthesized. Compound was isolated as a white solid. Overall yield (32%). $^1$H NMR (400 MHz, $CD_3OD$) δ ppm 8.63 (d, J=7.8 Hz, 1H), 8.55 (d, J=7.0 Hz, 1H), 8.43 (d, J=7.8 Hz, 1H), 8.23 (d, J=7.8 Hz, 1H), 8.13 (d, J=7.4 Hz, 1H), 7.76-7.58 (m, 2H), 5.75 (br. s., 1H), 4.51-4.34 (m, 1H), 3.58 (d, J=4.7 Hz, 1H), 2.99-2.80 (m, 2H), 2.54-2.11 (m, 4H), 1.76-1.53 (m, 4H), 2.07-1.51 (m, 6H), 1.54-1.35 (m, 2H), 1.27 (d, J=6.7 Hz, 2H), 0.95 (dd, J=6.3, 18.8 Hz, 6H). ESI-MS [M+H]+ calculated for $C_{32}H_{48}N_9O_6S$+ 686.34, found 686.6.

(2S,5S,13S)-13-acetamido-N—((S)-1-(benzo[d]thiazol-2-yl)-5-guanidino-1-oxopentan-2-yl)-2-isobutyl-3,7,14-trioxo-1,4,8-triazacyclotetradecane-5-carboxamide (VD2167): Following general procedures A, B, C, D, E, and G, compound VD2167 was synthesized. Compound was isolated as a white solid. Overall yield (32%). $^1$H NMR (400 MHz, DMSO-$d_6$) δ ppm 8.55 (d, J=6.7 Hz, 1H), 8.28 (dt, J=8.2, 13.5 Hz, 1H), 7.83-7.76 (m, 2H), 7.73-7.64 (m, 2H), 7.47 (d, J=6.7 Hz, 2H), 6.53 (br. s, 1H), 5.44 (br. s, 1H), 4.46-4.41 (m, 1H), 3.14 (d, J=6.7 Hz, 7H), 2.67 (br. s, 1H), 2.54 (br. s, 1H), 2.42-2.34 (m, 8H), 1.79 (s, 3H), 1.61 (br. s, 1H), 1.51-1.44 (m, 3H), 1.33-1.22 (m, 2H), 0.82 (dd, J=6.1, 19.4 Hz, 7H). ESI-MS [M+H]+ calculated for $C_{31}H_{46}N_9O_6S$+ 672.33, found 672.5.

(2S,5S,14S)-14-acetamido-N—((S)-1-(benzo[d]thiazol-2-yl)-5-guanidino-1-oxopentan-2-yl)-2-isobutyl-3,11,15-trioxo-1,4,10-triazacyclopentadecane-5-carboxamide (VD2169): Following general procedures A, B, C, D, E, and G, compound VD2169 was synthesized. Compound was isolated as a white solid. Overall yield (34%). $^1$H NMR (400 MHz, DMSO-$d_6$) δ ppm 8.60 (d, J=6.3 Hz, 1H), 8.34-8.19 (m, 1H), 8.06-7.84 (m, 1H), 7.76-7.63 (m, 1H), 7.55 (br. s., 1H), 7.40-7.27 (m, 1H), 5.49-5.36 (m, 1H), 5.00 (s, 1H), 4.35 (d, J=5.9 Hz, 2 H), 3.15 (d, J=6.3 Hz, 2H), 2.75 (br. s., 2H), 2.19-2.09 (m, 4H), 1.85 (br. s., 3H), 1.81 (s, 3H), 1.72 (br. s., 2H), 1.65-1.39 (m, 11H), 1.18 (br. s., 3H), 0.82 (dd, J=6.3, 14.1 Hz, 15H). ESI-MS [M+H]+ calculated for $C_{32}H_{48}N_9O_6S$+ 686.34, found 686.5.

(3S,6S,14S)-6-acetamido-N—((S)-1-(benzo[d]thiazol-2-yl)-5-guanidino-1-oxopentan-2-yl)-3-isobutyl-2,5,8-trioxo-1,4,9-triazacyclotetradecane-14-carboxamide (VD2173): Following general procedures A, B, C, D, E, and G and the general synthetic route for macrocyclic inhibitors in solid phase, compound VD2173 was synthesized. Compound was isolated as a white solid. Overall yield (55%). $^1$H NMR (400 MHz, DMSO-$d_6$) δ ppm 8.51 (d, J=6.7 Hz, 1H), 8.26 (dd, J=8.0, 15.1 Hz, 1H), 7.98 (d, J=7.4 Hz, 1H), 7.93-7.83 (m, 2H), 7.73-7.63 (m, 2H), 7.53 (br. s., 1H), 5.44-5.33 (m, 1H), 4.60-4.48 (m, 1H), 4.29-4.18 (m, 1H), 3.42 (br. s., 4H), 3.19-3.06 (m, 3H), 2.96 (br. s., 1H), 1.84 (s, 3H), 1.78-1.69 (m, 1H), 1.65-1.33 (m, 8H), 1.23-1.07 (m, 2H), 0.89-0.74 (m, 7H). ESI-MS [M+H]+ calculated for $C_{31}H_{46}N_9O_6S$+ 672.33, found 672.5.

2-(((3S,6S,14S)-6-acetamido-3-isobutyl-2,5,8-trioxo-1,4,9-triazacyclotetradecane-14-carbonyl)-L-arginyl)-N—((R)-1-amino-3-methyl-1-oxobutan-2-yl)benzo[d]thiazole-6-carboxamide (VD3056): Following the general synthetic route for macrocyclic inhibitors in solid phase, peptide coupling procedure A, and oxidation procedure H, compound VD3056 was synthesized. Compound was isolated as a white solid. Overall yield (50%). $^1$H NMR (400 MHz, DMSO-d6) δ ppm 0.76-0.88 (m, 6H), 0.95 (d, J=6.65 Hz, 6H), 1.22-1.25 (m, 1H), 1.46-1.61 (m, 1H), 1.84 (s, 3H), 2.09-2.17 (m, 1H), 3.15 (d, J=6.26 Hz, 2H), 4.20-4.36 (m, 2H), 4.49-4.58 (m, 1H), 5.34-5.42 (m, 1H), 7.11 (br. s., 1H), 7.52 (br. s., 1H), 7.83-8.02 (m, 1H), 8.14 (s, 1H), 8.27 (s, 1H), 8.38-8.43 (m, 1H), 8.52-8.58 (m, 1H), 8.81 (s, 1H). ESI-MS [M+H]+ calculated for $C_{37}H_{56}N_{11}O_8S$+ 814.40, found 814.6.

(3S,6S,14S)-6-acetamido-N—((S)-5-guanidino-1-oxo-1-(thiazol-2-yl)pentan-2-yl)-3-isobutyl-2,5,8-trioxo-1,4,9-triazacyclotetradecane-14-carboxamide (VD3076): Following the general synthetic route for macrocyclic inhibitors in solid phase and peptide coupling procedure A, compound VD3076 was synthesized. Compound was isolated as a white solid. Overall yield (55%). $^1$H NMR (400 MHz, $CD_3OD$) δ ppm 8.56-8.55 (m, 1H), 8.55 (d, J=7.8 Hz, 1H), 8.58-8.52 (m, 1H), 8.34-8.30 (m, 1H), 8.32 (d, J=7.8 Hz, 1H), 8.15 (d, J=7.8 Hz, 1H), 8.18-8.13 (m, 1H), 8.11 (s, 1H), 8.13-8.10 (m, 1H), 8.05 (d, J=2.7 Hz, 1H), 7.96 (t, J=5.9 Hz, 1H), 7.88 (d, J=6.7 Hz, 1H), 5.60 (br. s., 1H), 4.73-4.66 (m, 1H), 4.33 (br. s., 2H), 3.26 (dd, J=6.5, 11.5 Hz, 3H), 2.84-2.64 (m, 3H), 2.14 (t, J=9.2 Hz, 1H), 2.00 (s, 3H), 1.88-1.50 (m, 4H), 1.45-1.22 (m, 4H), 0.95 (d, J=5.9 Hz, 6H), 0.89 (d, J=5.9 Hz, 1H). ESI-MS [M+H]+ calculated for $C_{27}H_{44}N_9O_6S$+ 622.31, found 622.5.

(2S,5S,14S)-14-acetamido-N—((S)-1-(benzo[d]thiazol-2-yl)-5-guanidino-1-oxopentan-2-yl)-2-(3-guanidinopropyl)-3,8,15-trioxo-1,4,9-triazacyclopentadecane-5-carboxamide (VD2109): Following general procedures A, B, C, D, E, and G, compound VD2109 was synthesized. Compound was isolated as a white solid. Overall yield (35%). $^1$H NMR (400 MHz, DMSO-$d_6$) δ ppm 8.40 (d, J=5.7 Hz, 1H), 8.29-8.16 (m, 2H), 8.09 (d, J=7.2 Hz, 1H), 8.02 (d, J=6.6 Hz, 1H), 7.88-7.78 (m, 2H), 7.66 (dd, J=3.0, 6.3 Hz, 2H), 7.60-7.48 (m, 2H), 5.48-5.41 (m, 2H), 4.37-4.29 (m, 4H), 3.16-3.03 (m, 6H), 2.52 (br. s, 6H), 1.79 (s, 3H), 1.57 (d, J=7.8 Hz, 10H). ESI-MS [M+H]+ calculated for $C_{32}H_{49}N_{12}O_6S$+ 729.36, found 729.6.

(3S,6S,14S)-6-acetamido-N—((S)-1-(benzo[d]thiazol-2-yl)-5-guanidino-1-oxopentan-2-yl)-3-benzyl-2,5,8-trioxo-1,4,9-triazacyclotetradecane-14-carboxamide (VD3112): Following the general synthetic route for macrocyclic inhibitors in solid phase and peptide coupling procedure A, compound VD3112 was synthesized. Compound was isolated as a white solid. Overall yield (45%). $^1$H NMR (400 MHz, DMSO-$d_6$) δ ppm 8.55 (d, J=6.3 Hz, 2H), 8.25 (d, J=8.2 Hz, 2H), 8.08 (s, 2H), 7.80 (d, J=7.8 Hz, 2H), 7.71-7.51 (m, 2H), 7.28-7.11 (m, 5H), 5.56-5.35 (m, 1H), 4.60-4.40 (m, 1H), 4.31-4.23 (m, 1H), 3.20-2.91 (m, 13H), 2.01-1.90 (m, 1H), 1.78 (d, J=2.0 Hz, 3H), 1.58 (br. s., 8H). ESI-MS [M+H]+ calculated for $C_{34}H_{44}N_9O_6S$+ 706.31, found 706.50.

(3S,6S,14S)-6-acetamido-N—((S)-1-(benzo[d]thiazol-2-yl)-5-guanidino-1-oxopentan-2-yl)-3-methyl-2,5,8-trioxo-1,4,9-triazacyclotetradecane-14-carboxamide (VD3141): Following the general synthetic route for macrocyclic inhibitors in solid phase and peptide coupling procedure A, compound VD3141 was synthesized. Compound was isolated as a white solid. Overall yield (45%). $^1$H NMR (400 MHz, DMSO-$d_6$) δ ppm 8.58 (br. s., 1H), 8.25 (br. s., 2H), 8.15-8.02 (m, 1H), 7.66 (br. s., 2H), 7.51 (br. s., 2H), 5.56-5.37 (m, 1H), 4.53 (br. s., 3H), 4.21 (d, J=5.9 Hz, 2H), 3.13 (br. s., 2H), 2.95 (br. s., 1H), 2.01 (s, 3H), 1.85-1.75 (m, 4H), 1.59 (br. s., 9H), 1.38-1.09 (m, 5H). ESI-MS [M+H]+ calculated for $C_{28}H_{40}N_9O_6S$+ 630.28, found 630.4.

(3S,6S,14S)-6-acetamido-3-(3-amino-3-oxopropyl)-N—((S)-1-(benzo[d]thiazol-2-yl)-5-guanidino-1-oxopentan-2-yl)-2,5,8-trioxo-1,4,9-triazacyclotetradecane-14-carboxamide (VD3152): Following the general synthetic route for macrocyclic inhibitors in solid phase and peptide coupling procedure A, compound VD3152 was synthesized. Compound was isolated as a white solid. Overall yield (30%). $^1$H NMR (400 MHz, DMSO-$d_6$) δ ppm 9.19 (s, 1H), 8.98-8.81 (m, 2H), 8.78-8.67 (m, 1H), 8.60-8.50 (m, 1H), 8.38-8.24 (m, 1H), 8.24-8.13 (m, 1H), 7.89-7.81 (m, 1H), 7.41-7.32 (m, 1H), 7.29-7.11 (m, 1H), 6.21-5.98 (m, 2H), 5.25-5.08 (m, 1H), 4.94-4.82 (m, 1H), 4.05 (br. s., 2H), 3.79 (t, J=6.1 Hz, 6H), 3.15-3.04 (m, 6 H), 2.69-2.56 (m, 3H), 2.44-2.32 (m, 3H), 2.04 (s, 3H), 2.25 (br. s., 5H). ESI-MS [M+H]+ calculated for $C_{30}H_{43}N_{10}O_7S$+ 687.30, found 687.50.

(3S,6S,14S)-6-acetamido-N—((S)-1-(benzo[d]thiazol-2-yl)-5-guanidino-1-oxopentan-2-yl)-3-((S)-1-hydroxyethyl)-2,5,8-trioxo-1,4,9-triazacyclotetradecane-14-carboxamide (VD3157): Following the general synthetic route for macrocyclic inhibitors in solid phase and peptide coupling procedure A, compound VD3157 was synthesized. Compound was isolated as a white solid. Overall yield (35%). $^1$H NMR (400 MHz, DMSO-$d_6$) δ ppm 8.25 (br. s., 2H), 7.66 (br. s., 2H), 7.59-7.47 (m, 2H), 5.56-5.36 (m, 2H), 3.13 (br. s., 7H), 3.00-2.86 (m, 5H), 2.03 (s, 3H), 2.00-1.87 (m, 3H), 1.89-1.73 (m, 6H), 1.59 (br. s., 6H), 1.01 (d, J=6.7 Hz, 3H). ESI-MS [M+H]+ calculated for $C_{29}H_{42}N_9O_7S$+ 660.29, found 660.50.

(3S,6S,14S)-6-acetamido-N—((S)-1-(benzo[d]thiazol-2-yl)-5-guanidino-1-oxopentan-2-yl)-3-(4-hydroxybenzyl)-2,5,8-trioxo-1,4,9-triazacyclotetradecane-14-carboxamide (VD3158): Following the general synthetic route for macrocyclic inhibitors in solid phase and peptide coupling procedure A, compound VD3158 was synthesized. Compound was isolated as a white solid. Overall yield (38%). $^1$H NMR (400 MHz, DMSO-$d_6$) δ ppm 8.54 (d, J=6.3 Hz, 2H), 8.34-8.18 (m, 2H), 7.91-7.77 (m, 2H), 7.67 (br. s., 2H), 7.55-7.41 (m, 2H), 7.03-6.89 (m, 2H), 6.59 (d, J=6.7 Hz, 2H), 4.56 (s, 1H), 4.27 (d, J=5.9 Hz, 1H), 3.23-2.88 (m, 19H), 2.01 (s, 3H), 1.79 (s, 3H), 1.58 (br. s., 2H). ESI-MS [M+H]+ calculated for $C_{34}H_{44}N_9O_7S$+ 722.31, found 722.50.

(3S,6S,14S)-6-acetamido-3-(2-amino-2-oxoethyl)-N—((S)-1-(benzo[d]thiazol-2-yl)-5-guanidino-1-oxopentan-2-yl)-2,5,8-trioxo-1,4,9-triazacyclotetradecane-14-carboxamide (VD3166): Following the general synthetic route for macrocyclic inhibitors in solid phase and peptide coupling procedure A, compound VD3166 was synthesized. Compound was isolated as a white solid. Overall yield (41%). $^1$H NMR (400 MHz, DMSO-d6) δ ppm=8.48 (br. s., 1H), 8.26 (d, J=5.9 Hz, 2H), 7.97 (br. s., 1H), 7.89 (br. s., 1H), 7.67 (br. s., 2H), 7.46 (br. s., 1H), 7.36 (d, J=14.5 Hz, 1H), 6.81 (br. s., 1H), 5.41 (br. s., 2H), 4.56-4.42 (m, 1H), 4.24-4.18 (m, 1H), 3.15 (br. s., 6H), 3.07-3.00 (m, 2H), 2.68-2.61 (m, 5H), 2.33 (br. s., 1H), 1.85 (br. s., 11H), 1.60 (br. s., 2H). ESI-MS [M+H]+ calculated for $C_{29}H_{41}N_{10}O_7S$+ 673.29, found 673.50.

(3S,6S,14S)-6-acetamido-N—((S)-1-(benzo[d]thiazol-2-yl)-5-guanidino-1-oxopentan-2-yl)-3-isopropyl-2,5,8-trioxo-1,4,9-triazacyclotetradecane-14-carboxamide (VD3167): Following the general synthetic route for macrocyclic inhibitors in solid phase and peptide coupling procedure A, compound VD3167 was synthesized. Compound was isolated as a white solid. Overall yield (45%). $^1$H NMR (400 MHz, DMSO-d6) δ ppm=8.27-8.12 (m, 4H), 7.62 (br. s., 1H), 7.45 (br. s., 1H), 5.55-5.31 (m, 1H), 4.55 (m, 1H), 4.31-3.97 (m, 2H), 3.09 (br. s., 4H), 2.91 (br. s., 6H), 2.31 (d, J=12.9 Hz, 4H), 1.91 (s, 3H), 1.79 (br. s., 5H), 1.55 (br. s., 4H), 1.36-1.04 (m, 3H), 0.90-0.60 (m, 4H). ESI-MS [M+H]+ calculated for $C_{30}H_{44}N_9O_6S$+ 658.32, found 658.50.

(3S,6S,14S)-6-acetamido-N—((S)-1-(benzo[d]thiazol-2-yl)-5-guanidino-1-oxopentan-2-yl)-3-(2-(methylthio)ethyl)-2,5,8-trioxo-1,4,9-triazacyclotetradecane-14-carboxamide (VD3173): Following the general synthetic route for macrocyclic inhibitors in solid phase and peptide coupling procedure A, compound VD3173 was synthesized. Compound was isolated as a white solid. Overall yield (45%). $^1$H NMR (400 MHz, DMSO-d6) δ ppm=8.54 (d, J=6.3 Hz, 1H), 8.31-8.07 (m, 2H), 7.93 (d, J=8.2 Hz, 1H), 7.68 (br. s., 1H), 7.49 (br. s., 1H), 5.40 (br. s., 1H), 4.51 (br. s., 1H), 4.22 (br. s., 1H), 3.15 (br. s., 6H), 2.00 (d, J=1.2 Hz, 4H), 1.88-1.77 (s, 3H), 1.58 (br. s., 3H), 1.39-1.03 (m, 16H). ESI-MS [M+H]+ calculated for $C_{30}H_{43}N_9O_6S_2$+ 690.28, found 690.40.

(6S,14S)-6-acetamido-N—((S)-1-(benzo[d]thiazol-2-yl)-5-guanidino-1-oxopentan-2-yl)-2,5,8-trioxo-1,4,9-triazacyclotetradecane-14-carboxamide (VD3174): Following the general synthetic route for macrocyclic inhibitors in solid phase and peptide coupling procedure A, compound VD3174 was synthesized. Compound was isolated as a white solid. Overall yield (42%). $^1$H NMR (400 MHz, DMSO-d6) δ ppm=8.26 (br. s., 1H), 7.77 (br. s., 1H), 7.67 (br. s., 2H), 7.49 (br. s., 2H), 5.47-5.39 (m, 1H), 4.54-4.43 (m, 1H), 4.15-4.05 (m, 1H), 3.69 (br. s., 3H), 3.23-2.84 (m, 6H), 2.54 (s, 3H), 1.99-1.91 (s, 3H), 1.84 (d, J=3.1 Hz, 7H), 1.60 (br. s., 3H), 1.37-1.18 (m, 1H). ESI-MS [M+H]+ calculated for $C_{27}H_{37}N_9O_6S$+ 616.27, found 616.40.

(7S,10S,13S,E)-13-acetamido-10-isobutyl-9,12-dioxo-2-oxa-8,11-diaza-1(1,4)-benzenacyclotetradecaphan-4-ene-7-carboxylic acid (VD3198): This compound was prepared by using general procedures A, B, D, F, G, and I. Compound was isolated as an off-white solid. Yield (135 mg). $^1$H NMR (400 MHz, $CD_3OD$) δ ppm=7.11-6.98 (m, 2H), 6.74 (d, J=7.4 Hz, 2H), 5.71-5.59 (m, 1H), 5.57-5.45 (m, 2H), 4.67-4.59 (m, 2H), 4.53-4.39 (m, 3H), 4.15 (t, J=6.8 Hz, 1H), 3.68 (s, 2H), 3.00-2.90 (m, 1H), 2.82-2.71 (m, 1H), 2.63 (d, J=14.9 Hz, 1H), 2.32 (ddd, J=7.8, 12.1, 14.5 Hz, 2H), 2.07-2.04 (m, 1H), 1.99 (s, 2H), 1.64-1.35 (m, 5H), 0.95-0.83 (m, 7H).

5-benzyl 1-methyl L-glutamate hydrochloride:

$^1$H NMR (400 MHz, $CDCl_3$) δ ppm 7.38 (d, J=3.9 Hz, 5H), 4.73 (br. s., 2H), 3.71 (s, 3H), 3.49 (d, J=7.0 Hz, 2H), 1.22 (t, J=6.8 Hz, 2H).

Methyl ((S)-4-(benzyloxy)-2-((tert-butoxycarbonyl)amino)-4-oxobutanoyl)-L-leucinate: This compound was synthesized using general procedure A.

$^1$H NMR (400 MHz, $CDCl_3$) δ ppm 7.41-7.29 (m, 4H), 6.93-6.86 (m, 1H), 5.76-5.68 (m, 1H), 5.31 (s, 2H), 5.15 (d, J=3.5 Hz, 4H), 4.57 (d, J=4.3 Hz, 4H), 3.71 (s, 3H), 3.04 (dd, J=4.3, 17.2 Hz, 2H), 2.76 (d, J=6.3 Hz, 2H), 1.71-1.59 (m, 6H), 1.46 (s, 9H), 1.40 (s, 1H), 0.93 (t, J=5.1 Hz, 6H), 0.85 (br. s., 2H).

((S)-4-(benzyloxy)-2-((tert-butoxycarbonyl)amino)-4-oxobutanoyl)-L-leucine:

$^1$H NMR (400 MHz, $CDCl_3$) δ ppm 7.42-7.35 (m, 5H), 7.34-7.29 (m, 1H), 5.31 (s, 1H), 4.72 (s, 2H), 4.53 (d, J=5.9 Hz, 2H), 2.83 (d, J=6.7 Hz, 2H), 1.75-1.58 (m, 5H), 1.45 (s, 9H), 0.98-0.89 (m, 6H).

Benzyl (S)-4-((tert-butoxycarbonyl)amino)-5-(((S)-1-methoxy-4-methyl-1-oxopentan-2-yl)amino)-5-oxopentanoate:

$^1$H NMR (400 MHz, $CDCl_3$) δ ppm 7.41-7.32 (m, 6H), 6.65-6.58 (m, 1H), 5.28-5.21 (m, 1H), 5.14 (s, 2H), 4.59 (d, J=4.3 Hz, 1H), 4.26-4.16 (m, 1H), 3.72 (s, 3H), 2.55 (q, J=7.4 Hz, 3H), 2.21-2.10 (m, 2H), 2.01-1.89 (m, 2H), 1.73-1.60 (m, 4H), 1.44 (s, 11H), 0.93 (d, J=5.1 Hz, 7H).

((S)-5-(benzyloxy)-2-((tert-butoxycarbonyl)amino)-5-oxopentanoyl)-L-leucine:

$^1$H NMR (400 MHz, $CDCl_3$) δ ppm 7.53 (d, J=7.8 Hz, 1H), 7.38 (d, J=4.3 Hz, 4H), 7.34-7.29 (m, 1H), 5.67 (d, J=9.0 Hz, 1H), 4.71 (s, 2H), 4.59 (d, J=7.8 Hz, 2H), 4.42 (d, J=7.4 Hz, 1H), 2.54-2.37 (m, 3H), 1.91 (br. s., 1H), 1.75-1.58 (m, 5H), 1.43 (s, 11H), 0.92 (br. s., 8H).

Methyl (S)-2-((((S)-5-(benzyloxy)-2-((tert-butoxycarbonyl)amino)-5-oxopentanoyl)-L-leucyl)oxy)-6-(((benzyloxy)carbonyl)amino)hexanoate:

$^1$H NMR (400 MHz, $CDCl_3$) δ ppm 8.18 (br. s., 1H), 7.34 (br. s., 7H), 6.67 (br. s., 1H), 6.15 (br. s., 1H), 5.26-5.06 (m, 7H), 4.67-4.45 (m, 2H), 4.31 (br. s., 1H), 3.99 (br. s., 1H), 3.78 (br. s., 2H), 3.72 (s, 4H), 3.31-3.02 (m, 5H), 2.28-2.07 (m, 2H), 1.90-1.75 (m, 6H), 1.74-1.55 (m, 8H), 1.40 (d, J=15.3 Hz, 19H), 1.27 (br. s., 3H), 0.97-0.86 (m, 8H).

(S)-5-(((S)-1-(((S)-6-amino-1-methoxy-1-oxohexan-2-yl)oxy)-4-methyl-1-oxopentan-2-yl)amino)-4-((tert-butoxycarbonyl)amino)-5-oxopentanoic acid (VD2048):

$^1$H NMR (400 MHz, $CD_3OD$) δ ppm 4.51-4.39 (m, 2H), 3.77 (s, 1H), 3.71 (s, 2H), 2.72-2.64 (m, 2H), 1.85 (br. s., 3H), 1.79-1.67 (m, 2H), 1.63-1.56 (m, 2H), 1.43 (br. s., 9H), 1.29 (br. s., 2H), 0.98 (d, J=6.7 Hz, 6H), 0.95-0.86 (m, 4H).

N6-((benzyloxy)carbonyl)-N2-(tert-butoxycarbonyl)-L-lysyl-L-leucine (VD2125):

$^1$H NMR (400 MHz, $CDCl_3$) δ ppm 7.82-7.75 (m, 1H), 7.48-7.42 (m, 1H), 7.34 (br. s., 5H), 6.94 (d, J=8.2 Hz, 1H), 5.49-5.40 (m, 1H), 5.24 (br. s., 1H), 5.14 (br. s., 1H), 5.09 (s, 1H), 4.58 (d, J=3.5 Hz, 1H), 4.19-4.07 (m, 1H), 3.15 (d, J=5.5 Hz, 2H), 1.85-1.55 (m, 6H), 1.51-1.46 (m, 2H), 1.42 (s, 9H), 0.95-0.89 (m, 6H).

4-benzyl 1-methyl N6-((benzyloxy)carbonyl)-N2-(tert-butoxycarbonyl)-L-lysyl-L-leucyl-L-aspartate (VD2129):

$^1$H NMR (400 MHz, $CD_3OD$) δ ppm 7.40-7.26 (m, 10H), 5.19-5.02 (s, 4H), 4.53-4.39 (m, 3H), 3.99 (br. s., 3H), 3.69 (d, J=3.5 Hz, 3H), 3.10 (br. s., 3H), 2.45 (br. s., 3H), 2.22-2.12 (m, 1H), 1.96 (d, J=3.5 Hz, 1H), 1.70 (d, J=6.7 Hz, 3H), 1.59 (d, J=5.9 Hz, 2H), 1.42 (d, J=3.5 Hz, 9H), 1.00-0.86 (m, 7H).

N2-(N6-((benzyloxy)carbonyl)-N2-(tert-butoxycarbonyl)-L-lysyl)-Nw-((2,2,4,6,7-pentamethyl-2,3-dihydrobenzofuran-5-yl)sulfonyl)-L-arginine (VD2089):

$^1$H NMR (400 MHz, $CD_3OD$) δ ppm 7.34 (br. s., 5H), 5.09-5.04 (s, 2H), 4.63-4.38 (m, 2H), 3.03-2.97 (m, 4H), 2.60-2.54 (s, 6H), 2.54-2.49 (s, 3H), 2.12-2.05 (m, 6H), 2.02-1.97 (m, 6H), 1.43 (d, J=12.5 Hz, 9H).

5-benzyl 1-methyl N2-(N6-((benzyloxy)carbonyl)-N2-(tert-butoxycarbonyl)-L-lysyl)-Nw-((2,2,4,6,7-pentamethyl-2,3-dihydrobenzofuran-5-yl)sulfonyl)-L-arginyl-L-glutamate (VD2091):

$^1$H NMR (400 MHz, $CD_3OD$) δ ppm 7.33 (d, J=4.3 Hz, 10H), 5.15-5.01 (m, 4H), 4.51-4.33 (m, 2H), 4.02-3.95 (m, 1H), 3.68 (d, J=4.3 Hz, 6H), 3.10 (br. s., 3H), 2.99 (d, J=2.7 Hz, 6H), 2.57 (d, J=4.3 Hz, 4H), 2.53-2.42 (m, 6H), 2.07 (d, J=3.9 Hz, 6H), 1.65-1.54 (m, 6H), 1.47 (s, 6H), 1.43 (s, 9H).

(6S,9S,12S)-6-(4-aminobutyl)-12-(methoxycarbonyl)-2,2-dimethyl-4,7,10-trioxo-9-(3-(3-((2,2,4,6,7-pentamethyl-2,3-dihydrobenzofuran-5-yl)sulfonyl)guanidino)propyl)-3-oxa-5,8,11-triazapentadecan-15-oic acid (VD2092):

$^1$H NMR (400 MHz, $CD_3OD$) δ ppm 4.86 (br. s., 1H), 4.85-4.81 (m, 2H), 3.71-3.67 (m, 2H), 3.67 (br. s., 3H), 3.01-2.99 (m, 6H), 2.98 (br. s., 2H), 2.57-2.54 (s, 9H), 2.53-2.50 (m, 6H), 2.49 (br. s., 3H), 2.09-2.04 (m, 8H), 1.47-1.36 (m, 13H).

5-benzyl 1-methyl N6-((benzyloxy)carbonyl)-N2-(tert-butoxycarbonyl)-L-lysyl-L-leucyl-L-glutamate:

$^1$H NMR (400 MHz, $CDCl_3$) δ ppm 7.41-7.30 (m, 10H), 6.85 (d, J=7.4 Hz, 1H), 6.49 (d, J=7.8 Hz, 1H), 5.25-5.11 (m, 2H), 5.10 (s, 2H), 4.63-4.38 (m, 2H), 4.06 (d, J=5.5 Hz, 1H), 3.72 (s, 3H), 3.67 (s, 2H), 3.21 (d, J=6.3 Hz, 2H), 2.46-2.31 (m, 2H), 2.18 (dd, J=6.3, 13.3 Hz, 1H), 2.03-1.81 (m, 2H), 1.66 (s, 4H), 1.60-1.49 (m, 3H), 1.44 (s, 9H), 0.93 (dd, J=6.3, 9.8 Hz, 6H).

(6S,9S,12S)-6-(4-aminobutyl)-9-isobutyl-12-(methoxycarbonyl)-2,2-dimethyl-4,7,10-trioxo-3-oxa-5,8,11-triazapentadecan-15-oic acid (VD2135):

$^1$H NMR (400 MHz, $CDCl_3$) δ ppm 4.50-4.37 (m, 2H), 4.00 (d, J=6.3 Hz, 1H), 3.71 (s, 3H), 3.66 (s, 3H), 2.66 (t, J=7.0 Hz, 2H), 2.47-2.36 (m, 3H), 2.18 (dd, J=5.9, 13.3 Hz, 2H), 2.02-1.88 (m, 2H), 1.72 (dd, J=6.7, 13.3 Hz, 3H), 1.65-1.55 (m, 4H), 1.55-1.47 (m, 2H), 1.44 (s, 9H), 0.95 (dd, J=6.3, 16.0 Hz, 7H).

4-benzyl 1-methyl N6-((benzyloxy)carbonyl)-N2-(tert-butoxycarbonyl)-L-lysyl-L-leucyl-L-aspartate:

$^1$H NMR (400 MHz, $CD_3OD$) δ ppm 7.39-7.24 (m, 10H), 5.06 (br. s., 2H), 4.76 (br. s., 2H), 4.42 (d, J=6.7 Hz, 1H), 4.00 (br. s., 1H), 3.68 (dd, J=2.7, 13.7 Hz, 5H), 3.13 (br. s., 2H), 2.84 (d, J=5.9 Hz, 2H), 1.71 (d, J=5.9 Hz, 2H), 1.59 (d, J=4.3 Hz, 3H), 1.51 (d, J=5.1 Hz, 9H), 0.99-0.84 (m, 6H).

(6S,9S,12S)-6-(4-aminobutyl)-9-isobutyl-12-(methoxycarbonyl)-2,2-dimethyl-4,7,10-trioxo-3-oxa-5,8,11-triazatetradecan-14-oic acid:

$^1$H NMR (400 MHz, METHANOL-d4) δ ppm 4.77 (br. s., 1H), 4.48-4.39 (m, 1H), 4.02 (br. s., 1H), 3.70 (d, J=12.5 Hz, 3H), 3.35 (s, 1H), 2.86 (t, J=5.1 Hz, 1H), 2.76-2.68 (m, 1H), 1.73 (br. s., 2H), 1.66-1.52 (m, 4H), 1.44 (s, 9H), 0.95 (dd, J=6.1, 15.8 Hz, 6H).

Methyl (2S,5S,13S)-13-((tert-butoxycarbonyl)amino)-2-isobutyl-3,7,14-trioxo-1,4,8-triazacyclotetradecane-5-carboxylate:

$^1$H NMR (400 MHz, $CD_3OD$) δ ppm 8.05-7.96 (m, 1H), 4.77 (br. s., 1H), 4.49-4.35 (m, 1H), 4.01 (br. s., 1H), 3.75-3.71 (s, 3H), 3.28-3.13 (m, 2H), 2.99 (s, 1H), 2.90-2.83 (m, 2H), 1.82-1.50 (m, 8H), 1.44 (s, 9H), 0.94 (dd, J=6.1, 15.5 Hz, 7H).

Methyl (2S,5S,14S)-14-((tert-butoxycarbonyl)amino)-3,8,15-trioxo-2-(3-(3-((2,2,4,6,7-pentamethyl-2,3-dihydrobenzofuran-5-yl)sulfonyl)guanidino)propyl)-1,4,9-triazacyclopentadecane-5-carboxylate:

$^1$H NMR (400 MHz, $CD_3OD$) δ ppm 7.63-7.53 (m, 1H), 4.55 (d, J=9.8 Hz, 1H), 4.45 (br. s., 1H), 3.69 (s, 3H), 3.53-3.41 (m, 1H), 3.20-3.09 (m, 3H), 3.00 (s, 3H), 2.94-2.79 (m, 1H), 2.58 (s, 3H), 2.52 (s, 3H), 2.37 (d, J=8.6 Hz, 5H), 2.08 (s, 6H), 2.01 (s, 3H), 1.88-1.70 (m, 5H), 1.62 (br. s., 9H), 1.44 (d, J=13.7 Hz, 10H), 1.32-1.12 (m, 3H).

(2S,5S,14S)-14-((tert-butoxycarbonyl)amino)-2-isobutyl-3,8,15-trioxo-1,4,9-triazacyclopentadecane-5-carboxylic acid (VD1179): Following the general synthetic route for macrocyclic inhibitors in solid phase, compound VD1179 was synthesized. $^1$H NMR (400 MHz, METHANOL-d4) δ ppm 8.06-8.01 (m, 1H), 7.38-7.29 (m, 1H), 5.07 (br. s., 1H), 4.44 (br. s., 1H), 4.01 (br. s., 1H), 3.12 (br. s., 3H), 2.39 (d, J=5.5 Hz, 3H), 2.24-2.12 (m, 1H), 1.93 (d, J=2.7 Hz, 2H), 1.80-1.49 (m, 6H), 1.43 (br. s., 9H), 1.29 (br. s., 1H), 1.02-0.85 (m, 7H).

(3S,6S,14S)-6-acetamido-3-isopropyl-2,5,8-trioxo-1,4,9-triazacyclotetradecane-14-carboxylic acid (VD3161). Following the general synthetic route for macrocyclic inhibitors in solid phase, compound VD3161 was synthesized. Compound was isolated as an off-white solid. $^1$H NMR (400 MHz, DMSO-d6) δ ppm 8.15 (d, J=7.0 Hz, 1H), 8.07-7.91 (m, 1H), 7.89-7.74 (m, 1H), 7.67-7.49 (m, 1H), 6.85 (d, J=7.4 Hz, 1H), 4.59 (br. s., 1H), 4.24-4.06 (m, 1H), 3.64-3.56 (m, 1H), 3.00 (br. s., 2H), 2.80-2.66 (m, 2H), 2.43-2.29 (s, 3H), 1.86-1.80 (m, 3H), 1.42-1.08 (m, 4H), 0.89-0.74 (m, 6H).

Example 4. Synthesis of Macrocyclic Analogs Using Ring Closing Metathesis

An alternative method of synthesizing macrocyclic analogs is provided in FIGS. 4-7 and described herein. In general, the methods described in this example cover forming a macrocyclic analogs using ring closing metathesis, forming an alkenylene linkage between the two amino acid residues.

General Procedure A: Peptide Coupling in Solution Phase.

Appropriate N-protected amino acid treated with peptide coupling reagent EDCI/HOBt or HATU (1.3 eq) in DMF for 30 min. Cooled the reaction to 0-5° C. and added Amino acid methyl ester hydrochloride (1.1 eq.) followed by diisopropylethyl amine (3.0 eq.) at 0-5° C. and continue the stirring for 15 mins. Allowed the reaction to room temperature and continue the reaction overnight. Reaction monitored by TLC/LCMS. Solvent was removed under reduced pressure and residue partitioned between EtOAc and 5% aq. HCl, separated the layers and organic layer washed with aq. 5% HCl and saturated $NaHCO_3$ solution (2×) and brine (1×). Organic layer dried over anhydrous $Na_2SO_4$, filtered and concentrated. Crude product was purified by silica column chromatography.

General Procedure B: Boc-Deprotection.

Boc-protected peptide was treated with 4M HCl in dioxane 10 mL/1 g at room temperature for 3 hrs. Reaction monitored by TLC. Solvent removed on the rotavap, crude triturated with diethyl ether, filtered the product, dried and used in next step.

General Procedure D: Acetylation of Peptides.

The Boc de-protected compound was dissolved in DMF or DCM, cooled the reaction to 0-5° C., added N, N-diisopropylethylamine (3 mmol) followed by added acetic anhydride (1.5 mmol) and stirred the reaction for 1 h at room temperature. Reaction monitored by TLC or LCMS. Solvent was removed on reduced pressure, residue partitioned between ethyl acetate and ice cold water, separated the layers and organic layer washed with ice cold water (2×) and saturated NaCl solution, dried over anhydrous Na2SO4, filtered and concentrated to yield white solid.

General Procedure F: Hydrolysis of Esters.

A solution of ester (0.1 mmol) in THF (2 mL) was treated with 1M aqueous LiOH (2 mL). The reaction mixture was stirred for 3 h at room temperature, and the absence of starting material monitored by TLC. Most of the solvent was evaporated off, residue diluted with water and adjusted the pH ~3.0 using 5% aq. HCl and the product was extracted with ethyl acetate (3×100 mL). Combined ethyl acetate layer washed with saturated NaCl (25 mL), dried over anhydrous $Na_2SO_4$, filtered and concentrated to yield the corresponding cyclic acids.

General Procedure G: De-Protection of Pbf and Mtr.

The resulting Pbf/Mtr protected analogs (1.0 mmol) was dissolved in TFA/thioanisole/water (95:2.5:2.5 v/v/v) and the mixture was stirred at room temperature for 2-3 h. Reaction monitored by LCMS. Solvent was removed in vacuo and cold ether (40 mL) was added to the residue to yield a precipitate. Decant the ether solvent carefully and the crude product was purified by HPLC ($C_{18}$, 15×150 mm column; eluent: acetonitrile/water (0.05% TFA) to give the resulting compound.

General Procedure H: Ring Closing Metathesis (RCM) Macrocyclization.

Acyclic precursor (250 mg, 0.512 mmol) was dissolved in DCM (400 mL, 0.2 Mol.) degassed the reaction for 30 min by purging nitrogen gas and added the Grubbs $2^{nd}$ generation catalyst lot-1 (44 mg, 10 mol %) and heated the reaction to reflux temperature. Continue the reaction for 30 min and add the Grubbs $2^{nd}$ generation catalyst lot-2 (22 mg, 5 mol %) at reflux temperature and continue the reaction for 18 h under nitrogen atmosphere. Reaction monitored by TLC or LCMS. After completion of starting material, cooled the reaction room temperature and quenches the reaction by adding activated charcoal (100 mg) and stir the reaction for 1 h. Filter the reaction mass through celite bed and washed the bed with DCM, concentrated the filtrate and crude was purified by silica column. Off-white solid yielded as a product.

(7S,10S,13S,Z)-13-acetamido-N—((S)-1-(benzo[d]thiazol-2-yl)-5-guanidino-1-oxopentan-2-yl)-10-isobutyl-9,12-dioxo-2-oxa-8,11-diaza-1(1,4)-benzenacyclotetradecaphan-4-ene-7-carboxamide (VD4010). VD4010 was synthesized by using peptide coupling general procedure A and general procedure G followed by HPLC purification. White solid. Yield (63 mg). $^{1}$H NMR (400 MHz, DMSO-$d_6$) □=8.54 (d, J=5.5 Hz, 1H), 8.27 (dd, J=7.4, 14.5 Hz, 2H), 8.13-7.96 (m, 2H), 7.68 (d, J=5.1 Hz, 2H), 7.54-7.45 (m, 1H), 7.18 (br. s., 1H), 6.98 (d, J=7.4 Hz, 2H), 6.69 (d, J=7.8 Hz, 2H), 5.62-5.34 (m, 3H), 4.71-4.35 (m, 4H), 4.05 (d, J=6.3 Hz, 1H), 3.14 (d, J=6.3 Hz, 2H), 2.84 (br. s., 1H), 2.60 (d, J=11.0 Hz, 2H), 2.17 (br. s., 2H), 2.03-1.88 (m, 1H), 1.85 (s, 3H), 1.79-1.68 (m, 1H), 1.59 (br. s., 2H), 1.40 (d, J=6.3 Hz, 1H), 1.31-1.15 (m, 3H), 0.80-0.72 (m, 6H). ESI-MS [M+H]+ calcd for $C_{36}H_{47}N_8O_6S$+ 719.33, found 719.50.

(11S,14S,17S,Z)-17-acetamido-N—((S)-1-(benzo[d]thiazol-2-yl)-5-guanidino-1-oxopentan-2-yl)-14-isobutyl-8,13,16-trioxo-2-oxa-7,12,15-triaza-1(1,4)-benzenacyclooctadecaphan-4-ene-11-carboxamide (VD4018). VD4018 was synthesized by using peptide coupling general procedure A and general procedure G followed by HPLC purification. Off-white solid. Yield (17 mg). $^{1}$H NMR (400 MHz, DMSO-$d_6$) □=8.63 (s, 1H), 8.31-8.20 (m, 2H), 7.91 (d, J=7.8 Hz, 1H), 7.68 (br. s., 2H), 7.44 (br. s., 2H), 7.00 (d, J=8.2 Hz, 2H), 6.70 (d, J=8.6 Hz, 2H), 5.47 (br. s., 1H), 4.57 (br. s., 3H), 4.47 (br. s., 2H), 3.13 (br. s., 3H), 2.71-2.65 (m, 7H), 2.33 (s, 2H), 1.85 (s, 3H), 1.74 (s, 3H), 1.60 (br. s., 4H), 0.88-0.75 (m, 7H). ESI-MS [M+H]+ calcd for $C_{39}H_{51}N_9O_7S$+ 790.37, found 790.50.

(S)-2-((S)-2-((S)-2-acetamido-3-(4-(allyloxy)phenyl)propanamido)-4-methylpentanamido)-N5-allyl-N1-((S)-1-(benzo[d]thiazol-2-yl)-5-guanidino-1-oxopentan-2-yl)pentanediamide (VD4022). Compound VD4022 was synthesized using the general procedures A, B, D, F, and G. Off-white solid. Yield (6.7 mg). $^{1}$H NMR (400 MHz, DMSO-$d_6$) □=8.98 (s, 1H), 8.27 (br. s., 2H), 7.94 (br. s., 2H), 7.68 (br. s., 1H), 7.43 (br. s., 1H), 7.19-7.00 (m, 2H), 6.81 (br. s., 2H), 6.61 (s, 1H), 6.03 (s, 1H), 5.77 (s, 1H), 5.53-4.97 (m, 2H), 4.50 (br. s., 1H), 4.43 (s, 1H), 3.14 (br. s., 2H), 2.34 (s, 4H), 2.29 (s, 2H), 1.94 (br. s., 1H), 1.75 (br. s., 4H), 1.59 (br. s., 2H), 1.45 (br. s., 2H), 0.96-0.63 (m, 6H). ESI-MS [M+H]+ calcd for $C_{41}H_{56}N_9O_7S$+ 818.40, found 818.60

Methyl N5-allyl-N2-(tert-butoxycarbonyl)-L-glutaminate (VD3185). VD3185 was prepared by using peptide coupling general procedure A. Off-white solid, Yield 5.5 g (95%). $^{1}$H NMR (400 MHz, $CDCl_3$) □=6.51-6.38 (m, 1H), 5.84 (dd, J=5.7, 11.2 Hz, 1H), 5.45-5.27 (m, 1H), 5.27-5.09 (m, 2H), 4.28 (br. s., 1H), 3.91 (br. s., 2H), 3.75 (s, 3H), 2.66-2.44 (m, 1H), 2.43-2.28 (m, 1H), 2.28-2.16 (m, 1H), 1.95 (d, J=6.3 Hz, 1H), 1.45 (s, 9H). ESI-MS [M+H]+ calcd for $C_{14}H_{25}N_2O_5$+301.18, found 301.30.

Methyl ((S)-2-acetamido-3-(4-(allyloxy)phenyl)propanoyl)-L-leucinate (VD3186). VD3186 was prepared by using peptide coupling general procedure A. Off-white solid, Yield 440 mg (89%). $^{1}$H NMR (400 MHz, $CDCl_3$) □□=7.15 (br. s., 2H), 6.86 (d, J=7.0 Hz, 2H), 6.31-5.98 (m, 2H), 5.43 (d, J=17.6 Hz, 1H), 5.30 (d, J=9.8 Hz, 2H), 4.64 (br. s., 1H), 4.53 (br. s., 1H), 3.72 (d, J=4.3 Hz, 3H), 3.12-2.91 (m, 2H), 2.01 (br. s., 3H), 1.85 (br. s., 3H), 1.66-1.45 (m, 2H), 1.38 (br. s., 1H), 0.96-0.83 (m, 6H). ESI-MS [M+H]+ calcd for $C_{21}H_{30}N_2O_5$+391.22, found 391.30.

Methyl (S)-2-((S)-2-((S)-2-acetamido-3-(4-(allyloxy)phenyl)propanamido)-4-methylpentanamido)pent-4-enoate (VD3193). Compound VD3193 was synthesized using the general procedures A, B, D, and F. Off-white solid, Yield 312 mg (94%). $^{1}$H NMR (400 MHz, $CD_3OD$) □=7.17-7.10 (m, 2H), 6.88-6.81 (m, 2H), 6.05 (tdd, J=5.3, 10.8, 16.5 Hz, 1H), 5.85-5.70 (m, 2H), 5.44-5.34 (m, 1H), 5.23 (d, J=10.6 Hz, 1H), 5.17-5.03 (m, 3H), 4.57 (dd, J=5.7, 8.8 Hz, 1H), 4.51 (d, J=4.7 Hz, 2H), 4.47-4.38 (m, 2H), 4.20 (dd, J=3.9, 11.0 Hz, 1H), 3.71-3.67 (m, 3H), 3.05 (dd, J=5.5, 14.1 Hz, 1H), 2.94-2.87 (m, 1H), 2.84-2.76 (m, 1H), 2.62-2.42 (m, 3H), 1.60-1.53 (m, 1H), 0.93 (dd, J=6.1, 14.3 Hz, 5H), 0.81-0.76 (m, 1H), 0.74-0.66 (m, 2H). ESI-MS [M+H]+ calcd for $C_{26}H_{38}N_3O_6$+488.28, found 488.40.

Example 5. Synthesis of Macrocyclic Analogs

Various macrocyclic analogs were prepared according the schemes shown in FIGS. 8-11 and as described herein.

Hydrogenation.

Staring material (alkene) (250 mg; 0.544 mmol) dissolved in methanol (25 mL) followed by added Pd—C(50 mg) carefully and applied the hydrogen gas at room temperature continue the reaction for 3 h/until disappearance of the starting material by LCMS. After completion, reaction mass filtered through celite bed and washed the bed with methanol. Concentrated the filtrate, crude was purified by silica column chromatography yielded a white to off-white solid.

Intramolecular Click Chemistry.

To a solution of acyclic compound (100 mg; 0.229 mmol) in DCM (190 mL; 1.2 M) added DBU (103 uL; 0.687 mmol) under nitrogen atmosphere and stirred the reaction for 15 min followed by added Cu(I)Br (33 mg; 0.229 mmol) at room temperature and continue the reaction overnight (~16 h) till disappearance of the starting material. Reaction quenched by adding 3 M HCl (30 mL), separate the layers. Aqueous extracted with DCM (2×). Combined organic layer washed with water, brine, dried over anhydrous $Na_2SO_4$, filtered and concentrated. Crude was purified by column chromatography (Combiflash) yielded an Off-white solid.

Methyl (6S,9S,12S)-6-(4-azidobutyl)-9-isobutyl-2,2-dimethyl-4,7,10-trioxo-12-(prop-2-yn-1-yl)-3-oxa-5,8,11-triazatridecan-13-oate (VD4113). $^{1}$H NMR (400 MHz, $CDCl_3$) □□=4.54 (t, J=4.7 Hz, 1H), 4.41-4.32 (m, 1H), 3.96 (br. s., 1H), 3.81 (s, 3H), 3.68 (d, J=1.6 Hz, 2H), 3.27 (d, J=1.6 Hz, 1H), 3.19 (t, J=6.1 Hz, 2H), 2.68-2.61 (m, 2H), 2.00 (d, J=2.0 Hz, 1H), 1.76-1.65 (m, 1H), 1.61-1.44 (m, 7H), 1.34 (d, J=1.2 Hz, 9H), 0.84 (dd, J=4.7, 14.1 Hz, 7H).

t-Butyl 3-((S)-2-((S)-3-(4-(allyloxy)phenyl)-2-((tert-butoxycarbonyl)amino)propanamido)-3-methoxy-3-oxopropyl)-1H-indole-1-carboxylate (VD4146). $^{1}$H NMR (400 MHz, $CDCl_3$) □□=8.11 (d, J=7.4 Hz, 1H), 7.40-7.29 (m, 2H), 7.23-7.15 (m, 1H), 7.09 (d, J=7.0 Hz, 2H), 6.81 (d, J=7.0 Hz, 4H), 6.39 (d, J=7.0 Hz, 1H), 6.03 (dt, J=5.9, 11.0 Hz, 1H), 5.39 (d, J=17.2 Hz, 1H), 5.26 (d, J=10.2 Hz, 1H), 4.87 (d, J=5.5 Hz, 1H), 4.53-4.45 (m, 1H), 4.28 (br. s., 1H), 3.65 (s, 3H), 3.19 (d, J=5.1 Hz, 1H), 2.98 (d, J=5.5 Hz, 2H), 2.18 (d, J=1.2 Hz, 2H), 1.67 (s, 9H), 1.37 (s, 9H).

$N^{\alpha}$—((S)-3-(4-(allyloxy)phenyl)-2-((tert-butoxycarbonyl)amino)propanoyl)-1-(tert-butoxycarbonyl)-L-tryptophan (VD4147). $^{1}$H NMR (400 MHz, $CDCl_3$) □□=8.08 (d, J=5.9 Hz, 1H), 7.42 (br. s., 2H), 7.20 (d, J=6.3 Hz, 1H), 7.13-7.00 (m, 2H), 6.87-6.76 (m, 2H), 6.65 (br. s., 1H), 6.02

(dt, J=4.7, 11.0 Hz, 1H), 5.39 (d, J=17.2 Hz, 1H), 5.26 (d, J=10.6 Hz, 1H), 5.04-4.80 (m, 1H), 4.55-4.44 (m, 1H), 4.34 (br. s., 1H), 3.49 (br. s., 1H), 3.31-3.12 (m, 1H), 2.91 (d, J=7.0 Hz, 1H), 2.18 (d, J=1.2 Hz, 1H), 2.08 (dd, J=1.4, 18.2 Hz, 1H), 1.64 (s, 9H), 1.45-1.40 (m, 2H), 1.33 (br. s., 9H).

t-Butyl 3-((R)-2-((S)-3-(4-(allyloxy)phenyl)-2-((tert-butoxycarbonyl)amino)propanamido)-3-methoxy-3-oxopropyl)-1H-indole-1-carboxylate (VD4149). Compound VD4149 was synthesized using the peptide coupling general procedure A. $^1$H NMR (400 MHz, $CDCl_3$) □□=8.11 (d, J=6.7 Hz, 1H), 7.42 (d, J=7.4 Hz, 1H), 7.37-7.29 (m, 1H), 7.25-7.21 (m, 1H), 7.11-7.01 (m, 2H), 6.87-6.76 (m, 2H), 6.43 (d, J=5.5 Hz, 1H), 6.09-5.95 (m, 1H), 5.39 (d, J=17.2 Hz, 1H), 5.26 (d, J=10.6 Hz, 1H), 4.98-4.81 (m, 1H), 4.54-4.45 (m, 1H), 4.30 (br. s., 1H), 3.64 (s, 3H), 3.20-3.04 (m, 2H), 2.97 (d, J=5.9 Hz, 1H), 2.18 (s, 1H), 1.67 (s, 9H), 1.37 (s, 9H).

t-Butyl 3-((S)-2-((S)-3-(4-(allyloxy)phenyl)-2-((tert-butoxycarbonyl)amino)propanamido)-3-(((S)-1-methoxy-1-oxopent-4-en-2-yl)amino)-3-oxopropyl)-1H-indole-1-carboxylate (VD4150). $^1$H NMR (400 MHz, $CDCl_3$) □□=8.14 (d, J=7.4 Hz, 1H), 7.46 (s, 1H), 7.37-7.28 (m, 1H), 7.25-7.17 (m, 1H), 7.10 (d, J=7.8 Hz, 2H), 6.86 (d, J=7.4 Hz, 2H), 6.66 (d, J=7.0 Hz, 1H), 6.27-6.14 (m, 1H), 6.11-5.96 (m, 1H), 5.55-5.33 (m, 2H), 5.27 (d, J=10.2 Hz, 1H), 5.00-4.89 (m, 2H), 4.83-4.66 (m, 1H), 4.55-4.43 (m, 1H), 4.31 (br. s., 1H), 3.67 (s, 3H), 3.28 (d, J=9.8 Hz, 1H), 3.12-2.91 (m, 3H), 2.41 (q, J=6.9 Hz, 1H), 2.18 (d, J=0.8 Hz, 1H), 1.66 (s, 9H), 1.44-1.39 (m, 1H), 1.32 (s, 9H).

$N^{\alpha}$—((S)-3-(4-(allyloxy)phenyl)-2-((tert-butoxycarbonyl)amino)propanoyl)-1-(tert-butoxycarbonyl)-D-tryptophan (VD4151). $^1$H NMR (400 MHz, $CDCl_3$) □□=8.10 (d, J=6.7 Hz, 1H), 7.54 (d, J=6.7 Hz, 1H), 7.44 (br. s., 1H), 7.35-7.29 (m, 1H), 7.27-7.20 (m, 2H), 7.13-6.92 (m, 2H), 6.73 (br. s., 1H), 6.00 (dt, J=5.3, 11.1 Hz, 1H), 5.44-5.14 (m, 2H), 4.90 (br. s., 1H), 4.61-4.29 (m, 2H), 3.49 (br. s., 1H), 3.15 (br. s., 1H), 2.97-2.75 (m, 2H), 2.18 (d, J=0.8 Hz, 1H), 1.63 (s, 9H), 1.44-1.40 (m, 2H), 1.33 (br. s., 9H).

Methyl (7S,10S,13S,E)-13-acetamido-10-benzyl-9,12-dioxo-2-oxa-8,11-diaza-1(1,4)-benzenacyclotetradecaphan-4-ene-7-carboxylate (VD4098). $^1$H NMR (400 MHz, $CDCl_3$) □□=7.30-7.21 (m, 4H), 7.08 (d, J=6.7 Hz, 5H), 6.48 (d, J=7.8 Hz, 1H), 5.88 (d, J=8.2 Hz, 1H), 5.79 (d, J=6.7 Hz, 1H), 5.50-5.31 (m, 1H), 4.73-4.49 (m, 2H), 4.40 (d, J=6.7 Hz, 1H), 3.73 (d, J=2.0 Hz, 3H), 3.23-3.06 (m, 1H), 2.90-2.79 (m, 1H), 2.69-2.53 (m, 1H), 2.31 (br. s., 1H), 2.05 (d, J=1.6 Hz, 3H), 1.70 (br. s., 4H), 1.26 (br. s., 1H).

Methyl (7S,10S,13S)-13-acetamido-10-isobutyl-9,12-dioxo-2-oxa-8,11-diaza-1(1,4)-benzenacyclotetradecaphane-7-carboxylate (VD4063). $^1$H NMR (400 MHz, $CDCl_3$) □□=7.15-7.03 (m, 2H), 6.80 (d, J=7.8 Hz, 2H), 6.56 (br. s., 1H), 6.22 (br. s., 1H), 4.72 (br. s., 1H), 4.55 (br. s., 1H), 4.32 (d, J=12.5 Hz, 1H), 4.22 (br. s., 1H), 4.12 (d, J=7.4 Hz, 1H), 3.73 (s, 3H), 3.17 (dd, J=5.3, 12.3 Hz, 1H), 3.05-2.92 (m, 2H), 2.67 (t, J=12.1 Hz, 1H), 2.07 (s, 3H), 2.00 (br. s., 1H), 1.92 (d, J=9.0 Hz, 1H), 1.82 (d, J=7.0 Hz, 2H), 1.71-1.39 (m, 2H), 0.96 (d, J=6.7 Hz, 2H), 0.94-0.84 (m, 6H).

Methyl (7S,10S,13S)-13-acetamido-10-benzyl-9,12-dioxo-2-oxa-8,11-diaza-1(1,4)-benzenacyclotetradecaphane-7-carboxylate (VD4104).

$^1$H NMR (400 MHz, $CDCl_3$) □□□□7.24-7.19 (m, 2H), 7.14-6.98 (m, 2H), 6.77 (d, J=7.4 Hz, 1H), 6.40 (br. s., 1H), 6.24 (br. s., 1H), 5.60 (d, J=7.4 Hz, 1H), 4.59 (br. s., 1H), 4.41 (br. s., 1H), 4.19 (d, J=6.3 Hz, 1H), 4.08 (d, J=8.2 Hz, 2H), 3.67 (s, 3H), 3.20 (dd, J=4.9, 12.7 Hz, 1H), 3.08 (d, J=9.8 Hz, 1H), 2.97 (br. s., 1H), 2.86-2.72 (m, 2H), 2.69-2.56 (m, 1H), 2.07 (s, 3H), 1.90 (br. s., 1H), 1.67 (d, J=6.3 Hz, 1H), 1.52 (d, J=4.7 Hz, 1H), 1.38-1.23 (m, 1H), 1.19 (br. s., 1H), 0.95 (d, J=5.5 Hz, 1H).

Methyl (3S,6S,9S,Z)-3-acetamido-6-isobutyl-4,7-dioxo-11H-5,8-diaza-1(4,1)-triazolacyclotridecaphane-9-carboxylate (VD4084). $^1$H NMR (400 MHz, METHANOL-d4) □□=7.63 (br. s., 1H), 4.74 (br. s., 1H), 4.64 (d, J=11.3 Hz, 1H), 4.47-4.30 (m, 2H), 3.79-3.67 (s, 3H), 3.23 (q, J=6.9 Hz, 3H), 3.13 (br. s., 1H), 2.67 (br. s., 1H), 2.03 (s, 3H), 1.99 (br. s., 2H), 1.75 (br. s., 2H), 1.69-1.50 (m, 4H), 0.98-0.88 (m, 8H).

Methyl (3S,6S,9S,Z)-9-acetamido-6-isobutyl-5,8-dioxo-11H-4,7-diaza-1(4,1)-triazolacyclotridecaphane-3-carboxylate (VD4116). $^1$H NMR (400 MHz, $CD_3OD$) □□=7.64 (br. s., 1H), 5.50 (s, 1H), 4.49-4.39 (m, 1H), 4.13-4.06 (m, 1H), 3.79 (s, 3H), 3.35 (t, J=5.7 Hz, 3H), 2.68 (d, J=9.4 Hz, 3H), 2.56 (d, J=9.8 Hz, 1H), 2.09-2.00 (s, 3H), 1.94 (s, 1H), 1.83-1.69 (m, 5H), 1.38 (d, J=5.9 Hz, 2H), 1.24 (t, J=6.8 Hz, 1H), 0.99-0.87 (m, 6H).

(3S,6S,9S,Z)-3-acetamido-6-isobutyl-4,7-dioxo-11H-5,8-diaza-1(4,1)-triazolacyclotridecaphane-9-carboxylic acid (VD4087). $^1$H NMR (400 MHz, $CD_3OD$) □□=7.77 (br. s., 1H), 7.47-7.28 (m, 1H), 4.73 (br. s., 1H), 4.58 (d, J=9.0 Hz, 1H), 4.15 (d, J=8.2 Hz, 3H), 3.96 (br. s., 3H), 2.21 (br. s., 2H), 2.04 (s, 3H), 1.79 (br. s., 2H), 1.65-1.41 (m, 3H), 1.25-1.08 (m, 2H), 0.95-0.77 (m, 8H).

Methyl (7S,10S,13S)-10-((1-(tert-butoxycarbonyl)-1H-indol-3-yl)methyl)-13-((tert-butoxycarbonyl)amino)-9,12-dioxo-2-oxa-8,11-diaza-1(1,4)-benzenacyclotetradecaphane-7-carboxylate (VD4153). $^1$H NMR (400 MHz, $CDCl_3$) □□=8.12 (d, J=7.0 Hz, 1H), 7.73 (d, J=7.4 Hz, 2H), 7.39 (s, 2H), 7.34-7.29 (m, 2H), 7.06 (br. s., 2H), 6.77 (br. s., 1H), 6.15 (d, J=3.5 Hz, 1H), 5.35 (t, J=8.4 Hz, 2H), 4.33-3.91 (m, 4H), 3.56 (s, 3H), 3.35-3.17 (m, 2H), 2.83-2.60 (m, 1H), 1.84-1.71 (m, 1H), 1.66 (s, 9H), 1.39-1.36 (s, 9H), 1.29-1.18 (m, 2H), 1.10 (br. s., 2H).

Methyl (7S,10S,13S)-13-acetamido-10-((1-(tert-butoxycarbonyl)-1H-indol-3-yl)methyl)-9,12-dioxo-2-oxa-8,11-diaza-1(1,4)-benzenacyclotetradecaphane-7-carboxylate (VD4154). $^1$H NMR (400 MHz, $CDCl_3$) □□=8.23-8.09 (m, 1H), 7.79-7.68 (m, 1H), 7.42-7.32 (m, 1H), 7.22-6.99 (m, 2H), 6.76 (br. s., 2H), 6.52-6.23 (m, 2H), 5.45 (t, J=7.6 Hz, 1H), 4.61 (br. s., 1H), 4.41-4.27 (m, 1H), 4.23-3.96 (m, 2H), 3.73-3.61 (m, 2H), 3.58 (s, 3H), 3.39-3.19 (m, 1H), 3.10 (br. s., 2H), 2.90-2.74 (m, 1H), 2.65 (t, J=11.9 Hz, 1H), 2.08 (s, 3H), 1.80 (d, J=8.6 Hz, 1H), 1.66 (s, 2H), 1.58-1.54 (m, 4H), 1.46 (s, 9H), 1.24 (td, J=6.8, 14.2 Hz, 1H), 1.11 (br. s., 1H).

Methyl (7S,10R,13S)-10-((1-(tert-butoxycarbonyl)-1H-indol-3-yl)methyl)-13-((tert-butoxycarbonyl)amino)-9,12-dioxo-2-oxa-8,11-diaza-1(1,4)-benzenacyclotetradecaphane-7-carboxylate (VD4159). $^1$H NMR (400 MHz, $CDCl_3$) □□=8.13 (br. s., 1H), 7.88 (d, J=7.4 Hz, 1H), 7.78-7.68 (m, 1H), 7.48 (s, 1H), 7.37-7.29 (m, 3H), 7.21-7.00 (m, 3H), 6.92 (d, J=7.8 Hz, 2H), 6.76 (br. s., 1H), 6.29 (br. s., 1H), 5.79 (br. s., 1H), 5.32 (d, J=8.2 Hz, 2H), 4.57-4.24 (m, 5H), 4.16 (br. s., 2H), 3.66-3.47 (m, 4H), 3.37 (d, J=14.1 Hz, 1H), 2.70-2.56 (m, 1H), 1.95-1.80 (m, 1H), 1.67 (s, 9H), 1.48-1.43 (s, 9H), 0.99-0.82 (m, 2H).

(7S,10S,13S)-13-acetamido-N—((S)-1-(benzo[d]thiazol-2-yl)-5-guanidino-1-oxopentan-2-yl)-10-benzyl-9,12-dioxo-2-oxa-8,11-diaza-1(1,4)-benzenacyclotetradecaphane-7-carboxamide (VD4111). $^1$H NMR (400 MHz, DMSO-d6) δ=8.60 (d, J=5.9 Hz, 1H), 8.32-8.21 (m, 2H), 8.19 (d, J=7.0 Hz, 1H), 8.09 (d, J=9.4 Hz, 1 H), 7.74-7.63 (m, 2H), 7.53 (br. s., 1H), 7.07 (d, J=6.3 Hz, 2H), 6.97 (d, J=6.3 Hz, 3H), 6.71 (d, J=7.8 Hz, 1H), 6.37 (d, J=5.5 Hz, 1H), 5.47 (d, J=5.5 Hz, 1H), 4.44-4.25 (m, 2H), 3.99 (br. s., 2H), 3.16 (d, J=6.7 Hz, 2H), 2.93-2.83 (m, 2H), 2.69-2.59 (m, 4H), 1.97 (d, J=7.0 Hz, 2H), 1.88 (s, 4H), 1.81-1.56 (m, 4H), 1.45 (br. s., 4H), 1.37-1.15 (m, 4H).

(3S,6S,9R,Z)-3-acetamido-N—((S)-1-(benzo[d]thiazol-2-yl)-5-guanidino-1-oxopentan-2-yl)-6-isobutyl-4,7-dioxo-11H-5,8-diaza-1(4,1)-triazolacyclotridecaphane-9-carboxamide (VD4090). $^1$H NMR (400 MHz, DMSO-d6) δ8.57 (d, J=5.9 Hz, 1H), 8.27 (dd, J=7.8, 12.9 Hz, 2H), 8.12-8.01 (m, 1H), 7.88 (d, J=7.4 Hz, 2H), 7.75-7.65 (m, 1H), 7.50 (br. s., 1H), 5.46 (br. s., 1H), 4.68 (br. s., 1H), 4.57-4.46 (m, 2H), 4.39-4.21 (m, 4H), 3.13 (d, J=5.5 Hz, 3H), 2.03 (s, 3H), 1.95 (d, J=18.0 Hz, 2H), 1.88-1.82 (m, 2H), 1.79-1.52 (m, 6H), 1.44 (dd, J=6.3, 13.3 Hz, 2H), 1.33 (br. s., 1H), 0.94 (br. s., 2H), 0.80 (dd, J=6.1, 18.2 Hz, 6H).

(7S,10S,13S)-13-acetamido-N—((S)-1-(benzo[d]thiazol-2-yl)-5-guanidino-1-oxopentan-2-yl)-10-isobutyl-9,12-dioxo-2-oxa-8,11-diaza-1(1,4)-benzenacyclotetradecaphane-7-carboxamide (VD4072). $^1$H NMR (400 MHz, DMSO-d6) δ8.46 (d, J=6.3 Hz, 1H), 8.25 (dd, J=7.6, 17.0 Hz, 2H), 8.13 (d, J=7.0 Hz, 1H), 7.93 (d, J=9.0 Hz, 1H), 7.72-7.61 (m, 2H), 7.46 (br. s., 1H), 7.00 (d, J=7.0 Hz, 2H), 6.90 (d, J=7.8 Hz, 1H), 6.76 (d, J=7.8 Hz, 2H), 5.37 (br. s., 1H), 4.49 (d, J=4.7 Hz, 1H), 4.32 (d, J=8.6 Hz, 1H), 4.08-3.90 (m, 1H), 3.12 (d, J=5.9 Hz, 3H), 2.87 (d, J=7.8 Hz, 2H), 1.98-1.90 (m, 2H), 1.83 (s, 3H), 1.70 (br. s., 3H), 1.56 (br. s., 2H), 1.42-1.31 (m, 1H), 1.29-1.12 (m, 5H), 0.77-0.70 (m, 10H).

(10S,13S,16S,Z)-16-acetamido-N—((S)-1-(benzo[d]thiazol-2-yl)-5-guanidino-1-oxopentan-2-yl)-13-isobutyl-8,12,15-trioxo-2-oxa-7,11,14-triaza-1(1,4)-benzenacycloheptadecaphan-4-ene-10-carboxamide (VD4054). $^1$H NMR (400 MHz, DMSO-d6) □□□=8.48-8.36 (m, 1H), 8.34-8.23 (m, 2H), 8.17-8.08 (m, 1H), 7.69 (br. s., 2H), 7.47 (br. s., 1H), 7.02-6.89 (m, 2H), 6.78-6.68 (m, 1H), 5.68 (br. s., 1H), 5.49 (d, J=18.0 Hz, 2H), 5.03 (br. s., 1H), 4.75 (d, J=4.7 Hz, 1H), 4.61-4.49 (m, 2H), 4.38-4.27 (m, 1H), 3.80 (br. s., 1H), 3.13 (br. s., 4H), 1.96 (br. s., 2H), 1.87 (s, 3H), 1.75 (br. s., 3H), 1.66-1.45 (m, 4H), 1.37 (d, J=6.3 Hz, 2H), 0.87-0.73 (m, 11H).

(7S,10S,13S,E)-7-acetamido-N—((S)-1-(benzo[d]thiazol-2-yl)-5-guanidino-1-oxopentan-2-yl)-10-isobutyl-8,11-dioxo-2-oxa-9,12-diaza-1(1,4)-benzenacyclotetradecaphan-4-ene-13-carboxamide (VD4051). $^1$H NMR (400 MHz, DMSO-d6) □□□=8.79 (d, J=7.4 Hz, 1H), 8.33-8.25 (m, 2H), 8.20 (d, J=9.0 Hz, 1H), 8.13 (d, J=7.4 Hz, 1H), 7.75-7.64 (m, 2H), 7.53 (br. s., 1H), 7.07 (d, J=7.8 Hz, 2H), 6.67 (d, J=7.8 Hz, 1H), 5.60-5.36 (m, 2H), 4.72-4.54 (m, 2H), 4.37-4.25 (m, 1H), 4.17 (br. s., 1H), 3.16 (d, J=6.3 Hz, 2H), 2.98 (d, J=11.7 Hz, 3H), 1.79 (s, 3H), 1.64 (br. s., 4H), 1.41-1.32 (m, 3H), 1.24-1.14 (m, 4H), 0.83-0.72 (m, 10H).

Example 6. General Fmoc SPPS Procedure for Acetylated Dipeptide and Tripeptide Acids Leu-chlorotrityl chloride resin (0.618 meq/g) was swelled in dichloromethane for 30 min. The reagents were drained, and the resin washed 2× with 15 mL methylene chloride. The resin was then treated with the first Fmoc amino acid (2 eq), HBTU (2.5 eq), DIEA (3 eq) in DMF for 2 hours. Drained reagents and washed resin 4× with DMF. For tripeptides, the resin was then treated 2× with 20% piperidine/DMF for 20 min, drained and repeated. Washed resin 3× with DMF. The resin was then treated with second Fmoc amino acid (2 eq), HBTU (2.5 eq), DIEA (3 eq) in DMF for 2 hours. Drained reagents and washed resin 4× with DMF. The resin was then treated with 20% piperidine/DMF for 20 min, drained and repeated. Washed resin 3× with DMF. With either the dipeptide or tripeptide, the resin was then treated with acetic anhydride (2 eq) and DIEA (3 eq) in DMF for 2 hours. Drained reagents and washed resin 4× with DMF and 2× with methylene chloride. The resin was then treated with 25% HFIP/methylene chloride solution for 40 min, drained and repeated. The combined cleavage solutions were concentrated under vacuum to give the desired carboxylic acid.

hLeu-Chlorotrityl Chloride Resin hLeu-chlorotrityl chloride resin (0.17 meq/g) was swelled in dichloromethane for 30 min. The reagents were drained, and the resin washed 2× with 15 mL methylene chloride. The resin was then treated with the first Fmoc amino acid (2 eq), HBTU (2.5 eq), DIEA (3 eq) in DMF for 2 hours. Drained reagents and washed resin 4× with DMF. The resin was then treated 2× with 20% piperidine/DMF for 20 min, drained and repeated. Washed resin 3× with DMF. For tripeptides, the resin was then treated with second Fmoc amino acid (2 eq), HBTU (2.5 eq), DIEA (3 eq) in DMF for 2 hours. Drained reagents and washed resin 4× with DMF. The resin was then treated with 20% piperidine/DMF for 20 min, drained and repeated. Washed resin 3× with DMF. With either the dipeptide or tripeptide, the resin was then treated with acetic anhydride (2 eq) and DIEA (3 eq) in DMF for 2 hours. Drained reagents and washed resin 4× with DMF and 2× with methylene chloride. The resin was then treated with 25% HFIP/methylene chloride solution for 40 min, drained and repeated. The combined cleavage solutions were concentrated under vacuum to give the desired carboxylic acid.

Example 7. General Coupling of Tripeptide to H-Arg-Kbt HCl

A solution of the dipeptide or tripeptide acid (1.0 eq), prepared as described in Example 6, H-Arg(Pbf)-kbt HCl (1.0 eq), and HATU (1.1 eq) in DMF was cooled to ice bath temperature and then treated with DIEA (2.1 eq) and stirred under Ar(g) for 4 hours at ice bath temperature. The reaction was allowed to warm to room temperature and concentrated to dryness, then water was added forming a solid precipitate which was filtered off and dried. The solid was treated with a solution of 95% TFA/2.5% thioanisole/2.5% water for 2 hours. The reaction was concentrated in vacuo and purified by reversed phase C18 prep HPLC to give the desired compound. Table 1, shown below, depicts the compounds prepared by the methods of Examples 6 and 7. The synthesis of PK-1-18A1, PK-1-58A1, PK-1-54A1, PK-1-45A1 were reported in U.S. Patent Application Publication 2018/0066015, which is incorporated herein by reference.

TABLE 1
| ID | MW | Structure |
| --- | --- | --- |
| JH1140 | 817.03 | 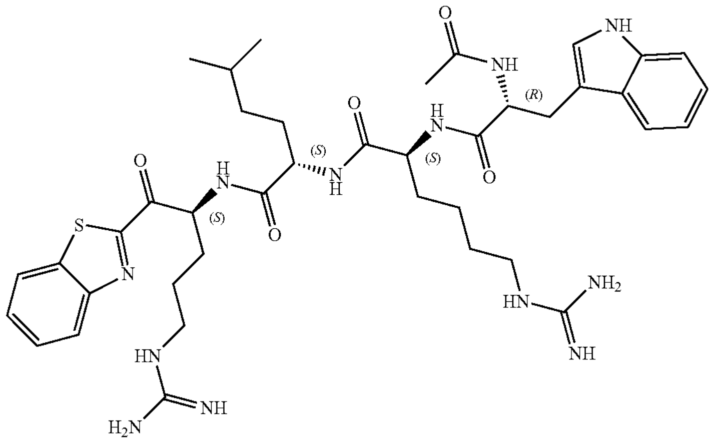 |
| JH1143-2 | 888.11 | 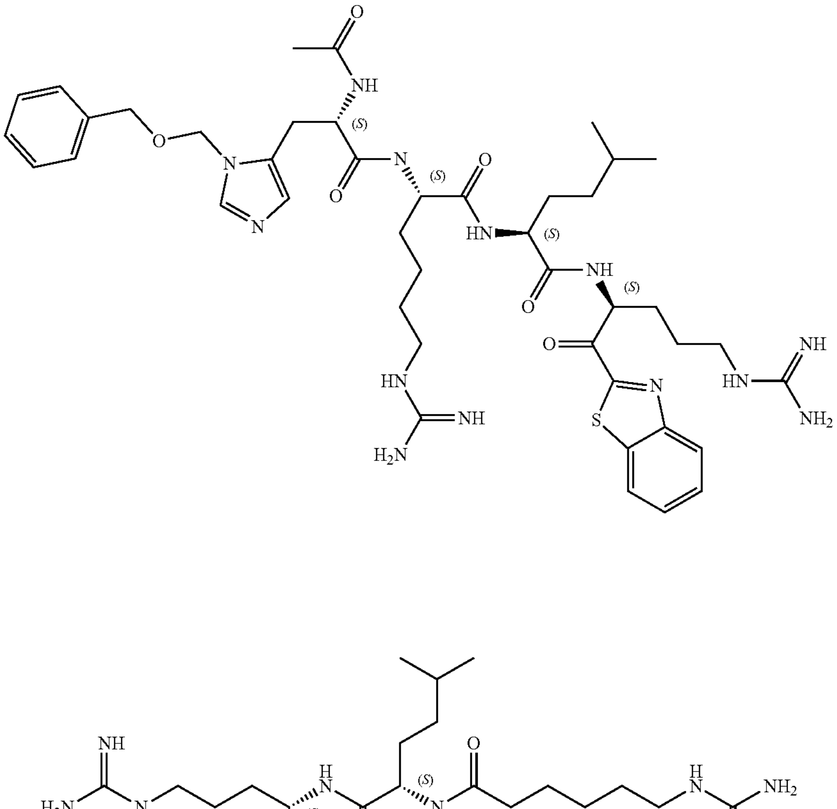 |
| JH1141-2 | 630.81 | 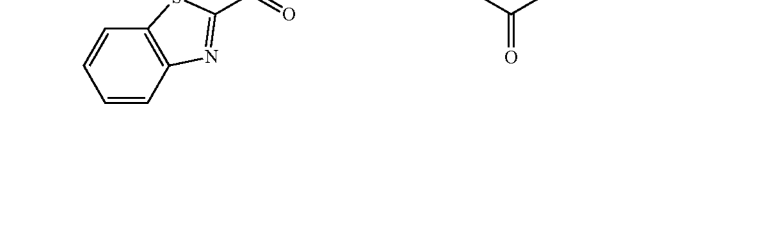 |

TABLE 1-continued
| ID | MW | Structure |
| --- | --- | --- |
| JH1142-2 | 717.89 | 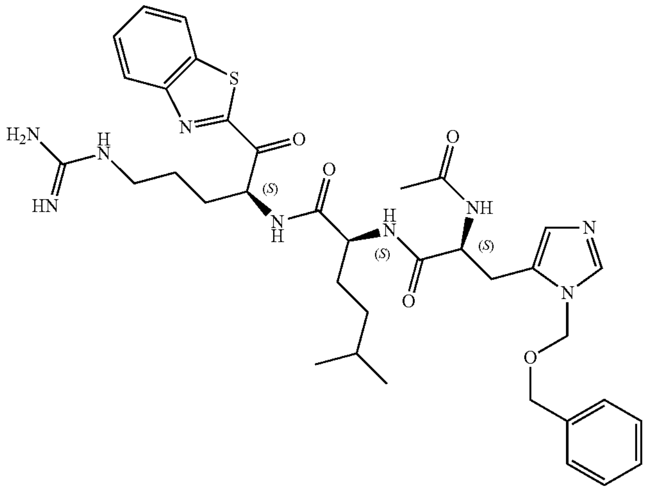 |
| JH1144 | 888.11 | 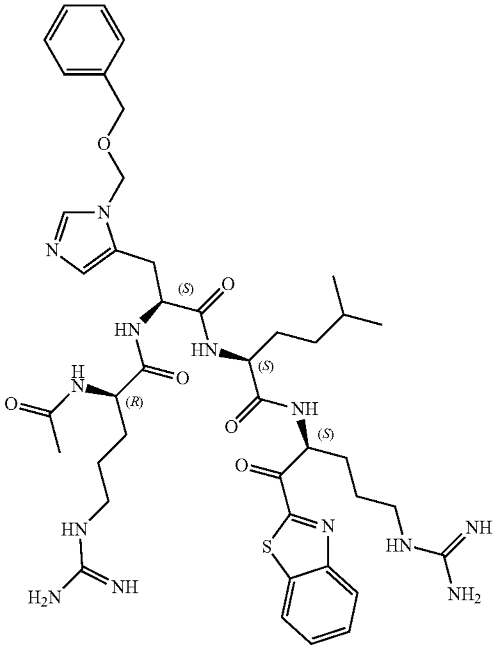 |

TABLE 1-continued
| ID | MW | Structure |
|---|---|---|
| MM1132-1 | 680.83 | 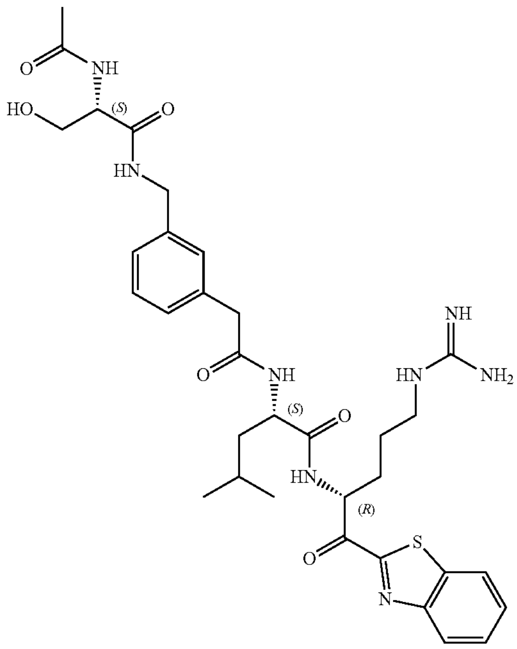 |
| MM1132-2 | 680.83 | 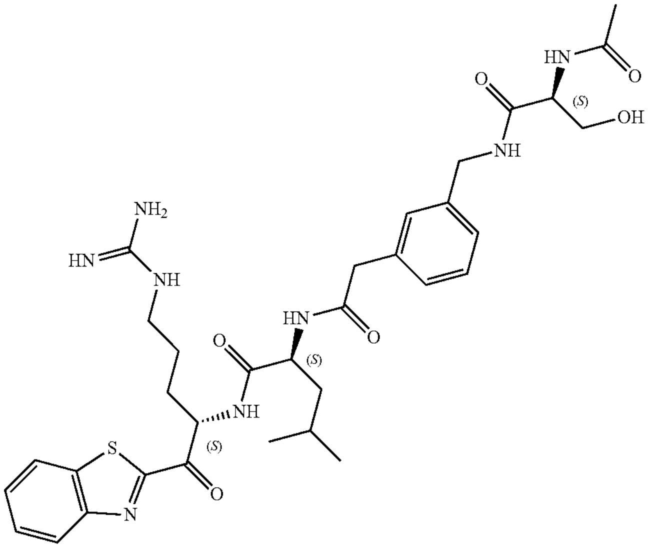 |
| MM1123 | 790.94 | 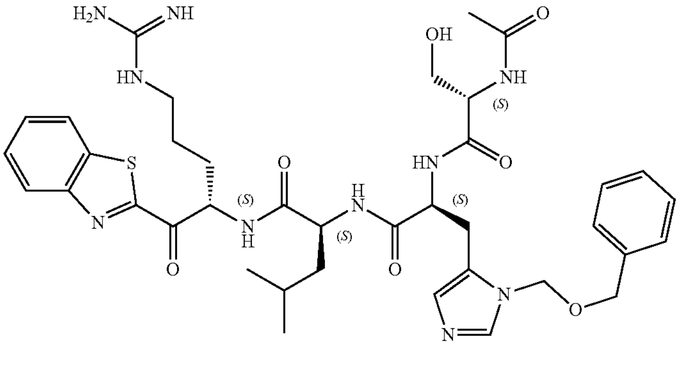 |

TABLE 1-continued
| ID | MW | Structure |
| --- | --- | --- |
| MM1180 | 867.98 | 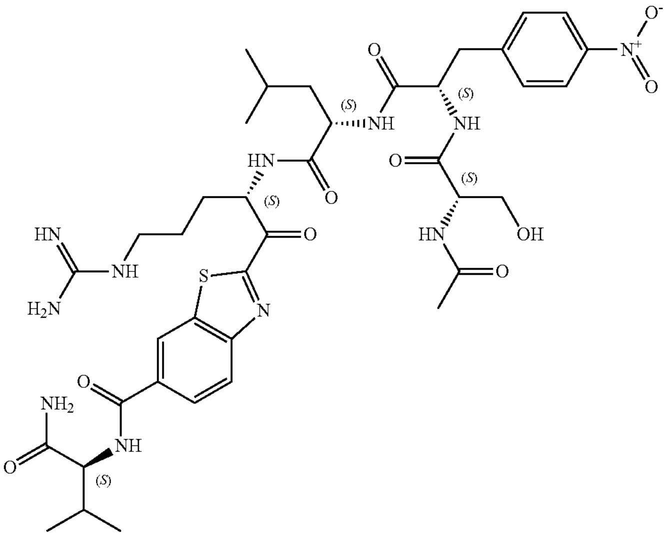 |
| MM1189 | 864.04 | 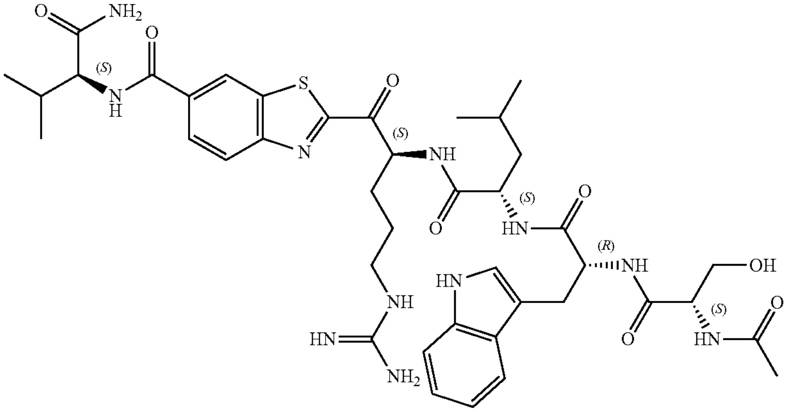 |
| JH1125-2 | 680.83 | 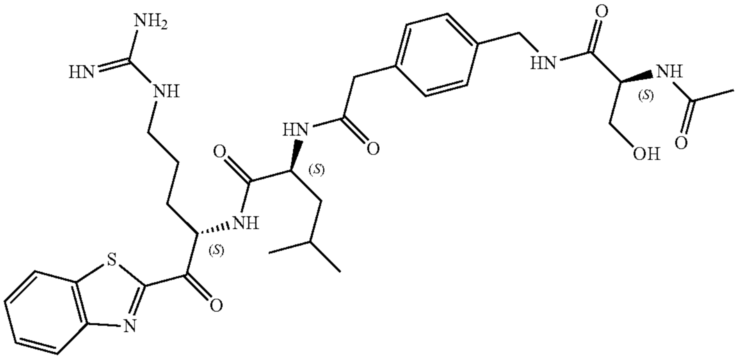 |

TABLE 1-continued
| ID | MW | Structure |
|---|---|---|
| JH1169 | 719.86 | 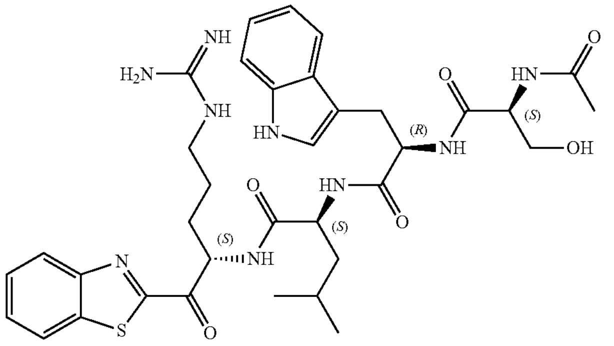 |
| PK-1-18A1 | 624.76 | 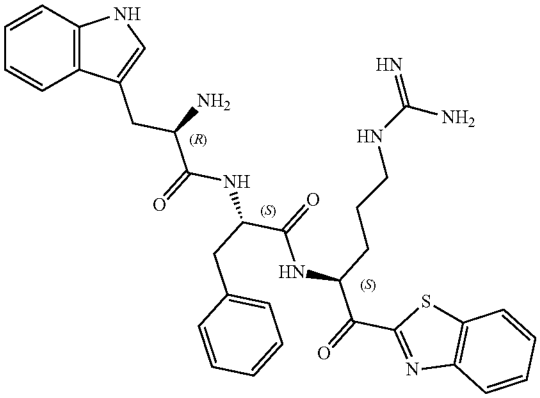 |
| PK-1-58A1 | 848.04 | 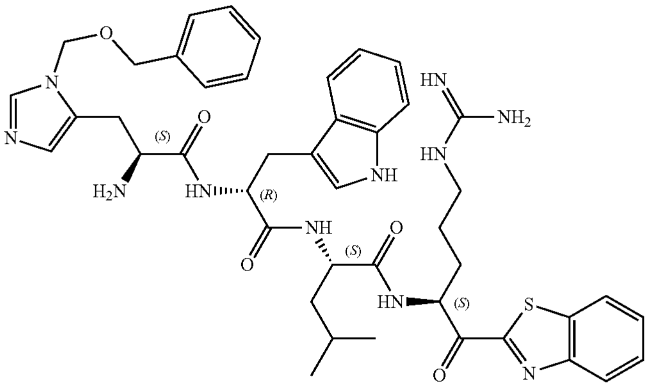 |
| PK-1-54A1 | 848.04 | 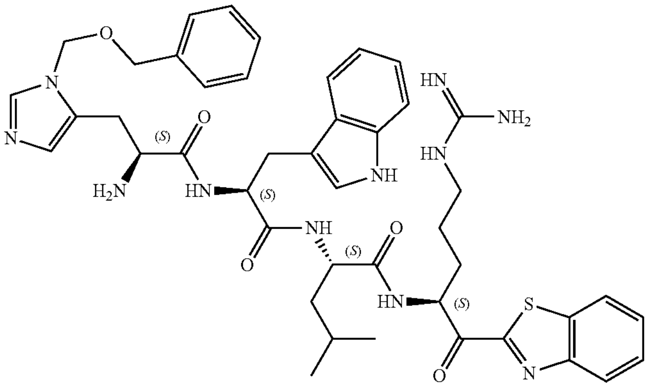 |

TABLE 1-continued
| ID | MW | Structure |
| --- | --- | --- |
| PK-1-45A1 | 668.77 | 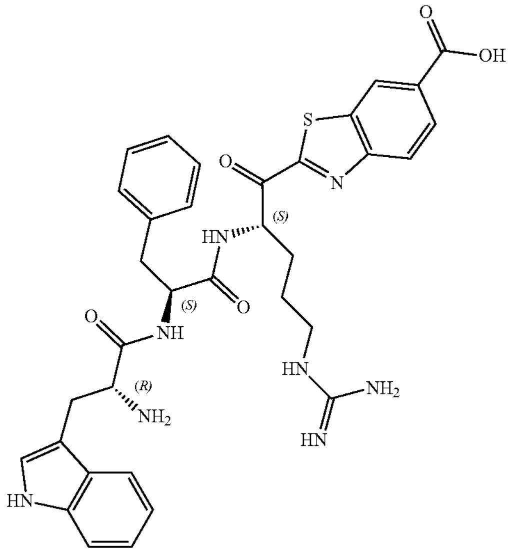 |
| PK-1-89A1 | 666.80 | 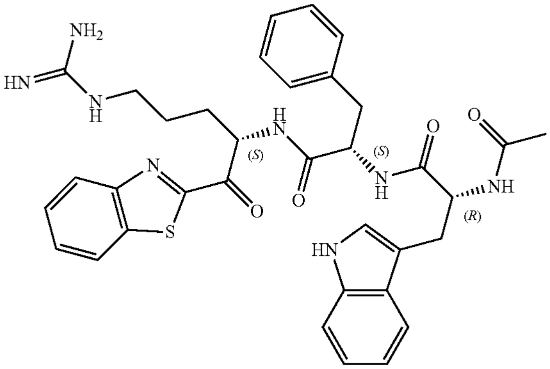 |
| PK-1-93A1 | 710.81 | 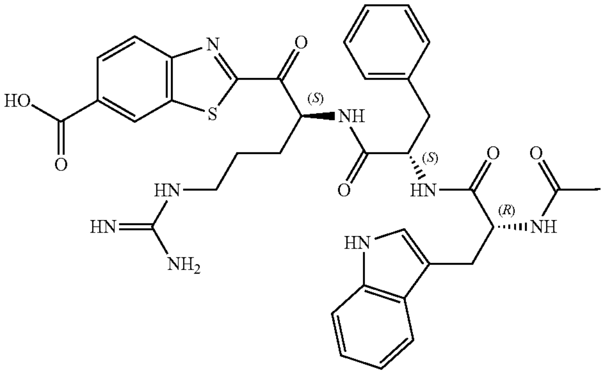 |

TABLE 1-continued

| ID | MW | Structure |
|---|---|---|
| ZFH6201-2 | 509.67 | 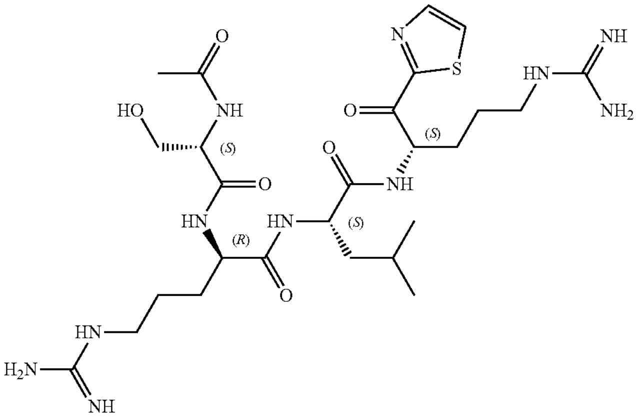 |

Example 8. Synthesis of Dipeptides

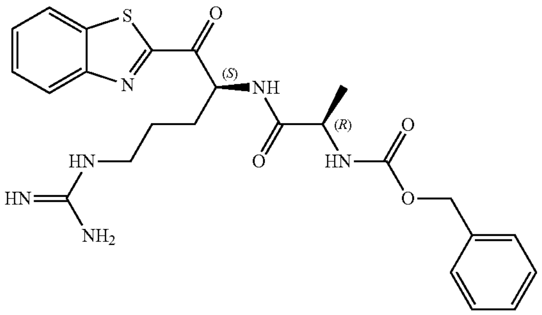

JH1162 (MW: 496.59)

A solution of Cbz-dAla-OH (14 mg, 0.046 mmol), H-Arg (Pbf)-kbt HCl (25 mg, 0.046 mmol), HATU (24 mg, 0.064 mmol) in DMF was cooled to ice bath temperature and then treated with DIEA (24 mg, 0.032 mL, 0.18 mmol)) and stirred under Ar(g) for 4 hours. The reaction was concentrated to dryness, water was added to form a solid which was filtered off and dried. The solid was then treated with a solution of 95% TFA/2.5% thioanisole/2.5% water for 2 hours. The reaction was concentrated and purified by prep HPLC to give the desired compound.

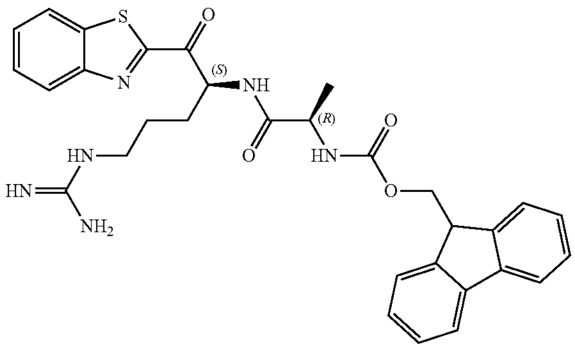

JH1161 (MW: 584.70)

A solution of Fmoc-dAla-OH (10 mg, 0.046 mmol), H-Arg(Pbf)-kbt HCl (25 mg, 0.046 mmol), HATU (24 mg, 0.064 mmol) in DMF was cooled to ice bath temperature and then treated with DIEA (24 mg, 0.032 mL, 0.18 mmol)) and stirred under Ar(g) for 4 hours. The reaction was concentrated to dryness, water was added to form a solid which was filtered off and dried. The solid was then treated with a solution of 95% TFA/2.5% thioanisole/2.5% water for 2 hours. The reaction was concentrated and purified by prep HPLC to give the desired compound.

Example 9. Biological Activity Data of Matriptase, Hepsin, HGFA, Factor Xa, and Thrombin The compounds prepared in Examples 1 to 8 were subjected to a series of inhibitions studies. The compounds were first tested in an HGFA enzymatic assay using the fluorogenic substrate Boc-QLR-AMC with a recombinant form of the HGFA serine protease domain.

Synthesis of Boc-QLR-AMC Fluorogenic Substrate:

Boc-R($NO_2$)-AMC: Under nitrogen atmosphere, pyridine (60 mL) was added into the round bottom flask containing Boc-R($NO_2$)—OH (4.653 g, 14.6 mmol) and 7-amino-4-methylcoumarin (3.829 g, 21.9 mmol). Diisopropylcarbodiimide (2.023 g, 16.0 mmol) was added and the mixture was stirred overnight. The mixture was filtered. The filtrate was concentrated then dried in vacuo. The resultant residue was purified by silica gel chromatography with dichloromethane/methanol combinations as eluent giving rise to Boc-R($NO_2$)-AMC (2.964 g) in 43% yield. MS (ESI): found $[M+H]^+$, 477.4.

HCl:$H_2N$—R($NO_2$)-AMC: 4 N HCl in dioxane (25 mL) was added into the round bottom flask containing Boc-R ($NO_2$)-AMC (2.964 g, 6.2 mmol) and the mixture stirred for 2 hours. The dioxane was removed in vacuo and to the resultant residue methanol was added then concentrated in vacuo three times, giving rise to the title compound in quantitative yield. MS (ESI): found $[M+H]^+$, 377.3.

Boc-QL-OH: Under nitrogen atmosphere, anhydrous DMF (10 mL) was added into the round bottom flask containing Boc-Q-OH (0.500 g, 2.0 mmol), H-L-OMe:HCl (0.406 g, 2.2 mmol), EDCI:HCl (0.467 g, 2.4 mmol), and HOBt (0.466 g, 3.1 mmol). N,N-diisopropylethylamine (0.787 g, 6.1 mmol) was added and the mixture was stirred overnight. The majority of DMF was removed in vacuo and to the resulting residue was added 20 mL of water. The precipitate was isolated by filtration then purified by silica gel chromatography with dichloromethane/methanol combinations as eluent to give Boc-QL-OMe (0.711 g) in 95% yield. MS (ESI): found $[M+Na]^+$, 396.4. Methanol/water (1:1 v/v, 10 mL) was added into the round bottom flask containing the Boc-QL-OMe (0.711 g, mmol) and LiOH (0.068 g, 2.8 mmol). The reaction was stirred overnight. The mixture was concentrated in vacuo and to the resulting residue was added 30 mL of water. 0.5 M HCl was added dropwise until pH=4.5 was reached, then the mixture was extracted three times with ethyl acetate. The ethyl acetate layers were collected, dried with $Na_2SO_4$, then concentrated in vacuo to give rise to Boc-QL-OH (0.603 g) in 49% yield. MS (ESI): found $[M+Na]^+$, 373.4.

Boc-QLR($NO_2$)-AMC: Under nitrogen atmosphere, anhydrous DMF (10 mL) was added into the round bottom flask containing Boc-QL-OH (0.603 g, 1.7 mmol), HCl·$H_2N$—R($NO_2$)-AMC (0.406 g, 2.2 mmol), EDCI:HCl (0.322 g, 1.7 mmol), and HOBt (0.257 g, 1.7 mmol). N,N-diisopropylethylamine (0.904 g, 7.0 mmol) was added and the mixture was stirred overnight. The majority of DMF was removed in vacuo and to the resulting residue was added 20 mL of water. The mixture was extracted three times with ethyl acetate. The ethyl acetate layers were collected, dried with $Na_2SO_4$, then concentrated in vacuo. The resultant residue was purified by silica gel chromatography with dichloromethane/methanol combinations as eluent giving rise to Boc-QLR($NO_2$)-AMC (0.250 g) in 20% yield. MS (ESI): found $[M+H]^+$, 718.5.

Boc-QLR-AMC: Into the solution of Boc-QLR($NO_2$)-AMC (0.250 g, 0.35 mmol) in MeOH (15 mL) was added Pd/C (10%) (0.111 g) followed by several drops of acetic acid. The mixture was stirred under hydrogen atmosphere for 21 hours. Additional Pd/C(10%) (0.184 g) was added with a few drops of acetic acid. The mixture was stirred for 24 hours, then filtered. The filtrate was concentrated. ⅕ of the resulting residue was purified by HPLC (C18, 15*150 mm column; eluent: acetonitrile/water (0.05% TFA)) to give the title compound (0.037 g) in 78% yield. $^1H$ NMR (400 MHz, METHANOL-$d_4$) δ ppm 0.92 (d, J=6.30 Hz, 3H) 0.98 (d, J=6.26 Hz, 3H) 1.45 (s, 9H) 1.54-2.14 (m, 9H) 2.25-2.41 (m, 2H) 2.49 (s, 3H) 3.17-3.29 (m, 2H) 4.00-4.14 (m, 1H) 4.34-4.47 (m, 1H) 4.49-4.61 (m, 1H) 6.28 (s, 1H) 7.46-7.60 (m, 1H) 7.71-7.80 (m, 1H) 7.80-7.89 (m, 1H). MS (ESI): found: $[M+H]^+$, 673.6.

Expression and purification of N-terminal His-tag HGFA serine protease domain: Using standard primers and standard PCR protocols, the nucleotide sequence encoding amino acids 373-655 of HGFA was synthesized. This PCR product was cloned into the SfoI-HindIII sites of a modified pFastBac HT baculovirus expression vector (Addgene, Cambridge, MA). This vector contains a six amino His tag followed by a seven amino spacer and a seven amino acid TEV cleavage site placed immediately downstream of the honey bee melittin signal peptide. Using a modified Bac to Bac Expression System (Life Technologies, Carlsbad, CA), recombinant HGFA bacmids were obtained by transforming DH10Bac *Escherichia coli* cells. To obtain HGFA containing baculovirus, purified bacmids were transfected into Sf9 insect cells. After 5 days in culture at 27° C., media was harvested from transfected Sf9 cells. This media was used to prepare baculovirus infected insect cells (BIICs). These BIIICs were used to infect High 5 insect cells. Four days post infection, media was harvested, and recombinant protein was prepared as follows. Media was chilled to 4° C. and spun at 4000×g for 20 minutes (all subsequent steps were performed at 4° C. unless noted). Clarified media was passed first through a Whatman GF/B 1 um (#1821-047, GE Healthcare Life Sciences, Piscataway, NJ) and then a 0.22 μm PES membrane (#99955, TPP Techno Plastic Products AG, Trasadingen, Switzerland) and then concentrated using a Pall Centramate tangential flow system and Centramate T-series Cassette (#OS010T12, Pall Corporation, Port Washington, NY). Concentrated media was then buffer exchanged in two steps, five volumes of 50 mM Na-phosphate, 500 mM NaCl, pH 6.2, followed by five volumes of 50 mM Na-phosphate, 500 mM NaCl, pH 7.5. The concentrated and buffered exchanged insect cell media was again filtered as above and made 25 mM imidazole (#I202, Sigma-Aldrich, St. Louis, MO) and was mixed with nickel agarose beads (#H-321-25, Gold Biotechnology, Inc., St. Louis MO). After mixing this slurry for 12 hours, nickel agarose beads were allowed to settle by gravity and then loaded into a column. Beads were washed with buffer (25 mM Na-phosphate, 500 mM NaCl, 25 mM imidazole, pH 8) and the bound protein eluted using (25 mM Na-phosphate, 500 mM NaCl, 250 mM imidazole, pH 8). Using a Amicon Ultra-4 Centrifugal filters (#UFC801008, Merck Millipore, Ltd., Tullagreen, Ireland), peak protein fractions were concentrated and run over a Superdex-200 10/300 GL column (GE Healthcare Life Sciences, Piscataway, NJ) in 10 mM Tris, 200 mM NaCl, 0.2 mM EDTA, pH 8. HGFA containing fractions were pooled, concentrated, made 50% glycerol, and stored at minus 20° C. Protein was quantitated using a modified Lowry protein assay (#500-0006, Bio-Rad Laboratories, Hercules, CA) and specific activity determined using Boc-QLR-AMC substrate.

Chromogenic kinetic enzyme assay of HGFA activity: The compounds (0-50 μM final concentration in reaction) were diluted in DMSO (2% DMSO final concentration in reaction) and then mixed with recombinant HGFA (12.5 nM final concentration in reaction) in TNC buffer (25 mM Tris, 150 mM NaCl, 5 mM $CaCl_2$, 0.01% TRITON X-100, pH 8). After incubating for thirty minutes at 25° C., chromogenic substrate, Pefachrome FVIIa, (#093-01, Enzyme Research Laboratories, South Bend, IN)) was added to a final concentration of 250 μM in a final reaction volume of 40 microliters. Changes in absorbance at 405 nm were measured over a 1 hour time period in a Biotek Synergy 2 plate reader (Winnoski, VT). Using the Gen 5 software program (Biotek, Winnoski, VT), a four-parameter curve fit was used to determine the inhibitor $IC_{50}$s from a plot of the mean reaction velocity versus the inhibitor concentration. The $IC_{50}$ values represent the average of three or more separate experimental determinations.

Chromogenic kinetic enzyme assays of thrombin and factor Xa activity: Compounds (0-20 μM final concentration) were serially diluted in DMSO (2% DMSO final concentration) and then mixed with recombinant thrombin (0.15 nM final concentration) or factor Xa (0.35 nM final concentration) in TNC buffer (25 mM Tris, 150 mM NaCl, 5 mM $CaCl_2$, 0.01% Triton X-100, pH 8) using clear 384 well plates. After incubating for 30 minutes at 25° C., the chromogenic substrate (S2238; D-Phe-Pip-Arg-pNA) for thrombin ($K_m$=14.5 μM) or (52222; Bz-Ile-Glu-Gly-Arg-pNA) for Factor Xa ($K_m$=200 μM) was added to a final concentration of $K_m$ (4×$K_m$ (50 μM) for thrombin) in a final reaction volume of 40 microliters. Changes in absorbance at 405 nm were measured over time in a Biotek Synergy 2 plate (Winnoski, VT). Using GraphPad Prism (GraphPad Software, San Diego, CA), a four-parameter curve fit was used to determine the inhibitor $IC_{50}$s from a plot of the mean reaction velocity versus the inhibitor concentration. The $IC_{50}$ values represent the average of three or more separate experimental determinations. Apparent $K_i$ values were calculated from the $IC_{50}$ values using the Cheng and Prusoff equation ($K_i=IC_{50}/(1+[S]/K_m)$).

Fluorescent kinetic enzyme assays of HGFA, matriptase, and hepsin activity: Compounds (0-20 μM final concentration in reaction) were diluted in DMSO (2% DMSO final concentration in reaction) and then mixed with either recombinant HGFA serine protease domain, matriptase (#3946-SE-010, R&D Systems, Minneapolis, Minnesota), or activated hepsin* (#4776-SE-010, R&D Systems, Minneapolis, Minnesota) in black 384 well plates (Corning #3575. Corning, NY). The final assay concentration for HGFA, matriptase, and hepsin, were 6.25 nM, 0.2 nM, and 0.3 nM, respectively in TNC buffer (25 mM Tris, 150 mM NaCl, 5 mM $CaCl_2$, 0.01% Triton X-100, pH 8). After thirty minutes of incubation at room temperature, Boc-QLR-AMC substrate was added (HGFA assay) or Boc-QAR-AMC substrate (matriptase, and hepsin assays). Fluorescence (excitation at 380 nm and emission at 460 nm) was kinetically measured at room temperature over a 1 hour time period using a Biotek Synergy 2 plate reader (Winnoski, VT). From a plot of the mean reaction velocity versus the inhibitor concentration, a non-linear four parameter curve fit was performed using GraphPad Prism (GraphPad Software, San Diego, CA) to determine inhibitor $IC_{50}$s. The $IC_{50}$ values were determined from the average of three or more separate experimental determinations. Apparent $K_i$ values were calculated using the Cheng and Prusoff equation ($K_i=IC_{50}/(1+[S]/K_m)$).

*Hepsin Activation: Hepsin was diluted 5.5-fold in TNC buffer (25 mM Tris, 150 mM NaCl, 5 mM $CaCl_2$, 0.01% Triton X-100, pH 8) and incubated at 37° C. After twenty-four hours, the Hepsin was diluted in glycerol to 50%. This stock Hepsin (1.2 M) was stored in a −20° C. freezer and diluted in TNC buffer for use in the hepsin assay described above.

Chromogenic Kinetic Enzyme Assay of Thrombin and Factor Xa: Inhibitors (11-pt serial dilutions, 0-20 μM final concentration) were serially diluted in DMSO (2% DMSO final concentration) and then mixed with recombinant thrombin (0.15 nM final concentration) (#1473-SE-010, R&D Systems, Minneapolis, Minnesota) or Factor Xa (0.35 nM final concentration) (#1063-SE-010, R&D Systems, Minneapolis, Minnesota) in TNC buffer (25 mM Tris, 150 mM NaCl, 5 mM $CaCl_2$, 0.01% Triton X-100, pH 8) using clear 384 well plates. After incubating for 30 minutes at 25° C., the chromogenic substrate (S2238; D-Phe-Pip-Arg-pNA) for thrombin ($K_m$=14.5 μM) or (S2222; Bz-1l*e*-Glu-Gly-Arg-pNA) for Factor Xa ($K_m$=200 μM) was added to a final concentration of $K_m$ (4×$K_m$ (50 μM) for thrombin) in a final reaction volume of 40 microliters. Changes in absorbance at 405 nm were measured over time in a Biotek Synergy 2 plate (Winnoski, VT). Using GraphPad Prism version 6.04 software program, (GraphPad Software, San Diego, CA, graphpad.com), a four parameter curve fit was used to determine the inhibitor $IC_{50}$s from a plot of the mean reaction velocity versus the inhibitor concentration.

The results of these assays are presented in Table 2.

TABLE 2
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD1135 | 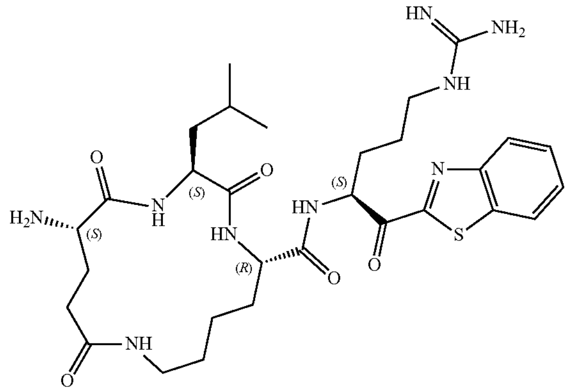 | 17500 | 0.23 | 2.6 | | | 643.8 | 644.5 |
| VD1185 | 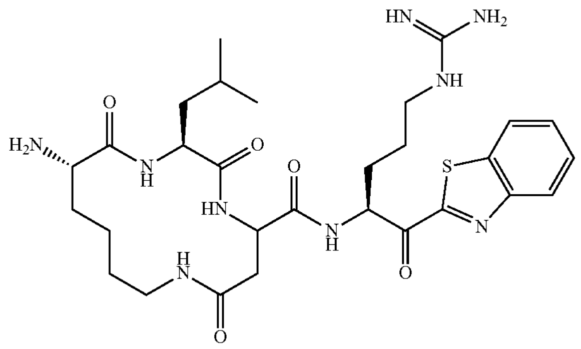 [SMILES: CC(C)C[C@@H]1NC(=O)[C@@H](N)CCCCNC(=O)CC(C(=O)N[C@@H](CCCNC(=N)N)C(=O)c2nc3ccccc3s2)NC1=O] | >20,000 | 1.1 | 92.0 | | | 629.8 | 630.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD2055 | 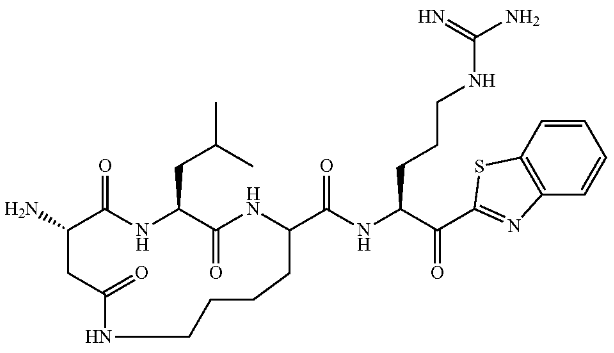 [SMILES: CC(C)C[C@@H]1NC(=O)[C@@H](N)CC(=O)NCCCCC(C(=O)N[C@@H](CCCNC(=N)N)C(=O)c2nc3ccccc3s2)NC1=O] | 11421 | 0.86 | 0.46 | nd | 1549 | 629.8 | 630.4 |
| VD2056 | 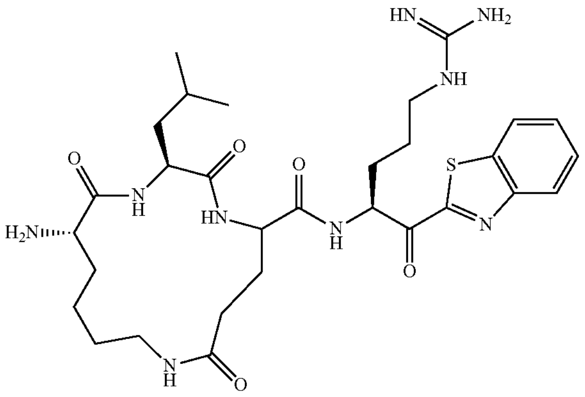 [SMILES: CC(C)C[C@@H]1NC(=O)[C@@H](N)CCCCNC(=O)CCC(C(=O)N[C@@H](CCCNC(=N)N)C(=O)c2nc3ccccc3s2)NC1=O] | >20,000 | 11.5 | 11.9 | | | 643.8 | 644.33 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD2064 | 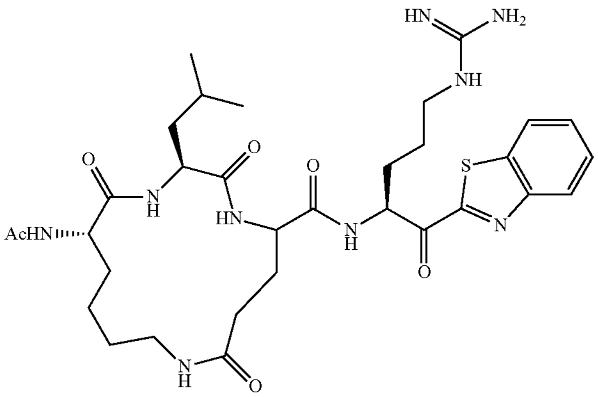 [SMILES: CC(=O)N[C@H]1CCCCNC(=O)CCC(C(=O)N[C@@H](CCCNC(=N)N)C(=O)c2nc3ccccc3s2)NC(=O)[C@H](CC(C)C)NC1=O] | 4466 | 4.4 | 1.7 | >20,000 | 723 | 685.9 | 686.6 |
| VD2167 | 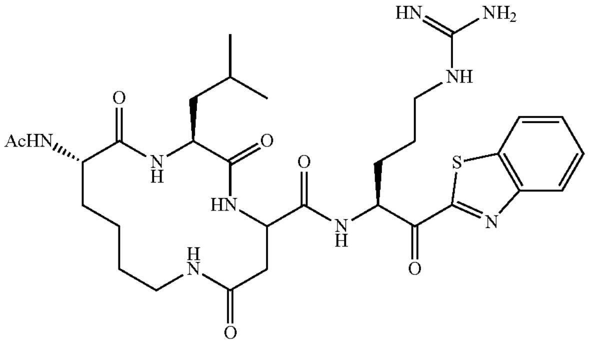 [SMILES: CC(=O)N[C@H]1CCCCNC(=O)CC(C(=O)N[C@@H](CCCNC(=N)N)C(=O)c2nc3ccccc3s2)NC(=O)[C@H](CC(C)C)NC1=O] | >20,000 | 19.6 | 25.1 | >20,000 | 1161 | 671.8 | 672.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD2169 | 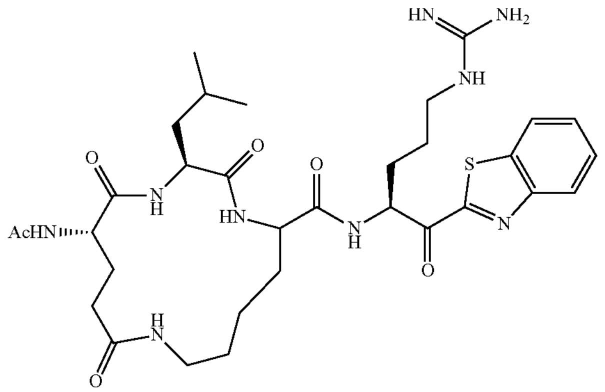 [SMILES: CC(=O)N[C@H]1CCC(=O)NCCCCC(C(=O)N[C@@H](CCCNC(=N)N)C(=O)c2nc3ccccc3s2)NC(=O)[C@H](CC(C)C)NC1=O] | >20,000 | 3.1 | 8.4 | >20,000 | 1714 | 685.9 | 686.5 |
| VD2173 | 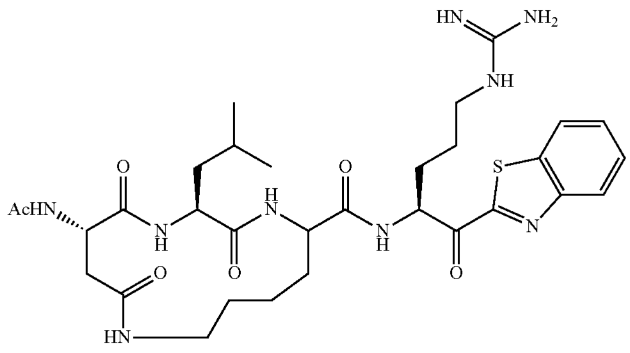 [SMILES: CC(=O)N[C@H]1CC(=O)NCCCCC(C(=O)N[C@@H](CCCNC(=N)N)C(=O)c2nc3ccccc3s2)NC(=O)[C@H](CC(C)C)NC1=O] | 3588 | 0.28 | 8.4 | 699.5 | 564 | 671.8 | 672.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD3056 | 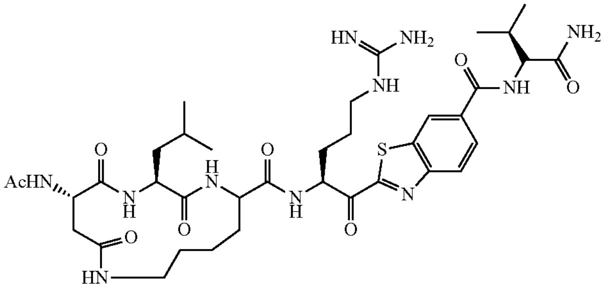 | 5378 | 11.2 | 5.4 | 33.9 | 118 | 814.0 | 814.6 |
| VD3076 | 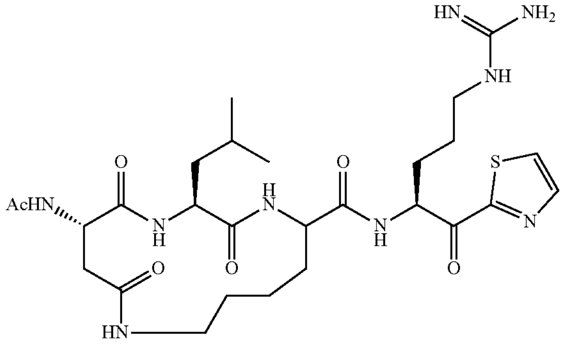 [SMILES: CC(=O)N[C@H]1CC(=O)NCCCCC(C(=O)N[C@@H](CCCNC(=N)N)C(=O)c2nccs2)NC(=O)[C@H](CC(C)C)NC1=O] | >20,000 | 41.3 | 136 | 7939 | 1363 | 621.8 | 622.5 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| VD2109 | 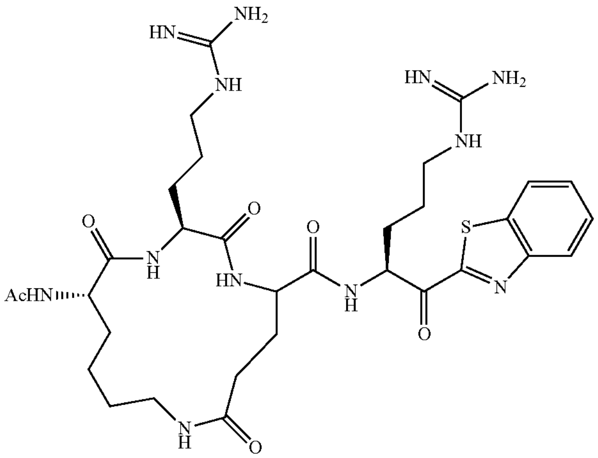 [SMILES: CC(=O)N[C@H]1CCCCNC(=O)CCC(C(=O)N[C@@H](CCCNC(=N)N)C(=O)c2nc3ccccc3s2)NC(=O)[C@H](CCCNC(=N)N)NC1=O] | 5046 | 0.13 | 0.08 | | | 729.6 | |
| VD2109A | 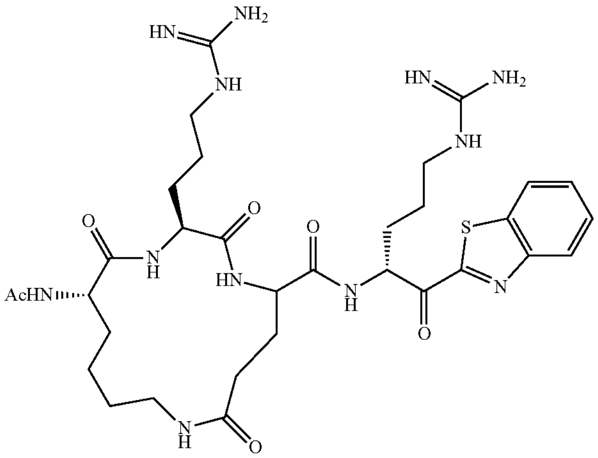 [SMILES: CC(=O)N[C@H]1CCCCNC(=O)CCC(C(=O)N[C@H](CCCNC(=N)N)C(=O)c2nc3ccccc3s2)NC(=O)[C@H](CCCNC(=N)N)NC1=O] | 4092 | 0.19 | 0.14 | | | 728.87 | 729.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD2109B | 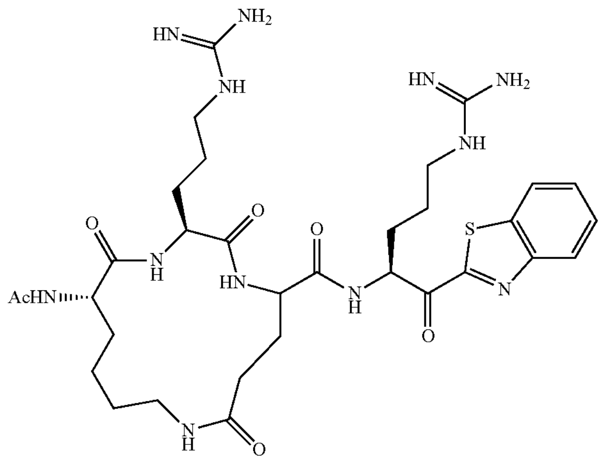 [SMILES: CC(=O)N[C@H]1CCCCNC(=O)CCC(C(=O)N[C@@H](CCCNC(=N)N)C(=O)c2nc3ccccc3s2)NC(=O)[C@H](CCCNC(=N)N)NC1=O] | 2523 | 0.07 | 0.04 | >20000 | 155 | 728.87 | 729.6 |
| VD3112 | 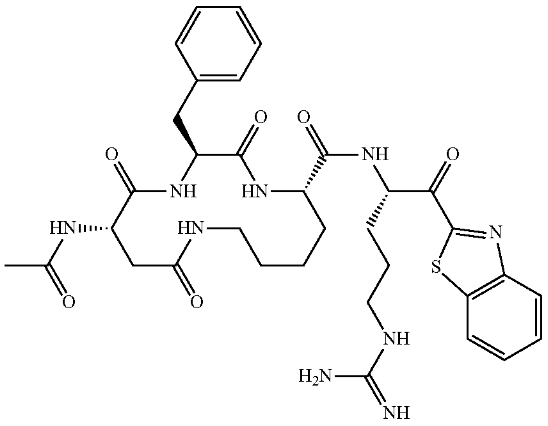 [SMILES: CC(=O)N[C@H]1CC(=O)NCCCC[C@@H](C(=O)N[C@@H](CCCNC(=N)N)C(=O)c2nc3ccccc3s2)NC(=O)[C@H](Cc2ccccc2)NC1=O] | 3173 | 3.4 | 17.4 | 1087 | 1526 | 705.8 | 706.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD3141 | 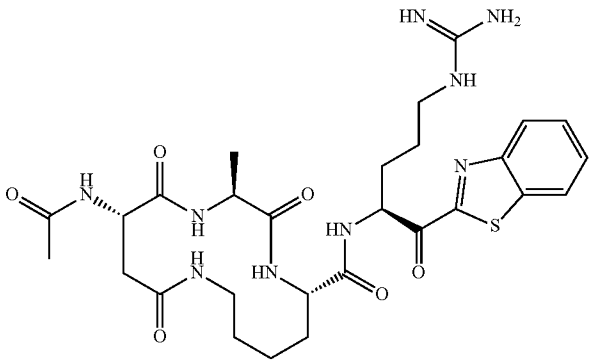 [SMILES: CC(=O)N[C@H]1CC(=O)NCCCC[C@@H](C(=O)N[C@@H](CCCNC(=N)N)C(=O)c2nc3ccccc3s2)NC(=O)[C@H](C)NC1=O] | 13705 | 2.5 | 8.8 | >20000 | >20000 | 629.7 | 630.4 |
| VD3152 | 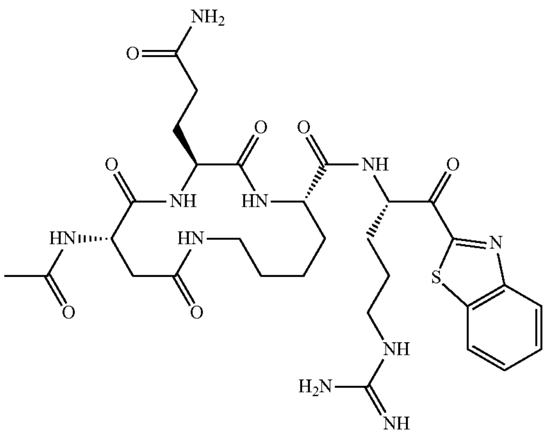 [SMILES: CC(=O)N[C@H]1CC(=O)NCCCC[C@@H](C(=O)N[C@@H](CCCNC(=N)N)C(=O)c2nc3ccccc3s2)NC(=O)[C@H](CCC(N)=O)NC1=O] | 16108 | 7.7 | 22.2 | >20000 | >20000 | 686.8 | 687.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD3157 | 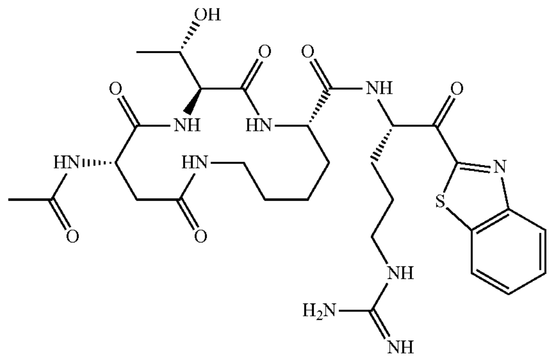 [SMILES: CC(=O)N[C@H]1CC(=O)NCCCC[C@@H](C(=O)N[C@@H](CCCNC(=N)N)C(=O)c2nc3ccccc3s2)NC(=O)[C@H]([C@H](C)O)NC1=O] | 11777 | 3.7 | 5.8 | >20000 | 13341 | 659.8 | 660.5 |
| VD3158 | 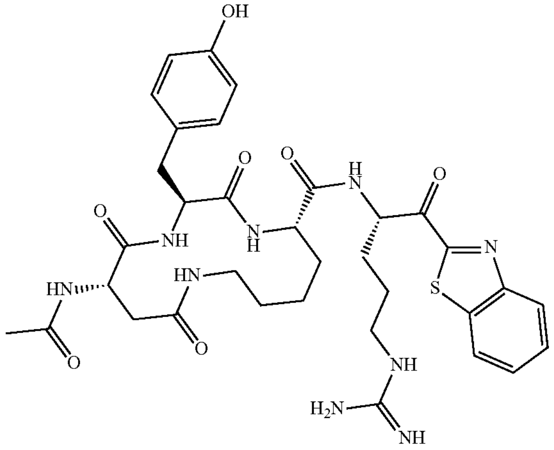 [SMILES: CC(=O)N[C@H]1CC(=O)NCCCC[C@@H](C(=O)N[C@@H](CCCNC(=N)N)C(=O)c2nc3ccccc3s2)NC(=O)[C@H](Cc2ccc(O)cc2)NC1=O] | >20,000 | 6.1 | 44.0 | >20000 | 16962 | 721.8 | 722.5 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| VD3166 | 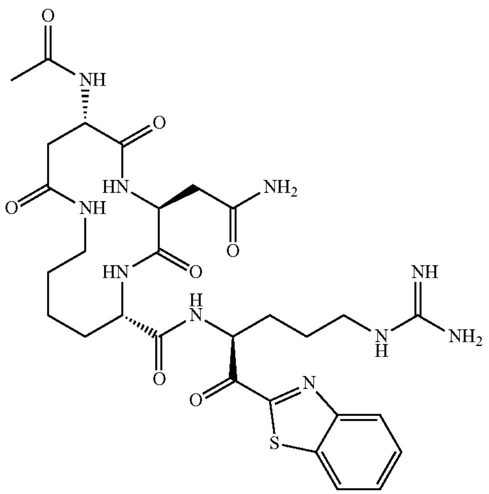 [SMILES: CC(=O)N[C@H]1CC(=O)NCCCC[C@@H](C(=O)N[C@@H](CCCNC(=N)N)C(=O)c2nc3ccccc3s2)NC(=O)[C@H](CC(N)=O)NC1=O] | 15837 | 3.8 | 10.1 | >20000 | 4653 | 672.8 | 673.5 |
| VD3167 | 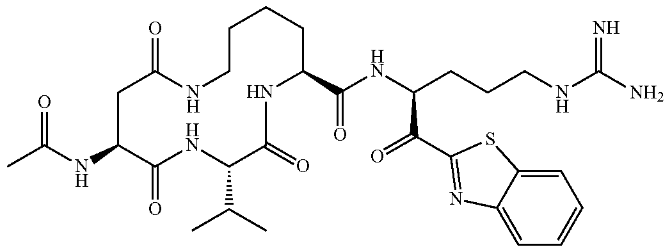 [SMILES: CC(=O)N[C@H]1CC(=O)NCCCC[C@@H](C(=O)N[C@@H](CCCNC(=N)N)C(=O)c2nc3ccccc3s2)NC(=O)[C@H](C(C)C)NC1=O] | 1832 | 3.2 | 7.8 | >20000 | 1514 | 657.8 | 658.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD3173 | 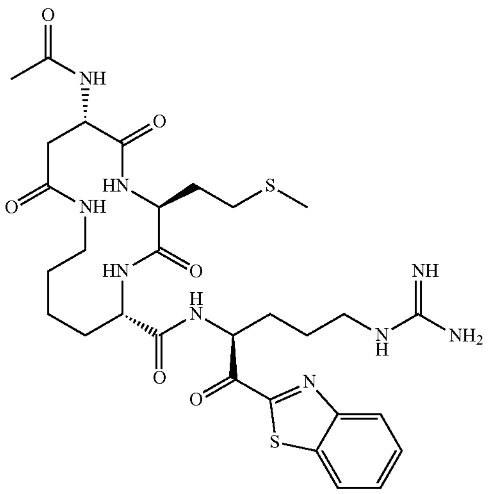 [SMILES: CSCC[C@@H]1NC(=O)[C@@H](NC(C)=O)CC(=O)NCCCC[C@@H](C(=O)N[C@@H](CCCNC(=N)N)C(=O)c2nc3ccccc3s2)NC1=O] | 3240 | 0.98 | 5.9 | >20000 | 1395 | 689.9 | 690.4 |
| VD3174 | 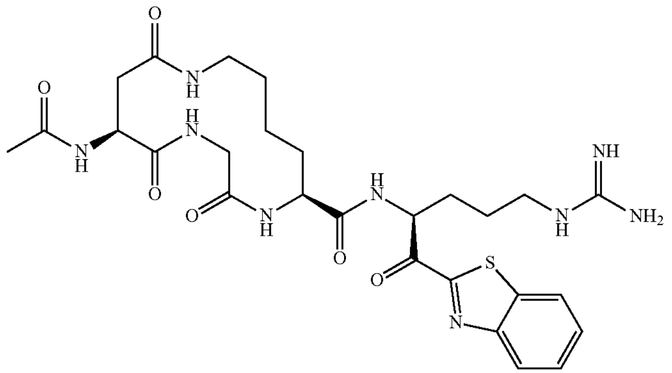 [SMILES: CC(=O)N[C@H]1CC(=O)NCCCC[C@@H](C(=O)N[C@@H](CCCNC(=N)N)C(=O)c2nc3ccccc3s2)NC(=O)CNC1=O] | 4312 | 6.3 | 5.9 | >20000 | 6183 | 615.7 | 616.4 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4010 | 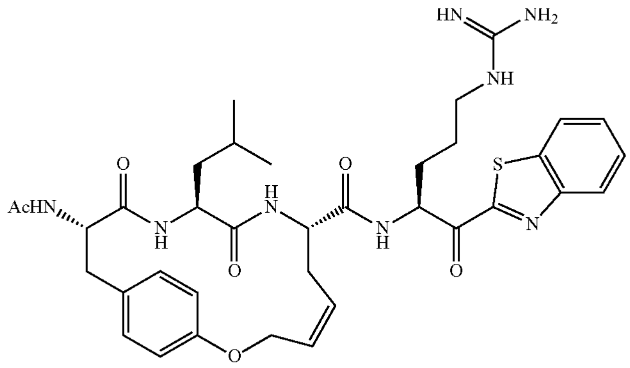 [SMILES: CC(=O)N[C@H]1Cc2ccc(cc2)OC/C=C\C[C@@H](C(=O)N[C@@H](CCCNC(=N)N)C(=O)c2nc3ccccc3s2)NC(=O)[C@H](CC(C)C)NC1=O] | 11.15 | 3.238 | 0.1413 | >20000 | 121.70 | 718.9 | 719.5 |
| VD4010A | 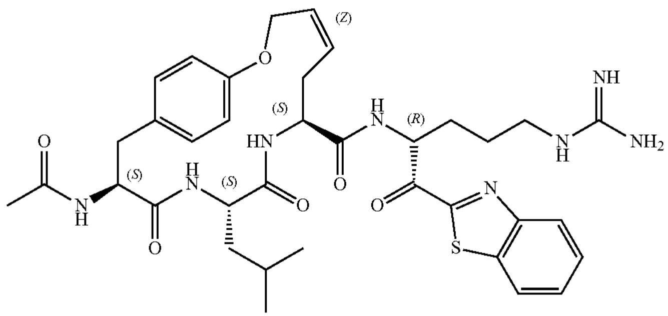 | 196.93 | 31.61 | 1.14 | | | 718.9 | |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| VD4118B | 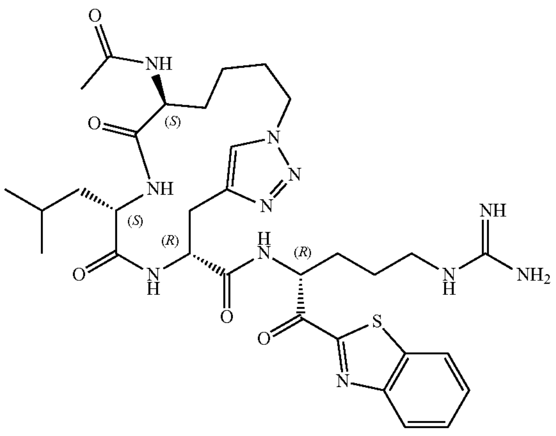 | 10872 | 91.21 | 136.9 | >20000 | 9544.3 | 695.8 | 696.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4118 | 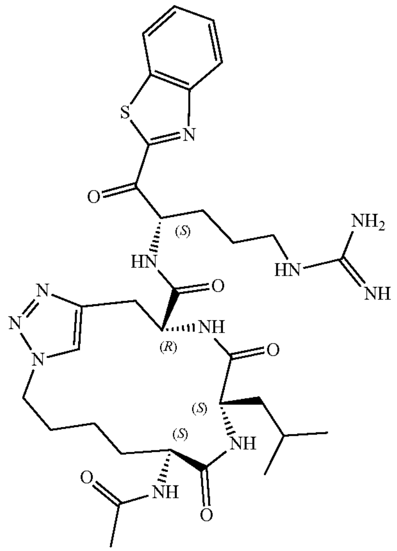 | 15646 | 19.5 | 117.1 | >20000 | 1934.5 | 695.8 | 696.6 |
| VD4111A | 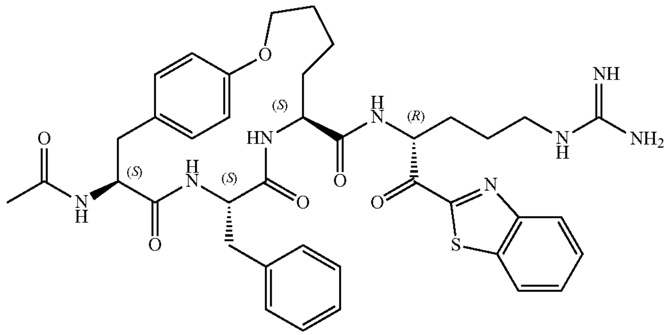 | 3277 | 329.9 | 12.72 | | | 754.91 | 755.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| --- | --- | --- | --- | --- | --- | --- | --- | --- |
| VD4111 | 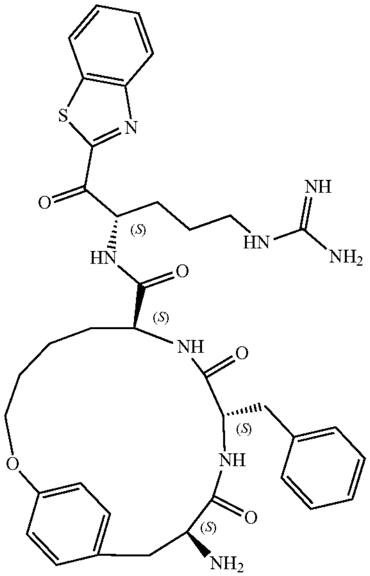 | 11.95 | 16.98 | 0.3314 | >20000 | 8697 | 754.91 | 755.5 |
| VD4090 | 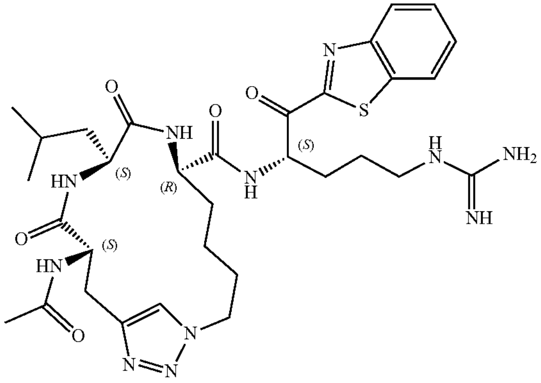 | 3077 | 39.15 | 14.14 | >20000 | 4294 | 695.84 | 696.6 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| VD4072 | 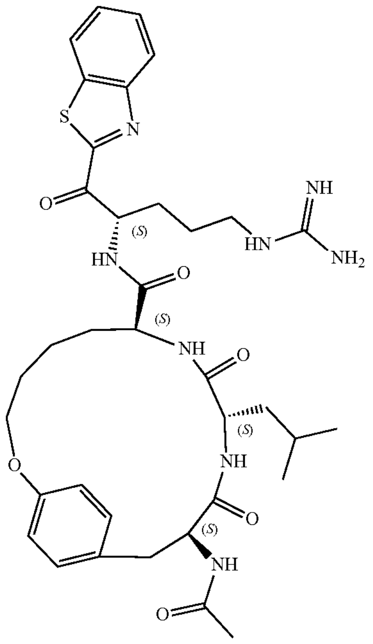 | 7.991 | 7.76 | 0.1753 | >20000 | 2646 | 720.89 | 721.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4054A | 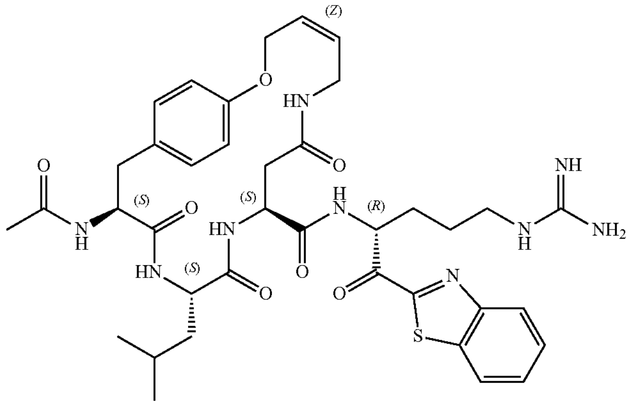 | >20000 | 76.57 | 14.01 | | | 775.9 | 776.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4054 | 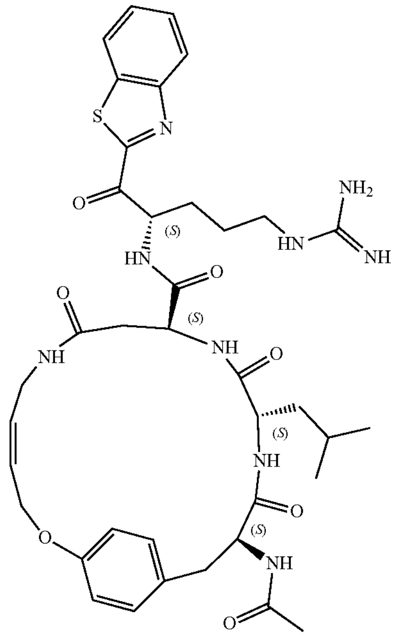 | >20000 | 72.56 | 0.6426 | >20000 | 3185 | 775.9 | 776.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4051 | 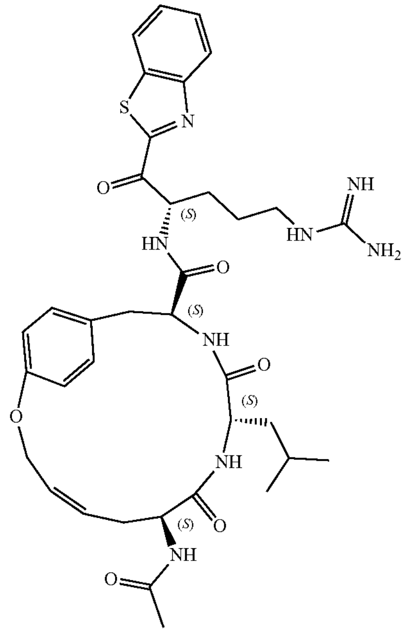 | >20000 | 80.22 | 102.2 | >20000 | 8814.00 | 718.87 | 719.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4018 | 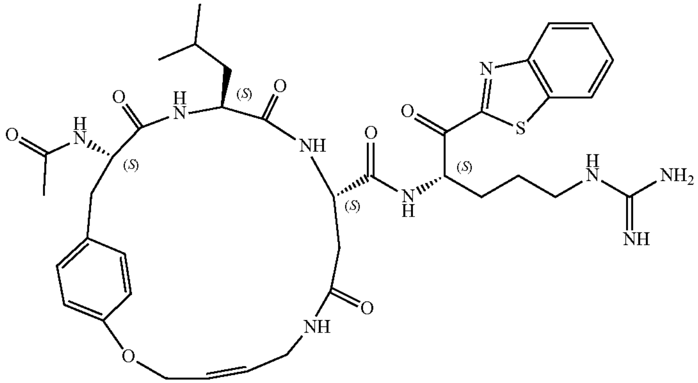 | 6500 | 9.84 | 6.31 | >20000 | 1240.00 | 789.95 | 791.5 |
| VD4158 | 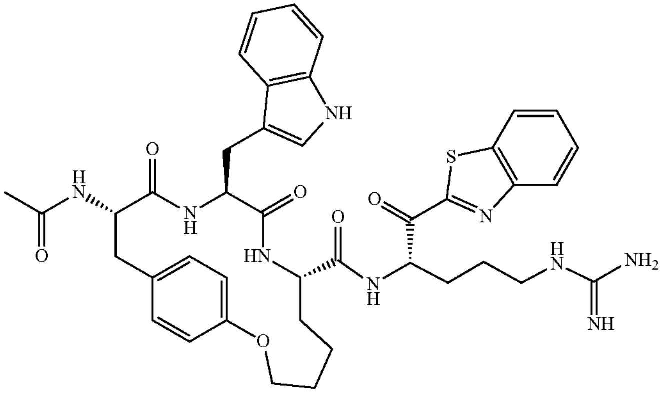 [SMILES: CC(=O)N[C@H]1Cc2ccc(cc2)OCCCC[C@@H](C(=O)N[C@@H](CCCNC(=N)N)C(=O)c2nc3ccccc3s2)NC(=O)[C@H](Cc2c[nH]c3ccccc23)NC1=O] | 85.23 | 56.81 | 2.84 | >20000 | 9530 | 793.94 | 794.7 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4162B | 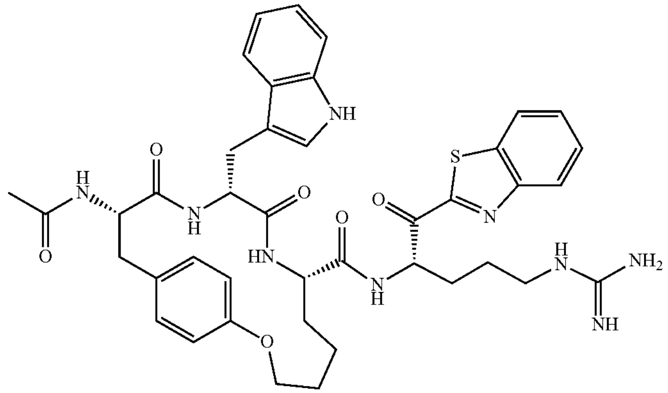 [SMILES: CC(=O)N[C@H]1Cc2ccc(cc2)OCCCC[C@@H](C(=O)N[C@@H](CCCNC(=N)N)C(=O)c2nc3ccccc3s2)NC(=O)[C@@H](Cc2c[nH]c3ccccc23)NC1=O] | 3.35 | 2.88 | 0.54 | 14599 | 1114.2 | 793.94 | 794.6 |
| VD4162A | 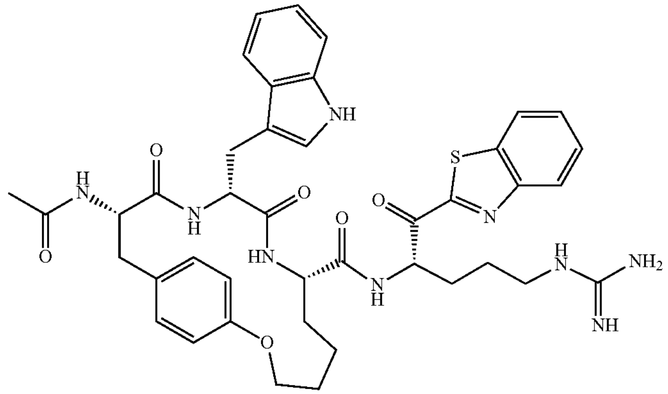 [SMILES: CC(=O)N[C@H]1Cc2ccc(cc2)OCCCC[C@@H](C(=O)N[C@@H](CCCNC(=N)N)C(=O)c2nc3ccccc3s2)NC(=O)[C@@H](Cc2c[nH]c3ccccc23)NC1=O] | 51.99 | 30.77 | 3.05 | >20000 | 7472.3 | 793.94 | 794.7 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| --- | --- | --- | --- | --- | --- | --- | --- | --- |
| VD4192B | 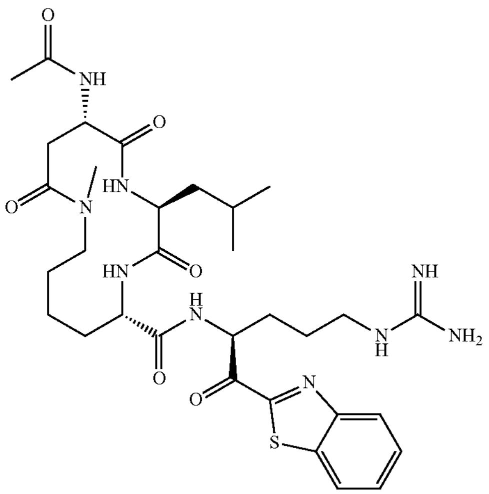 [SMILES: CC(=O)N[C@H]1CC(=O)N(C)CCCC[C@@H](C(=O)N[C@@H](CCCNC(=N)N)C(=O)c2nc3ccccc3s2)NC(=O)[C@H](CC(C)C)NC1=O] | 12272.67 | 1.1 | 14.9 | 17061.00 | 678.10 | 685.85 | 686.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4192C1 | 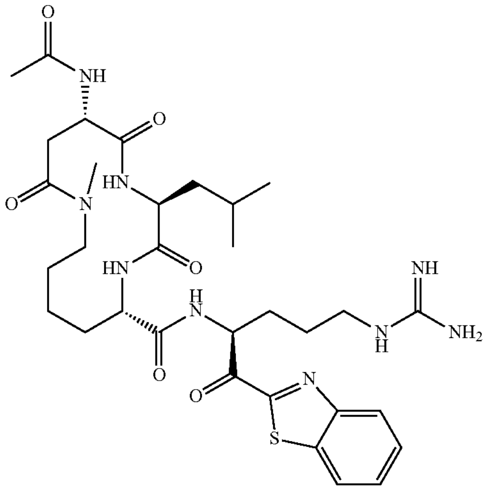 [SMILES: CC(=O)N[C@H]1CC(=O)N(C)CCCC[C@@H](C(=O)N[C@@H](CCCNC(=N)N)C(=O)c2nc3ccccc3s2)NC(=O)[C@H](CC(C)C)NC1=O] | 7733 | 110.62 | 0.97 | >20000 | >20000 | 685.85 | 686.6 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| VD4192C2 | 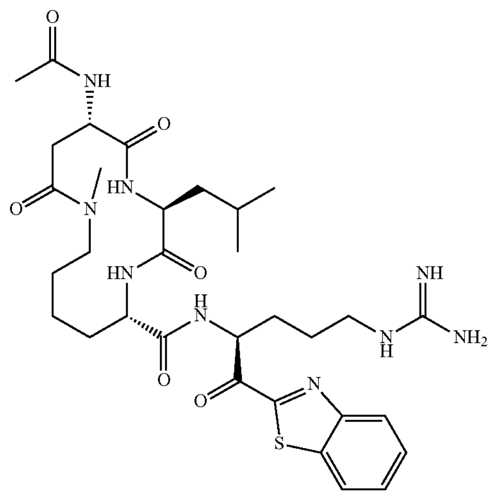 [SMILES: CC(=O)N[C@H]1CC(=O)N(C)CCCC[C@@H](C(=O)N[C@@H](CCCNC(=N)N)C(=O)c2nc3ccccc3s2)NC(=O)[C@H](CC(C)C)NC1=O] | 8561 | 23.49 | 1.75 | >20000 | 18540.3 | 685.85 | 686.5 |
| VD4022 | 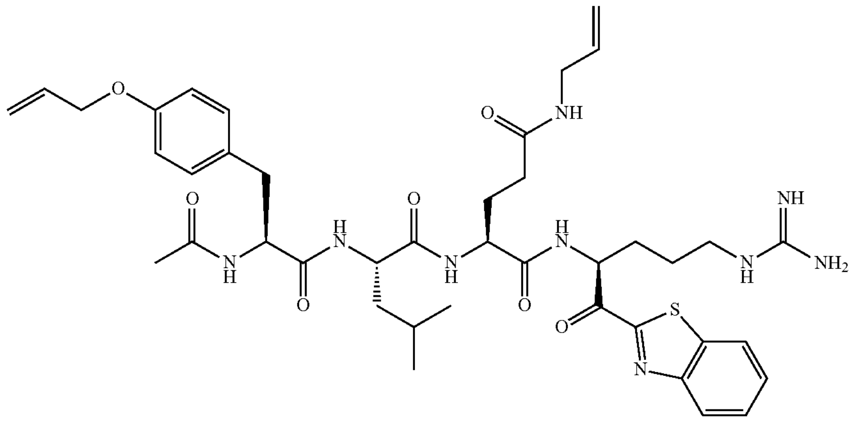 [SMILES: C=CCNC(=O)CC[C@H](NC(=O)[C@H](CC(C)C)NC(=O)[C@H](Cc1ccc(OCC=C)cc1)NC(C)=O)C(=O)N[C@@H](CCCNC(=N)N)C(=O)c1nc2ccccc2s1] | 4750 | 19.1 | 10.1 | | | 818.01 | 819.5 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| MM1132-1 | 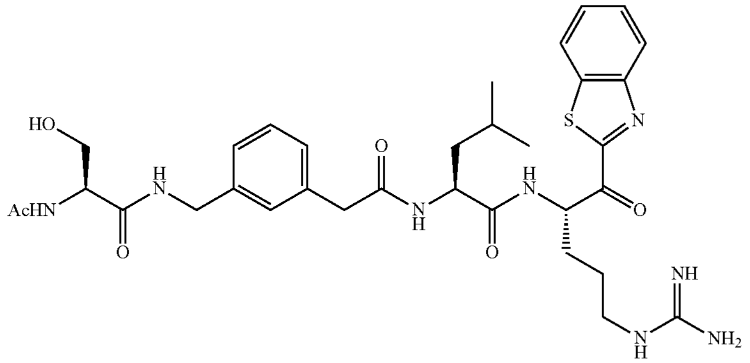 [SMILES: CC(=O)N[C@@H](CO)C(=O)NCc1cccc(CC(=O)N[C@@H](CC(C)C)C(=O)N[C@@H](CCCNC(=N)N)C(=O)c2nc3ccccc3s2)c1] | | | | | | 680.83 | 681.6 |
| MM1132-2 | 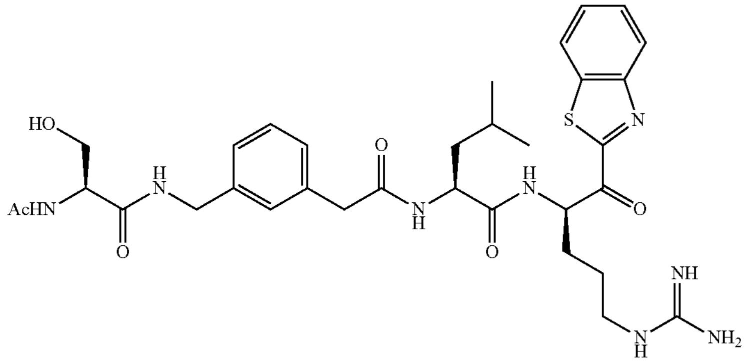 [SMILES: CC(=O)N[C@@H](CO)C(=O)NCc1cccc(CC(=O)N[C@@H](CC(C)C)C(=O)N[C@H](CCCNC(=N)N)C(=O)c2nc3ccccc3s2)c1] | | | | | | 680.83 | 681.6 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| MM1123 | 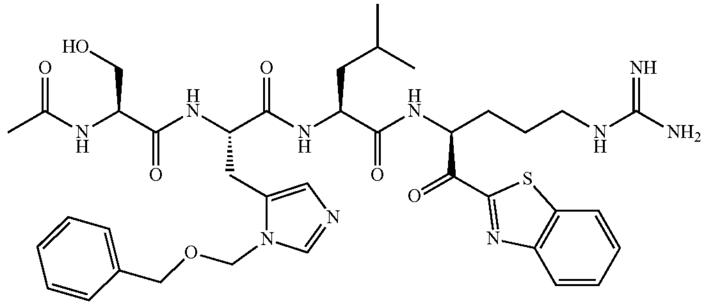 [SMILES: CC(=O)N[C@@H](CO)C(=O)N[C@@H](Cc1cncn1COCc1ccccc1)C(=O)N[C@@H](CC(C)C)C(=O)N[C@@H](CCCNC(=N)N)C(=O)c1nc2ccccc2s1] | | | | | | 790.94 | 791.5 |
| MM1180 | 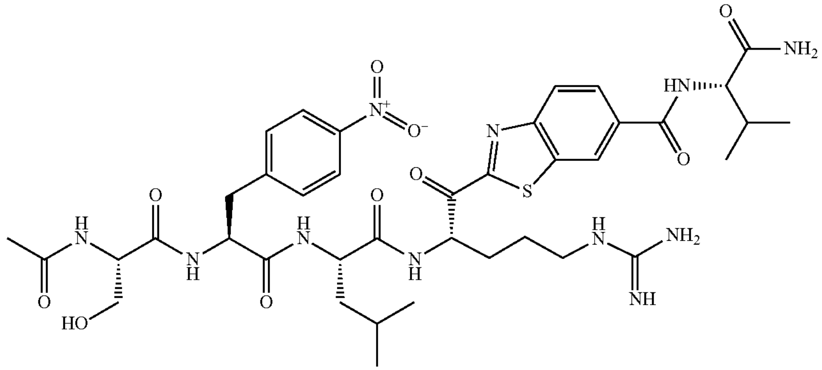 | | | | | | 867.98 | 869.3 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| MM1189 | 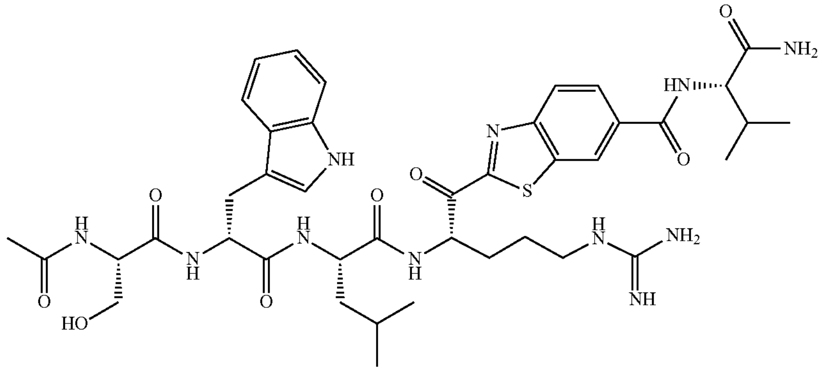 [SMILES: CC(=O)N[C@@H](CO)C(=O)N[C@H](Cc1c[nH]c2ccccc12)C(=O)N[C@@H](CC(C)C)C(=O)N[C@@H](CCCNC(=N)N)C(=O)c1nc2ccc(C(=O)N[C@H](C(N)=O)C(C)C)cc2s1] | | | | | | 862.02 | 863.3 |
| JH1169 | 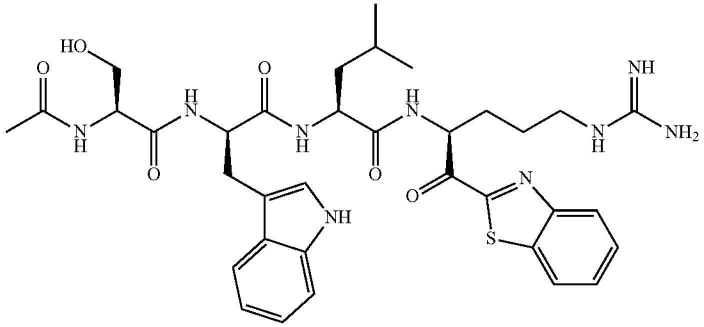 [SMILES: CC(=O)N[C@@H](CO)C(=O)N[C@H](Cc1c[nH]c2ccccc12)C(=O)N[C@@H](CC(C)C)C(=O)N[C@@H](CCCNC(=N)N)C(=O)c1nc2ccccc2s1] | | | | | | 719.86 | 720.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| --- | --- | --- | --- | --- | --- | --- | --- | --- |
| JH1196 | 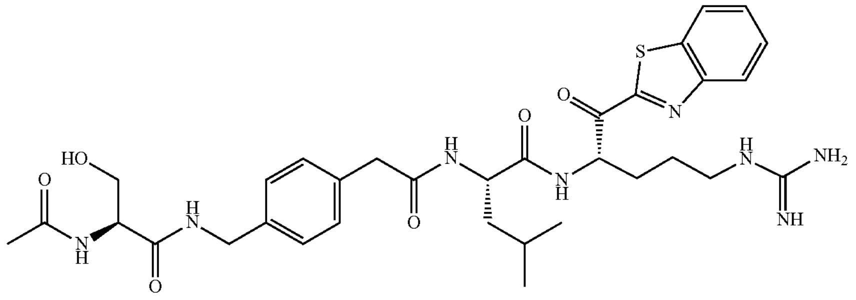 [SMILES: CC(=O)N[C@@H](CO)C(=O)NCc1ccc(CC(=O)N[C@@H](CC(C)C)C(=O)N[C@@H](CCCNC(=N)N)C(=O)c2nc3ccccc3s2)cc1] | | | | | | 680.83 | 681.5 |
| JH1144 | 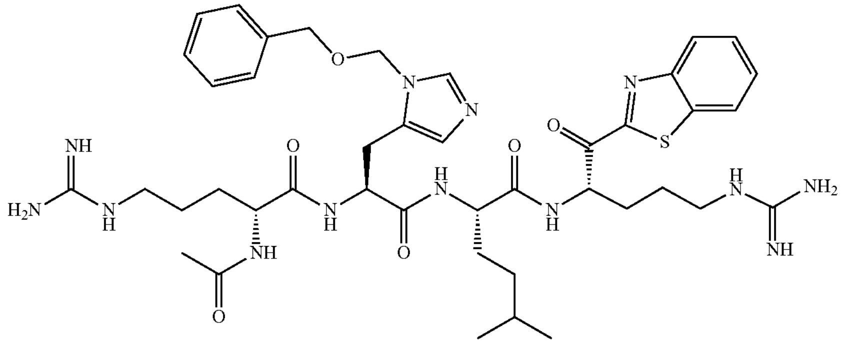 [SMILES: CC(=O)N[C@H](CCCNC(=N)N)C(=O)N[C@@H](Cc1cncn1COCc1ccccc1)C(=O)N[C@@H](CCC(C)C)C(=O)N[C@@H](CCCNC(=N)N)C(=O)c1nc2ccccc2s1] | | | | | | 874.08 | 875.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| --- | --- | --- | --- | --- | --- | --- | --- | --- |
| JH1143-2 | 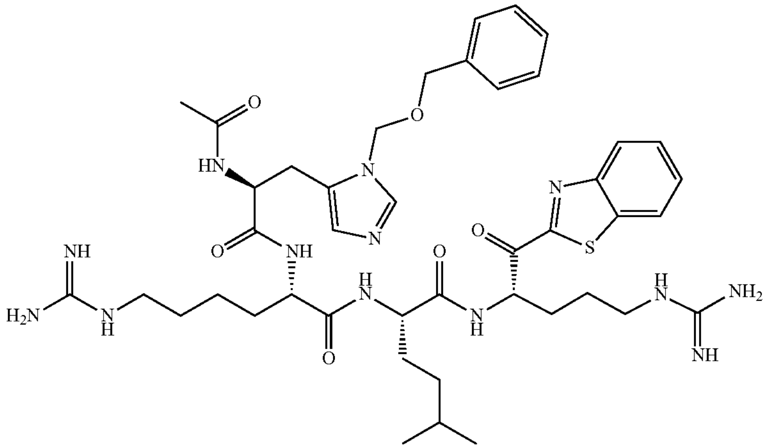 [SMILES: CC(=O)N[C@@H](Cc1cncn1COCc1ccccc1)C(=O)N[C@@H](CCCCNC(=N)N)C(=O)N[C@@H](CCC(C)C)C(=O)N[C@@H](CCCNC(=N)N)C(=O)c1nc2ccccc2s1] | | | | | | 888.11 | 889.5 |
| JH1162 | 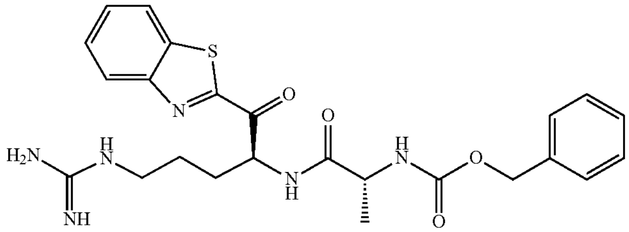 [SMILES: C[C@@H](NC(=O)OCc1ccccc1)C(=O)N[C@@H](CCCNC(=N)N)C(=O)c1nc2ccccc2s1] | | | | | | 496.59 | 497.5 |
| JH1161 | 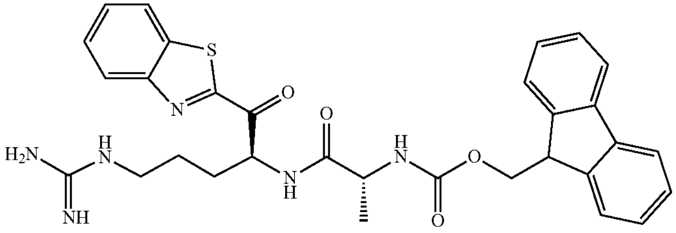 [SMILES: C[C@@H](NC(=O)OCC1c2ccccc2-c2ccccc21)C(=O)N[C@@H](CCCNC(=N)N)C(=O)c1nc2ccccc2s1] | | | | | | 584.7 | 584.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| JH1142-2 | 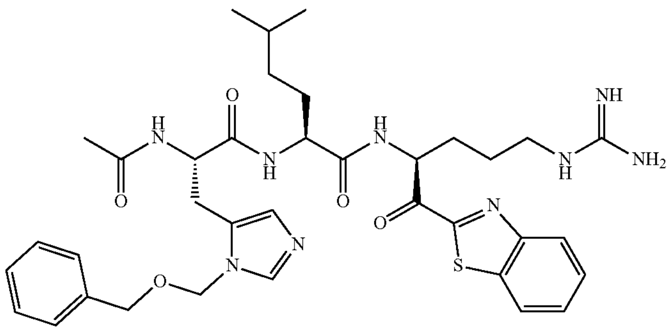 [SMILES: CC(=O)N[C@@H](Cc1cncn1COCc1ccccc1)C(=O)N[C@@H](CCC(C)C)C(=O)N[C@@H](CCCNC(=N)N)C(=O)c1nc2ccccc2s1] | | | | | | 717.89 | 718.5 |
| JH1141-2 | 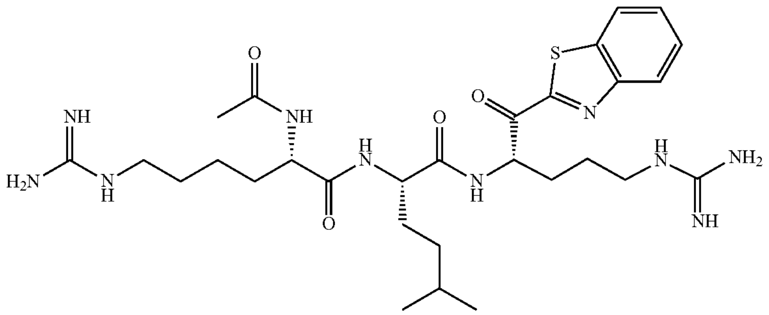 [SMILES: CC(=O)N[C@@H](CCCCNC(=N)N)C(=O)N[C@@H](CCC(C)C)C(=O)N[C@@H](CCCNC(=N)N)C(=O)c1nc2ccccc2s1] | | | | | | 630.81 | 631.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| JH1140-2 | 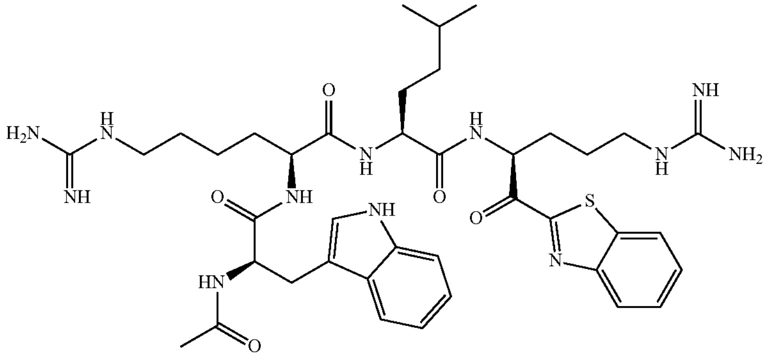 [SMILES: CC(=O)N[C@H](Cc1c[nH]c2ccccc12)C(=O)N[C@@H](CCCCNC(=N)N)C(=O)N[C@@H](CCC(C)C)C(=O)N[C@@H](CCCNC(=N)N)C(=O)c1nc2ccccc2s1] | | | | | | 817.03 | 818.7 |
| PK-1-45A1 | 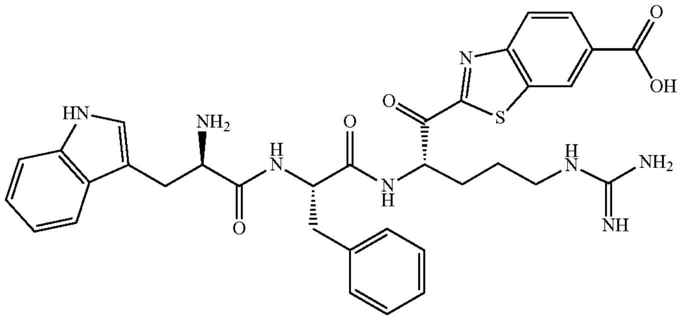 [SMILES: N=C(N)NCCC[C@H](NC(=O)[C@H](Cc1ccccc1)NC(=O)[C@H](N)Cc1c[nH]c2ccccc12)C(=O)c1nc2ccc(C(=O)O)cc2s1] | | | | | | 668.77 | 669.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| PK-1-89A1 | 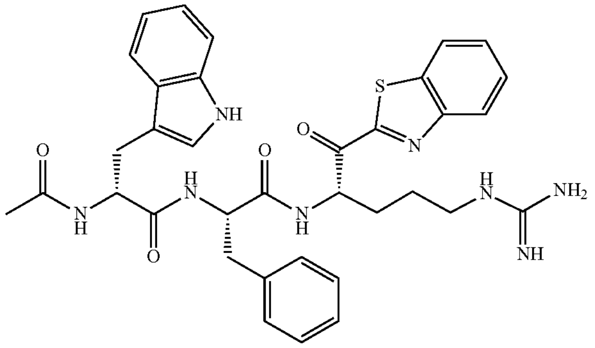 [SMILES: CC(=O)N[C@H](Cc1c[nH]c2ccccc12)C(=O)N[C@@H](Cc1ccccc1)C(=O)N[C@@H](CCCNC(=N)N)C(=O)c1nc2ccccc2s1] | | | | | | 666.8 | 667.5 |
| PK-1-93A1 | 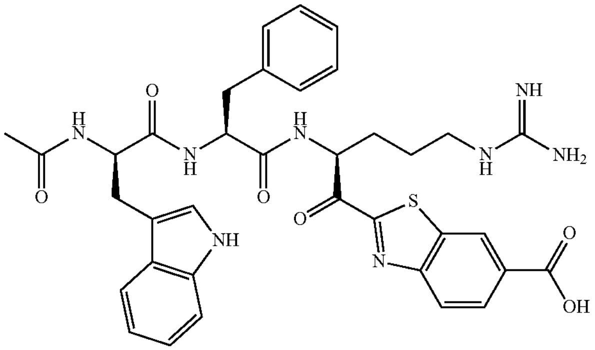 [SMILES: CC(=O)N[C@H](Cc1c[nH]c2ccccc12)C(=O)N[C@@H](Cc1ccccc1)C(=O)N[C@@H](CCCNC(=N)N)C(=O)c1nc2ccc(C(=O)O)cc2s1] | | | | | | 710.81 | 711.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| PK-1-18A1 | 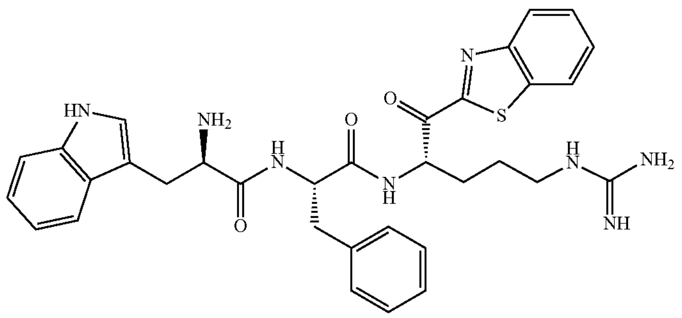 [SMILES: N=C(N)NCCC[C@H](NC(=O)[C@H](Cc1ccccc1)NC(=O)[C@H](N)Cc1c[nH]c2ccccc12)C(=O)c1nc2ccccc2s1] | | | | | | 624.76 | 625.5 |
| ZFH6201-2 | 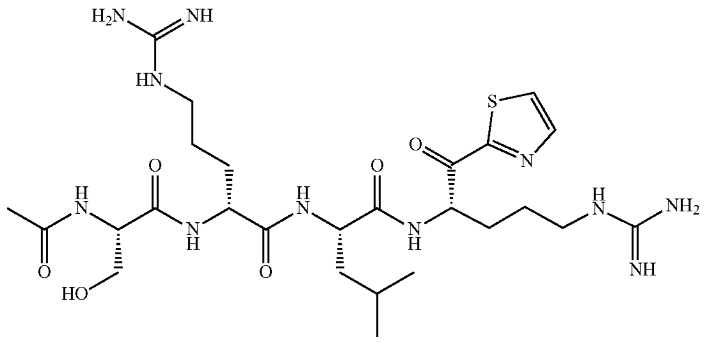 [SMILES: CC(=O)N[C@@H](CO)C(=O)N[C@H](CCCNC(=N)N)C(=O)N[C@@H](CC(C)C)C(=O)N[C@@H](CCCNC(=N)N)C(=O)c1nccs1] | | | | | | 509.67 | 510.5 |

TABLE 2-continued
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| Biological activity data of matriptase, hepsin, HGFA, Factor Xa, and thrombin. | | | | | | | | |
| PK-1-58A1 | 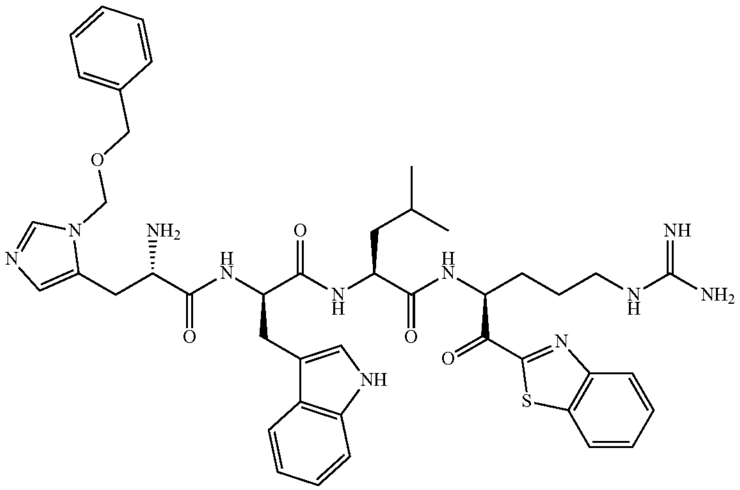 [SMILES: CC(C)C[C@H](NC(=O)[C@@H](Cc1c[nH]c2ccccc12)NC(=O)[C@@H](N)Cc1cncn1COCc1ccccc1)C(=O)N[C@@H](CCCNC(=N)N)C(=O)c1nc2ccccc2s1] | | | | | | 848.04 | 849.5 |

TABLE 2-continued
| Biological activity data of matriptase, hepsin, HGFA, Factor Xa, and thrombin. | | | | | | | | |
|---|---|---|---|---|---|---|---|---|
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
| PK-1-54A1 | 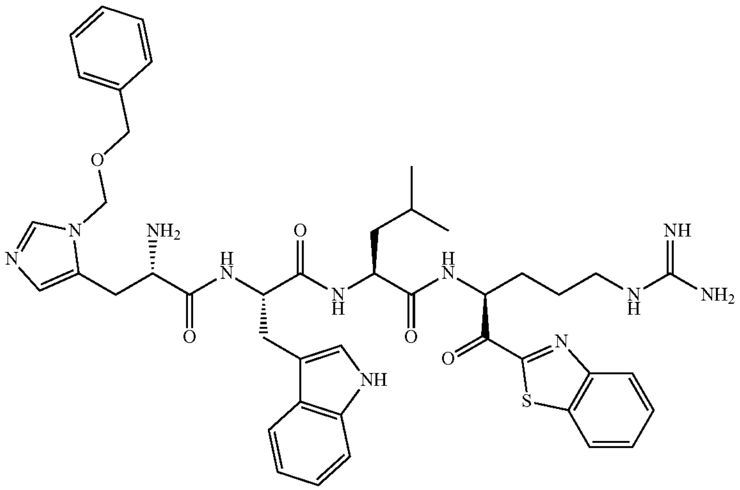 [SMILES: CC(C)C[C@H](NC(=O)[C@H](Cc1c[nH]c2ccccc12)NC(=O)[C@@H](N)Cc1cncn1COCc1ccccc1)C(=O)N[C@@H](CCCNC(=N)N)C(=O)c1nc2ccccc2s1] | | | | | | 848.04 | 849.5 |
| MM2030 | 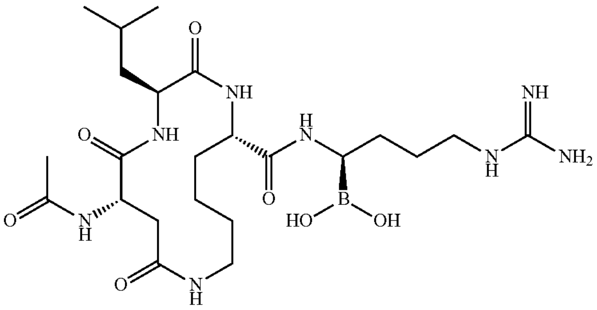 [SMILES: CC(=O)N[C@H]1CC(=O)NCCCC[C@@H](C(=O)N[C@@H](CCCNC(=N)N)B(O)O)NC(=O)[C@H](CC(C)C)NC1=O] | | | | | | 554.56 | (M + H)− H2O 527.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| MM2001 | 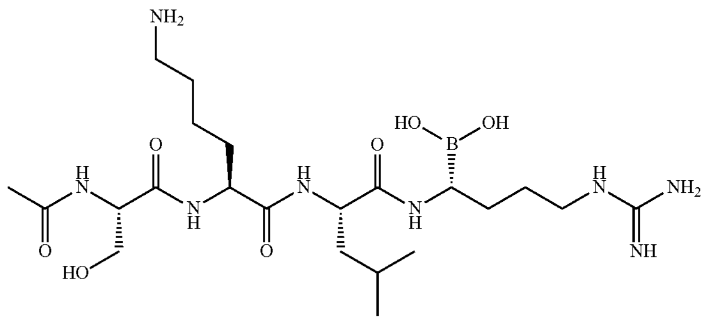 [SMILES: CC(=O)N[C@@H](CO)C(=O)N[C@@H](CCCCN)C(=O)N[C@@H](CC(C)C)C(=O)N[C@@H](CCCNC(=N)N)B(O)O] | | | | | | 544.46 | (M + H)− H2O 527.5 |
| MM1119 | 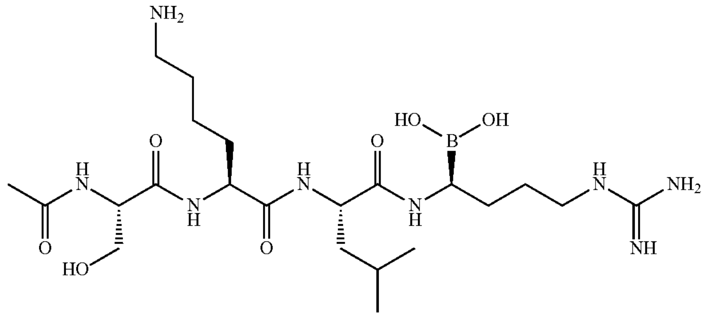 [SMILES: CC(=O)N[C@@H](CO)C(=O)N[C@@H](CCCCN)C(=O)N[C@@H](CC(C)C)C(=O)N[C@H](CCCNC(=N)N)B(O)O] | | | | | | 544.46 | (M + H)− H2O 527.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| VD4112A | 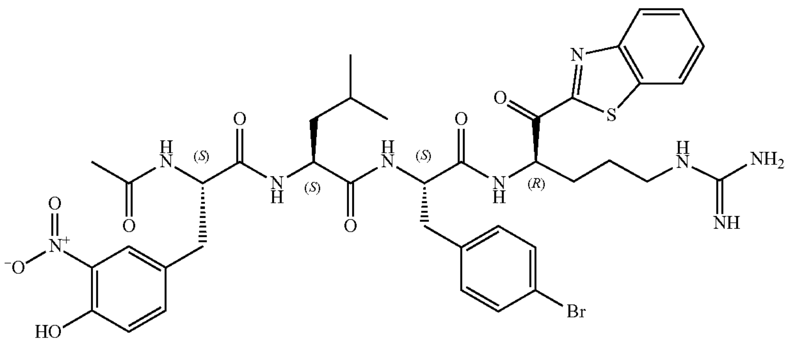 | 3515 | 111.4 | 23.94 | | | 880.8 | 881.6 |
| VD4112 | 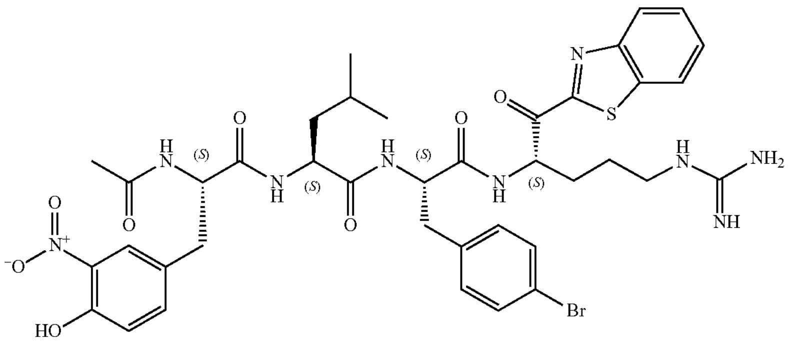 | 13968 | 9.495 | 1.154 | | | 880.8 | 881.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| MM3116 Ac-IQFR-kbt | 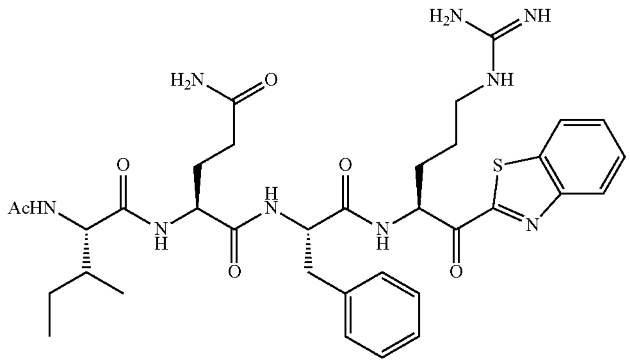 [SMILES: CCC(C)[C@H](NC(C)=O)C(=O)N[C@@H](CCC(N)=O)C(=O)N[C@@H](Cc1ccccc1)C(=O)N[C@@H](CCCNC(=N)N)C(=O)c1nc2ccccc2s1] | 30.18 | 0.923 | 0.14 | >20 | 791.9 | 721.88 | M + H 722.6 |
| MM3122 Ac-GQFR-kbt | 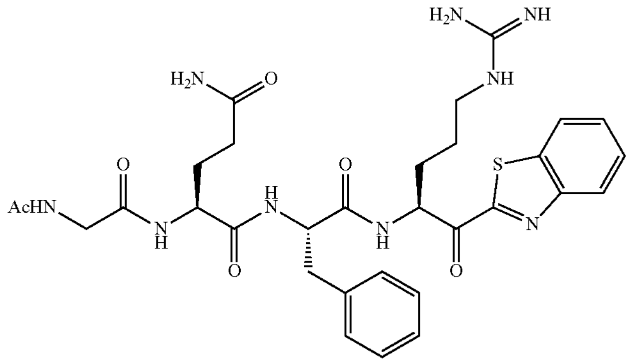 [SMILES: CC(=O)NCC(=O)N[C@@H](CCC(N)=O)C(=O)N[C@@H](Cc1ccccc1)C(=O)N[C@@H](CCCNC(=N)N)C(=O)c1nc2ccccc2s1] | 32.54 | 0.314 | 0.194 | >20 | 700.3 | 665.77 | M + H 666.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| MM3123 Ac-PQFR-kbt | 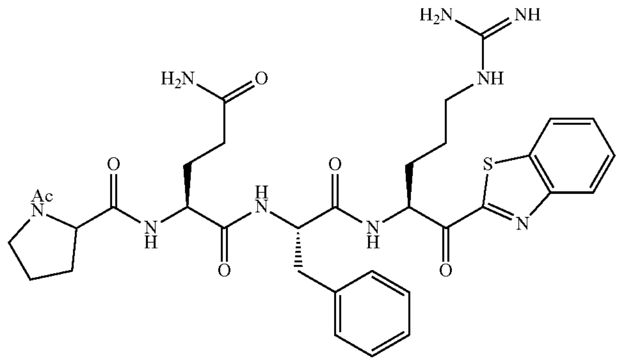 | 74.98 | 0.316 | 0.136 | >20 | 199.2 | 705.84 | M + H 706.5 |
| MM3130 Ac-MQFR-kbt | 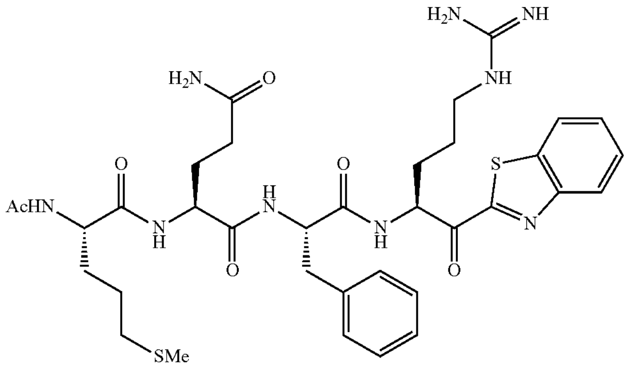 [SMILES: CSCCC[C@H](NC(C)=O)C(=O)N[C@@H](CCC(N)=O)C(=O)N[C@@H](Cc1ccccc1)C(=O)N[C@@H](CCCNC(=N)N)C(=O)c1nc2ccccc2s1] | 36.45 | 0.552 | 0.135 | >20 | 341.8 | 739.91 | M + H 740.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| MM3131 Ac-LQFR-kbt | 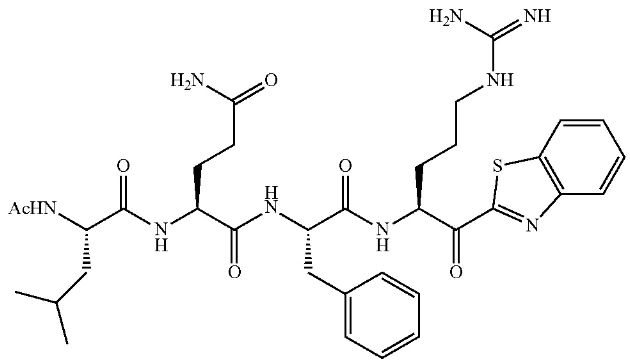 [SMILES: CC(=O)N[C@@H](CC(C)C)C(=O)N[C@@H](CCC(N)=O)C(=O)N[C@@H](Cc1ccccc1)C(=O)N[C@@H](CCCNC(=N)N)C(=O)c1nc2ccccc2s1] | 98.17 | 1.8 | 0.247 | >20 | 219.1 | 721.88 | M + H 722.6 |
| MM3144 Ac-QFR-kbt | 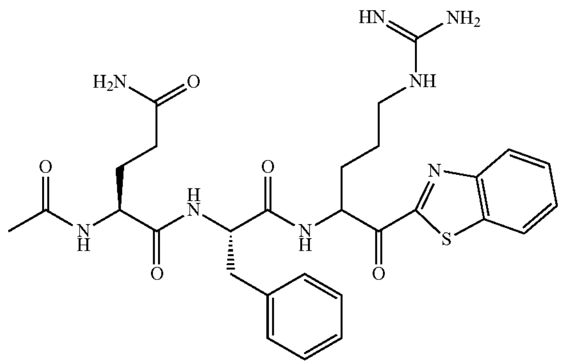 [SMILES: CC(=O)N[C@@H](CCC(N)=O)C(=O)N[C@@H](Cc1ccccc1)C(=O)NC(CCCNC(=N)N)C(=O)c1nc2ccccc2s1] | 13.83 | 0.128 | 0.078 | >20 | 1.4 | 608.72 | M + H 609.5 |

TABLE 2-continued
Biological activity data of matriptase, hepsin, HGFA, Factor Xa, and thrombin.
| Compound | Structure | HGFA ($IC_{50}$ nM) | Matriptase ($IC_{50}$ nM) | Hepsin ($IC_{50}$ nM) | Thrombin* ($IC_{50}$ nM) | Factor Xa* ($IC_{50}$ nM) | MW | LC/MS |
|---|---|---|---|---|---|---|---|---|
| JH1125-2 | 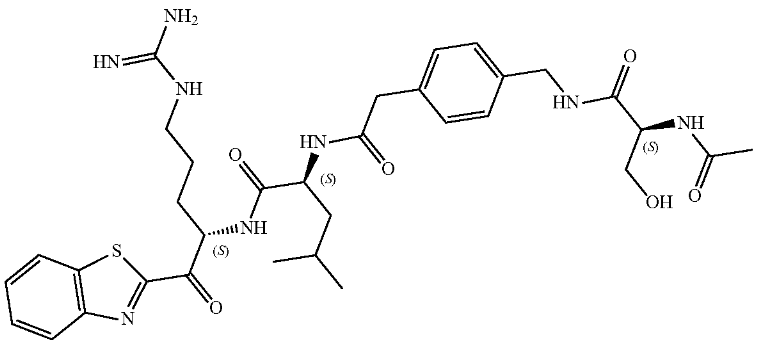 | | | | | | 680.83 | |
*chromogenic assay Example 10. Design of P3-P4 Hybrid Piperidine Carbamate Dipeptide Inhibitors There are several disadvantages associated with peptide-derived inhibitors as drugs, including high conformational flexibility, susceptibility to proteolytic degradation leading to high clearance and low half-life, and poor membrane permeability resulting is low oral bioavailability. The attributes of peptides leading to their poor drug-like properties stem from several reasons: their high molecular weight, high polarity, their large number of amide bonds susceptible to enzymatic hydrolysis, and their multiple H-bond-donors and acceptors, all of which make for problematic cell permeability. Reduction of peptidyl character of the drugs typically enhances the cellular permeability, proteolytic stability, and oral bioavailability. Thus, the goal in the study was to rationally design novel inhibitors of HGFA, matriptase and hepsin which have much less peptide character. To that end, non-peptidyl functional groups were introduced into the P4 and P3 positions of the tetrapeptide inhibitors 1a and 1b, in order to make binding interactions in the corresponding S4 and S3 subsite pockets of the three proteases.

Using existing X-ray crystal structures of HGFA (PDB code 2WUC), matriptase (PDB code 2GV7), and hepsin (PDB code 1Z8G) bound to benzamidine inhibitors, Ac-SKLR-kbt (1b) and Ac-KQLR-kbt (1a) were computationally docked to generate a binding model to the three proteases. SRI 31215, reported by Galemmo et al. is a non-peptide cyclic urea benzamidine (cub) inhibitor of matriptase and hepsin which binds the S1, S3 and S4 pockets but not the S2. When overlaid on 1b, the piperidine was positioned close to the P3 amino acid nitrogen suggesting that a piperidine ring attached through a two-atom linker such as a carbamate from the P2 position would place the piperidine in a similar position to that of SRI 31215. Previous structure-activity relationship (SAR) studies and reported PS-SCL (positional scanning of substrate combinatorial libraries) studies on matriptase, hepsin, and HGFA indicated that all three proteases require substrates with an Arg (R) at the P1 and prefer Leu (L) at the P2 position.

It was hypothesized that the low potency of SRI 31215 is partly reflected by the lack of binding in the S2 pocket (Leu of 1b). Based on this analysis and inspired by the SRI 31215 structure, novel hybrid dipeptide inhibitors were designed with the preferred Leu (L) in the P2 position, but which contained the piperidine group of SRI 31215 in the P3 position installed via a carbamate from the P2 Leu as suggested by the model. In another set of analogs, a P4 position library was created with alkyl or aryl sulfonyl substituents on the piperidine nitrogen to identify compounds to access the S4 pocket with optimal substitution for both potency and selectivity for the individual proteases.

Example 11. Synthesis of P2-P1 Leu-Arg-Kbt Dipeptides Capped with Substituted Piperidine Carbamates at the P3 and P4 Positions Starting materials, reagents, and solvents were purchased from commercial vendors unless otherwise noted. $^1H$ NMR spectra were measured on a Varian 400 MHz NMR instrument. The chemical shifts were reported as 6 ppm relative to TMS using a residual solvent peak as the reference unless otherwise noted. The following abbreviations were used to express the multiplicities: s=singlet; d=doublet; t=triplet; q=quartet; m=multiplet; br=broad. High-performance liquid chromatography (HPLC) was carried out on GILSON GX-281 using Waters C18 5 M, 4.6*50 mm and Waters Prep C18 5 M, 19*150 mm reverse phase columns, eluted with a gradient system of 5:95 to 95:5 acetonitrile:water with a buffer consisting of 0.05% TFA. Mass spectra (MS) were performed on HPLC/MSD using electrospray ionization (ESI) for detection. All reactions were monitored by thin layer chromatography (TLC) carried out on Merck silica gel plates (0.25 mm thick, 60F254), visualized by using UV (254 nm) or dyes such as $KMnO_4$, p-Anisaldehyde and CAM (Cerium Ammonium Molybdate or Hanessian's Stain). Silica gel chromatography was carried out on a Teledyne ISCO CombiFlash purification system using pre-packed silica gel columns (12 g-330 g sizes). All compounds used for biological assays were greater than 95% purity based on NMR and HPLC by absorbance at 220 nm and 254 nm wavelengths.

Figure 12:
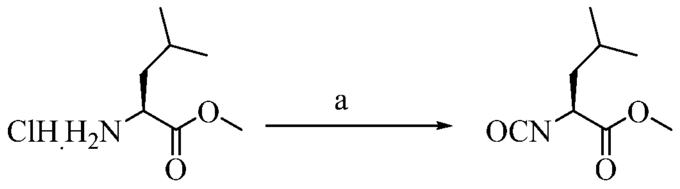
FIG. 12 presents general synthetic routes for A) amino acid isocyanates 2 a-b and B) piperidine alcohols 3 a-e. Reagents: a) tricholoromethyl chloroformate, 1,4-dioxane; b) Grignard reagent, THF.
Figure 12:
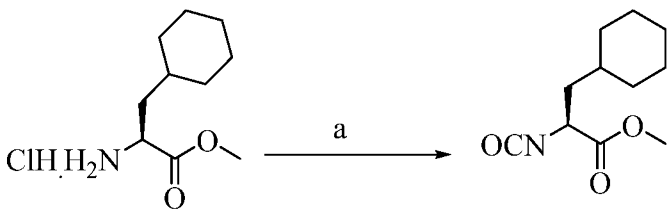
Figure 12:
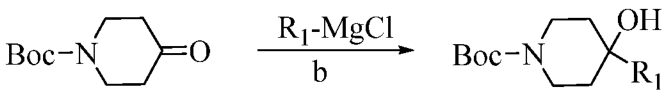
Figure 12:
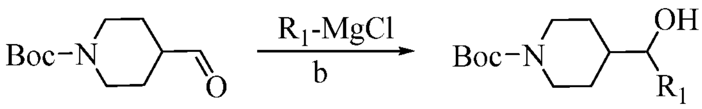
Figure 13:
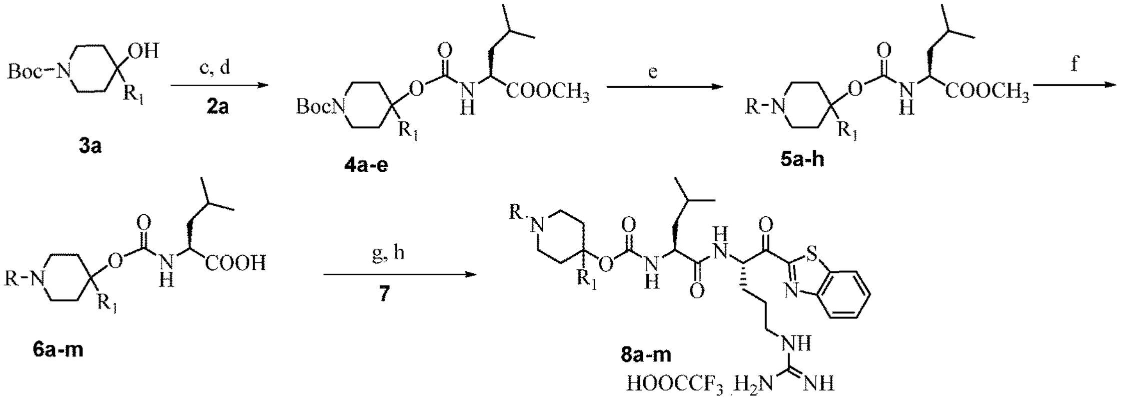
FIG. 13 presents general synthetic routes for hybrid piperidine dipeptide ketobenzothiazole (kbt) inhibitors. Reagents: c) Compd 2a or 2b, TEA, ACN; d) 4N HCl in dioxane; e) $RSO_2Cl$, TEA, THF; f) aq. LiOH, THF; g) EDCI, HOBt, DIEA, DMF or HATU, DIEA, DMF; h) TFA:water:thioanisole (95:2.5:2.5), followed by RP-HPLC.
Figure 13:
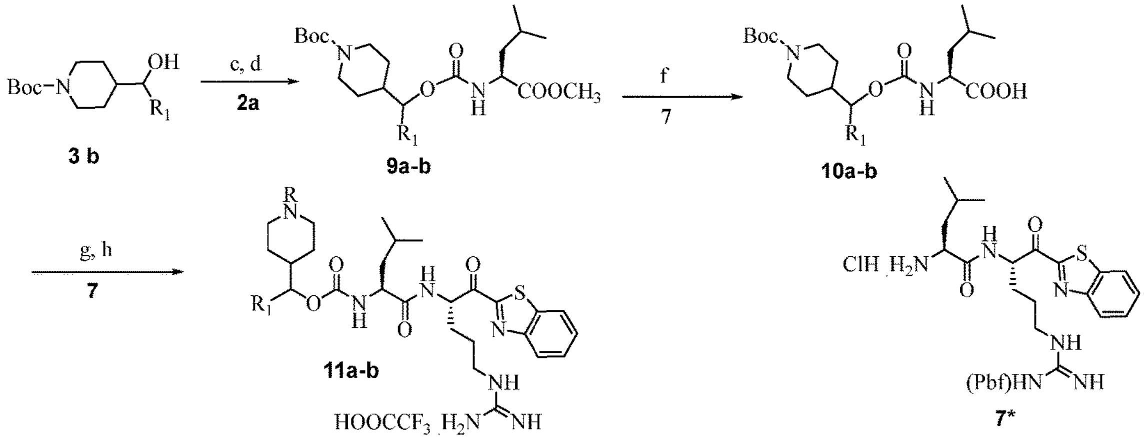

Construction of the target compounds which were selected based on the computational binding model of 1a, 1b, and SRI 31215 is shown in FIGS. 13 and 14. Shown in FIG. 12, step A, the leucine amino acid isocyanate was prepared by refluxing leucine methyl ester hydrochloride with trichloromethyl chloroformate (2a). The cyclohexyl alanine (Cha) isocyanate 2b was formed in a similar fashion. As seen in FIG. 12, step B, Grignard reactions with commercially available tert-butyl 4-oxopiperidine-1-carboxylate gave 1-Boc-4-piperidinol derivatives 3a-c and likewise reaction with tert-butyl 4-formylpiperidine-1-carboxylate gave 3d-e in good yield. Shown in FIG. 13, step A, leucine isocyanate 2 was then treated with piperidinol derivatives (3a-e) yielding the corresponding carbamate esters (4a-e) or 9a-b (FIG. 12, step B). Treatment of the carbamates 4a-e with dry HCl in dioxane followed by reaction with alkyl sulfonyl chloride gave the corresponding sulfonamides (5a-h). Hydrolysis of substituted piperidine esters 5a-h or 9a-b (FIG. 13, step B) with LiOH in aqueous THF provided the carboxylic acids (6a-m or 10a-b) which were then reacted with the Pbf side chain protected Arg-kbt (7) using standard amide coupling conditions (EDC/HOBt or HATU) to give piperidine dipeptides which were subjected to global side-chain deprotection with a cocktail of TFA/water/thioanisole. Reverse phase preparatory HPLC purification was then conducted to produce final target compounds (8a-m and 11a-b) in high purity.

The carbamates and precursors were synthesized in accordance with FIGS. 13 and 14 and the procedures described herein. Note that synthesis of H-Arg(Pbf)-kbt-HCl 7 has been reported previously in Z. Han et al., *ChemMedChem,* 2016, 11, 585-599.

Synthesis of amino acid methyl ester isocyanates 2a-b: The leucine amino acid methyl ester hydrochloride (4.55 g, 25 mmol) was placed in a dry RB flask and then dried overnight on the vacuum pump. The flask was flushed with nitrogen and dry dioxane (60 mL) was added followed by trichloromethyl chloroformate (7.42 g, 37.5 mmol). After refluxing for 14 hours, the solvent was removed on the rotary evaporator to yield pure isocyanates 2a-b as colorless oils.

Synthesis of compounds 3a-e: To a 250 mL round bottom flask kept under nitrogen atmosphere was added a 2.0 M solution (1.40 mL, 2.76 mmol) of the appropriate Grignard reagent in THF and the solution was cooled to 0-5° C. A solution of the appropriate aldehyde (0.5 g, 2.50 mmol) in dry THF (5 mL) was added dropwise to the cooled Grignard solution over ~20 minutes. The reaction mixture was allowed to warm up to room temperature and stirred for 5 hours under nitrogen. The disappearance of the aldehyde was monitored by TLC. The reaction mixture was cooled to 0-5° C. and acidified to pH ~3.0 using 5% aqueous hydrochloric acid. The organic solvent was evaporated off and the residue was extracted with ethyl acetate (2×50 mL). The combined organic extracts were washed with brine (10 mL) dried over anhydrous $Na_2SO_4$, filtered, and concentrated. The crude product was purified by column chromatography to yield alcohols 3a-c and 3d-e as oils.

Synthesis of carbamates 4a-d and 9a-b: A solution of compound Boc-(4-hydroxy) piperidine (3) (2.02 g, 10 mmol) in dry acetonitrile (20 mL) was treated with trimethylamine (2.02 g; 20 mmol) followed by an appropriate amino acid methyl ester isocyanate 2 (11 mmol). The resulting reaction mixture was refluxed for 3 hours and then allowed to cool to room temperature. The disappearance of the alcohol was monitored by TLC. The solvent was evaporated, and the residue was taken up in ethyl acetate (100 mL) and the organic layer was washed with 5% aqueous HCl (2×20 mL) and saturated NaCl (20 mL). The organic layer was dried over anhydrous sulfate, filtered, and concentrated to yield an oily product. Purification by flash chromatography yielded 4a-d and 9a-b esters as colorless oils/solids. The above purified compound 4d was dissolved in dry DCM (5 mL) and added to a solution of 4 M HCl in dioxane (15 mL) with stirring. The reaction mixture was stirred for 2 hours at room temperature. The disappearance of the starting material was monitored by TLC. The solvent was evaporated under reduced pressure and compound 4e was used in the next step without further purification.

Synthesis of sulfonyl compounds 5a-h: A solution of compound 4e (100 mg, 0.32 mmol) in dry THF (3 mL) was treated with triethyl amine (0.13 mL, 0.64 mmol) followed by addition of appropriate sulfonyl chloride (63 mg, 0.32 mmol) while stirring, and the reaction was continued for 12 hours. Residue was dissolved in ethyl acetate (50 mL) and washed with 5% HCl (2×20 mL) and saturated NaCl (20 mL), dried over sodium sulfate, filtered and concentrated to yield crude product, which was purified by column chromatography to yield the corresponding esters 5a-h as colorless oils.

Synthesis of acids 6a-m and 10a-b: A solution of ester 4, or 5 or 9 (0.28 g, 0.557 mmol) in tetrahydrofuran (2 mL) was treated with 1 M aqueous LiOH (2 mL). The reaction mixture was stirred for 3 hours at room temperature while monitoring the disappearance of the ester by TLC. Most of the solvent was evaporated off and the solution was acidified to pH ~3 using 5% hydrochloric acid (2 mL). The aqueous layer was extracted with ethyl acetate (2×25 mL) and the combined organic layer was washed with brine (10 mL). The organic layer was dried over anhydrous sodium sulfate, filtered, and concentrated to yield compounds 6a-m and 10a-b.

Synthesis of compounds 8a-m and 11a-b: EDCI (0.28 mmol) and HOBt (0.28 mmol) were added to a solution of compound 6 or 10 (100 mg, 0.222 mmol) in dry DMF (2 mL) and the mixture was stirred for 30 minutes at room temperature. The reaction was cooled to 0-5° C., Arg (Pbf)-kbt HCl (7) (129 mg, 0.222 mmol) was added followed by DIEA (115 mg, 0.888 mmol), and the reaction was stirred for 15 min. The reaction as allowed to come to room temperature and stirred for 12 hours. The reaction was concentrated under reduced pressure and the residue was partitioned between ethyl acetate (25 mL) and 10% citric acid (2×10 mL). The layers were separated, and the ethyl acetate was further washed with aqueous $NaHCO_3$ (10 mL) and saturated NaCl solution (10 mL). The organic layer was dried over $Na_2SO_4$, filtered, and concentrated. The deprotection of the crude product was accomplished by stirring in 1.0 mL of a TFA-thioanisole-water mixture (95:2.5:2.5) for 2-3 hours. After concentrating in vacuo, the crude material was dissolved in DMSO and purified using reverse phase HPLC (0.05% TFA/acetonitrile/water gradient). The pure fractions were pooled, frozen, and lyophilized to give the pure dipeptides 8a-m and 11a-b as white powders.

t-Butyl 4-hydroxy-4-phenylpiperidine-1-carboxylate (3a):

Compound was isolated as a sticky oil. Yield (0.47 g), $^1$H NMR (400 MHz, $CDCl_3$) δ ppm 7.49 (d, J=7.8 Hz, 2H), 7.38 (t, J=7.6 Hz, 2H), 7.30 (d, J=7.4 Hz, 1H), 4.04 (d, J=12.9 Hz, 2H), 3.25 (t, J=12.5 Hz, 2H), 2.01 (dt, J=4.5, 13.2 Hz, 2H), 1.74 (d, J=13.7 Hz, 2H), 1.62 (s, 1H), 1.49 (s, 9H). LCMS (ESI+) expected m/z 277.17, found 278.30 ($M+H^+$).

t-Butyl 4-benzyl-4-hydroxypiperidine-1-carboxylate (3b):

Compound was isolated as an oil. Yield (0.43 g), $^1$H NMR (400 MHz, $CDCl_3$) δ ppm 7.38-7.20 (m, 4H), 7.10 (t, J=7.5 Hz, 1H), 3.94 (d, J=12.9 Hz, 2H), 3.15 (t, J=12.5 Hz, 2H), 2.65 (s, 2H), 1.64-1.50 (m, 4H), 1.51 (s, 9H). LCMS (ESI+) expected m/z 291.18, found 292.30 ($M+H^+$).

t-Butyl 4-hydroxy-4-phenethylpiperidine-1-carboxylate (3c):

Oil, yield (0.24 g), $^1$H NMR (400 MHz, $CDCl_3$) δ ppm 7.32-7.27 (m, 2H), 7.20 (d, J=7.0 Hz, 3H), 3.83 (d, J=10.2 Hz, 3H), 3.26-3.13 (m, 3H), 2.76-2.68 (m, 3H), 1.85-1.76 (m, 3H), 1.61 (d, J=4.3 Hz, 5H), 1.47 (s, 9H). LCMS (ESI+) expected m/z 305.20, found 306.40 ($M+H^+$).

t-Butyl 4-(hydroxy(phenyl)methyl)piperidine-1-carboxylate (3d):

Compound was isolated as an oil. Yield (0.56 g), $^1$H NMR (400 MHz, $CDCl_3$) δ ppm 0.49 (d, J=7.8 Hz, 2H), 7.38 (t, J=7.6 Hz, 2H), 7.30 (d, J=7.4 Hz, 1H), 4.04 (d, J=12.9 Hz, 2H), 3.25 (t, J=12.5 Hz, 2H), 2.01 (dt, J=4.5, 13.2 Hz, 2H), 1.74 (d, J=13.7 Hz, 2H), 1.62 (s, 1H), 1.58-1.47 (m, 2H), 1.45 (s, 9H). LCMS (ESI+) expected m/z 291.18, found 292.30 ($M+H^+$).

t-Butyl 4-(1-hydroxy-2-phenylethyl)piperidine-1-carboxylate (3e):

Compound was isolated as an oil. Yield (0.50 g), $^1$H NMR (400 MHz, $CDCl_3$) δ ppm 7.29 (d, J=0.8 Hz, 1H), 7.25 (s, 1H), 7.21 (s, 1H), 7.20-7.14 (m, 2H), 4.53 (d, J=5.5 Hz, 1H), 4.10-4.03 (m, 1H), 3.55 (br. s., 1H), 2.84 (dd, J=3.1, 13.7 Hz, 1H), 2.69-2.50 (m, 2H), 1.99 (s, 2H), 1.82 (d, J=12.9 Hz, 1H), 1.72-1.60 (m, 2H), 1.58-1.47 (m, 2H), 1.40 (d, J=3.5 Hz, 9H). LCMS (ESI+) expected m/z 305.20, found 306.40 ($M+H^+$).

t-Butyl4-(((((S)-1-methoxy-4-methyl-1-oxopentan-2-yl) carbamoyl)oxy) (phenyl)methyl)piperidine-1-carboxylate (9a):

Compound was isolated as an oil. Yield (124 mg), $^1$H NMR (400 MHz, $CDCl_3$) δ ppm 7.38-7.29 (m, 5H), 4.80 (br. s., 1H), 4.47 (br. s., 1H), 4.39 (d, J=7.4 Hz, 1H), 4.17-4.10 (m, 1H), 3.74 (s, 3H), 2.71-2.54 (m, 2H), 2.05 (s, 1H), 1.66-1.55 (m, 5H), 1.46 (br. s., 1H), 1.45 (s, 9H), 1.31-1.25 (m, 2H), 1.21-1.12 (m, 1H), 0.95 (td, J=3.1, 6.3 Hz, 6H). LCMS (ESI+) expected m/z 462.27, found 463.40 ($M+H^+$).

t-Butyl 4-(1-((((S)-1-methoxy-4-methyl-1-oxopentan-2-yl)carbamoyl)oxy)-2-phenylethyl)piperidine-1-carboxylate (9b):

Compound was isolated as an oil. Yield (152 mg), $^1$H NMR (400 MHz, $CDCl_3$) δ ppm 7.29-7.26 (m, 1H), 7.22-7.18 (m, 1H), 7.16 (d, J=7.8 Hz, 2H), 4.94-4.86 (m, 1H), 4.53 (d, J=5.1 Hz, 1H), 4.06 (q, J=7.2 Hz, 2H), 5.13-3.83 (m, 2H), 3.66 (d, J=3.1 Hz, 1H), 3.59-3.52 (m, 1H), 3.26-3.19 (m, 1H), 2.84 (dd, J=3.3, 13.5 Hz, 1H), 2.62 (d, J=9.4 Hz, 2H), 1.99 (s, 1H), 1.82 (d, J=13.3 Hz, 1H), 1.70-1.62 (m, 3H), 1.53-1.50 (m, 1H), 1.41 (s, 9H), 1.20 (t, J=7.2 Hz, 2H), 0.89-0.87 (m, 6H). LCMS (ESI+) expected m/z 476.29, found 476.40 (M+H$^+$).

t-Butyl (S)-4-(((1-methoxy-4-methyl-1-oxopentan-2-yl)carbamoyl)oxy)-4-phenylpiperidine-1-carboxylate (4a):

Compound was isolated as an oil. Yield (125 mg), $^1$H NMR (400 MHz, $CDCl_3$) δ ppm 7.42-7.38 (m, 2H), 7.32-7.28 (m, 1H), 7.23-7.17 (m, 2H), 4.07-3.82 (m, 2H), 3.64 (s, 3H), 3.25-3.10 (m, 2H), 1.96 (s, 2H), 1.70-1.61 (m, 3H), 1.40 (s, 9H), 1.17 (t, J=7.6 Hz, 1H), 0.90-0.82 (m, 9H). LCMS (ESI+) expected m/z 448.26, found 449.40 (M+H$^+$).

t-Butyl (S)-4-benzyl-4-(((1-methoxy-4-methyl-1-oxopentan-2-yl)carbamoyl)oxy)piperidine-1-carboxylate (4b):

Compound was isolated as an oil. Yield (200 mg), $^1$H NMR (400 MHz, $CDCl_3$) δ ppm 7.36-7.28 (m, 3H), 7.20 (d, J=7.4 Hz, 2H), 5.03 (dd, J=8.2, 18.4 Hz, 2H), 4.48 (dt, J=4.5, 8.9 Hz, 2H), 3.73 (s, 3H), 3.10 (br. s., 1H), 2.76 (s, 1H), 1.64-1.55 (m, 4H), 1.53-1.49 (m, 2H), 1.46 (s, 9H), 0.96-0.93 (m, 6H). LCMS (ESI+) expected m/z 462.27, found 463.40 (M+H$^+$).

t-Butyl (S)-4-(((1-methoxy-4-methyl-1-oxopentan-2-yl)carbamoyl)oxy)-4-phenethylpiperidine-1-carboxylate (4c):

Compound was isolated as an oil. Yield (215 mg), $^1$H NMR (400 MHz, $CDCl_3$) δ ppm 7.32-7.27 (m, 3H), 7.20 (d, J=6.7 Hz, 2H), 4.92-4.84 (m, 1H), 4.48 (br. s., 1H), 3.95-3.79 (m, 2H), 3.73 (s, 1H), 3.26-3.13 (m, 2H), 2.76-2.69 (m, 2H), 1.84-1.77 (m, 2H), 1.61 (d, J=4.3 Hz, 5H), 1.47 (s, 9H), 0.94 (dd, J=3.3, 6.5 Hz, 6H). LCMS (ESI+) expected m/z 476.29, found 477.50 (M+H$^+$).

Methyl (((1-acetyl-4-phenethylpiperidin-4-yl)oxy)carbonyl)-L-leucinate (4d):

Compound was isolated as an oil. Yield (150 mg), $^1$H NMR (400 MHz, $CDCl_3$) δ ppm 7.33-7.27 (m, 2H), 7.20 (d, J=7.4 Hz, 3H), 5.00-4.90 (m, 1H), 4.52-4.43 (m, 1H), 4.36 (d, J=12.9 Hz, 1H), 3.73 (s, 3H), 3.61 (d, J=13.3 Hz, 1H), 3.53-3.43 (m, 1H), 3.11-3.02 (m, 1H), 2.76-2.69 (m, 2H), 2.11 (s, 3H), 1.85-1.78 (m, 2H), 1.74-1.57 (m, 9H), 1.53-1.46 (m, 2H), 0.94 (dd, J=2.9, 6.5 Hz, 7H). LCMS (ESI+) expected m/z 418.25, found 419.50 (M+H$^+$).

t-Butyl (S)-4-(((1-methoxy-4-methyl-1-oxopentan-2-yl)carbamoyl)oxy)piperidine-1-carboxylate (4e):

Compound was isolated as an oil. Yield (2.4 g), $^1$H NMR (400 MHz, $CDCl_3$) δ ppm 5.06 (d, J=8.6 Hz, 1H), 4.80 (br. s., 2H), 4.52-4.44 (m, 1H), 4.37 (d, J=5.1 Hz, 1H), 3.74 (s, 3H), 3.24-3.14 (m, 2H), 1.85 (br. s., 3H), 1.60 (dd, J=7.4, 12.5 Hz, 4H), 1.46 (s, 9H), 0.97-0.92 (m, 8H). LCMS (ESI+) expected m/z 372.23, found 373.40 (M+H$^+$).

t-Butyl (S)-4-(((3-cyclohexyl-1-methoxy-1-oxopropan-2-yl)carbamoyl)oxy)-4-phenylpiperidine-1-carboxylate (4f):

Compound was isolated as an oil. Yield (0.37 g), $^1$H NMR (400 MHz, $CDCl_3$) δ ppm 7.48 (d, J=7.4 Hz, 2H), 7.38 (t, J=7.6 Hz, 2H), 7.29 (d, J=7.4 Hz, 1H), 4.83 (d, J=8.6 Hz, 1H), 4.49 (d, J=5.5 Hz, 1H), 4.09-3.99 (m, 2H), 3.73 (s, 3H), 3.26 (br. s., 2H), 2.01 (br. s., 2H), 1.83-1.58 (m, 13H), 1.49 (s, 9H), 1.41-1.30 (m, 2H), 1.30-1.10 (m, 6H), 0.99-0.83 (m, 4H). LCMS (ESI+) expected m/z 488.29, found 489.40 (M+H$^+$).

Methyl (((1-(ethylsulfonyl)piperidin-4-yl)oxy)carbonyl)-L-leucinate (5a):

Compound was isolated as an oil. Yield (150 mg), $^1$H NMR (400 MHz, $CDCl_3$) δ ppm 5.94 (br. s., 2H), 5.12 (br. s., 1H), 4.84 (br. s., 1H), 4.37 (d, J=3.1 Hz, 1H), 3.75 (s, 1H), 3.56-3.44 (m, 2H), 3.23 (dd, J=3.5, 7.8 Hz, 2H), 3.01-2.93 (m, 2H), 1.96 (d, J=3.1 Hz, 2H), 1.86-1.64 (m, 4H), 1.64-1.49 (m, 2H), 1.37 (t, J=7.2 Hz, 3H), 0.97 (d, J=5.9 Hz, 6H). LCMS (ESI+) expected m/z 364.17, found 365.30 (M+H$^+$).

Methyl (((1-(phenylsulfonyl)piperidin-4-yl)oxy)carbonyl)-L-leucinate (5b):

Compound was isolated as an oil. Yield (159 mg), $^1$H NMR (400 MHz, $CDCl_3$) δ ppm 7.78 (d, J=7.8 Hz, 2H), 7.66-7.60 (m, 1H), 7.59-7.53 (m, 2H), 5.00 (d, J=8.6 Hz, 1H), 4.92-4.85 (m, 1H), 4.69 (br. s., 1H), 4.53-4.43 (m, 1H), 4.38-4.28 (m, 2H), 3.72 (s, 3H), 3.26 (br. s., 2H), 2.96 (br. s., 2H), 1.95 (d, J=3.9 Hz, 2H), 1.78 (br. s., 2H), 1.70-1.55 (m, 3H), 1.53-1.43 (m, 2H), 0.97-0.88 (m, 6H). LCMS (ESI+) expected m/z 412.17, found 413.30 (M+H$^+$).

Methyl (((1-((3-fluorophenyl)sulfonyl)piperidin-4-yl)oxy)carbonyl)-L-leucinate (5c):

Compound was isolated as an oil. Yield (148 mg), $^1$H NMR (400 MHz, $CDCl_3$) δ ppm 7.61-7.50 (m, 2H), 7.48 (d, J=7.8 Hz, 1H), 7.39-7.30 (m, 1H), 5.01 (d, J=8.2 Hz, 1H), 4.91-4.80 (m, 1H), 4.72 (br. s., 1H), 4.48 (d, J=5.1 Hz, 1H), 4.37-4.28 (m, 1H), 3.73 (s, 3H), 3.23 (br. s., 2H), 3.03 (br. s., 2H), 1.96 (br. s., 2H), 1.80 (br. s., 2H), 1.62 (s, 2H), 1.54-1.44 (m, 2H), 0.93 (br. s., 6H). LCMS (ESI+) expected m/z 430.16, found 431.30 (M+H$^+$).

Methyl (((1-((2-fluorophenyl)sulfonyl)piperidin-4-yl)oxy)carbonyl)-L-leucinate (5d):

Compound was isolated as an oil. Yield (126 mg), $^1$H NMR (400 MHz, $CDCl_3$) δ ppm 8.00 (t, J=7.4 Hz, 1H), 7.86 (t, J=7.4 Hz, 1H), 7.81-7.71 (m, 1H), 7.63-7.56 (m, 1H), 7.43-7.35 (m, 1H), 5.31 (s, 1H), 5.03 (d, J=9.4 Hz, 1H), 4.83-4.73 (m, 1H), 4.53-4.42 (m, 1H), 4.34 (d, J=4.7 Hz, 1H), 3.73 (s, 3H), 3.41 (br. s., 2H), 3.17 (d, J=7.8 Hz, 2H), 1.95 (br. s., 2H), 1.79 (br. s., 2H), 1.71-1.57 (m, 6H), 1.54-1.43 (m, 2H), 0.93 (d, J=4.3 Hz, 6H). LCMS (ESI+) expected m/z 430.16, found 431.30 (M+H$^+$).

Methyl (((1-((4-chlorophenyl)sulfonyl)piperidin-4-yl)oxy)carbonyl)-L-leucinate (5e):

Compound was isolated as an oil. Yield (150 mg), $^1$H NMR (400 MHz, $CDCl_3$) δ ppm 7.71 (d, J=7.4 Hz, 2H), 7.53 (d, J=7.8 Hz, 2H), 5.01 (d, J=8.2 Hz, 1H), 4.72 (br. s., 1H), 4.52-4.43 (m, 1H), 4.38-4.28 (m, 1H), 3.73 (s, 3H), 3.19 (br. s., 2H), 3.02 (br. s., 2H), 1.95 (br. s., 2H), 1.80 (br. s., 2H), 1.62 (br. s., 4H), 1.54-1.42 (m, 2H), 0.94 (br. s., 6H). LCMS (ESI+) expected m/z 446.13, found 447.20 (M+H$^+$).

Methyl (((1-((2,4-dinitrophenyl)sulfonyl)piperidin-4-yl)oxy)carbonyl)-L-leucinate (5f):

Compound was isolated as a yellow solid. Yield (136 mg), $^1$H NMR (400 MHz, $CDCl_3$) δ ppm 8.54-8.47 (m, 2H), 8.23 (d, J=8.6 Hz, 1H), 5.08 (d, J=8.2 Hz, 1H), 4.86 (br. s., 1H), 4.40-4.31 (m, 1H), 3.74 (s, 3H), 3.56-3.31 (m, 4H), 1.97 (d, J=4.3 Hz, 2H), 1.84 (d, J=5.9 Hz, 2H), 1.74-1.56 (m, 2H), 1.55-1.45 (m, 2H), 1.32-1.21 (m, 2H), 0.94 (t, J=4.9 Hz, 6H). LCMS (ESI+) expected m/z 502.10, found 503.20 (M+H$^+$).

Methyl (((1-((5-chloro-2-methoxyphenyl)sulfonyl)piperidin-4-yl)oxy)carbonyl)-L-leucinate (5g):

Compound was isolated as an oil. Yield (167 mg), $^1$H NMR (400 MHz, $CDCl_3$) δ ppm 7.88 (d, J=2.3 Hz, 1H), 7.51-7.44 (m, 1H), 6.97 (d, J=9.0 Hz, 1H), 5.05 (d, J=8.6 Hz, 1H), 4.77 (br. s., 1H), 4.40-4.31 (m, 1H), 3.93 (s, 3H), 3.74 (s, 3H), 3.48 (d, J=5.9 Hz, 2H), 3.22-3.11 (m, 2H), 1.93 (br. s., 2H), 1.80-1.68 (m, 2H), 1.62 (s, 2H), 1.55-1.46 (m, 2H), 0.94 (d, J=5.5 Hz, 6H). LCMS (ESI+) expected m/z 476.14, found 477.30 (M+H$^+$).

Methyl (((1-(mesitylsulfonyl)piperidin-4-yl)oxy)carbonyl)-L-leucinate (5h):

Compound was isolated as an oil. Yield (162 mg), $^1$H NMR (400 MHz, $CDCl_3$) δ ppm 6.96 (s, 2H), 5.05 (d, J=8.6 Hz, 1H), 4.89-4.78 (m, 1H), 4.36 (d, J=5.1 Hz, 1H), 3.74 (s, 3H), 3.36 (br. s., 2H), 3.11 (d, J=7.8 Hz, 2H), 2.62 (s, 6H), 2.31 (s, 3H), 1.90 (br. s., 3H), 1.80-1.65 (m, 4H), 1.56-1.45

(m, 2H), 0.95 (d, J=5.5 Hz, 6H). LCMS (ESI+) expected m/z 454.21, found 455.40 (M+H$^+$). [0326](((1-(tert-butoxycarbonyl)piperidin-4-yl)(phenyl)methoxy)carbonyl)-L-leucine (10a):

Compound was isolated as an off white solid. Yield (110 mg), $^1$H NMR (400 MHz, $CDCl_3$) δ ppm 7.40-7.28 (m, 5H), 5.56-5.39 (m, 1H), 4.43-4.28 (m, 1H), 4.21-3.99 (m, 1H), 2.63 (br. s., 1H), 1.90 (br. s., 2H), 1.84-1.63 (m, 4H), 1.45 (s, 9H), 1.28 (d, J=9.4 Hz, 3H), 1.04-0.85 (m, 7H). LCMS (ESI+) expected m/z 448.26, found 449.40 (M+H$^+$).

((1-(1-(tert-butoxycarbonyl)piperidin-4-yl)-2-phenylethoxy)carbonyl)-L-leucine (10b):

Compound was isolated as an off white solid. Yield (270 mg), $^1$H NMR (400 MHz, $CDCl_3$) δ ppm 7.36-7.30 (m, 2H), 7.26-7.20 (m, 3H), 4.62-4.58 (m, 1H), 4.22-4.09 (m, 3H), 3.62 (s, 2H), 2.91 (dd, J=3.3, 13.5 Hz, 2H), 2.75-2.57 (m, 4H), 1.88 (d, J=12.5 Hz, 2H), 1.72 (t, J=12.7 Hz, 2H), 1.47 (s, 9H), 1.34-1.23 (m, 2H), 1.02-0.92 (m, 6H). LCMS (ESI+) expected m/z 462.27, found 463.40 (M+H$^+$).

(((1-(tert-butoxycarbonyl)-4-phenylpiperidin-4-yl)oxy)carbonyl)-L-leucine (6a):

Compound was isolated as a thick oil. Yield (165 mg), $^1$H NMR (400 MHz, $CDCl_3$) δ ppm 7.51-7.46 (m, 2H), 7.38 (t, J=7.6 Hz, 2H), 7.30 (d, J=7.0 Hz, 1H), 4.08-4.00 (m, 2H), 3.72 (s, 1H), 3.26 (dt, J=2.3, 12.9 Hz, 3H), 2.45 (s, 1H), 2.00 (dd, J=4.9, 13.1 Hz, 2H), 1.75 (d, J=12.5 Hz, 2H), 1.50 (s, 2H), 1.49 (s, 9H), 1.01-0.93 (m, 6H). LCMS (ESI+) expected m/z 434.24, found 435.40 (M+H$^+$).

(((4-benzyl-1-(tert-butoxycarbonyl)piperidin-4-yl)oxy)carbonyl)-L-leucine (6b):

Compound was isolated as an off white solid. Yield (174 mg), $^1$H NMR (400 MHz, $CDCl_3$) δ ppm 7.36-7.28 (m, 3H), 7.20 (d, J=7.8 Hz, 2H), 6.43 (br. s., 1H), 4.76 (dd, J=4.3, 11.7 Hz, 1H), 4.11 (d, J=10.2 Hz, 1H), 3.87 (br. s., 2H), 3.10 (br. s., 2H), 2.77 (s, 2H), 2.26 (d, J=11.3 Hz, 1H), 1.93-1.76 (m, 4H), 1.66-1.50 (m, 5H), 1.46 (s, 9H), 1.28 (t, J=6.5 Hz, 1H), 0.95 (d, J=6.7 Hz, 6H). LCMS (ESI+) expected m/z 448.26, found 449.40 (M+H$^+$).

(((1-acetyl-4-phenethylpiperidin-4-yl)oxy)carbonyl)-L-leucine (6c):

Compound was isolated as an off white solid. Yield (200 mg), $^1$H NMR (400 MHz, $CDCl_3$) δ ppm 7.33-7.28 (m, 2H), 7.20 (d, J=7.0 Hz, 3H), 6.45 (br. s., 1H), 4.75 (dd, J=2.3, 11.3 Hz, 1H), 4.10 (d, J=9.4 Hz, 1H), 2.72 (br. s., 2H), 2.16 (br. s., 3H), 2.09 (s, 1H), 1.80 (br. s., 4H), 1.68 (br. s., 4H), 0.99 (d, J=8.2 Hz, 2H), 0.95 (d, J=6.3 Hz, 6H). LCMS (ESI+) expected m/z 404.23, found 405.40 (M+H$^+$).

(((1-acetylpiperidin-4-yl)oxy)carbonyl)-L-leucine (6d):

Compound was isolated as an off white solid. Yield (370 mg), $^1$H NMR (400 MHz, CHLOROFORM-d) δ ppm 5.20 (br. s., 1H), 4.89 (br. s., 1H), 4.78-4.72 (m, 1H), 4.37 (d, J=3.9 Hz, 2H), 4.18-4.07 (m, 2H), 3.72-3.53 (m, 3H), 3.40 (br. s., 2H), 2.14 (s, 3H), 1.98-1.83 (m, 2H), 1.83-1.62 (m, 2H), 1.57 (ddd, J=5.3, 8.9, 13.6 Hz, 2H), 0.97 (d, J=6.3 Hz, 6H). LCMS (ESI+) expected m/z 300.17, found 301.30 (M+H$^+$).

(S)-2-((((1-(tert-butoxycarbonyl)-4-phenylpiperidin-4-yl)oxy)carbonyl)amino)-3-cyclohexylpropanoic acid (6e):

Compound was isolated as an off white solid. Yield (314 mg), $^1$H NMR (400 MHz, $CDCl_3$) δ ppm 7.48 (d, J=7.4 Hz, 2H), 7.38 (t, J=7.6 Hz, 2H), 7.29 (d, J=7.4 Hz, 1H), 4.83 (d, J=8.6 Hz, 1H), 4.49 (d, J=5.5 Hz, 1H), 4.09-3.99 (m, 2H), 3.73 (s, 3H), 3.26 (br. s., 2H), 2.01 (br. s., 2H), 1.83-1.58 (m, 13H), 1.49 (s, 9H), 1.41-1.30 (m, 2H), 1.30-1.10 (m, 6H), 0.99-0.83 (m, 4H). LCMS (ESI+) expected m/z 474.27, found 475.40 (M+H$^+$).

(((1-(ethylsulfonyl)piperidin-4-yl)oxy)carbonyl)-L-leucine (6f):

Compound was isolated as an oil. Yield (120 mg), $^1$H NMR (400 MHz, $CDCl_3$) δ ppm 6.40 (br. s., 1H), 5.62 (br. s., 1H), 5.07 (d, J=8.2 Hz, 1H), 4.85 (br. s., 1H), 4.38 (br. s., 2H), 3.50 (br. s., 2H), 3.22 (br. s., 3H), 2.97 (q, J=7.2 Hz, 2H), 1.97 (br. s., 3H), 1.86-1.66 (m, 4 H), 1.63-1.53 (m, 2H), 1.37 (t, J=7.2 Hz, 3H), 1.02-0.93 (m, 6H). LCMS (ESI+) expected m/z 350.15, found 351.20 (M+H$^+$).

(((1-(phenylsulfonyl)piperidin-4-yl)oxy)carbonyl)-L-leucine (6g):

Compound was isolated as a white solid. Yield (118 mg), $^1$H NMR (400 MHz, $CDCl_3$) δ ppm 7.78 (d, J=7.4 Hz, 2H), 7.65-7.53 (m, 3H), 5.00 (d, J=8.6 Hz, 1H), 4.76 (dd, J=4.1, 11.2 Hz, 1H), 4.69 (br. s., 1H), 4.38-4.28 (m, 1H), 4.02 (br. s., 1H), 3.30 (br. s., 2H), 3.17 (br. s., 1H), 2.92 (br. s., 2H), 1.95 (d, J=3.9 Hz, 2H), 1.85-1.72 (m, 2H), 1.71-1.62 (m, 2H), 1.57-1.47 (m, 2H), 0.97-0.90 (m, 6H). LCMS (ESI+) expected m/z 398.15, found 399.30 (M+H$^+$).

(((1-((4-chlorophenyl)sulfonyl)piperidin-4-yl)oxy)carbonyl)-L-leucine (6h):

Compound was isolated as a white solid. Yield (140 mg), $^1$H NMR (400 MHz, $CDCl_3$) δ ppm 7.71 (d, J=8.2 Hz, 2H), 7.53 (d, J=8.2 Hz, 2H), 6.28 (br. s., 1H), 4.98 (d, J=8.2 Hz, 1H), 4.81-4.68 (m, 1H), 4.33 (br. s., 1H), 3.24 (br. s., 2H), 2.99 (br. s., 2H), 1.96 (br. s., 2H), 1.85-1.64 (m, 4H), 1.61-1.49 (m, 1H), 0.95 (d, J=5.5 Hz, 6H). LCMS (ESI+) expected m/z 432.11, found 432.30 (M+H$^+$).

(((1-((2-fluorophenyl)sulfonyl)piperidin-4-yl)oxy)carbonyl)-L-leucine (6i):

Compound was isolated as an off white solid. Yield (120 mg), $^1$H NMR (400 MHz, $CDCl_3$) δ ppm 7.86 (t, J=7.2 Hz, 1H), 7.60 (q, J=6.7 Hz, 1H), 7.32-7.29 (m, 1H), 7.25-7.20 (m, 1H), 5.02 (d, J=8.6 Hz, 1H), 4.78 (br. s., 1H), 4.38-4.31 (m, 1H), 3.44 (br. s., 2H), 3.15 (d, J=7.4 Hz, 2H), 1.96 (br. s., 2H), 1.83-1.64 (m, 4H), 1.58-1.50 (m, 2H), 1.27 (br. s., 1H), 0.95 (d, J=6.3 Hz, 6H). LCMS (ESI+) expected m/z 416.14, found 417.30 (M+H$^+$).

(((1-((3-fluorophenyl)sulfonyl)piperidin-4-yl)oxy)carbonyl)-L-leucine (6j):

Compound was isolated as an off white solid. Yield (110 mg), $^1$H NMR (400 MHz, $CDCl_3$) δ ppm 7.59-7.53 (m, 2H), 7.48 (d, J=7.4 Hz, 1H), 7.32 (d, J=7.0 Hz, 1H), 6.70 (br. s., 1H), 5.79 (br. s., 1H), 5.01 (d, J=8.2 Hz, 1H), 4.82-4.68 (m, 1H), 4.32 (br. s., 1H), 4.14-3.98 (m, 1H), 3.28 (br. s., 2H), 2.99 (br. s., 2H), 1.96 (br. s., 2H), 1.79 (br. s., 2H), 1.68 (d, J=9.4 Hz, 2H), 1.53 (br. s., 2H), 1.26 (br. s., 1H), 0.94 (d, J=5.1 Hz, 6H). LCMS (ESI+) expected m/z 416.14, found 417.30 (M+H$^+$).

(((1-((2,4-dinitrophenyl)sulfonyl)piperidin-4-yl)oxy)carbonyl)-L-leucine (6k):

Compound was isolated as an off white solid. Yield (90 mg), $^1$H NMR (400 MHz, $CDCl_3$) δ ppm 11.08-10.99 (m, 1H), 9.09 (d, J=2.3 Hz, 1H), 8.53-8.39 (m, 1H), 7.35 (d, J=9.4 Hz, 1H), 4.11 (m, 2H), 3.94 (m, 2H), 3.83-3.75 (m, 2H), 3.71-3.58 (m, 4H), 2.18 (m, 3H), 1.07-0.93 (m, 6H). LCMS (ESI+) expected m/z 488.12, found 489.30 (M+H$^+$).

(((1-((5-chloro-2-methoxyphenyl)sulfonyl)piperidin-4-yl)oxy)carbonyl)-L-leucine (61):

Compound was isolated as an off white solid. Yield (100 mg), $^1$H NMR (400 MHz, $CDCl_3$) δ ppm 7.88 (s, 1H), 7.47 (dd, J=2.3, 8.6 Hz, 1H), 6.97 (d, J=9.0 Hz, 1H), 5.02 (d, J=8.6 Hz, 1H), 4.78 (br. s., 1H), 4.36 (d, J=3.1 Hz, 1H), 3.92 (s, 3H), 3.51 (d, J=6.3 Hz, 2H), 3.16 (d, J=9.4 Hz, 2H), 1.94 (br. s., 2H), 1.79-1.66 (m, 4H), 1.55 (t, J=8.6 Hz, 2H), 0.96 (d, J=5.9 Hz, 6H). LCMS (ESI+) expected m/z 462.12, found 463.30 (M+H$^+$).

(((1-(mesitylsulfonyl)piperidin-4-yl)oxy)carbonyl)-L-leucine (6m):

Compound was isolated as an off white solid. Yield (130 mg), $^1$H NMR (400 MHz, $CDCl_3$) δ ppm 6.95 (s, 2H), 5.15 (d, J=8.2 Hz, 1H), 4.82 (br. s., 1H), 4.35 (br. s., 1H), 3.36 (br. s., 2H), 3.11 (br. s., 2H), 2.61 (s, 6H), 2.30 (s, 3H), 2.18 (s, 2H), 1.88 (d, J=3.5 Hz, 2H), 1.82-1.69 (m, 3H), 1.62-1.52 (m, 2H), 0.96 (d, J=5.9 Hz, 6H). LCMS (ESI+) expected m/z 440.20, found 441.40 ($M+H^+$).

4-phenylpiperidin-4-yl ((S)-1-(((S)-1-(benzo[d]thiazol-2-yl)-5-guanidino-1-oxopentan-2-yl)amino)-4-methyl-1-oxopentan-2-yl)carbamate (8a):

Compound was isolated as a white solid. Yield (65%), $^1$H NMR (400 MHz, $CD_3OD$) δ ppm 8.23-8.20 (m, 1H), 8.15-8.11 (m, 1H), 7.68-7.59 (m, 1H), 7.34 (d, J=3.9 Hz, 3H), 7.29-7.18 (m, 4H), 5.71-5.64 (m, 1H), 3.88-3.79 (m, 1H), 3.23-3.18 (m, 3H), 3.12 (s, 1H), 2.68-2.63 (m, 3H), 2.44 (s, 2H), 1.90-1.77 (m, 2H), 1.60-1.49 (m, 1H), 1.26 (d, J=6.7 Hz, 2H), 1.07-0.88 (m, 6H). LCMS (ESI+) expected m/z 607.30, found 608.5 ($M+H^+$).

4-benzylpiperidin-4-yl((S)-1-(((S)-1-(benzo[d]thiazol-2-yl)-5-guanidino-1-oxopentan-2-yl)amino)-4-methyl-1-oxopentan-2-yl)carbamate (8b):

Compound was isolated as a white solid. Yield (68%), $^1$H NMR (400 MHz, $CDCl_3$) δ ppm 8.17 (d, J=7.8 Hz, 1H), 7.96 (d, J=7.4 Hz, 1H), 7.65-7.50 (m, 4H), 6.94 (br. s., 2H), 5.79 (br. s., 1H), 4.76 (dd, J=4.9, 10.8 Hz, 1H), 4.15 (d, J=5.5 Hz, 1H), 3.45 (br. s., 2H), 3.16 (br. s., 2H), 2.81 (br. s., 4H), 2.37-2.06 (m, 3H), 1.93-1.58 (m, 8H), 1.61-1.38 (m, 3H), 0.98-0.85 (m, 6H). LCMS (ESI+) expected m/z 621.31, found 622.4 ($M+H^+$).

1-acetyl-4-phenethylpiperidin-4-yl ((S)-1-(((S)-1-(benzo[d]thiazol-2-yl)-5-guanidino-1-oxopentan-2-yl)amino)-4-methyl-1-oxopentan-2-yl)carbamate (8c):

Compound was isolated as a white solid. Yield (55%), $^1$H NMR (400 MHz, CHLOROFORM-d) δ ppm=8.19 (d, J=7.04 Hz, 1H), 7.92-8.06 (m, 2H), 7.43-7.76 (m, 7H), 6.95 (br. s., 1H), 5.79 (d, J=7.83 Hz, 2H), 4.71-4.85 (m, 1H), 4.04-4.26 (m, 2H), 3.16 (br. s., 1H), 2.11-2.49 (m, 8H), 1.40-1.95 (m, 10H), 0.83-1.03 (m, 6H). LCMS (ESI+) expected m/z 677.34, found 587.5 ($M-Bn^+$).

4-phenylpiperidin-4-yl ((S)-1-(((S)-1-(benzo[d]thiazol-2-yl)-5-guanidino-1-oxopentan-2-yl)amino)-3-cyclohexyl-1-oxopropan-2-yl)carbamate (8d):

Compound was isolated as a white solid. Yield (60%), $^1$H NMR (400 MHz, $CDCl_3$) δ ppm=8.20 (d, J=7.83 Hz, 2H), 7.92-8.04 (m, 2H), 7.75 (br. s., 1H), 7.37-7.68 (m, 9H), 6.97 (br. s., 2H), 5.81 (br. s., 2H), 4.70-4.88 (m, 2H), 4.08-4.29 (m, 2H), 3.41-3.63 (m, 1H), 3.17 (br. s., 1H), 2.51 (br. s., 2H), 2.10-2.39 (m, 4H), 1.43-1.93 (m, 8H), 0.79-1.36 (m, 11H). LCMS (ESI+) expected m/z 646.33, found 647.5 ($M+H^+$).

1-acetylpiperidin-4-yl ((S)-1-(((S)-1-(benzo[d]thiazol-2-yl)-5-guanidino-1-oxopentan-2-yl)amino)-4-methyl-1-oxopentan-2-yl)carbamate (8e):

Compound was isolated as a white solid. Yield (65%), $^1$H NMR (400 MHz, DMSO-d6) δ ppm 8.57 (d, J=5.5 Hz, 1H), 8.30-8.21 (m, 1H), 7.68 (quin, J=6.5 Hz, 1H), 7.51 (br. s., 1H), 7.25 (d, J=8.2 Hz, 1H), 5.41 (br. s., 1H), 4.65 (br. s., 1H), 4.08 (d, J=6.7 Hz, 1H), 3.84 (d, J=13.3 Hz, 1H), 3.59 (br. s., 1H), 3.24 (br. s., 1H), 3.15 (d, J=5.5 Hz, 2H), 1.99 (s, 3H), 1.75 (br. s., 2H), 1.58 (dd, J=6.3, 14.5 Hz, 3H), 1.41-1.31 (m, 3H), 0.82 (d, J=6.7 Hz, 6H).

LCMS (ESI+) expected m/z 573.28, found 574.5 ($M+H^+$).

1-(phenylsulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8f):

Compound was isolated as a white solid. Yield (55%), $^1$H NMR (400 MHz, $CDCl_3$) δ ppm 8.17 (d, J=6.7 Hz, 1H), 8.03-7.92 (m, 2H), 7.83 (br. s., 1H), 7.79-7.66 (m, 3H), 7.64-7.50 (m, 4H), 7.46 (d, J=7.4 Hz, 1H), 6.98 (br. s., 1H), 5.83-5.71 (m, 1H), 5.52 (d, J=5.5 Hz, 1H), 5.33 (br. s., 1H), 4.64 (br. s., 2H), 4.16 (br. s., 1H), 3.34-3.07 (m, 2H), 2.88 (br. s., 2H), 2.17 (br. s., 1H), 1.91 (br. s., 3H), 1.75 (br. s., 4H), 1.57 (dt, J=7.0, 15.7 Hz, 4H), 0.89 (d, J=6.7 Hz, 6H). LCMS (ESI+) expected m/z 671.26, found 672.4 ($M+H^+$).

1-((2-fluorophenyl)sulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8g):

Compound was isolated as a white solid. Yield (60%), $^1$H NMR (400 MHz, $CDCl_3$) δ ppm=8.16 (d, J=7.83 Hz, 1H), 7.97 (d, J=7.83 Hz, 1H), 7.86 (br. s., 1H), 7.70 (d, J=7.83 Hz, 1H), 7.50-7.64 (m, 4H), 7.45 (d, J=6.65 Hz, 1H), 7.29-7.37 (m, 1H), 6.88 (br. s., 1H), 5.74 (br. s., 1H), 5.33 (d, J=6.65 Hz, 1H), 4.68 (br. s., 1H), 3.84-4.28 (m, 5H), 3.44-3.62 (m, 2H), 3.24 (br. s., 4H), 2.90-3.04 (m, 2H), 2.17 (br. s., 2H), 1.93 (m, 3H), 1.76 (m, 2H), 1.45-1.68 (m, 2H), 0.77-1.01 (m, 6H). LCMS (ESI+) expected m/z 689.25, found 690.4 ($M+H^+$).

1-(ethylsulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8h):

Compound was isolated as a white solid. Yield (62%), $^1$H NMR (400 MHz, $CDCl_3$) δ ppm=8.18 (d, J=7.43 Hz, 1H), 7.97 (d, J=7.83 Hz, 1H), 7.73 (d, J=7.43 Hz, 1H), 7.46-7.65 (m, 4H), 5.75 (br. s., 2H), 5.55 (br. s., 1H), 4.82 (br. s., 1H), 4.22 (br. s., 1H), 3.45 (br. s., 2H), 3.05-3.31 (m, 4H), 2.96 (q, J=7.30 Hz, 2H), 2.10-2.28 (m, 3H), 1.50-2.03 (m, 7H), 1.34 (t, J=7.43 Hz, 3H), 0.94 (d, J=7.04 Hz, 6H). LCMS (ESI+) expected m/z 623.26, found 624.4 ($M+H^+$).

1-((4-chlorophenyl)sulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8i):

Compound was isolated as a white solid. Yield (65%), $^1$H NMR (400 MHz, $CDCl_3$) d ppm=8.19 (d, J=7.43 Hz, 1H), 8.00 (d, J=7.04 Hz, 1H), 7.44-7.75 (m, 5H), 7.38 (d, J=7.04 Hz, 2H), 6.93 (br. s., 1H), 5.83 (br. s., 1H), 5.42 (d, J=7.43 Hz, 1H), 4.66 (br. s., 1H), 4.15 (br. s., 1H), 3.17-3.41 (m, 6H), 2.94 (br. s., 4H), 1.93 (m, 2H), 1.76 (m., 4H), 1.19-1.37 (m, 1H), 0.75-0.93 (m, 6H). LCMS (ESI+) expected m/z 705.22, found 706.4 ($M+H^+$).

1-((3-fluorophenyl)sulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8j):

Compound was isolated as a white solid. Yield (65%), $^1$H NMR (400 MHz, $CDCl_3$) δ ppm=8.16 (d, J=7.83 Hz, 1H), 7.97 (d, J=7.83 Hz, 1H), 7.86 (br. s., 1H), 7.70 (d, J=7.83 Hz, 1H), 7.50-7.64 (m, 4H), 7.45 (d, J=6.65 Hz, 1H), 7.29-7.37 (m, 1H), 6.88 (br. s., 1H), 5.74 (br. s., 1H), 5.33 (d, J=6.65 Hz, 1H), 4.68 (br. s., 1H), 3.84-4.28 (m, 5H), 3.44-3.62 (m, 2H), 3.24 (br. s., 4H), 2.90-3.04 (m, 2H), 2.17 (br. s., 2H), 1.93 (m, 3H), 1.76 (m, 2H), 1.45-1.68 (m, 2H), 0.77-1.01 (m, 6H). LCMS (ESI+) expected m/z 689.25, found 690.5 ($M+H^+$).

1-((2,4-dinitrophenyl)sulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8k):

Compound was isolated as an off-white solid. Yield (60%), $^1$H NMR (400 MHz, $CDCl_3$) δ ppm 8.75-8.66 (m, 1H), 8.48-8.45 (m, 1H), 8.19 (s, 3H), 8.03-7.98 (m, 2H), 7.67-7.53 (m, 5H), 7.16-7.06 (m, 1H), 5.33-5.27 (m, 1H), 3.95-3.88 (m, 1H), 3.52-3.47 (m, 1H), 2.68 (s, 2H), 1.87 (br. s., 52H), 1.02-0.87 (m, 6H). LCMS (ESI+) expected m/z 761.23, found 762.5 ($M+H^+$).

1-((5-chloro-2-methoxyphenyl)sulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (81):

Compound was isolated as a white solid. Yield (63%), $^1$H NMR (400 MHz, $CDCl_3$) δ ppm 8.12-8.24 (m, 1H), 7.71-8.02 (m, 4H), 7.40-7.65 (m, 4H), 6.95 (d, J=8.61 Hz, 1H), 5.60-5.85 (m, 1H), 5.46 (d, J=7.04 Hz, 1H), 4.74 (br. s., 1H), 3.96-4.28 (m, 7H), 3.90 (s, 2 H), 3.47 (d, J=4.70 Hz, 2H), 3.13 (m., 2H), 2.18 (br. s., 2H), 1.49-2.00 (m, 8H), 0.91 (d, J=6.78 Hz, 6H). LCMS (ESI+) expected m/z 735.24, found 736.4 ($M+H^+$).

1-(mesitylsulfonyl)piperidin-4-yl ((S)-1-(((S)-1-(benzo[d]thiazol-2-yl)-5-guanidino-1-oxopentan-2-yl)amino)-4-methyl-1-oxopentan-2-yl)carbamate (8m):

Compound was isolated as a white solid. Yield (64%), $^1$H NMR (400 MHz, $CDCl_3$) δ ppm 8.17 (d, J=7.04 Hz, 1H), 7.97 (t, J=6.26 Hz, 2H), 7.76 (d, J=5.09 Hz, 1H), 7.50-7.65 (m, 4H), 6.94 (s, 2H), 5.68-5.86 (m, 1H), 4.77 (br. s., 1H), 4.21 (br. s., 1H), 3.01-3.57 (m, 6H), 2.58 (s, 3H), 2.30 (s, 3H), 2.19 (s, 2H), 1.50-1.94 (m, 6H), 0.91 (d, J=6.39 Hz, 6H). LCMS (ESI+) expected m/z 713.31, found 714.5 ($M+H^+$).

phenyl(piperidin-4-yl)methyl ((S)-1-(((S)-1-(benzo[d]thiazol-2-yl)-5-guanidino-1-oxopentan-2-yl)amino)-4-methyl-1-oxopentan-2-yl)carbamate (11a):

Compound was isolated as a white solid. Yield (50%), $^1$H NMR (400 MHz, $CD_3OD$) δ ppm 8.23-8.20 (m, 1H), 8.15-8.11 (m, 1H), 7.68-7.59 (m, 1H), 7.34 (d, J=3.9 Hz, 3H), 7.29-7.18 (m, 4H), 5.71-5.64 (m, 1H), 3.88-3.79 (m, 1H), 3.23-3.18 (m, 3H), 3.12 (s, 1H), 2.68-2.63 (m, 3H), 2.44 (s, 2H), 1.90-1.77 (m, 2H), 1.60-1.49 (m, 1H), 1.26 (d, J=6.7 Hz, 2H), 1.07-0.88 (m, 6H). LCMS (ESI+) expected m/z 621.32, found 622.5 ($M+H^+$).

2-phenyl-1-(piperidin-4-yl)ethyl ((S)-1-(((S)-1-(benzo[d]thiazol-2-yl)-5-guanidino-1-oxopentan-2-yl)amino)-4-methyl-1-oxopentan-2-yl)carbamate (11b):

Compound was isolated as a white solid. Yield (52%), $^1$H NMR (400 MHz, DMSO-d6) δ ppm 8.65-8.56 (m, 1H), 8.41 (s, 1H), 8.36 (d, J=4.7 Hz, 1H), 8.30-8.23 (m, 2H), 7.68 (dd, J=2.3, 5.1 Hz, 2H), 7.53-7.44 (m, 1H), 7.29 (d, J=8.2 Hz, 1H), 7.18 (d, J=8.2 Hz, 1H), 5.52-5.35 (m, 1H), 4.55-4.45 (m, 1H), 4.06-3.96 (m, 1H), 3.56 (d, J=11.0 Hz, 1H), 3.18-3.11 (m, 2H), 2.42 (s, 2H), 1.97 (d, J=5.1 Hz, 1H), 1.74 (dd, J=3.9, 9.4 Hz, 3H), 1.65-1.51 (m, 3H), 1.40-1.29 (m, 2H), 0.86 (d, J=2.3 Hz, 6H). LCMS (ESI+) expected m/z 635.33, found 544.4 ($M-Bn^+$).

Example 12. Biological Activity Data of Matriptase, Hepsin, HGFA, Factor Xa, and Thrombin Fluorescent inhibitor and chromogenic proteolytic assays were performed for compounds prepared in Example 11 in general accordance with the procedures described in Example 9.

Using the fluorogenic protease substrates, Boc-QAR-AMC (matriptase and hepsin) or Boc-QLR-AMC (HGFA) in previously published kinetic enzyme assays (Z. Han et al., *ACS Med. Chem. Lett.,* 2014, 5, 1219-1224), the activities of all target compounds using eleven different concentrations of compound were tested. Inhibitors were pre-incubated with protease followed by the addition of the substrate. Inhibition of substrate proteolysis derived fluorescence was monitored kinetically over a period of one hour. Shown in Table 3 are the experimentally determined $IC_{50}$ values of each compound for their concentration-dependent inhibition of HGFA, matriptase, and hepsin.

The majority of compounds tested showed good activity and excellent selectivity for matriptase and hepsin over HGFA (Table 3). The most potent inhibitors identified were 8b and 8c which have $IC_{50}$ values 0.6 and 0.5 nM for hepsin and 30 and 70 nM for matriptase, respectively. Compound 8d was also made, which replaced the P2 Leu with the unnatural amino acid cyclohexyl alanine (Cha), but it was found that the activity lowered for all three proteases (Table 3). Inhibitors with substituted alkyl or aryl sulfonyl groups at the R2/P4 position attached on the piperidine ring nitrogen generally were found to exhibit better potency against hepsin relative to matriptase. As examples, ethyl sulfonyl (8h) and acetyl (8e) analogs showed the best activity of all aryl sulfonyl analogs at the R2/P4 position, clearly demonstrating that smaller functional groups are preferred in the S4 pocket of matriptase and hepsin.

To introduce more flexibility into the piperidine carbamate, two additional analogs 11a-b which have a methylene spacer between the piperidine ring and the carbamate linker to the Leu P2 position were made. In these analogs, the R1 substituent was then not a tertiary group on the piperidine ring but rather a secondary group on the spacer. It was found that these two inhibitors exhibited excellent potency against both hepsin and matriptase with $IC_{50}$ values 8 nM and 2 nM, respectively. It was also found that these two inhibitors exhibited moderate effect in inhibiting HGFA ($IC_{50}$ values 14 μM and 6 μM) but were less active than the corresponding matched pairs 8a and 8b ($IC_{50}$ values of 0.78 and 1.2 μM). SAR data also revealed that adding the methylene linker between the aryl and carbamate group decreased the activity against matriptase and hepsin. Similar to that found for 8a and 8b, the benzyl group on the R1 position of the piperidine having an additional methylene spacer was optimal to the phenyl group in 11a and 11b.

It is noteworthy that all hybrid piperidine dipeptides displayed only weak or no activity against HGFA with the analogs 8a and 8b containing phenyl and benzyl groups at the R1 position having the best $IC_{50}$ values of 0.78 and 1.2 μM, respectively. Increasing the alkyl linker length between the phenyl and piperidine ring as in compound 8c resulted in loss of any activity up to 20 μM. Evaluation of the SAR derived from different sulfonyl and acyl groups at the R2 position showed only moderate effects on HGFA activity. Interestingly, when tested in the enzyme assays, it was found that SRI 31215 only had weak activity for HGFA ($IC_{50}$ 20 μM). Furthermore, all other benzamidine inhibitors reported to date showed either no or weak potency for HGFA as well.

To determine the target selectivity profile, a handful of compounds were tested against the similar trypsin-like serine proteases, Factor Xa and thrombin. In general, it was found that all compounds tested had good selectivity over both Factor Xa and thrombin. However, it was found that 8c with an acetyl on R2 and a phenethyl group off of R1 had some inhibition of Factor Xa ($IC_{50}$ 2.0 μM) and thrombin ($IC_{50}$ 7.7 μM). A notable piece of SAR is that that 8b which has no substitution at R2 and a shorter benzyl R1 showed no activity against thrombin (>20 μM) and a 4-fold higher $IC_{50}$ relative to 8c.

TABLE 3
Biological activity and selectivity of hybrid piperidine dipeptide kbt HGFA, matriptase and hepsin serine protease inhibitors, 8a-m and 11a-b.
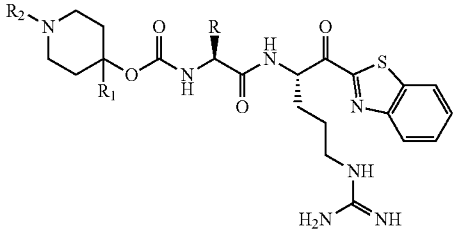
8
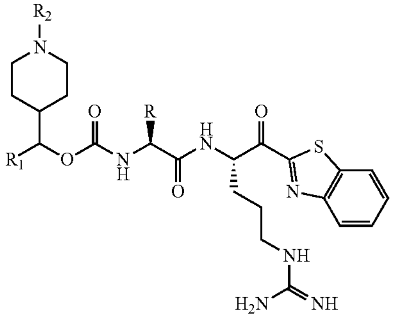
11
| Compound | R | R1 | R2 | Matriptase $IC_{50}$ (uM)[a] | Hepsin $IC_{50}$ (μM)[a] | HGFA $IC_{50}$ (μM)[a] | Factor Xa $IC_{50}$ (μM)[a] | Thrombin $IC_{50}$ (μM)[a] |
|---|---|---|---|---|---|---|---|---|
| 8a | Leu | 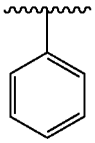 [SMILES: *c1ccccc1] | H | 0.09 | 0.005 | 0.78 | NT | >20 |
| 8b | Leu | 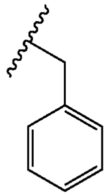 [SMILES: *Cc1ccccc1] | H | 0.03 | 0.0006 | 1.2 | 6.5 | >20 |
| 8c | Leu | 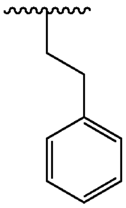 [SMILES: *CCc1ccccc1] | 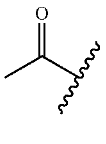 [SMILES: *C(C)=O] | 0.07 | 0.0005 | >20 | 2.0 | 7.7 |
| 8d | Cha | 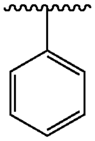 [SMILES: *c1ccccc1] | H | 2.1 | 0.09 | >20 | 9.0 | >20 |
| 8e | Leu | H | 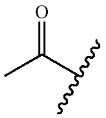 [SMILES: *C(C)=O] | 0.64 | 0.02 | >20 | NT | NT |
| 8f | Leu | H | 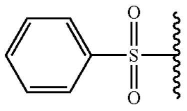 [SMILES: *S(=O)(=O)c1ccccc1] | 0.81 | 0.02 | 8.6 | >20 | >20 |
| 8g | Leu | H | 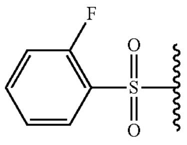 [SMILES: *S(=O)(=O)c1ccccc1F] | 4.5 | 0.07 | 18 | NT | NT |

TABLE 3-continued
Biological activity and selectivity of hybrid piperidine dipeptide kbt HGFA, matriptase and hepsin serine protease inhibitors, 8a-m and 11a-b.
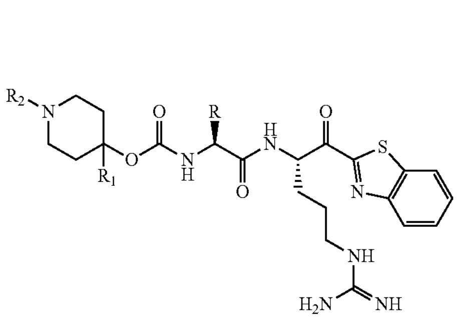
8
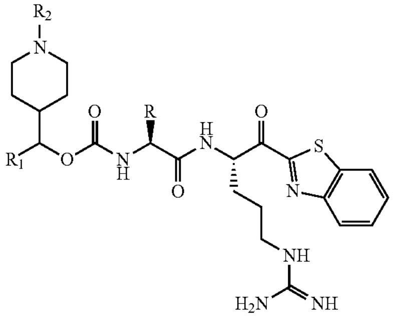
11
| Compound | R | R1 | R2 | Matriptase $IC_{50}$ (uM)[a] | Hepsin $IC_{50}$ (μM)[a] | HGFA $IC_{50}$ (μM)[a] | Factor Xa $IC_{50}$ (μM)[a] | Thrombin $IC_{50}$ (μM)[a] |
|---|---|---|---|---|---|---|---|---|
| 8h | Leu | H | 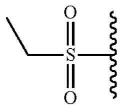 [SMILES: *S(=O)(=O)CC] | 0.73 | 0.01 | >20 | >20 | >20 |
| 8i | Leu | H | 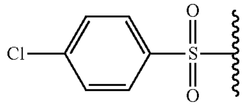 [SMILES: *S(=O)(=O)c1ccc(Cl)cc1] | 2.4 | 0.06 | 9.0 | NT | NT |
| 8j | Leu | H | 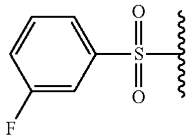 [SMILES: *S(=O)(=O)c1cccc(F)c1] | 7.5 | 0.07 | >20 | NT | NT |
| 8k | Leu | H | 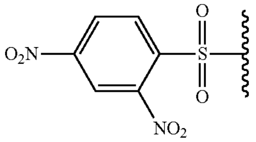 [SMILES: *S(=O)(=O)c1ccc([N+](=O)[O-])cc1[N+](=O)[O-]] | 10 | 0.11 | >20 | NT | NT |
| 8l | Leu | H | 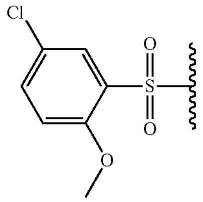 [SMILES: *S(=O)(=O)c1cc(Cl)ccc1OC] | 4.0 | 0.06 | 6.3 | NT | NT |
| 8m | Leu | H | 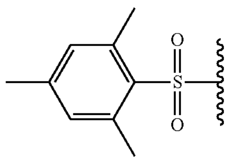 [SMILES: *S(=O)(=O)c1c(C)cc(C)cc1C] | >20 | 0.11 | 8.8 | NT | NT |

TABLE 3-continued

Biological activity and selectivity of hybrid piperidine dipeptide kbt HGFA, matriptase and hepsin serine protease inhibitors, 8a-m and 11a-b.

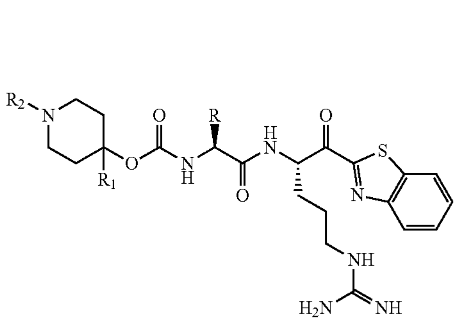

8

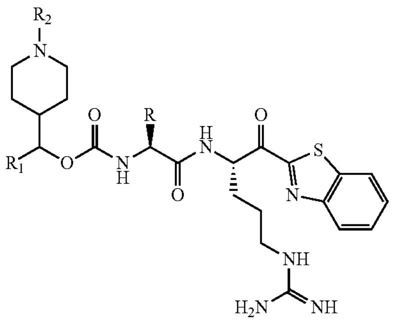

11

| Compound | R | R1 | R2 | Matriptase $IC_{50}$ (uM)[a] | Hepsin $IC_{50}$ (μM)[a] | HGFA $IC_{50}$ (μM)[a] | Factor Xa $IC_{50}$ (μM)[a] | Thrombin $IC_{50}$ (μM)[a] |
|---|---|---|---|---|---|---|---|---|
| 11a | Leu | 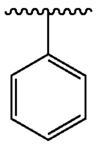 [SMILES: *c1ccccc1] | H | 1.1 | 0.008 | 14 | >20 | >20 |
| 11b | Leu | 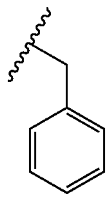 | H | 0.02 | 0.002 | 6.0 | NT | NT |

NT = Not tested

[a]$IC_{50}$ values are an average of three experiments

Example 13. KLK5 Inhibitors

The following compounds were tested for their ability to inhibit KLK5 using the following protocol.

Fluorescent Kinetic Enzyme Inhibitor Assay of KLK5: Inhibitors (11-pt serial dilutions, 0-20 μM final concentration in reaction) were serially diluted in DMSO (2% DMSO final concentration) and then mixed with KLK5 (#1108-SE-010, R&D Systems, Minneapolis, Minnesota) in black 384 well plates (Corning #3575. Corning, NY). The final assay concentration for KLK5 is 7.5 nM in TNC buffer (25 mM Tris, 150 mM NaCl, 5 mM $CaCl_2$), 0.01% Triton X-100, pH 8). After thirty minutes incubation at room temperature, Boc-VPR-AMC substrate was added. The final substrate concentrations for assay is 100 μM. Changes in fluorescence (excitation at 380 nm and emission at 460 nm) were measured at room temperature over time in a Biotek Synergy 2 plate reader (Winnoski, VT). Using GraphPad Prism version 6.04 software program, (GraphPad Software, San Diego, CA, graphpad.com), a four parameter curve fit was used to determine the inhibitor $IC_{50}$s from a plot of the mean reaction velocity versus the inhibitor concentration. The $IC_{50}$ values represent the average of three or more separate experimental determinations. Results are shown in Table 4, below.

TABLE 4

| Compound | KLK5 $IC_{50}$ (nM) | Compound | KLK5 $IC_{50}$ (nM) |
|---|---|---|---|
| VD4010 | 1832 | MM2030 | 18103 |
| VD4072 | 5231 | AcSKLRkbt | 2120 |
| VD4090 | 9388 | AcKQLRkbt | 1786 |
| VD4111 | 647.2 | AcSQLRkt | 3943 |
| VD3112 | 2526 | FmocPRkbt | 3682 |
| VD2173 | 193.2 | FmocWRkbt | 4394 |
| VD4158 | 3561 | AcWFRkbt | >20000 |
| ZFH7116 | 137 | Leupeptin | >20000 |

Example 14. SHAI Inhibitors of HGFA, Matriptase and Hepsin, Show TMPRSS2-Dependent Antiviral Activity Selected compounds were tested for their ability to show TMPRSS2-dependent antiviral activity using the following protocols. Table 5 below lists the compounds tested, followed by a summary of data obtained from the compounds.

TABLE 5
| Comp. ID | Structure |
| --- | --- |
| Ac-SKLR kbt V-amide, ZFH7116 | 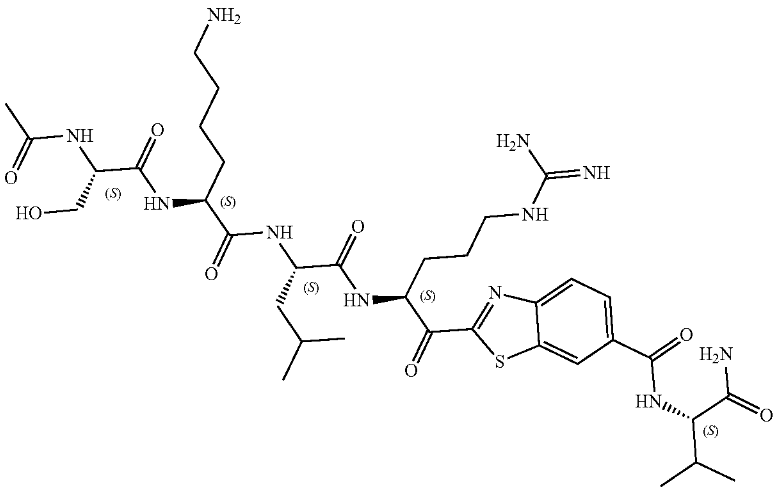 |
| Ac-dWFR-kbt, PK-1-89A1 | 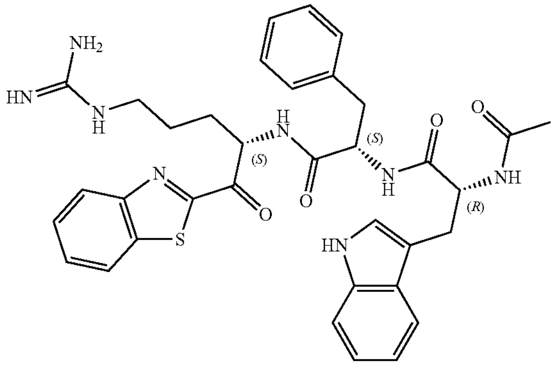 |
| VD3173 | 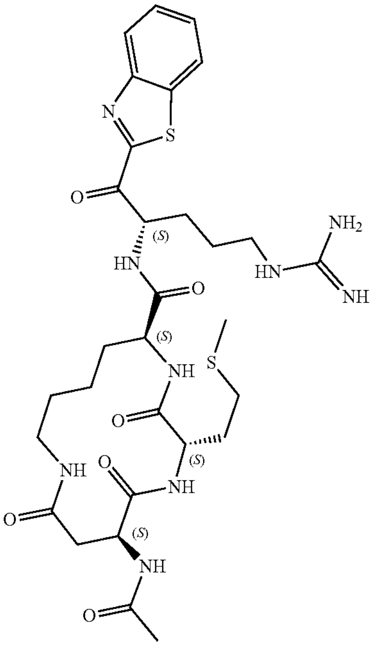 |

TABLE 5-continued
| Comp. ID | Structure |
| --- | --- |
| VD2173 | 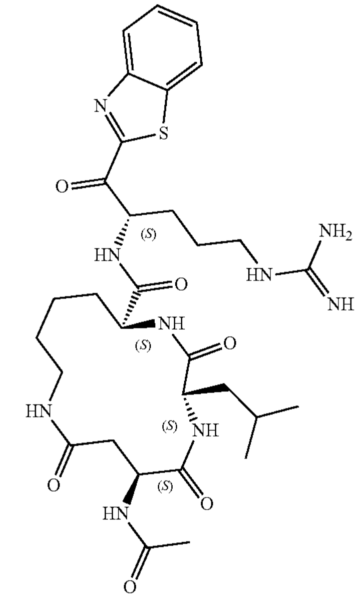 |
| VD3152 | 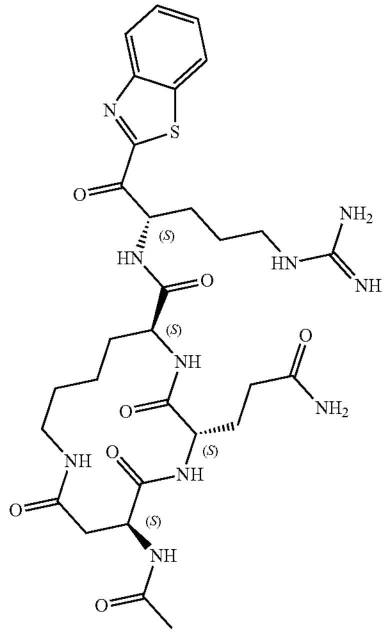 |

TABLE 5-continued
| Comp. ID | Structure |
| --- | --- |
| VD4051 | 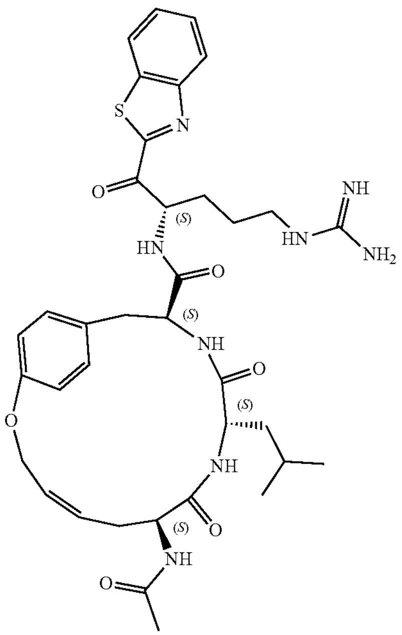 |
| Ac-WFR-kbt, PK-1-102A1 | 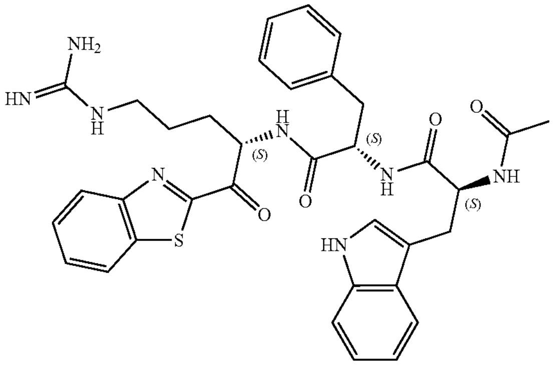 |
| LLR kbt V-amide, ZFH7182 | 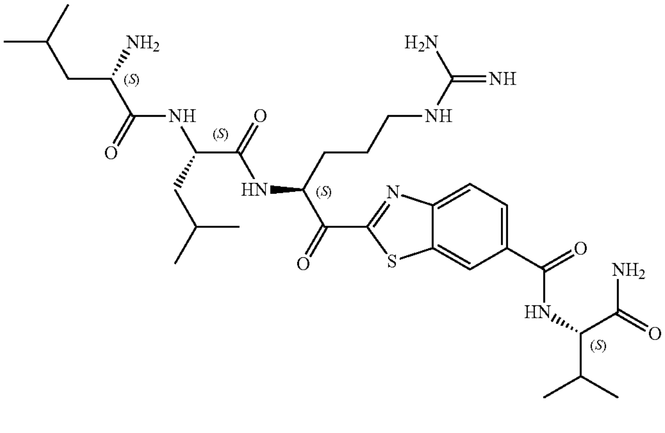 |

TABLE 5-continued
| Comp. ID | Structure |
| --- | --- |
| Ac-WLFR-kbt, ZFH7064 | 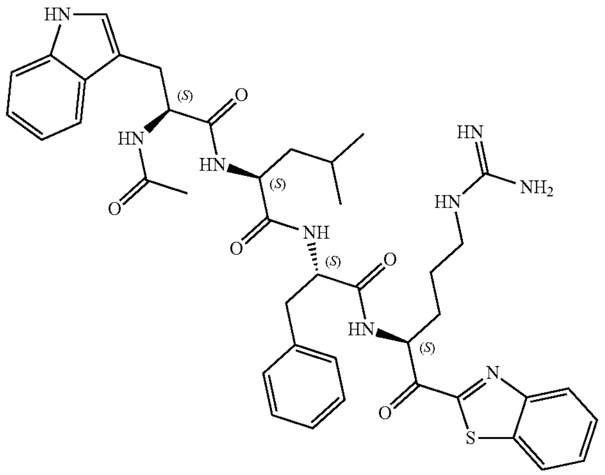 |
| Ac-FLFR-kbt, ZFH7063 | 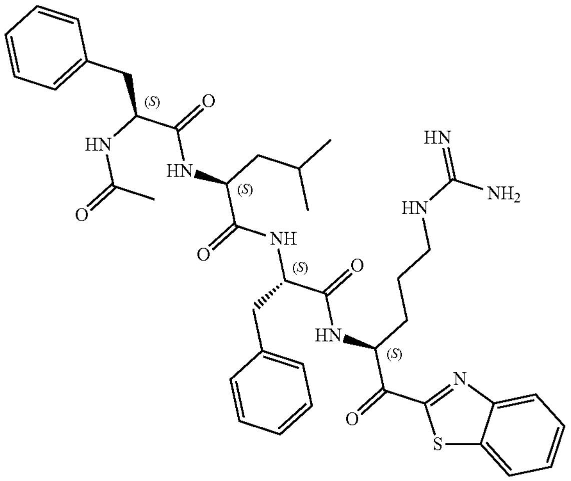 |
| Ac-SKLR kbt, ZFH7053 | 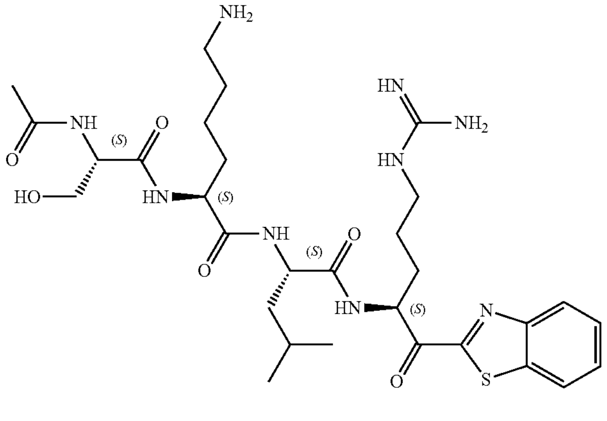 |

TABLE 5-continued
| Comp. ID | Structure |
| --- | --- |
| Ac-KQLR-kbt, ZFH7006 | 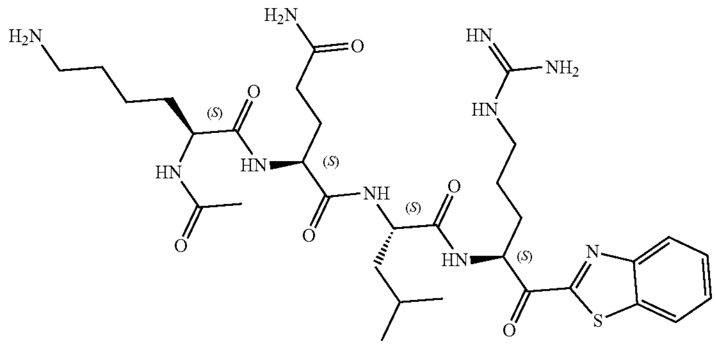 |
| Ac-LLR-kt, ZFH6201-1 | 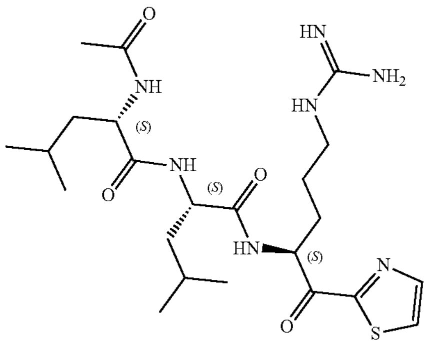 |
| Ac-SQLR-kt, ZFH6138 | 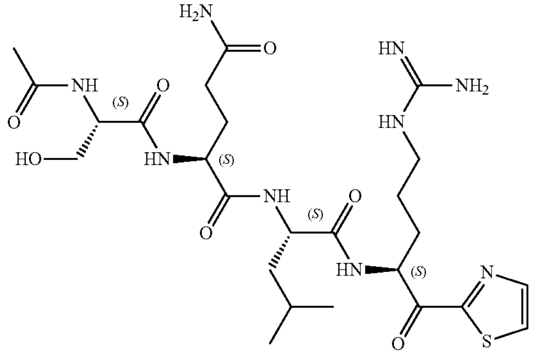 |
| Ac-KQFR-kt, ZFH6101 | 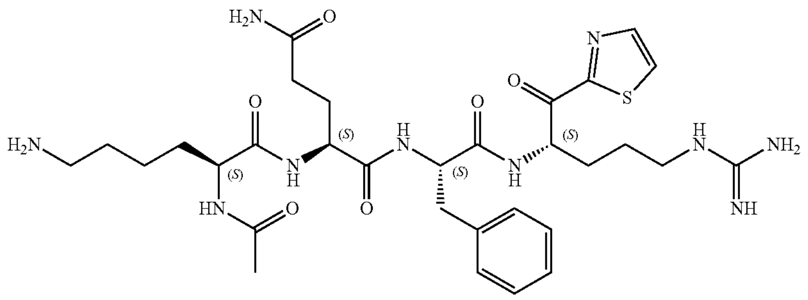 |

TABLE 5-continued
| Comp. ID | Structure |
|---|---|
| Ac-SKFR-kt, ZFH6095 | 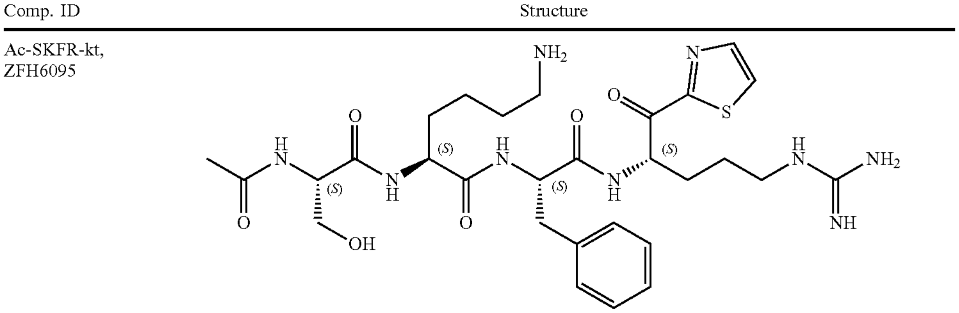 |
| PK-1-18A1, dWFR kbt | 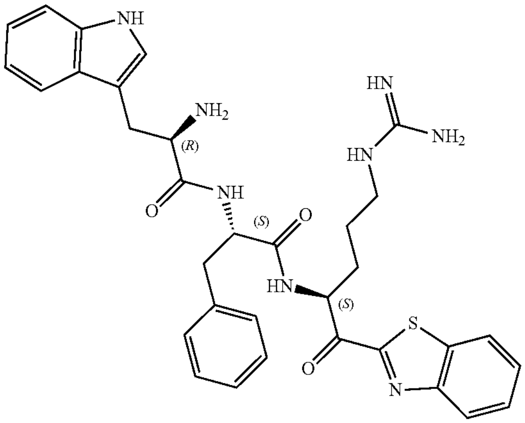 |
| PK-1-45A1, dWFR-kbt-COOH | 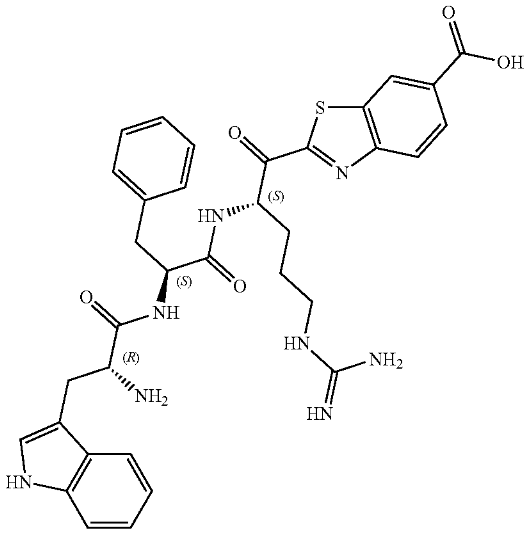 |
| MM3116 | 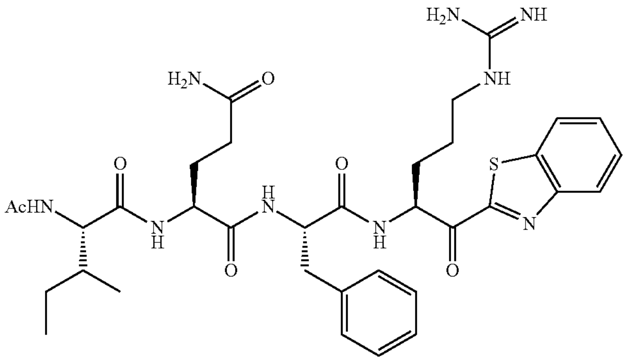 [SMILES: CCC(C)[C@H](NC(C)=O)C(=O)N[C@@H](CCC(N)=O)C(=O)N[C@@H](Cc1ccccc1)C(=O)N[C@@H](CCCNC(=N)N)C(=O)c1nc2ccccc2s1] |

TABLE 5-continued
| Comp. ID | Structure |
|---|---|
| MM3122 | 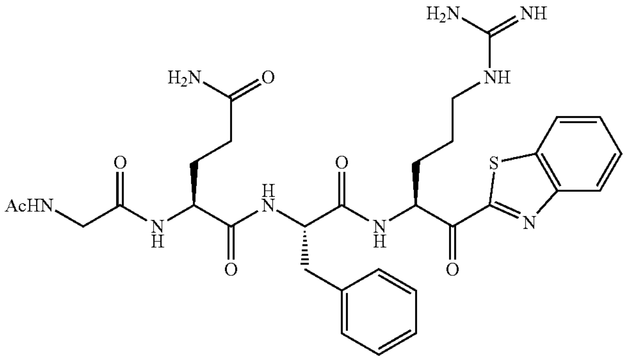 [SMILES: CC(=O)NCC(=O)N[C@@H](CCC(N)=O)C(=O)N[C@@H](Cc1ccccc1)C(=O)N[C@@H](CCCNC(=N)N)C(=O)c1nc2ccccc2s1] |
| MM3123 | 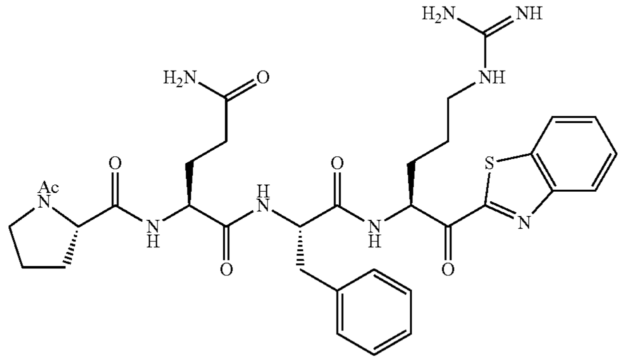 |
| MM3130 | 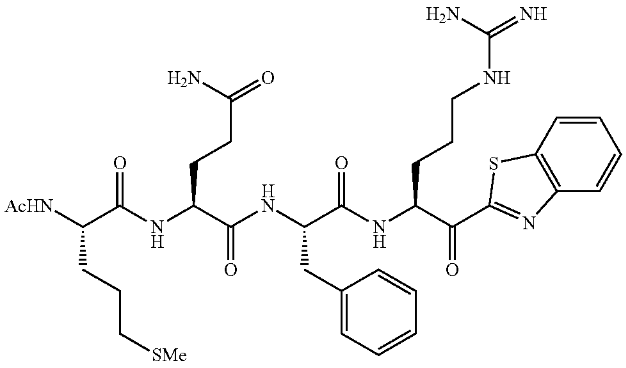 [SMILES: CSCCC[C@H](NC(C)=O)C(=O)N[C@@H](CCC(N)=O)C(=O)N[C@@H](Cc1ccccc1)C(=O)N[C@@H](CCCNC(=N)N)C(=O)c1nc2ccccc2s1] |
| MM3131 | 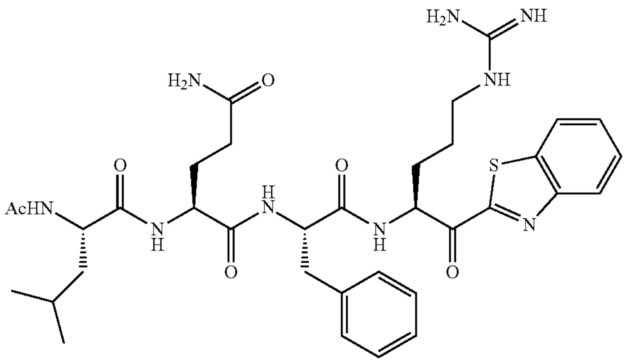 [SMILES: CC(=O)N[C@@H](CC(C)C)C(=O)N[C@@H](CCC(N)=O)C(=O)N[C@@H](Cc1ccccc1)C(=O)N[C@@H](CCCNC(=N)N)C(=O)c1nc2ccccc2s1] |

TABLE 5-continued

| Comp. ID | Structure |
|---|---|
| MM3142 | 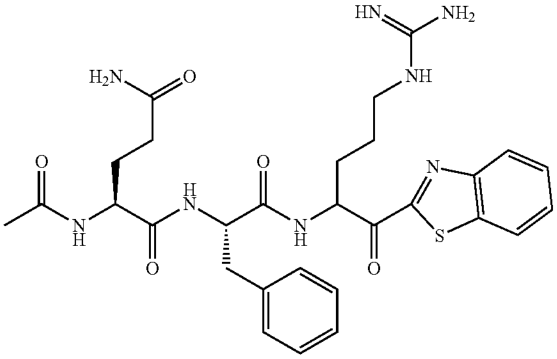 [SMILES: CC(=O)N[C@@H](CCC(N)=O)C(=O)N[C@@H](Cc1ccccc1)C(=O)NC(CCCNC(=N)N)C(=O)c1nc2ccccc2s1] |

We analyzed pseudotype entry driven by the spike protein of SARS-CoV-2 (SARS-2-S) or the glycoprotein of vesicular stomatitis virus (VSV-G) into the TMPRSS2-positive human lung cell line Calu-3. VSV-G was used as a control, as it does not depend on proteolytic (TMPRSS2) activation for host cell entry. Besides Calu-3 cells, we further used Vero cells (African green monkey, kidney) as a control, as these cells do not express TMPRSS2 and therefore any reduction in SARS-2-S-driven entry would be either related to unspecific side effects or cytotoxicity. Each compound was tested in three separate experiments with independent pseudotype batches. We treated cells (96-well format) with different concentration of inhibitor or solvent (DMSO) diluted in medium (50 µl/well) for 2 h at 37° C. and 5% $CO_2$, then we added 50 µl of pseudotype on top and incubated for 16 h at 37° C. and 5% $CO_2$.

Next, we measured virus-encoded firefly luciferase activity in cell lysates (indicator of pseudotype entry into target cells). The data was normalized against control (DMSO-treated cells=100% pseudotype entry) and plotted with GraphPad Prism (version 8.3.0), to calculate effective concentration EC50 and perform statistics (comparison against the respective control; two-way ANOVA with Dunnett's posttest).

Figure 14A:
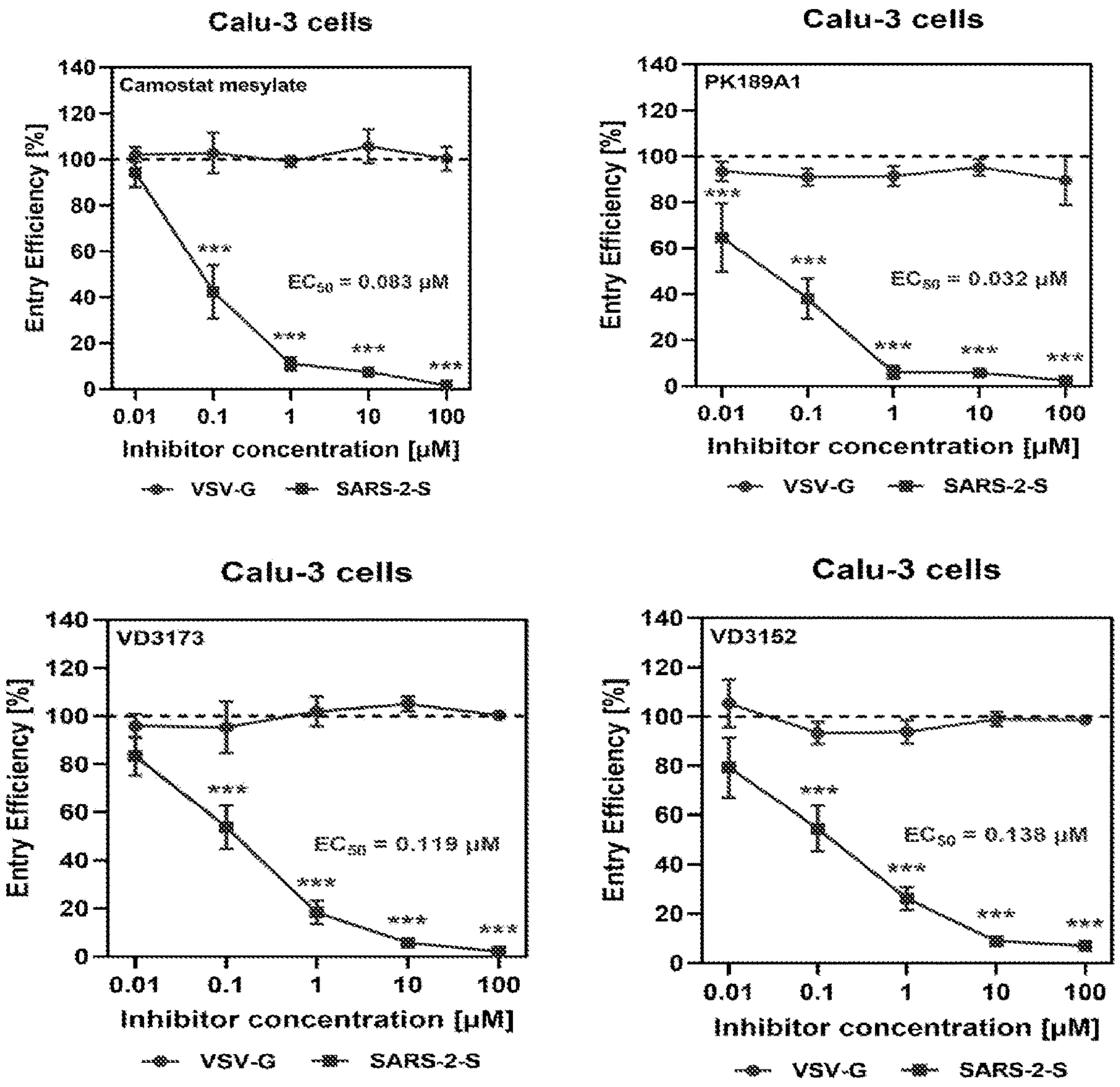
FIGS. 14A, 14B, and 14C present the cellular entry efficiency of replication-competent chimeric VSV using the Spike protein of SARS-CoV-2 in Vero cells in the presence of different compounds described herein.
Figure 14B:
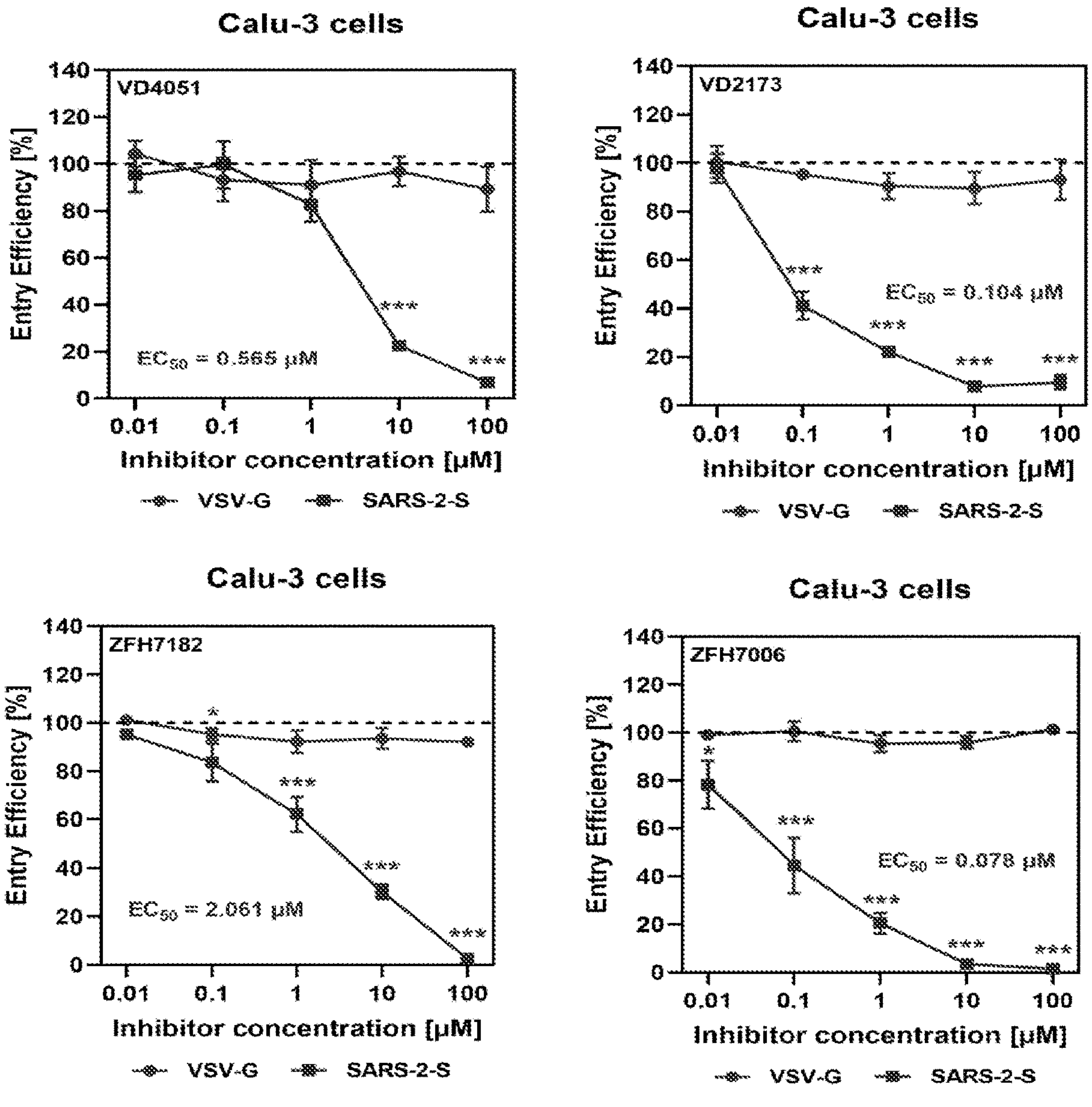
Figure 14C:
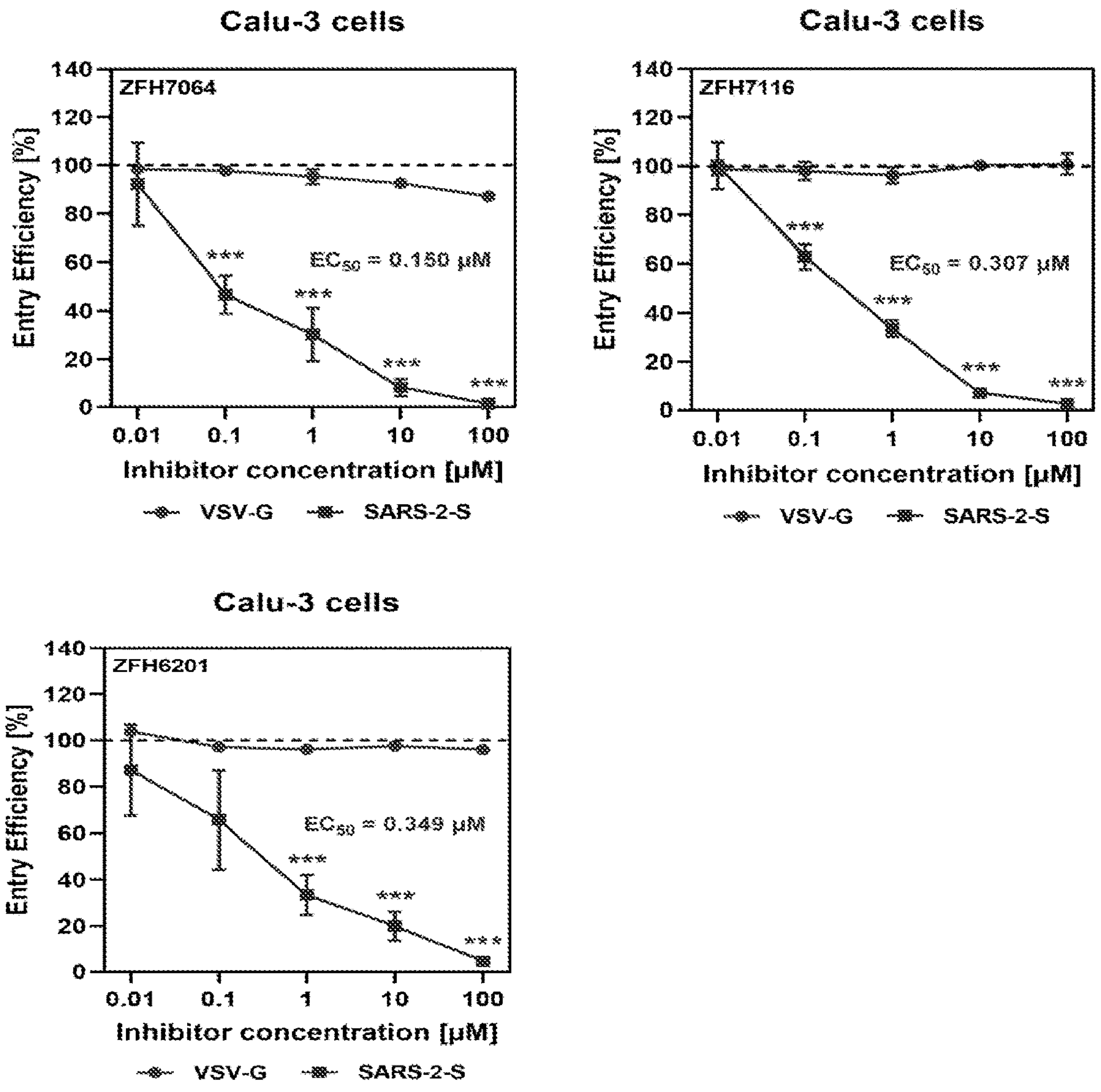

As summarized in Table 6, the compounds tested showed potent inhibition of VSV pseudotypes using the Spike protein of SARS-CoV-2 (VSVpp (SARS-2-S) for viral entry into Calu-3 cells. PK-1-89 is showing the best $EC_{50}$ of 32 nM and cyclic peptide VD2173 has an $EC_{50}$ of 104 nM. Ac-WLFR-kbt (ZFH7064) also having a $P_2$ Phe showed excellent potency. Furthermore, ZFH7006 (Ac-KQLR-kbt) which contains a $P_3$ Gln also predicted from PS-SCL shows the next best activity with an $EC_{50}$ of 78 nM with VD2173 the third best overall ($EC_{50}$ 104 nM). Cyclic peptides, VD3173 and VD3152 also show almost equivalent activity while VD4051 exhibited the second least potency of all 10 compounds at still a pretty respectable $EC_{50}$ of 565 nM. The worst activity was displayed by ZFH7182 (Ac-LLR-kbt V amide) with an $EC_{50}$ of 2 µM. Further, there is significant structure-activity relationships (SAR) among the ten compounds. For example, it appears that TMPRSS2 does not prefer large groups extending beyond the kbt S1'C-terminal portion of the inhibitor since both ZFH7116 and ZFH7182 lose activity relative to unsubstituted kbt analogs, ZFH6201 and ZFH7006/ZFH7064. Raw data are also shown in FIGS. 14A-14C. Importantly none of the compounds showed inhibition of cell entry into TMPRSS2 negative Vero cells by VSVpp (SARS-2-S) or VSVpp (SARS-2-S). Also, entry into Calu-3 cells by pseudotypes bearing the VSV glycoprotein (VSVpp VSV-G) was not affected.

TABLE 6

| Structure | HGFA $IC_{50}$ (nM) | Matriptase $IC_{50}$ (nM) | Hepsin $IC_{50}$ (nM) | Calu-3 $EC_{50}$ (nM) |
|---|---|---|---|---|
| Ac-SKLR kbt V amide, ZFH7116 | 26 | 11 | 0.5 | 307 |
| Ac-dWFR-kbt, PK-1-89 | 346 | 29 | 100 | 32 |
| Cyclo(DMK)R-kbt, VD3173 | 3,240 | 1.0 | 5.9 | 119 |
| Cyclo(DLK)R-kbt, VD2173 | 5,262 | 1.4 | 10 | 104 |
| Cyclo(DQK)R-kbt, VD3152 | 16,108 | 7.7 | 22 | 138 |
| Cyclo(allylLY)R-kbt, VD4051 | >20,000 | 14 | 20 | 565 |
| H-LLR-kbt V-amide ZFH7182 | 44 | 50 | 0.01 | 2060 |
| Ac-WLFR-kbt, ZFH7064 | 266 | 12 | 0.79 | 150 |
| Ac-KQLR-kbt, ZFH7006 | 60 | 1.1 | 0.17 | 78 |
| Ac-LLR-kt, ZFH6201 | 506 | 56 | 4.6 | 349 |

Example 15. Cell-Based TMPRSS2 Fluorogenic Enzyme Inhibition Assay

Figure 15A:
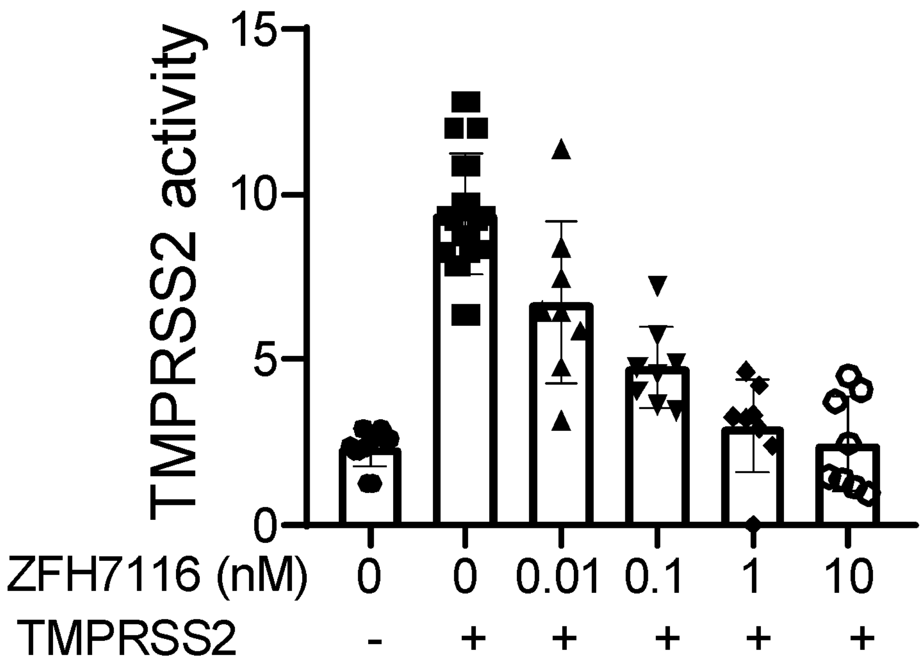
FIGS. 15A and 15B present bar graphs of TMPRSS2 activity of inhibitors ZFH7116 and VD2173, respectively.
Figure 15B:
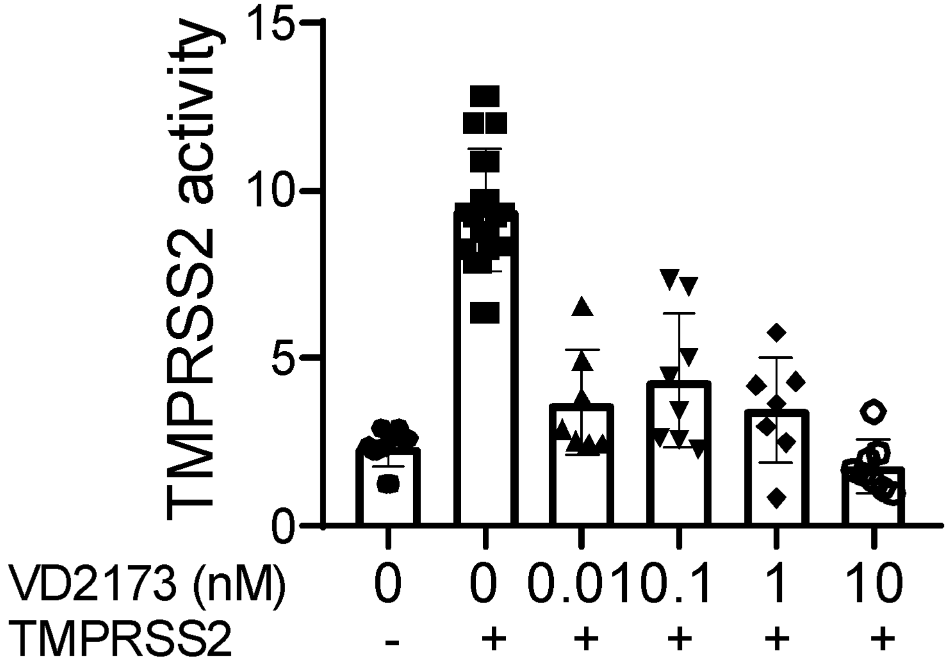

A PLX304 plasmid-containing human TMPRSS2 open reading frame from the ORFeome Collaboration (Dana-Farber Cancer Institute, Broad Institute of Harvard and Massachusetts Institute of Technology [HsCD00435929]) was obtained from DNASU Plasmid Repository, and a control PLX304 vector was obtained from Addgene (Watertown, MA, USA). HEK-293T cells were grown in DMEM supplemented with 10% FBS and seeded in a black, 96-well plate (75,000 cells/well). The following day, cells were transfected overnight with either a control plasmid (PLX) or TMPRSS2 (PLX-TMPRSS2) via TransIT LT-1 transfection reagent (Mirus Bio) in 100 µL of OptiMEM per well. The media was replaced the next day. Twenty-four hours after transfection, the media was replaced with 80 µL of phosphate-buffered saline (PBS). Inhibitors (ZFH7116 and VD2173) or PBS alone were added to the wells in the indicated 5 concentrations and incubated at 25° C. for 15 minutes. The fluorogenic substrate Boc-QAR-AMC (R&D Biosystems) was then added to each well to a final concentration of 100 μM. Fluorescence (excitation 365 nm, emission 410 nm) was kinetically measured every 15 minutes at 37° C. using a GloMax plate reader (Promega). Results of this assay are presented in FIGS. 15A and 15B.

ZFH7116 inhibited TMPRSS2 in a dose dependent manner in concentrations ranging between 10,000 nM-10 nM ($IC_{50}$=51 nM). We then tested VD2173 effect on TMPRSS2 proteolytic activity in the same range of concentrations. VD2173 demonstrated even stronger potency towards TMPRSS2 compared with ZFH7116 ($IC_{50}$=6.9 nM). These data demonstrate that both ZFH7116 and VD2173 mediate their function by inhibiting TMPRSS2 at least in part.

When introducing elements of the present invention or the preferred embodiments(s) thereof, the articles “a”, “an”, “the” and “said” are intended to mean that there are one or more of the elements. The terms “comprising”, “including” and “having” are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A compound of Formula (IIA), (IIB), (IIC), (IID), (IIE), (IIF), (IIG), or (IIH) a salt thereof, or a stereoisomer thereof:

(IIA)

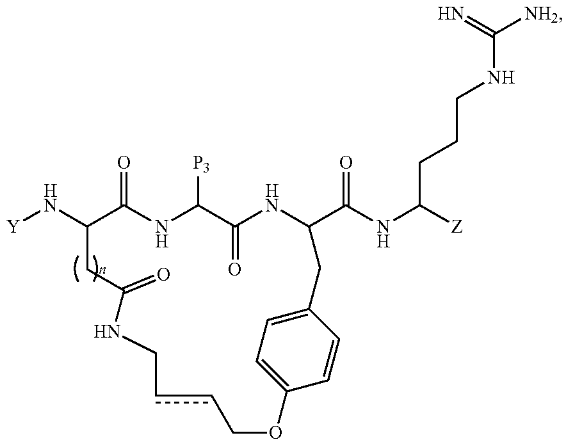

-continued (IIB)

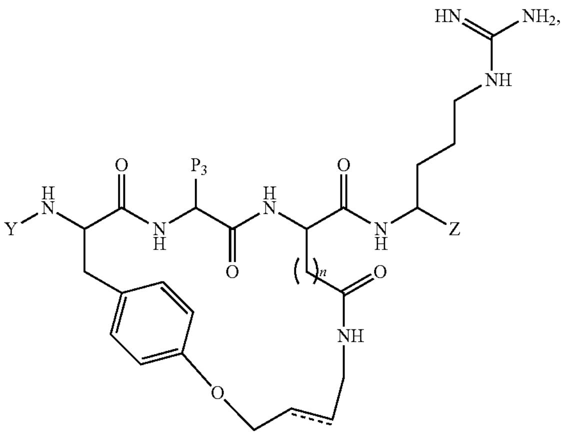

-continued (IIC)

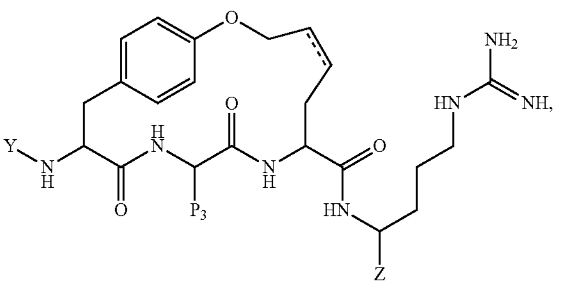

(IID)

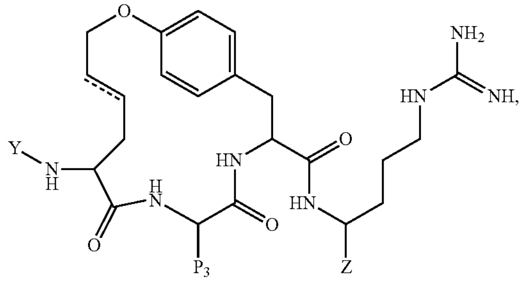

(IIE)

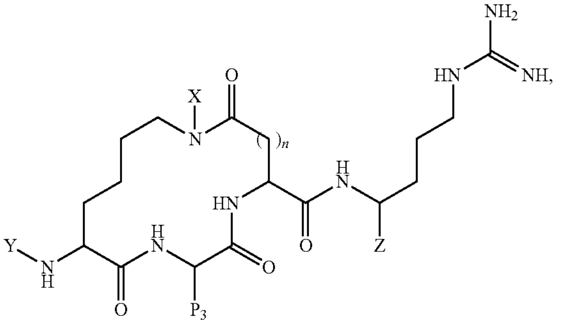

(IIF)

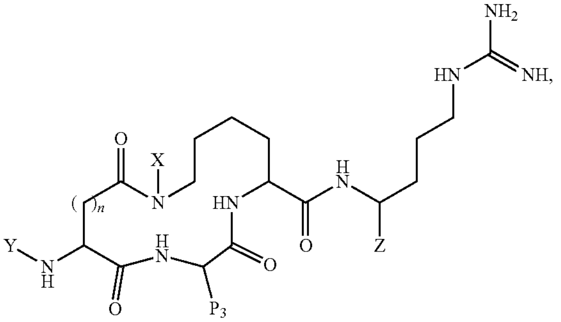

(IIG)

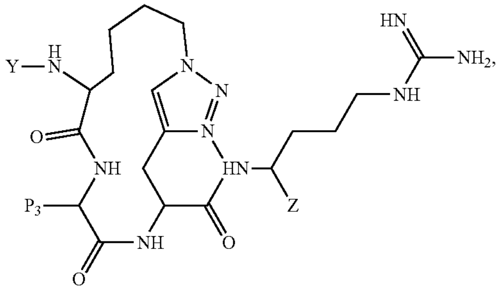

or

-continued (IIH)

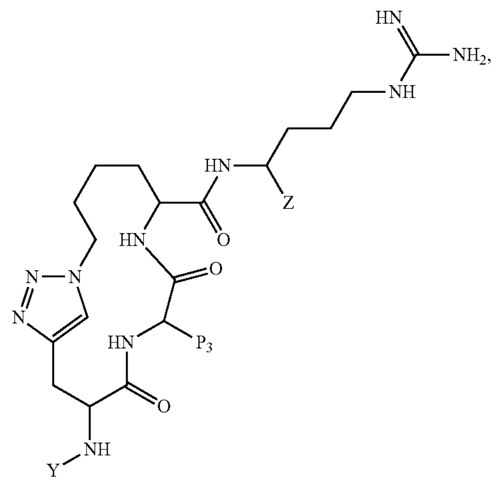

wherein:

each n is independently 1 or 2;

each $P_3$ is independently hydrogen or a side chain of a natural or unnatural amino acid;

each X is independently hydrogen or methyl;

each Y is independently hydrogen, acetyl, tert-butyloxycarbonyl (Boc), benzyloxycarbonyl (Cbz), fluorenylmethyloxycarbonyl (Fmoc), benzyl, —C(O)R, —SOOR, —COOR, —C(O)NHR, substituted or unsubstituted $—(CH_2)_x$aryl, substituted or unsubstituted $—(CH_2)_x$heteroaryl, substituted or unsubstituted $—(CH_2)_x$cycloalkyl, or substituted or unsubstituted $—(CH_2)_x$heterocycle;

each x is independently 0, 1, or 2;

each R is independently $C_1$ to $C_6$ alkyl, $C_3$ to $C_6$ cycloalkyl, substituted or unsubstituted heterocycle, substituted or unsubstituted alkylheterocycle, aralkyl, or aryl; and each Z is independently

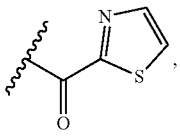

,

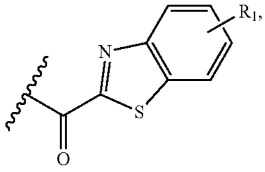

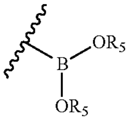

, or

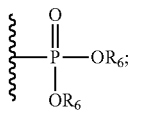

$R_1$ is hydrogen,

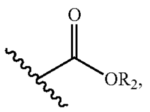 or 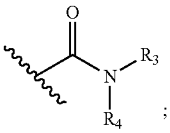 ;

$R_2$ and $R_3$ are each independently hydrogen, substituted or unsubstituted alkyl, substituted or unsubstituted cycloalkyl, substituted or unsubstituted aryl, substituted or unsubstituted aralkyl, substituted or unsubstituted heteroaryl, or substituted or unsubstituted heteroarylalkyl;

$R_4$ is hydrogen, substituted or unsubstituted alkyl, or a residue of an amino acid, or $R_3$ and $R_4$ can form a ring;

each $R_5$ is independently hydrogen, substituted or unsubstituted alkyl, or $R_5$ moieties can form a ring; and each $R_6$ is substituted or unsubstituted aryl.

2. The compound of claim 1 wherein the compound of Formula (IIA)-(IIH) includes one or more of the following:

each Y is independently hydrogen, acetyl, tert-butyloxycarbonyl (Boc), benzyloxycarbonyl (Cbz), or fluorenylmethyloxycarbonyl (Fmoc);

each $P_3$ is independently a side chain of Ala, Gly, Val, Leu, Lys, Arg, Asn, Phe, Gln, Thr, D-Trp, Tyr, Met, Agp, hCha, hTyr, hPhe, Orn, DAB, DAB(Z), Nle(O-Bzl), Arg($NO_2$), Arg$(Z)_2$, Lys(2-ClZ), hLeu, Dht, Idc, Igl, Chg, hAbu, Hyp, Glu(Bz), Met(O), Dap, Phe(F5), Glu(Me), hArg; or a combination thereof.

3. The compound of claim 1 wherein $R_2$ and $R_3$ are each independently hydrogen, alkyl, cycloalkyl, aryl, aralkyl, heteroaryl, or heteroarylalkyl.

4. The compound of claim 1 wherein $R_4$ is hydrogen, alkyl, or a residue of an amino acid, or $R_3$ and $R_4$ can form a piperazine or piperidine ring.

5. The compound of claim 1 wherein each $R_5$ is independently hydrogen, alkyl, or the $R_5$ moieties can form a ring.

6. The compound of claim 1 wherein each $R_6$ is aryl.

7. The compound of claim 1 wherein each Z is independently:

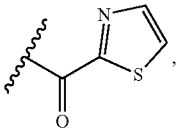,

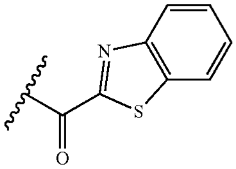, or

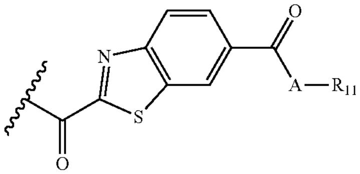

wherein A is —O— or NH and $R_{11}$ is H, methyl, benzyl, optionally substituted alkyl, optionally substituted aryl, heterocycle, or a residue of an α-amino acid.

8. The compound of claim 7 wherein A is NH and A and $R_{11}$ form a residue of an α-amino acid.

9. A pharmaceutical composition comprising a therapeutically effective amount of at least one compound of claim 1 or a salt thereof.

10. A compound selected from the group consisting of:

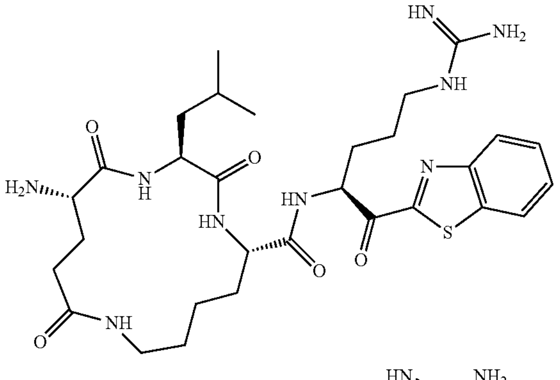,

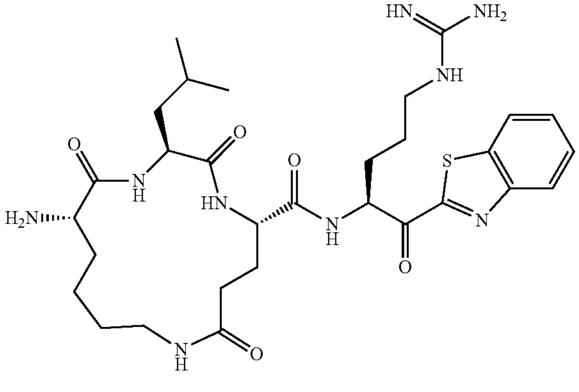,

-continued
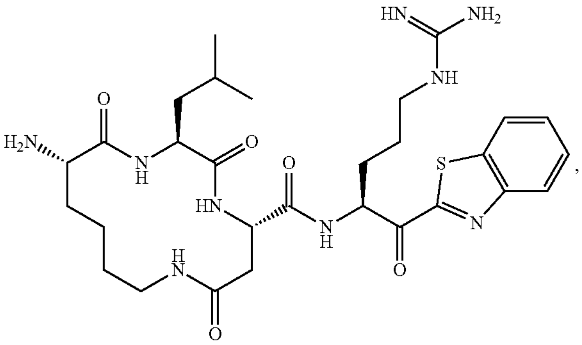
,
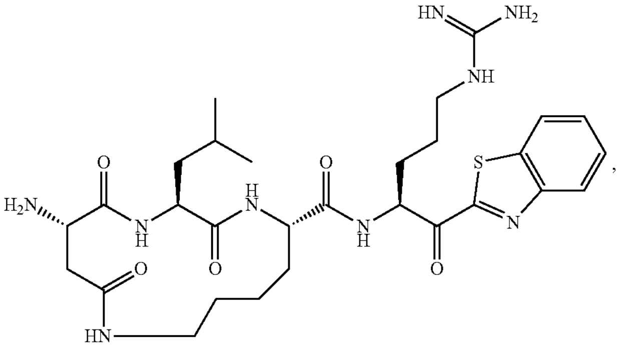
,
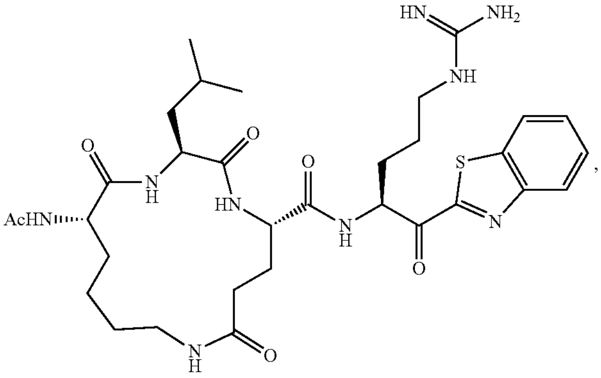
,
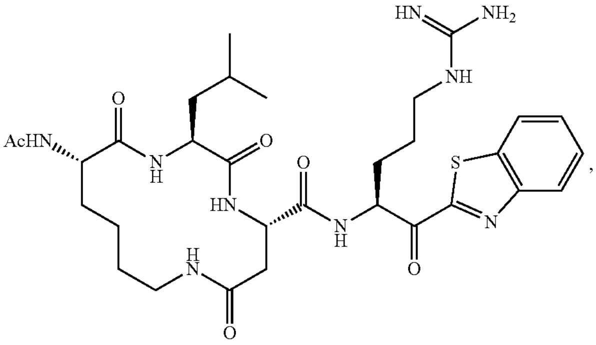
,

-continued
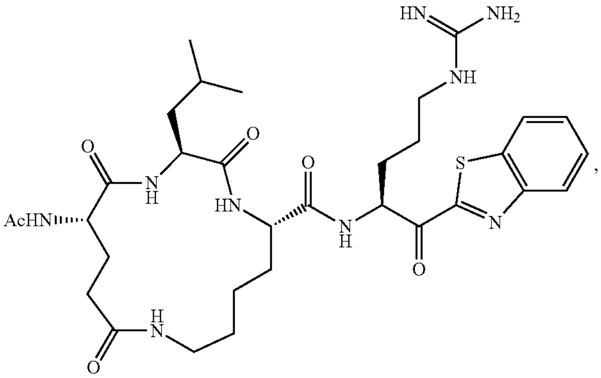
,
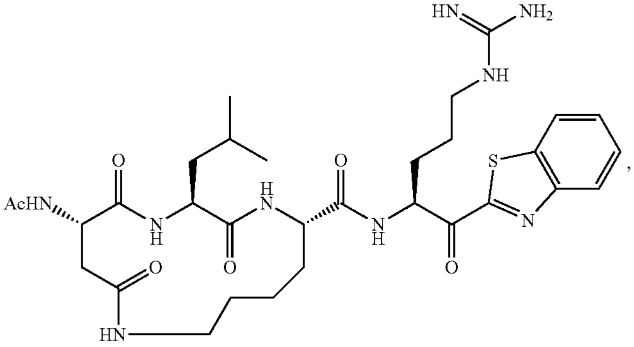
,
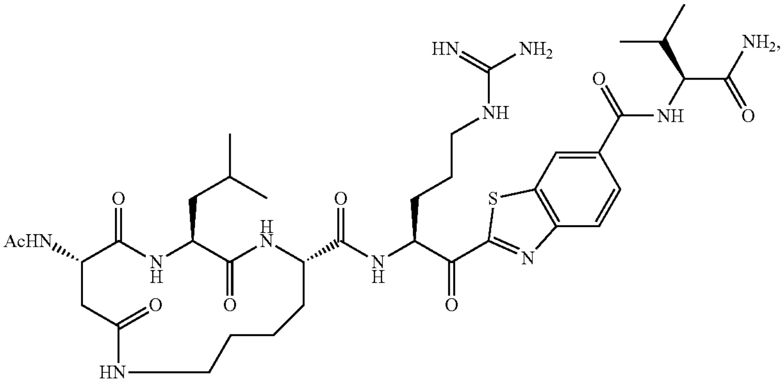
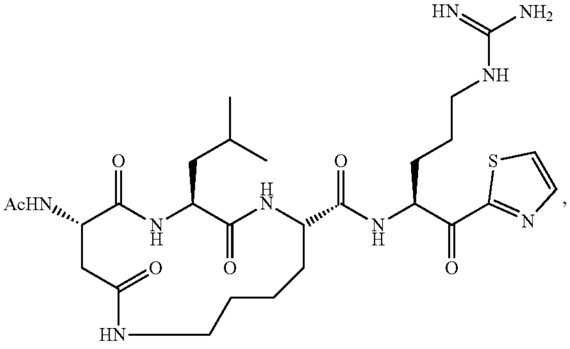
,

-continued
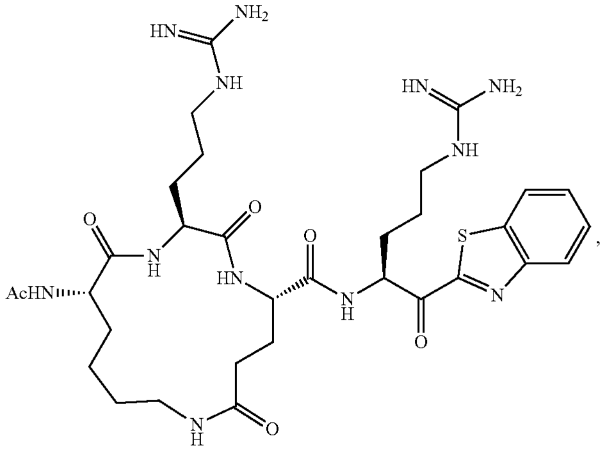
,
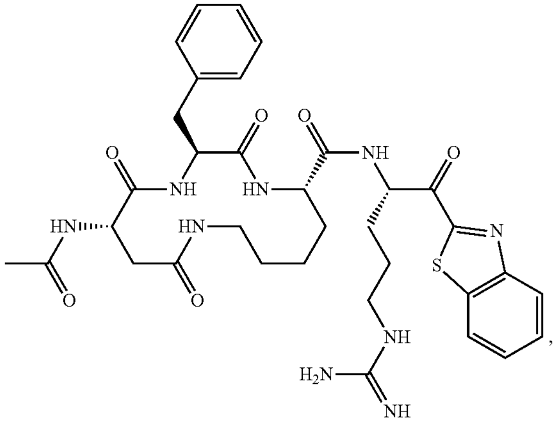
,
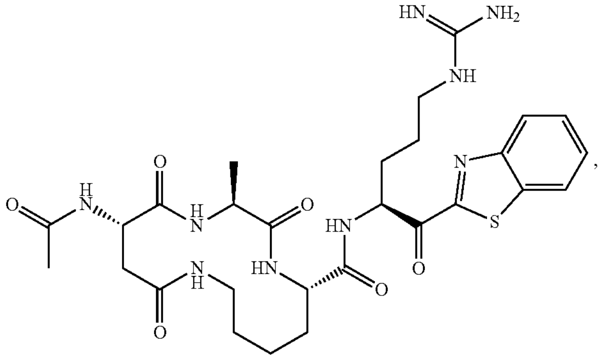
,
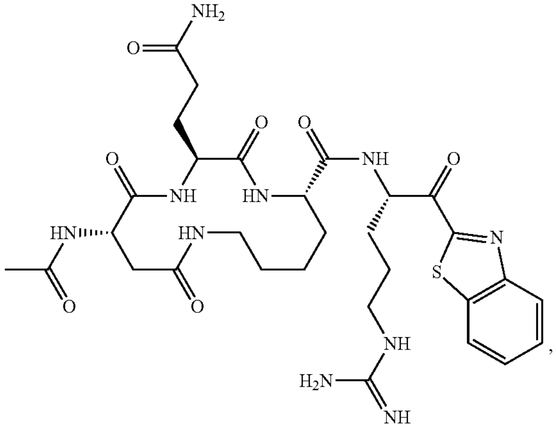
,
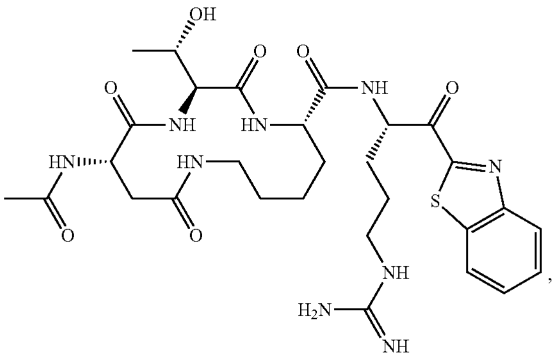
, -continued
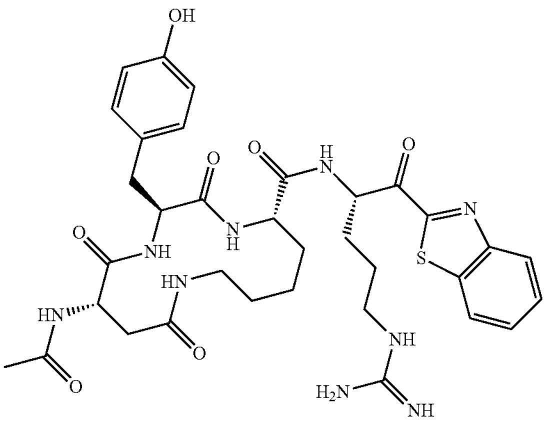
,
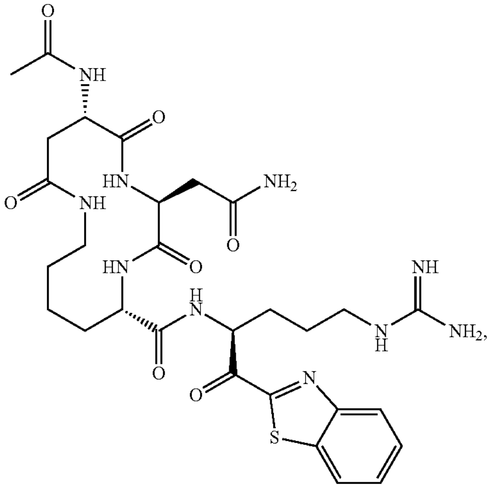
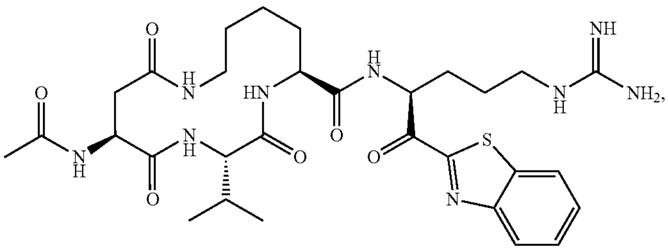
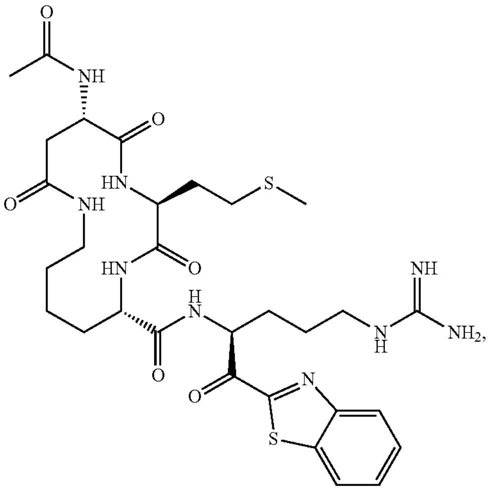
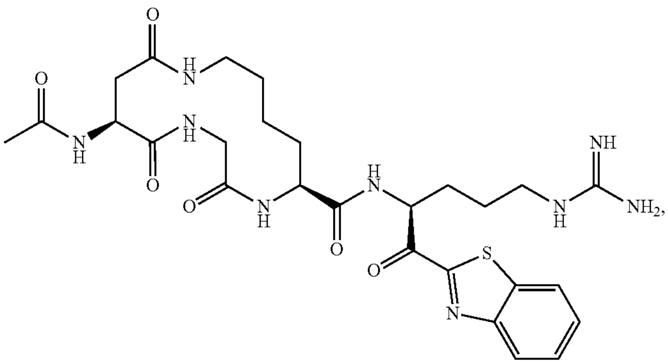

-continued
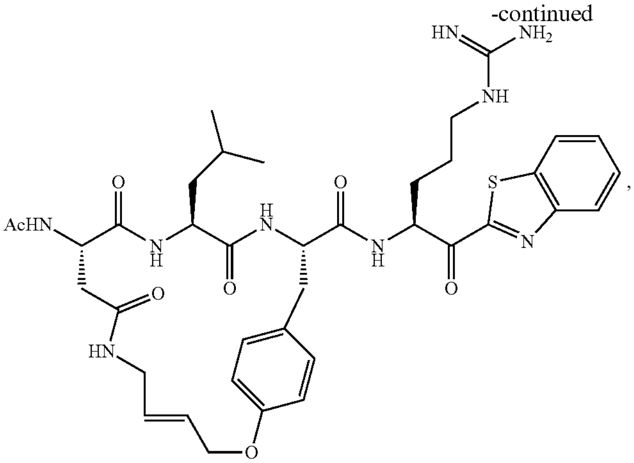
,
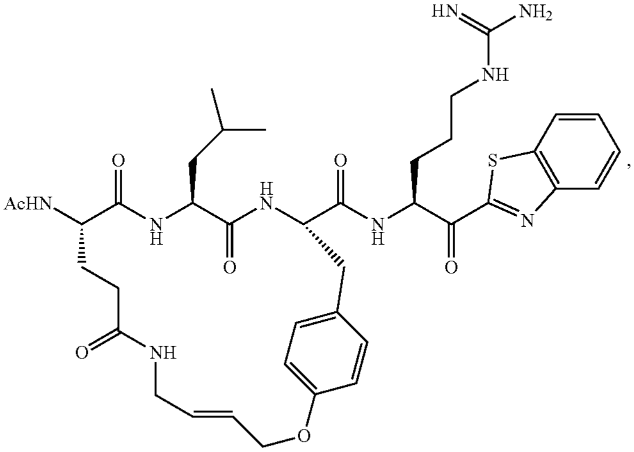
,
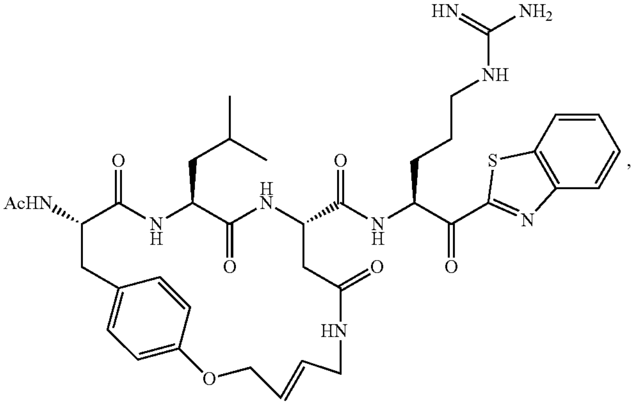
,
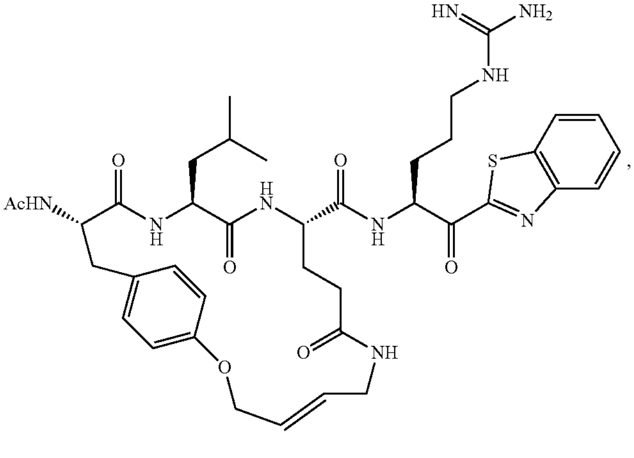
,

-continued
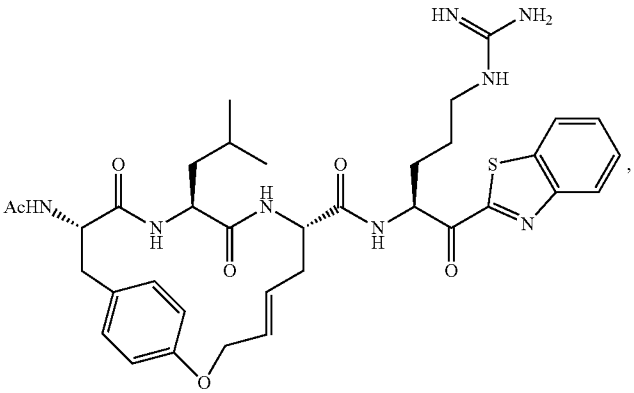
,
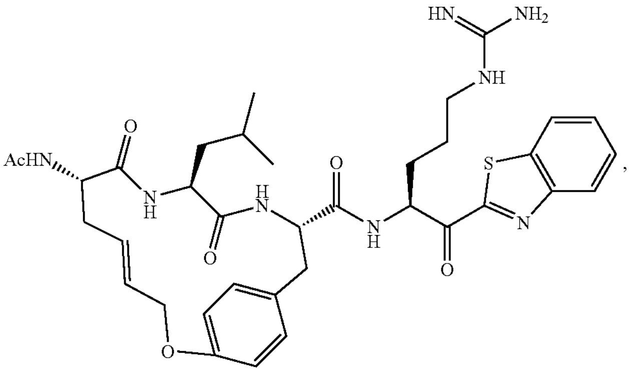
,
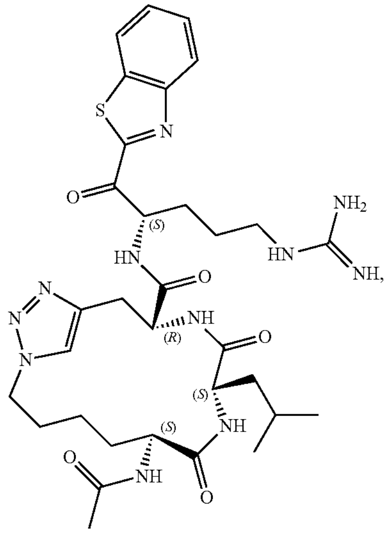
,
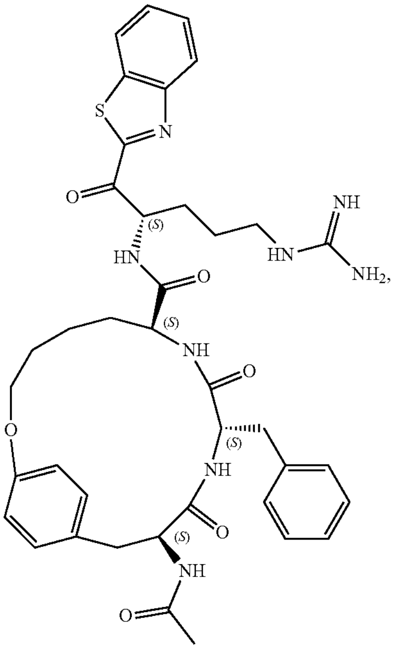
,

-continued
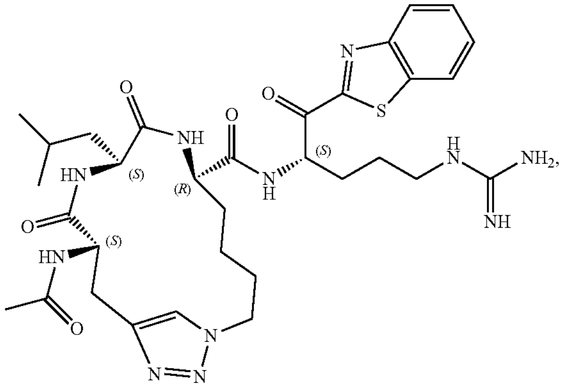
,
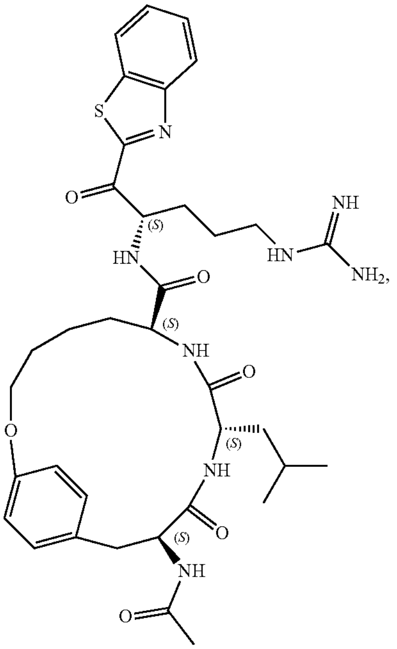
,
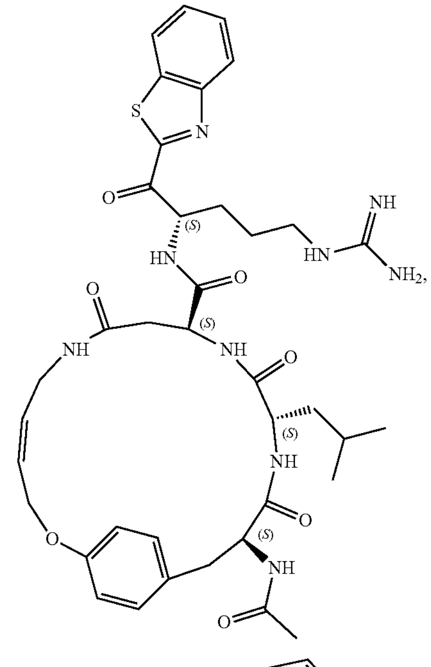
,
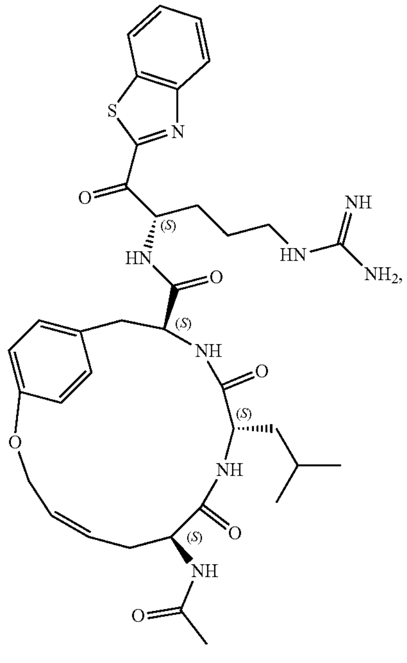
,
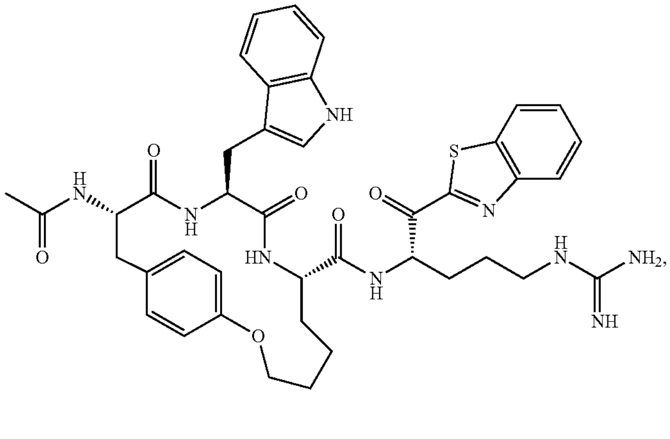
, -continued
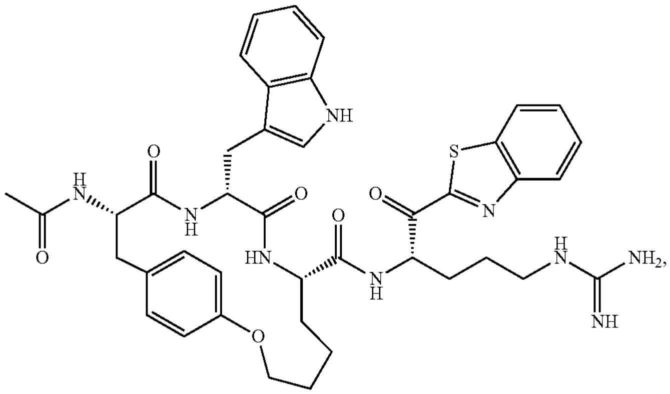
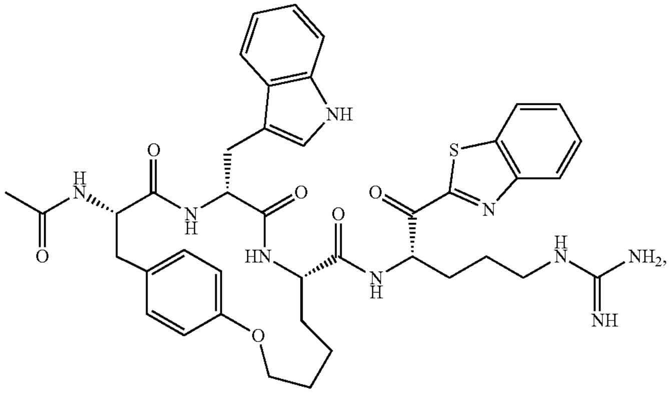
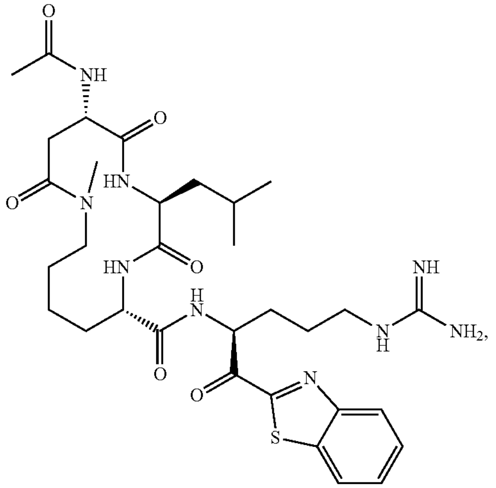
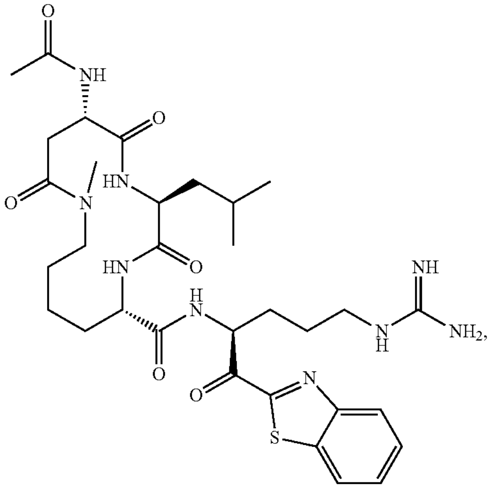

-continued
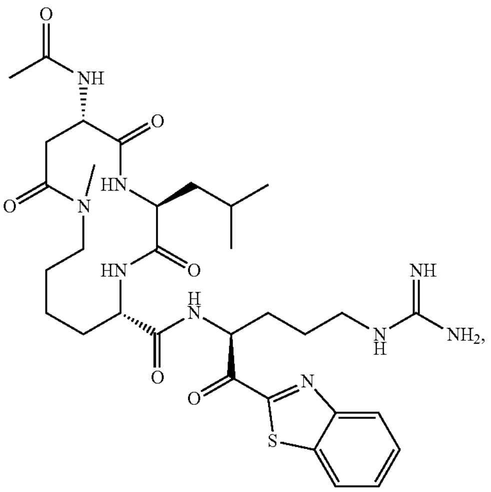
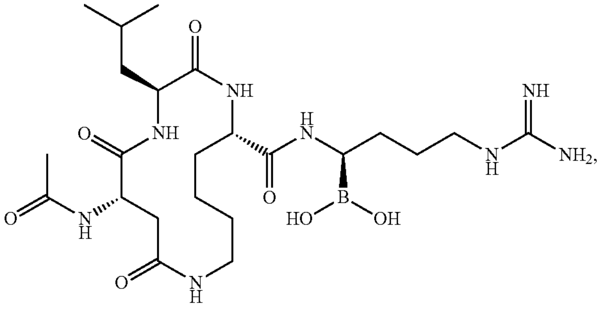
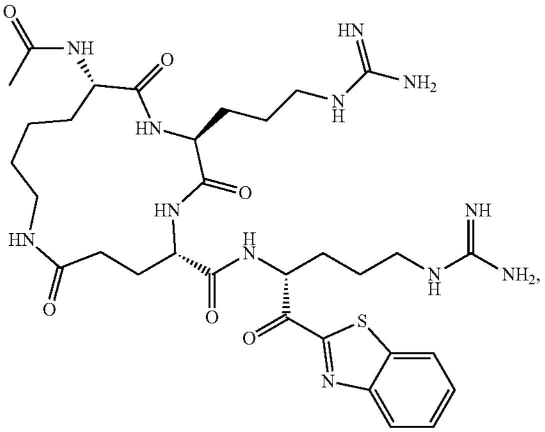
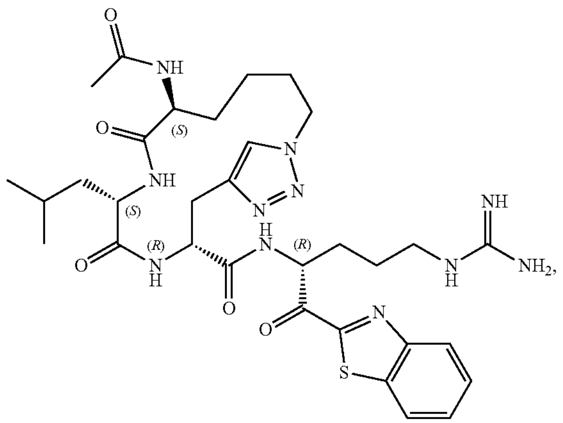
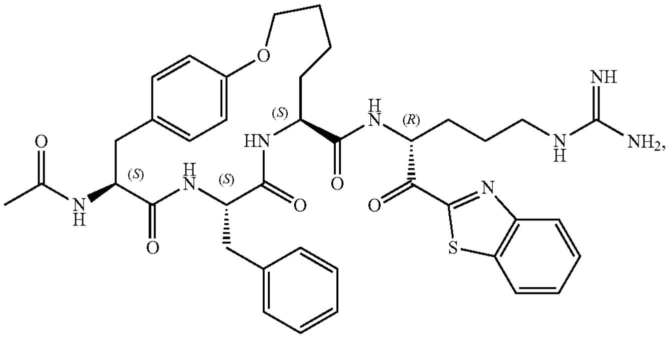
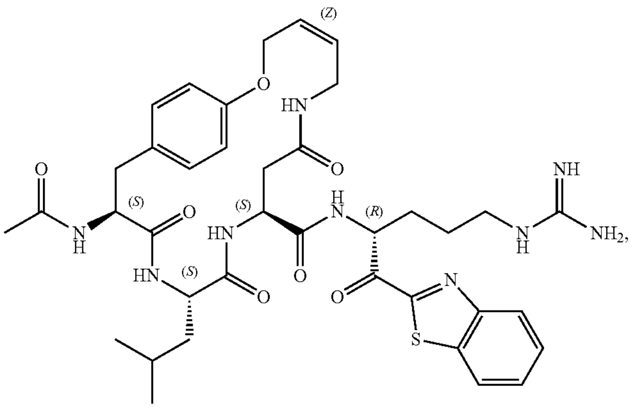
and -continued
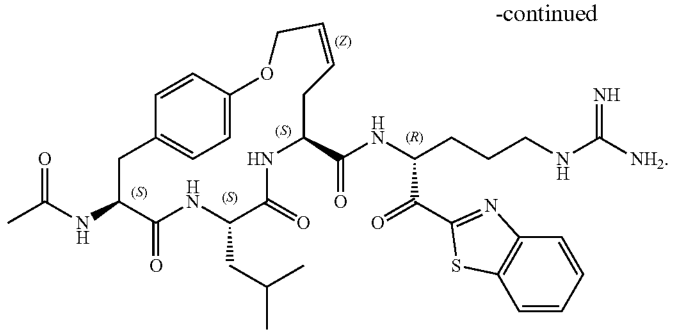
* * * * *

SEQUENCE LISTING

```
<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Lys Gln Leu Arg
1


<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Lys His Leu Arg
1


<210> SEQ ID NO 3
<211> LENGTH: 4
<212> TYPE: PRT
<213> ORGANISM: Artificial Sequence
<220> FEATURE:
<223> OTHER INFORMATION: Synthetic

<400> SEQUENCE: 3

Trp Gln Leu Arg
1


<210> SEQ ID NO 4
<211> LENGTH: 4
<212> TYPE: PRT
<213> ORGANISM: Artificial Sequence
<220> FEATURE:
<223> OTHER INFORMATION: Synthetic

<400> SEQUENCE: 4

Lys Phe Leu Arg
1


<210> SEQ ID NO 5
<211> LENGTH: 4
<212> TYPE: PRT
<213> ORGANISM: Artificial Sequence
```

<220> FEATURE:
<223> OTHER INFORMATION: Synthetic

<400> SEQUENCE: 5

Lys Phe Leu Arg
1

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Arg Gln Leu Arg
1

<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ser Gln Leu Arg
1

<210> SEQ ID NO 8
<211> LENGTH: 4
<212> TYPE: PRT
<213> ORGANISM: Artificial Sequence
<220> FEATURE:
<223> OTHER INFORMATION: Synthetic

<400> SEQUENCE: 8

Lys Arg Leu Arg
1

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Trp Arg Leu Arg
1

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Ser Lys Leu Arg
1

<210> SEQ ID NO 11
<211> LENGTH: 4
<212> TYPE: PRT
<213> ORGANISM: Artificial Sequence
<220> FEATURE:

<223> OTHER INFORMATION: Synthetic

<400> SEQUENCE: 11

Ser His Leu Arg
1

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Trp Lys Leu Arg
1

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Ser Lys Phe Arg
1

<210> SEQ ID NO 14
<211> LENGTH: 4
<212> TYPE: PRT
<213> ORGANISM: Artificial Sequence
<220> FEATURE:
<223> OTHER INFORMATION: Synthetic

<400> SEQUENCE: 14

Asn Lys Leu Arg
1

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Ser Arg Leu Arg
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

<400> SEQUENCE: 16

Thr Lys Leu Arg
1

<210> SEQ ID NO 17
<211> LENGTH: 4
<212> TYPE: PRT
<213> ORGANISM: Artificial Sequence
<220> FEATURE:
<223> OTHER INFORMATION: Synthetic -continued

```
<400> SEQUENCE: 17

Ser Trp Leu Arg
1


<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Arg Lys Leu Arg
1


<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Phe Leu Phe Arg
1


<210> SEQ ID NO 20
<211> LENGTH: 4
<212> TYPE: PRT
<213> ORGANISM: Artificial Sequence
<220> FEATURE:
<223> OTHER INFORMATION: Synthetic

<400> SEQUENCE: 20

Trp Leu Phe Arg
1
```